US012668646B2

(12) United States Patent
Lindsey et al.

(10) Patent No.: US 12,668,646 B2
(45) Date of Patent: Jun. 30, 2026

(54) CROSS-LINKING COMPOUNDS AND METHODS OF USE THEREOF

(71) Applicant: North Carolina State University, Raleigh, NC (US)

(72) Inventors: Jonathan S. Lindsey, Raleigh, NC (US); Hikaru Fujita, Ishikawa (JP); Nobuyuki Matsumoto, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 1064 days.

(21) Appl. No.: 17/628,943

(22) PCT Filed: Jul. 24, 2020

(86) PCT No.: PCT/US2020/043446
§ 371 (c)(1),
(2) Date: Jan. 21, 2022

(87) PCT Pub. No.: WO2021/016537
PCT Pub. Date: Jan. 28, 2021

(65) Prior Publication Data

US 2022/0275111 A1 Sep. 1, 2022

Related U.S. Application Data

(60) Provisional application No. 62/878,363, filed on Jul. 25, 2019, provisional application No. 62/878,361, filed on Jul. 25, 2019.

(51) Int. Cl.
*C08B 33/00* (2006.01)
*A61K 51/06* (2006.01)

(52) U.S. Cl.
CPC ............ *C08B 33/00* (2013.01); *A61K 51/065* (2013.01)

(58) Field of Classification Search
CPC ...................................................... C08B 33/00
See application file for complete search history.

(56) References Cited

U.S. PATENT DOCUMENTS 3,710,795 A 1/1973 Higuchi et al.
RE28,819 E 5/1976 Thompson
(Continued)

FOREIGN PATENT DOCUMENTS

WO 2006010165 A2 1/2006
WO 2010128120 A1 11/2010
(Continued)

OTHER PUBLICATIONS

Adinolfi, M. et al., European Journal of Organic Chemistry, "Glycosylated Eumelanin Building Blocks by Thioglycosylation of 5,6-Diacetoxyindole with an Expedient Selenium-Based Dynamic-Mixture Methodology", 2012, pp. 4333-4338 (Year: 2012).*
(Continued)

*Primary Examiner* — Bahar Craigo
(74) *Attorney, Agent, or Firm* — Myers Bigel, P.A.

(57) ABSTRACT

Compounds comprising a cross-linking moiety and a protecting group are described herein along with their methods of use. The cross-linking moiety may comprise an indoxyl and the protecting group may comprise a sugar (e.g., a glucuronide or glucoside), phosphoester, or sulfoester group. The cross-linking moiety and protecting group may be attached to each other via an oxygen atom, sulfur atom, or linker. In some embodiments, the linker attaching the cross-linking moiety and protecting group is a self-immolative linker. A compound of the present invention may cross-link under physiological conditions and/or in vivo.

15 Claims, 11 Drawing Sheets

(56) References Cited

U.S. PATENT DOCUMENTS

| | | | |
|---|---|---|---|
| 4,328,245 | A | 5/1982 | Yu et al. |
| 4,358,603 | A | 11/1982 | Yu |
| 4,409,239 | A | 10/1983 | Yu |
| 4,410,545 | A | 10/1983 | Yu et al. |
| 4,522,811 | A | 6/1985 | Eppstein et al. |
| 5,816,259 | A | 10/1998 | Rose |
| 5,952,366 | A | 9/1999 | Pandey et al. |
| 6,080,383 | A | 6/2000 | Rose |
| 6,208,553 | B1 | 3/2001 | Gryko et al. |
| 6,212,093 | B1 | 4/2001 | Lindsey |
| 6,272,038 | B1 | 8/2001 | Clausen et al. |
| 6,407,330 | B1 | 6/2002 | Lindsey et al. |
| 6,420,648 | B1 | 7/2002 | Lindsey |
| 6,451,942 | B1 | 9/2002 | Li et al. |
| 6,468,503 | B2 | 10/2002 | Rose |
| 6,559,374 | B2 | 5/2003 | Lindsey et al. |
| 6,603,070 | B2 | 8/2003 | Lindsey et al. |
| 6,642,376 | B2 | 11/2003 | Lindsey et al. |
| 6,657,884 | B2 | 12/2003 | Bocian et al. |
| 6,728,129 | B2 | 4/2004 | Lindsey et al. |
| 6,759,509 | B1 | 7/2004 | King et al. |
| 6,765,092 | B2 | 7/2004 | Lindsey et al. |
| 6,849,730 | B2 | 2/2005 | Lindsey et al. |
| 6,916,982 | B2 | 7/2005 | Loewe et al. |
| 6,924,375 | B2 | 8/2005 | Lindsey et al. |
| 6,944,047 | B2 | 9/2005 | Rotenberg et al. |
| 6,946,552 | B2 | 9/2005 | Lindsey et al. |
| 7,005,237 | B2 | 2/2006 | Lindsey |
| 7,022,862 | B2 | 4/2006 | Lindsey et al. |
| 7,148,361 | B2 | 12/2006 | Lindsey et al. |
| 7,153,975 | B2 | 12/2006 | Lindsey et al. |
| 7,317,108 | B2 | 1/2008 | Lindsey et al. |
| 7,323,561 | B2 | 1/2008 | Lindsey et al. |
| 7,332,599 | B2 | 2/2008 | Yu et al. |
| 7,378,520 | B2 | 5/2008 | Lindsey et al. |
| 7,501,507 | B2 | 3/2009 | Balakumar et al. |
| 7,501,508 | B2 | 3/2009 | Lindsey et al. |
| 7,514,067 | B2 | 4/2009 | Kassis et al. |
| 7,534,807 | B2 | 5/2009 | Kim et al. |
| 7,582,751 | B2 | 9/2009 | Lindsey et al. |
| 7,615,221 | B2 | 11/2009 | Mayers et al. |
| 7,633,007 | B2 | 12/2009 | Lindsey et al. |
| 7,745,618 | B2 | 6/2010 | Kiper et al. |
| 7,799,910 | B2 | 9/2010 | Lindsey et al. |
| 7,807,136 | B2 | 10/2010 | Mayers et al. |
| 7,884,280 | B2 | 2/2011 | Lindsey |
| 7,919,770 | B2 | 4/2011 | Youngblood et al. |
| 7,994,312 | B2 | 8/2011 | Lindsey et al. |
| 8,097,609 | B2 | 1/2012 | Borbas et al. |
| 8,168,159 | B2 | 5/2012 | Kassis et al. |
| 8,187,824 | B2 | 5/2012 | Lindsey |
| 8,207,329 | B2 | 6/2012 | Lindsey et al. |
| 8,278,340 | B2 | 10/2012 | Melander et al. |
| 8,394,953 | B2 | 3/2013 | Kassis |
| 8,603,437 | B2 | 12/2013 | Kassis et al. |
| 9,186,425 | B2 | 11/2015 | Kassis et al. |
| 9,303,165 | B2 | 4/2016 | Lindsey et al. |
| 9,320,815 | B2 | 4/2016 | Kassis |
| 9,365,722 | B2 | 6/2016 | Lindsey et al. |
| 9,499,638 | B2 | 11/2016 | Okamoto et al. |
| 2003/0228324 | A1 | 12/2003 | Malcolm et al. |
| 2005/0059727 | A1 | 3/2005 | Nair et al. |
| 2005/0113290 | A1 | 5/2005 | Rose |
| 2006/0018908 | A1 | 1/2006 | Mayers et al. |
| 2009/0203879 | A1 | 8/2009 | Gengrinovitch |
| 2011/0142756 | A1 | 6/2011 | Mayers et al. |
| 2011/0152252 | A1 | 6/2011 | Johannes et al. |
| 2011/0318322 | A1 | 12/2011 | Bossard |
| 2014/0141062 | A1 | 5/2014 | Gadek et al. |
| 2016/0095934 | A1 | 4/2016 | Wang et al. |
| 2017/0042979 | A1 | 2/2017 | Stefano |
| 2017/0119784 | A1 | 5/2017 | Karaboga et al. |
| 2017/0266161 | A1 | 9/2017 | Vafai et al. |
| 2019/0142642 | A1 | 5/2019 | Burnet et al. |

FOREIGN PATENT DOCUMENTS

| | | | | |
|---|---|---|---|---|
| WO | 2013078106 | A1 | | 5/2013 |
| WO | 2015149070 | A1 | | 10/2015 |
| WO | WO2016141207 | A1 | * | 9/2016 |
| WO | 2018035281 | A1 | | 2/2018 |
| WO | 2018102252 | A1 | | 6/2018 |
| WO | 2019165171 | A2 | | 8/2019 |

OTHER PUBLICATIONS

Corani, A. et al., The Journal of Physical Chemistry, "Bottom-Up Approach to Eumelanin Photoprotection: Emission Dynamics in Parallel Sets of Water-Soluble 5,6-Dihydroxyindole-Based Model Systems", 2012, vol. 116, pp. 13151-13158 (Year: 2012).*

Afonso et al. "Synthesis of 2,4,6-Tri-substituted-1,3,5-Triazines" Molecules, 11:81-102 (2006).

Al et al. "In Vivo Covalent Cross-Linking of Photon-Converted Rare-Earth Nanostructures for Tumour Localization and Theranostics" Nature Communications, 7:10432 (2016).

Alderson et al. "Characterization of a CC49-Based Single-Chain Fragment-□-Lactamase Fusion Protein for Antibody-Directed Enzyme Prodrug Therapy" Bioconjugate Chemistry, 17(2):410-480 (2006).

Alouane et al. "Self-Immolative Spacers: Kinetic Aspects, Structure-Property Relationships, and Applications" Angewandte Chemie International Edition, 54(26): 7492-7509 (2015).

Andreani et al. "Synthesis and Screening for Antiacetylcholinesterase Activity of (1-Benzyl-4-oxopiperidin-3-ylidene) methylindoles and -pyrroles Related to Donepezil" Journal of Medicinal Chemistry, 44(23):4011-4014 (2001).

Annison et al. "Acetylated, propionylated or butyrylated starches raise large bowel short-chain fatty acids preferentially when fed to rats" The Journal of Nutrition, 133(11):3523-3528 (2003).

Antunes et al. "Synthesis and Evaluation of [18F]-FEAnGA as a PET Tracer for beta-Glucuronidase Activity" Bioconjugate Chemistry, 21(5):911-920 (2010).

Bagshawe, K. D. "Antibody Directed Enzymes Revive Anti-Cancer Prodrugs Concept" British Journal of Cancer, 56:531-532 (1987).

Bagshawe, K. D. "Towards generating cytotoxic agents at cancer sites" British Journal of Cancer, 60:275-281 (1989).

Barandov et al. "A New Bifunctional Chelator Enables Facile Biocoupling and Radiolabeling as the Basis for a Bioconjugation Kit" ChemBioChem, 15(7):986-994 (2014).

Beloqui et al. "A simple route to highly active single-enzyme nanogels" Chemical Science, 9(4):1006-1013 (2018).

Blotny, Grzegorz "Recent Applications of 2,4,6-Trichloro-1,3,5-Triazine and Its Derivatives in Organic Synthesis" Tetrahedron, 62:9507-9522 (2006).

Bosslet et al. "Molecular and functional characterisation of a fusion protein suited for tumour specific prodrug activation" British Journal of Cancer, 65:234-238 (1992).

Bowers et al. "Salt Effects on beta-Glucosidase: pH-Profile Narrowing" Biochimica et Biophysica Acta, 1774:1500-1507 (2007).

Breitinger, Hans-Georg "Synthesis and characterization of 2,3-di-O-alkylated amyloses: hydrophobic substitution destabilizes helical conformation" Biopolymers, 69:301-310 (2003).

Calissendorff et al. "Lugol's solution and other iodide preparations: perspectives and research directions in Graves' disease" Endocrine, 58:467-473 (2017).

Chen et al. "In silico design, synthesis, and biological evaluation of radioiodinated quinazolinone derivatives for alkaline phosphatase-mediated cancer diagnosis and therapy" Molecular Cancer Therapeutics, 5(12):3001-3013 (2006).

Chen et al. "Glucuronides in Anti-Cancer Therapy" Current Medicinal Chemistry, 3:139-150 (2003).

Chen et al. "Membrane-Localized Activation of Glucuronide Prodrugs by beta-Glucuronidase Enzymes" Cancer Gene Therapy, 14:187-200 (2007).

Chen et al. "Molecular-Docking-Guided Design, Synthesis, and Biologic Evaluation of Radioiodinated Quinazolinone Prodrugs" Journal of Medicinal Chemistry, 50:663-673 (2007).

(56) References Cited

OTHER PUBLICATIONS

Cooksey, Christopher J. "Tyrian Purple: 6,6'-Dibromoindigo and Related Compounds" Molecules, 6:736-769 (2001).
Cotson et al. "Studies in Enzyme Cytochemistry. IV. Kinetics of Aerial Oxidation of Indoxyl and Some of Its Halogen Derivatives" Proceedings of The Royal Society B, 148:506-519 (1958).
Cowley et al. "Triazinylaniline Derivatives as Fluorescence Probes. Part 1." J. Chem. Soc. Perkin Trans. 2:1495-1500 (1991).
Dale et al. "Reversible Inhibitors of beta-Glucosidase" Biochemistry, 24:3530-3539 (1985).
De Groot et al. "Elongated Multiple Electronic Cascade and Cyclization Spacer Systems in Activatible Anticancer Prodrugs for Enhanced Drug Release" The Journal of Organic Chemistry, 66:8815-8830 (2001).
De La Rica et al. "Enzyme-responsive nanoparticles for drug release and diagnostics" Advanced Drug Delivery Reviews, 64(11):967-978 (2012).
Dilworth et al. "The Radiopharmaceutical Chemistry of Technetium and Rhenium" The Chemistry of Molecular Imaging, 1st ed., pp. 137-164 (2015).
Ding et al. "Bioconjugated PLGA-4-arm-PEG branched polymeric nanoparticles as novel tumor targeting carriers" Nanotechnology, 22(165101):1-13 (2011).
Dommerholt et al. "Readily Accessible Bicyclononynes for Bioorthogonal Labeling and Three-Dimensional Imaging of Living Cells." Angewandte Chemie International Edition, 49:9422-9425 (2010).
Driguez, Pierre-Alexandre "Dichlorotetrakis(1,1-dimethylethyl)di-µ-hydroxyditin" Encyclopedia of Reagents for Organic Synthesis. pp. 1-3 (2001).
Dubowchik et al. "Cathepsin B-Labile Dipeptide Linkers for Lysosomal Release of Doxorubicin from Internalizing Immunoconjugates" Bioconjugate Chemistry, 13:855-869 (2002).
Dumoulin et al. "Cross-linked amylose as matrix for drug controlled release. X-ray and FT-IR structural analysis" Carbohydrate Polymers, 37:361-370 (1998).
Ehmann et al. "Beta-Particle Interactions" Radiochemistry and Nuclear Methods of Analysis, John Wiley and Sons, Inc., p. 155 (1991).
Enciso et al. "Rapid, semi-automated convergent synthesis of low generation triazine dendrimers using microwave assisted reactions" Polymer Chemistry, 5:4635-4640 (2014).
Esser-Kahn et al. "Protein-Cross-Linked Polymeric Materials through Site-Selective Bio-Conjugation" Angewandte Chemie, 47:3751-3754 (2008).
Ferreira et al. "The Natural Constituents of Historical Textile Dyes" Chemical Society Reviews, 33:329-336 (2004).
Fräbel et al. "Engineering of New-to-Nature Halogenated Indigo Precursors in Plants" Metabolic Engineering, 46:20-27 (2018).
Fujita et al. "Enzymatically triggered chromogenic cross-linking agents under physiological conditions" New Journal of Chemistry, 44(3):719-743 (2020).
Gao et al. "Rapid and efficient crossing blood-brain barrier: hydrophobic drug delivery system based on propionylated amylose helix nanoclusters" Biomaterials, 113:133-144 (2017).
Gessler et al. "V-Amylose at atomic resolution: X-ray structure of a cycloamylose with 26 glucose residues (cyclomaltohexaicosaose)" Proceedings of the National Academy of Sciences USA, 96:4246-4251 (1999).
Gilmore et al. "N-Terminal Protein Modification through a Biomimetic Transamination Reaction" Angewandte Chemie, 45:5307-5311 (2006).
Gisbert-Garzaran et al. "Self-immolative chemistry in nanomedicine" Chemical Engineering Journal, 340:24-31 (2018).
Gotor et al. "Optical pH Sensor Covering the Range from PH 0-14 Compatible with Mobile-Device Readout and Based on a Set of Rationally Designed Indicator Dyes" Analytical Chemistry, 89:8437-8444 (2017).
Graaf et al. "Beta-glucuronidase-mediated drug release" Current Pharmaceutical Design, 8(15):1391-1403 (2002).
Grinda et al. "A Heterodimeric Glucuronide Prodrug for Cancer Tritherapy: the Double Role of the Chemical Amplifier" ChemMedChem, 6:2137-2141 (2011).
Gröst et al. "PYRROC: The First Functionalized Cycloalkyne that Facilitates Isomer-Free Generation of Organic Molecules by SPAAC" Organic and Biomolecular Chemistry, 13:3866-3870 (2015).
Gu et al. "Protein Nanocapsule Weaved with Enzymatically Degradable Polymeric Network" Nano Letters, 9(12):4533-4538 (2009).
Hancock et al. "The other double helix-the fascinating chemistry of starch" Journal of Chemical Education, 77(8):988-992 (2000).
Hermanson et al. "The Reactions of Bioconjugation" Bioconjugate Techniques, Third Edition, Chapter 3, pp. 229-258 (2013).
Ho et al. "Synthesis and Biologic Evaluation of a Radioiodinated Quinazolinone Derivative for Enzyme-Mediated Insolubilization Therapy" Bioconjugate Chemistry, 13:357-364 (2002).
Holt et al. "Studies in Enzyme Cytochemistry. III. Relationships between Solubility, Molecular Association and Structure in Indigoid Dyes" Proceedings of the Royal Society of London B, 148:495-505 (1958).
Houba et al. "A Novel Doxorubicin-Glucuronide Prodrug DOX-GA3 for Tumour-Selective Chemotherapy: Distribution and Efficacy in Experimental Human Ovarian Cancer" British Journal of Cancer, 84:550-557 (1999).
Houba et al. "Characterization of Novel Anthracycline Prodrugs Activated by Human beta-Glucuronidase for Use in Antibody-Directed Enzyme Prodrug Therapy" Biochemical Pharmacology, 52:455-463 (1996).
Hu et al. "Enzyme-responsive nanomaterials for controlled drug delivery" Nanoscale, 6(21):12273-12286 (2014).
Immel et al. "The hydrophobic topographies of amylose and its blue iodine complex" Starch/Stärke, 52(1):1-8 (2000).
Jacobsen et al. "Amine Landscaping to Maximize Protein-Dye Fluorescence and Ultrastable Protein-Ligand Interaction" Cell Chemical Biology, 24:1040-1047 (2017).
Kadokawa, Jun-ichi "Preparation and applications of amylose supramolecules by means of phosphorylase-catalyzed enzymatic polymerization" Polymers, 4:116-133 (2012).
Kassis et al. "Novel Prodrugs for Targeting Diagnostic and Therapeutic Radionuclides to Solid Tumors" Molecules, 13:391-404 (2008).
Keller et al. "A thermally-cleavable linker for solid-phase synthesis" Tetrahedron Letters, 46(7):1181-1184 (2005).
Kempton et al. "Mechanism of Agrobacterium β-Glucosidase: Kinetic Studies" Biochemistry, 31:9961-9969 (1992).
Kerr et al. "Development and Activities of a New Melphalan Prodrug Designed for Tumor Selective Activation" Bioconjugate Chemistry, 9(2):255-259 (1996).
Kida et al. "Partially-methylated amyloses as effective hosts for inclusion complex formation with polymeric guests" ChemComm, pp. 1559-1561 (2007).
Kiernan, J. A. "Indigogenic Substrates for Detection and Localization of Enzymes" Biotechnic & Histochemistry, 82:73-103 (2007).
Koniev et al. "Developments and recent advancements in the field of endogenous amino acid selective bond forming reactions for bioconjugation" Chemical Society Reviews, 44:5495-5551 (2015).
Krishnaswamy et al. "Fascinating Organic Molecules from Nature. 2. The Blue of Blue Jeans and Royal Purple" Resonance, 17:1022-1033 (2012).
Kunishima et al. "Development of acid-catalyzed fluorous benzylating reagents based on a triazinedione core" Journal of Fluorine Chemistry, 190:68-74 (2016).
Lee et al. "Functionalization of a Triazine Dendrimer Presenting Four Maleimides on the Periphery and a DOTA Group at the Core" Molecules, 21(335):1-16 (2016).
Leenders et al. "Novel Anthracycline-Spacer-beta-Glucuronide, -beta-Glucoside, and -beta-Galactoside Prodrugs for Application in Selective Chemotherapy" Bioorganic & Medicinal Chemistry, 7:1597-1610 (1999).
Li et al. "Nanogels for Intracellular Delivery of Biotherapeutics" Journal of Controlled Release, 259:16-28 (2017).
Liang et al. "A Biocompatible Condensation Reaction for Controlled Assembly of Nanostructures in Living Cells" Nature Chemistry, 2:54-60 (2010).

(56) References Cited

OTHER PUBLICATIONS

Liu et al. "Sequential molecule-triggered release system based on acetylated amylose helix aggregates" ChemComm, 53:10680-10683 (2017).
Lu et al. "Catalytic synthesis of a new series of alkyl uronates and evaluation of their physicochemical properties" Molecules, 21(1301):1-15 (2016).
Mann et al. "Transferrin conjugation confers mucosal molecular targeting to a model HIV-1 trimeric gp 140 vaccine antigen" Journal of Controlled Release, 158:240-249 (2012).
Martini et al. "Technetium Complexes and Radiopharmaceuticals with Scorpionate Ligands" Molecules, 23(8):2039 (2018).
Mayers, G. L. "Targeted Molecular Brachytherapy," Drug Development Research, 67(1):94-106 (2006).
Mckay et al. "Click Chemistry in Complex Mixtures: Bioorthogonal Bioconjugation" Chemistry & Biology, 21:1075-1101 (2014).
Melvin et al. "The improved synthesis of beta-D-glucuronides using TEMPO and t-butyl hypochlorite" Tetrahedron etters, 40(6):1201-1202 (1999).
Mindt et al. "A Click Approach to Structurally Diverse Conjugates Containing a Central Di-1,2,3-triazole Metal Chelate" ChemMedChem, 4:529-539 (2009).
Mindt et al. "Molecular Assembly of Multifunctional 99mTc Radiopharmaceuticals Using 'Clickable' Amino Acid Derivatives" ChemMedChem, 5:2026-2038 (2010).
Mu et al. "Development of Endogenous Enzyme-Responsive Nanomaterials for Theranostics" Chemical Society Reviews, 47(15):5554-5573 (2018).
Mürdter et al. "Dose Optimization of a Doxorubicin Prodrug (HMR 1826) in Isolated Perfused Human Lungs: Low Tumor pH Promotes Prodrug Activation by beta-Glucuronidase" The Journal of Pharmacology and Experimental Therapeutics, 301:223-228 (2002).
Natrajan et al. "Zwitterionic Reagents for Labeling, Cross-Linking and Improving the Performance of Chemiluminescent Immunoassays" Organic & Biomolecular Chemistry, 10:1883-1895 (2012).
Niikura et al. "Versatile Glycoblotting Nanoparticles for High-Throughput Protein Glycomics" Chemistry a European Journal, 11(13):3825-3834 (2005).
Nishimura et al. "High-Throughput Protein Glycomics: Combined Use of Chemoselective Glycoblotting and MALDI-TOF/TOF Mass Spectrometry" Angewandte Chemie, 44:91-96 (2004).
Niu et al. "New Insights into the Solubilization of Bodipy Dyes" Tetrahedron Letters, 50:3840-3844 (2009).
Noga et al. "Controlled shielding and deshielding of gene delivery polyplexes using hydroxyethyl starch (HES) and alpha-amylase" Journal of Controlled Release, 159:92-103 (2012).
Noga et al. "The effect of molar mass and degree of hydroxyethylation on the controlled shielding and deshielding of hydroxyethyl starch-coated polyplexes" Biomaterials, 34:2530-2538 (2013).
O'Neill et al. "Enzymatic synthesis using glycoside phosphorylases" Carbohydrate Research, 403:23-37 (2015).
Orita et al. "Highly efficient deacetylation by use of the neutral organotin catalyst [tBu2SnOH (CI)] 2" Chemistry—A European Journal, 7(15):3321-3327 (2001).
Padalkar et al. "Synthesis of Novel Fluorescent 1,3,5-Trisubstituted Triazine Derivatives and Photophysical Property Evaluation of Fluorophores and Their BSA Conjugates" Heterocyclic Communications, 18:127-134 (2012).
Pearson et al. "Histochemical beta-Glucuronidase Distribution in Mammalian Tissue as Detected by 5-Bromo-4-Chloroindol-3-yl-beta-D-glucopyruroniside" Department of the Army, Technical Manuscript 366, pp. 1-12 (1967).
Pospisil et al. "Computational and Biological Evaluation of Quinazolinone Prodrug for Targeting Pancreatic Cancer" Chemical Biology & Drug Design, 79:926-934 (2012).
Pospisil et al. "Computational Modeling and Experimental Evaluation of a Novel Prodrug for Targeting the Extracellular Space of Prostate Tumors" Cancer Research, 67(5):2197-2204 (2007).
Pospisil et al. "Computational and Biological Evaluation of Quinazolinone Prodrug for Targeting Pancreatic Cancer" Molecular Diagnostics and Treatment of Pancreatic Cancer, Chapter 17, pp. 385-403 (2014).
Putseys et al. "Amylose-inclusion complexes: formation, identity and physico-chemical properties" Journal of Cereal Science, 51:238-247 (2010).
Qian et al. "Targeted Drug Delivery via the Transferrin Receptor-Mediated Endocytosis Pathway" Pharmacological Reviews, 54(4):561-587 (2002).
Rabiger et al. "Synthesis of 5-Iodo- and 5-Nitro-3-Indolyl Phosphates as Cytochemical Substrates for Acid Phosphatase" Journal of Heterocyclic Chemistry, 7:307-311 (1970).
Rachmawati et al. "Synthesis of telechelic and three-arm polytetrahydrofuran-block-amylose" Macromolecular Chemistry and Physics, 216(10):1091-1102 (2015).
Renoux et al. "A New Cyclopamine Glucuronide Prodrug with Improved Kinetics of Drug Release" Organic & Biomolecular Chemistry, 9:8459-8464 (2011).
Renoux et al. "Targeting the tumour microenvironment with an enzyme-responsive drug delivery system for the efficient therapy of breast and pancreatic cancers" Chemical Science, 8:3427-3433 (2017).
Roberts et al. "Chemistry for peptide and protein PEGylation" Advanced Drug Delivery Reviews, 54:459-476 (2002).
Rodrigues et al. "Development of a humanized disulfide-stabilized anti-p185HER2 Fv-beta-lactamase fusion protein for activation of a cephalosporin doxorubicin prodrug" Cancer Research, 55:63-70 (1995).
Romhild et al. "Glycated 99mTc-Tricarbonyl-Labeled Peptide Conjugates for Tumor Targeting by 'Click-to-Chelate'" ChemMedChem, 12:66-74 (2017).
Rooseboom et al. "Enzyme-Catalyzed Activation of Anticancer Prodrugs" Pharmacological Reviews, 56:53-102 (2004).
Rose, S. "A Proposal for a New Direction to Treat Cancer" Journal of Theoretical Biology, 195:111-128 (1998).
Rosen et al. "Targeting the N Terminus for Site-Selective Protein Modification" Nature Chemical Biology, 13:697-705 (2017).
Russell et al. "Oxidation of Carbanions. IV. Oxidation of Indoxyl to Indigo in Basic Solution" Journal of the American Chemical Society, 91:3851-3859 (1969).
Schatz et al. "Polysaccharide-block-polypeptide Copolymer Vesicles: Towards Synthetic Viral Capsids" Angewandte Chemie International Edition, 48(14):2572-2575 (2009).
Scheck et al. "Regioselective Labeling of Antibodies through N-Terminal Transamination" ACS Chemical Biology, 2:247-251 (2007).
Senter et al. "Anti-tumor Effects of Antibody-Alkaline Phosphatase Conjugates in Combination with Etoposide Phosphate" Proceedings of the National Academy of Sciences USA, 85:4842-4846 (1988).
Sharma et al. "Antibody-Directed Enzyme Prodrug Therapy (ADEPT) for Cancer" In Macromolecular Anticancer Therapeutics, Chapter 11, pp. 393-406 (2010).
Shiraishi et al. "A coumarin-thiourea conjugate as a fluorescent probe for Hg (II) in aqueous media with a broad pH range 2-12" Organic & Biomolecular Chemistry, 8(6):1310-1314 (2010).
Siemers et al. "Construction, Expression, and Activities of L49-sFv-□-Lactamase, a Single-Chain Antibody Fusion Protein for Anticancer Prodrug Activation," Bioconjugate Chemistry, 8:510-519 (1997).
Steffensen et al. "Dendrimers Based on [1,3,5]-Triazines" Journal of Polymer Science Part A: Polymer Chemistry, 44(11):3411-3433 (2006).
Sun et al. "Conjugation Reaction with 8-Arm PEG Markedly Improves the Immunogenicity of *Mycobacterium tuberculosis* CFP10-TB10.4 Fusion Protein" Bioconjugate Chemistry, 28:1658-1668 (2017).
Tanaka et al. "Synthesis of Aza-Bridged Calix(4-Methoxy)Triazines toward Flattened π-Conjugated Macrocycles" Heterocycles, 79:609-616 (2009).
Taniguchi et al. "PhotochemCAD 3: Diverse Modules for Photophysical Calculations with Multiple Spectral Databases" Photochemistry and Photobiology, 94:277-289 (2018).

(56) References Cited

OTHER PUBLICATIONS

Thirumurugan et al. "Click Chemistry for Drug Development and Diverse Chemical-Biology Applications" Chemical Reviews, 113:4905-4979 (2013).
Tietze et al. "Proof of Principle in the Selective Treatment of Cancer by Antibody-Directed Enzyme Prodrug Therapy: The Development of a Highly Potent Prodrug" Angewandte Chemie International Edition, 41:759-761 (2002).
Tranoy-Opalinski et al. "beta-Glucuronidase-responsive prodrugs for selective cancer chemotherapy: an update" European Journal of Medicinal Chemistry, 74:302-313 (2014).
Trifonov et al. "Overview and Assessment of the Histochemical Methods and Reagents for the Detection of beta-Galactosidase Activity in Transgenic Animals" Anatomical Science International, 91:56-67 (2016).
Veronese "Peptide and protein PEGylation: a review of problems and solutions" Biomaterials, 22:405-417 (2001).
Wang et al. "Evaluation of Chemical, Physical, and Biologic Properties of Tumor-Targeting Radioiodinated Quinazolinone Derivative" Bioconjugate Chemistry, 18:754-764 (2007).
Wardman, P. "Chemical radiosensitizers for use in radiotherapy" Clinical Oncology, 19(6):397-417 (2007).
Witte et al. "Production of unnaturally linked chimeric proteins using a combination of sortase-catalyzed transpeptidation and click chemistry" Nature Protocols, 8(9):1808-1819 (2013).
Witus et al. "Site-specific Protein Bioconjugation via a Pyridoxal 5'-Phosphate-Mediated N-Terminal Transamination Reaction" Current Protocols in Chemical Biology, 2(2):125-134 (2010).
Wulff et al. "Modification of amylose and investigation of its inclusion behavior" Carbohydrate Research, 307:19-31 (1998).
Xue et al. "Bystander effect produced by radiolabeled tumor cells in vivo" Proceedings of the National Academy of Sciences, 99(21):13765-13770 (2002).
Yan et al. "Encapsulation of single enzyme in nanogel with enhanced biocatalytic activity and stability" Journal of the American Chemical Society, 128:11008-11009 (2006).
Yang et al. "Enzyme-mediated hydrolytic activation of prodrugs" Acta Pharmaceutica Sinica B, 1(3):143-159 (2011).
Yeh et al. "Killing of Human Tumor Cells in Culture with Adriamycin Conjugates of Human Transferrin" Clinical Immunology and Immunopathology, 32:1-11 (1984).
Yuan et al. "Detection of Glutathione in Vitro and in Cells by the Controlled Self-Assembly of Nanorings" Analytical Chemistry, 85:1280-1284 (2013).
Zhang et al. "Applications of CBT-Cys Click Reaction: Past, Present, and Future" Science China Chemistry, 61:1088-1098 (2018).
Zhang et al. "Quantitation of Tolyporphins, Diverse Tetrapyrrole Secondary Metabolites with Chlorophyll-Like Absorption, from a Filamentous Cyanobacterium-Microbial Community" Phytochemical Analysis, 29:205-216 (2018).
Zhu et al. "Solid-tumor radionuclide therapy dosimetry: New paradigms in view of tumor microenvironment and angiogenesis" Medical Physics, 37(6):2974-2984 (2010).
International Search Report and the Written Opinion of the International Searching Authority corresponding to International Patent Application No. PCT/US2020/043446 (13 pages) (mailed Dec. 15, 2020).
Rossiter et al. "Halogenated Indole-3-acetic Acids as Oxidatively Activated Prodrugs with Potential for Targeted Cancer Therapy" Bioorganic & Medicinal Chemistry Letters, 12:2523-2526 (2002).
Extended European Search Report corresponding to European Patent Application No. 20843756.6 (9 pages) (dated Jul. 13, 2023).
Nagata et al. "Synthesis of a 1,2-cis-indoxyl galactoside as a chromogenic glycosidase substrate" RSC Advances, 9:28241-28247 (2019).

* cited by examiner

1

2

3

4

34

1

CROSS-LINKING COMPOUNDS AND METHODS OF USE THEREOF

FIELD

The present invention concerns cross-linking compounds and methods of use thereof.

BACKGROUND

The construction of nanostructures upon enzymatic action under physiological conditions constitutes a new research arena that might be termed "synthetic chemistry in vivo." The formation of covalently cross-linked nanostructures in vivo is particularly attractive because the resulting scaffold can be exploited for further reactions such as bioconjugation.

However, new compounds and methods are needed.

SUMMARY

One aspect of the present invention is directed to compounds that can cross-link such as under physiological conditions and/or in vivo. A compound of the present invention may comprise a cross-linking moiety and a protecting group. The cross-linking moiety may comprise an indoxyl. In some embodiments, the protecting group comprises a sugar (e.g., a glucuronide or glucoside). The cross-linking moiety and protecting group may be attached to each other via an oxygen atom, sulfur atom, or linker. In some embodiments, the linker attaching the cross-linking moiety and protecting group is a self-immolative linker.

Another aspect of the present invention is directed to a compound having a structure of Formula I.

I

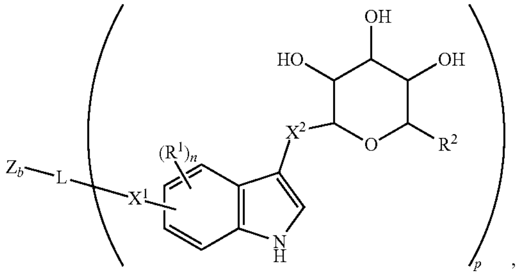

wherein:

Z is each independently a hydrogen, hydroxyl, amino, enzyme, polyiodide binding matrix, a targeting agent, a circulation enhancing agent, water solubilizing group, chromophore, or bioconjugatable group;

L is a linker (e.g., a hydrocarbon or polymer such as polyethylene glycol (PEG) each of which may be unsubstituted or substituted);

$X^1$ is absent or is —O— or —S—;

each $R^1$ is independently selected from a halogen, alkyl, alkenyl, alkynyl, —OH, alkoxy, acyloxy, carboxy, carboxylic ester, haloalkyl, boronate ester, thioalkoxy, and amino;

each $R^2$ is independently —$CH_2OH$ or —C(O)OH;

each $X^2$ is independently —O—, —S—, or a self-immolative linker, p is an integer of 1 to 6;

b is an integer of 1 to 6; and each n is independently an integer of 1 to 4;

or a pharmaceutically acceptable salt thereof.

Another aspect of the present invention is directed to a compound having a structure of Formula II:

II

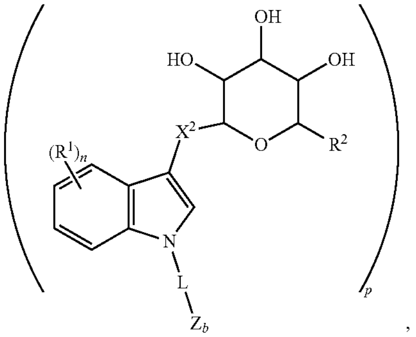

wherein:

Z is a hydrogen, hydroxyl, amino, enzyme, polyiodide binding matrix, a targeting agent, a circulation enhancing agent, water solubilizing group, chromophore, or bioconjugatable group;

L is a linker (e.g., a hydrocarbon or polymer such as polyethylene glycol (PEG) each of which may be unsubstituted or substituted);

each $R^1$ is independently selected from a halogen, alkyl, alkenyl, alkynyl, —OH, alkoxy, acyloxy, carboxy, carboxylic ester, boronate ester, haloalkyl, thioalkoxy, and amino;

each $R^2$ is independently —$CH_2OH$ or —C(O)OH;

each $X^2$ is independently —O—, —S—, or a self-immolative linker, p is an integer of 1 to 6;

b is an integer of 1 to 6; and each n is independently an integer of 1 to 4;

or a pharmaceutically acceptable salt thereof.

A further aspect of the present invention is directed to a method of using a compound of Formula I or Formula II to form a cross-linked compound, optionally wherein the cross-linked compound is a cross-linked deposit. In some embodiments, the cross-linked compound comprises an enzyme, polyiodide binding matrix, or bioconjugatable group.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 9A shows the effect of pH on the reaction progress [33 (100 μM), enzyme (200 nM), 0.05 M phosphate buffer, n=3]. FIG. 9B shows the effect of the enzyme concentration [33 (100 μM), 0.05 M phosphate buffer, 2 h, n=3]. FIG. 9C shows the effect of the concentration of 33 [enzyme (200 nM), 0.01 M phosphate buffer (pH 7, 0.05 M NaCl), 2 or 14 h, n=3). Yields were determined by absorption spectroscopy of solubilized indigoid dye.

DETAILED DESCRIPTION OF EXAMPLE EMBODIMENTS

Figure 1:
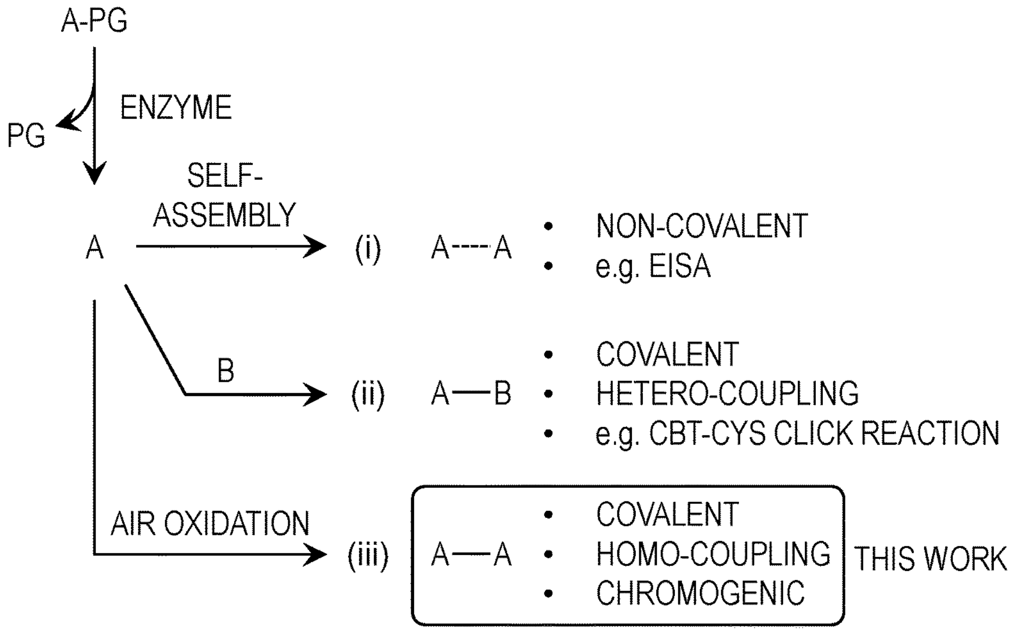
FIG. 1 is a schematic showing enzyme-triggered reactions of molecule A protected with a protecting group (PG) (A-PG); (i) shows self-assembly of A; (ii) shows hetero-coupling of A with acceptor B; and (iii) shows homo-coupling of A in the presence of $O_2$ according to aspects of the present invention.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

It will also be understood that, as used herein, the terms "example," "exemplary," and grammatical variations thereof are intended to refer to non-limiting examples and/or variant embodiments discussed herein, and are not intended to indicate preference for one or more embodiments discussed herein compared to one or more other embodiments.

The term “about,” as used herein when referring to a measurable value such as an amount or concentration and the like, is meant to encompass variations of ±10%, ±5%, ±1%, ±0.5%, or even ±0.1% of the specified value as well as the specified value. For example, “about X” where X is the measurable value, is meant to include X as well as variations of ±10%, ±5%, ±1%, ±0.5%, or even ±0.1% of X. A range provided herein for a measureable value may include any other range and/or individual value therein.

Unless indicated otherwise, nomenclature used to describe chemical groups or moieties as used herein follow the convention where, reading the name from left to right, the point of attachment to the rest of the molecule is at the right hand side of the name. For example, the group “alkylamino” is attached to the rest of the molecule at the amino end, whereas the group “aminoalkyl” is attached to the rest of the molecule at the alkyl end.

Unless indicated otherwise, where a chemical group is described by its chemical formula, including a terminal bond moiety indicated by “-” or “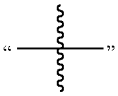”, it will be understood that the attachment is read from the side in which the bond appears. For example, —O-heteroaryl is attached to the rest of the molecule at the oxygen end.

“Alkyl” as used herein alone or as part of another group, refers to a fully saturated straight or branched chain hydrocarbon containing from 1 to 20 carbon atoms, which can be referred to as a C1-C20 alkyl. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. “Loweralkyl” as used herein, is a subset of alkyl, and, in some embodiments, refers to a saturated straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term “alkyl” or “loweralkyl” is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, polyalkoxy such as polyethylene glycol, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_a$, haloalkyl-$S(O)_a$, alkenyl-$S(O)_a$, alkynyl-$S(O)_a$, cycloalkyl-$S(O)_a$, cycloalkylalkyl-$S(O)_a$, aryl-$S(O)_a$, arylalkyl-$S(O)_a$, heterocyclo-$S(O)_a$, heterocycloalkyl-$S(O)_a$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where a is 0, 1, 2 or 3.

“Alkenyl” as used herein alone or as part of another group, refers to a straight or branched chain hydrocarbon containing from 1 to 20 carbon atoms (or in loweralkenyl 1 to 4 carbon atoms) that can include 1 to 8 double bonds in the normal chain, and can be referred to as a C1-C20 alkenyl. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term “alkenyl” or “loweralkenyl” is intended to include both substituted and unsubstituted alkenyl or loweralkenyl unless otherwise indicated and these groups may be substituted with groups as described in connection with alkyl and loweralkyl above.

“Alkynyl” as used herein alone or as part of another group, refers to a straight or branched chain hydrocarbon containing from 1 to 20 carbon atoms (or in loweralkynyl 1 to 4 carbon atoms) which include 1 triple bond in the normal chain, and can be referred to as a C1-C20 alkynyl. Representative examples of alkynyl include, but are not limited to, 2-propynyl, 3-butynyl, 2-butynyl, 4-pentynyl, 3-pentynyl, and the like. The term “alkynyl” or “loweralkynyl” is intended to include both substituted and unsubstituted alkynyl or loweralkynyl unless otherwise indicated and these groups may be substituted with the same groups as set forth in connection with alkyl and loweralkyl above.

“Halo” or “halogen” as used herein refers to any suitable halogen, including —F, —Cl, —Br, and —I.

“Mercapto” as used herein refers to an —SH group.

“Azido” as used herein refers to an $—N_3$ group.

“Cyano” as used herein refers to a —CN group.

“Hydroxyl” as used herein refers to an —OH group.

“Nitro” as used herein refers to an $—NO_2$ group.

“Alkoxy” as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

“Acyl” as used herein alone or as part of another group refers to a $—C(O)R^{20}$ group, wherein $R^{20}$ is an alkyl, alkenyl, alkynyl, cycloalkyl, or aryl.

“Acyloxy” as used herein alone or as part of another group refers to a $—OC(O)R^{20}$ group, wherein $R^{20}$ is an alkyl, alkenyl, alkynyl, cycloalkyl, or aryl.

“Haloalkyl” as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

“Alkylthio” as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

“Aryl” as used herein alone or as part of another group, refers to a monocyclic carbocyclic ring system or a bicyclic carbocyclic fused ring system having one or more aromatic rings. Representative examples of aryl include, but are not limited to, azulenyl, indanyl, indenyl, naphthyl, phenyl, tetrahydronaphthyl, and the like. The term “aryl” is intended to include both substituted and unsubstituted aryl unless otherwise indicated and these groups may be substituted with the same groups as set forth in connection with alkyl and loweralkyl above.

“Arylalkyl” as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —$NHR^{21}$, wherein $R^{21}$ is an alkyl group.

"Ester" as used herein alone or as part of another group refers to a —$C(O)OR^{22}$ radical, wherein $R^{22}$ is an alkyl, cycloalkyl, alkenyl, alkynyl, or aryl.

"Formyl" as used herein refers to a —C(O)H group.

"Carboxylic acid" as used herein refers to a —C(O)OH group.

"Carboxylic ester" as used herein refers to a —$C(O)OR^{23}$ group, wherein $R^{23}$ is an alkyl, cycloalkyl, alkenyl, alkynyl or aryl.

"Boronate ester" as used herein refers to a —$B(O)OR^{23}$ group, wherein $R^{23}$ is an alkyl, cycloalkyl, alkenyl, alkynyl or aryl.

"Phosphate ester" or "phosphoester" as used herein refers to a —$P(O)(OR^{23})_2$ group, wherein each $R^{23}$ is independently an alkyl, cycloalkyl, alkenyl, alkynyl or aryl.

"Sulfoester" as used herein refers to a —$S(O)_2(OR^{23})$ group, wherein $R^{23}$ is an alkyl, cycloalkyl, alkenyl, alkynyl or aryl.

"Heteroatom" as used herein refers to O, S or N.

"Heterocycle" or "heterocyclyl" as used herein, means a monocyclic heterocycle, a bicyclic heterocycle, or a tricyclic heterocycle containing at least one heteroatom in a ring.

"Pharmaceutically acceptable" as used herein means that the compound, anion, cation, or composition is suitable for administration to a subject to achieve the treatments described herein, without unduly deleterious side effects in light of the severity of the disease and necessity of the treatment.

As used herein, the terms "increase," "increases," "increased," "increasing," "improve," "enhance," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

Provided according to embodiments of the present invention are cross-linking compounds and methods of use thereof. A compound of the present invention may comprise a cross-linking moiety and a protecting group. The cross-linking moiety may comprise an indoxyl. In some embodiments, the protecting group may be a group that is cleaved by one or more endogenous enzymes in a subject and/or biological sample such as one or more endogenous enzymes in circulation, extracellular space (e.g., tumor extracellular space), and/or in a lysosome of a cell. Example groups that may be cleaved and/or protecting groups include, but are not limited to, amide groups, phosphoester groups, sulfoester groups, glycosyl groups, glucosides, glucuronides, groups that are labile to peroxidases, and/or groups that are known as self-immolative linkers. In some embodiments, the protecting group comprises a sugar (e.g., a glucoside or glucuronide), a phosphate (e.g., a phosphoester group), or a sulfur (e.g., a sulfoester group). Such groups can conveniently be attached using standard techniques of bioconjugation. Removal of a protecting group (PG) (e.g., by native enzymatic action) can reveal one or more cross-linking moieties, which may undergo self-reaction to create a cross-linked compound and/or a deposit comprising the cross-linked compound. In some embodiments, a compound of the present invention can cross-link with itself and/or another compound under physiological conditions and/or in vivo. In some embodiments, the protecting group comprises a sugar (e.g., a glucuronide or glucoside). The cross-linking moiety and protecting group may be attached to each other via an oxygen atom, sulfur atom, or linker. In some embodiments, the linker attaching the cross-linking moiety and protecting group is a self-immolative linker.

In some embodiments, a cross-linking compound of the present invention comprises an indoxyl and a glucuronide or glucoside, which may be attached to each other via an oxygen atom, sulfur atom, or linker. A cross-linking compound of the present invention may have a structure of Formula I or Formula II:

I

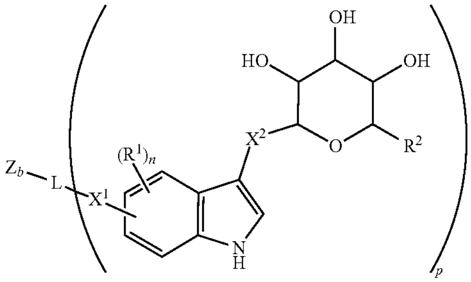

, or

II

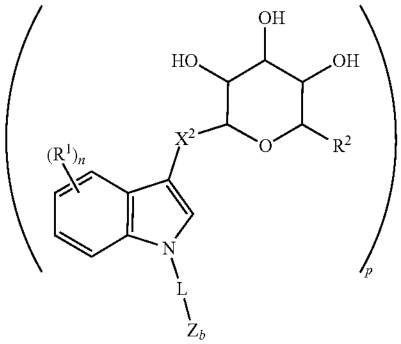

, wherein:

Z is each independently a hydrogen, hydroxyl, amino, enzyme, polyiodide binding matrix, a targeting agent, a circulation enhancing agent, water solubilizing group, chromophore, or bioconjugatable group;

L is a linker (e.g., a hydrocarbon or polymer such as polyethylene glycol (PEG) each of which may be unsubstituted or substituted);

$X^1$, if present, is absent or is —O— or —S—;

each $R^1$ is independently selected from a halogen, alkyl, alkenyl, alkynyl, —OH, alkoxy, acyloxy, carboxy, carboxylic ester, boronate ester, haloalkyl, thioalkoxy, and amino;

each $R^2$ is independently —$CH_2OH$ or —C(O)OH;

each $X^2$ is independently —O—, —S—, or a self-immolative linker, p is an integer of 1 to 6;

b is an integer of 1 to 6; and each n is independently an integer of 1 to 4;

or a pharmaceutically acceptable salt thereof.

In the compound of Formula I, the moiety to which p applies has the structure of:

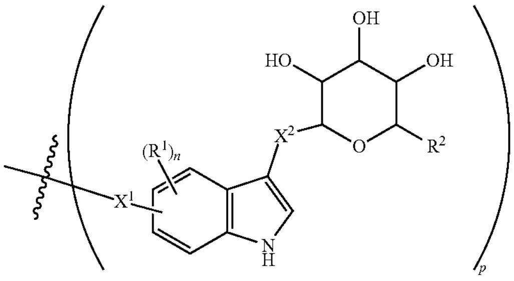
, wherein $R^1$, $R^2$, $X^1$, $X^2$, p, and n are each as defined herein. When p in the compound of Formula I is an integer of 2 to 6, each of the moieties to which p applies may be separately attached to the same atom or a different atom in the linker, L, (e.g., a multivalent linker) as defined herein. In some embodiments, in the compound of Formula I, two or more moieties to which p applies are attached to the same atom in the linker, L. In some embodiments, in the compound of Formula I, two or more moieties to which p applies are attached to different atoms in the linker, L. Similarly, when b in the compound of Formula I is an integer of 2 to 6, each Z may be separately attached to the same atom or a different atom in the linker, L, (e.g., a multivalent linker) as defined herein. In some embodiments, in the compound of Formula I, two or more Z are attached to the same atom in the linker, L. In some embodiments, in the compound of Formula I, two or more Z are attached to different atoms in the linker, L. The same atom or two or more different atoms in the linker, L, of the compound of Formula I may be attached to one or more Z and/or one or more moieties to which p applies.

In the compound of Formula II, the moiety to which p applies has the structure of:

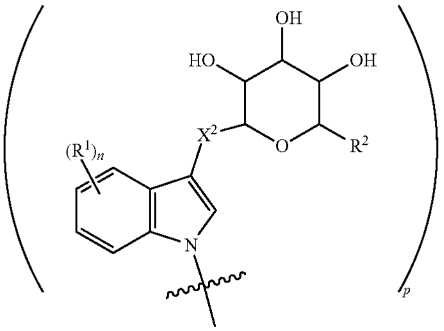

wherein $R^1$, $R^2$, $X^2$, p, and n are each as defined herein. When p in the compound of Formula II is an integer of 2 to 6, each of the moieties to which p applies may be separately attached to the same atom or a different atom in the linker, L, (e.g., a multivalent linker) as defined herein. In some embodiments, in the compound of Formula II, two or more moieties to which p applies are attached to the same atom in the linker, L. In some embodiments, in the compound of Formula II, two or more moieties to which p applies are attached to different atoms in the linker, L. Similarly, when b in the compound of Formula II is an integer of 2 to 6, each Z may be separately attached to the same atom or a different atom in the linker, L, (e.g., a multivalent linker) as defined herein. In some embodiments, in the compound of Formula II, two or more Z are attached to the same atom in the linker, L. In some embodiments, in the compound of Formula II, two or more Z are attached to different atoms in the linker, L. The same atom or two or more different atoms in the linker, L, of the compound of Formula I may be attached to one or more Z and/or one or more moieties to which p applies.

A compound of the present invention may comprise one or more (e.g., 1, 2, 3, or more) cross-linking unit(s). In some embodiments, a compound of the present invention comprises at least two cross-linking units that are optionally attached via a linker and the compound may further comprise a bioconjugatable group and/or chromophore. A cross-linking unit may comprise an indoxyl group. In some embodiments, a crosslinking unit may have a structure of:

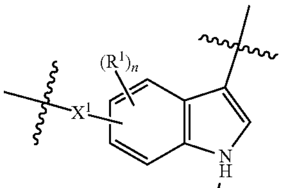
, or

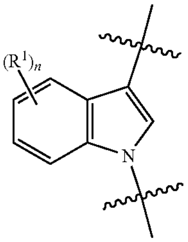
, wherein $X^1$, $R^1$, and n are each as defined herein.

In some embodiments, the compound has a structure of Formula I and Z, L, $X^1$, $R^1$, $R^2$, $X^2$, p, b, and n are each as defined herein. In some embodiments, the compound is a compound of Formula I and $X^1$ is O. In some embodiments, the compound is a compound of Formula I and $X^1$ is S.

In some embodiments, the compound has a structure of Formula II and Z, L, $R^1$, $R^2$, $X^2$, p, b, and n are each as defined herein. As one of skill in the art will recognize, L in the compound of Formula II may be attached to the depicted nitrogen via a carbon-nitrogen bond such as, for example, via a $-(CH_2)_q-$, alkenyl, alkynyl, aryl, $-C(O)-$, or $-CH_2C(O)-$ each of which may be substituted or unsubstituted, where q is an integer of 2 to 5, 10, or 20.

In some embodiments, the compound has a structure of Formula I':

I'

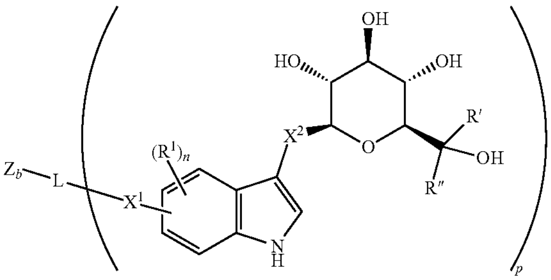
, wherein:

R' and R'' are both hydrogen or together form an oxo; and

Z, L, $X^1$, $R^1$, $X^2$, p, b, and n are each as defined herein.

In some embodiments, R' and R'' in the compound of Formula I' are both hydrogen. In some embodiments, R' and R'' in the compound of Formula I' together form an oxo. In some embodiments, p in the compound of Formula I' is 1, 2, 3, 4, 5, or 6. In some embodiments, b in the compound of Formula I' is 1, 2, 3, 4, 5, or 6.

In some embodiments, the compound has a structure of Formula II':

II'

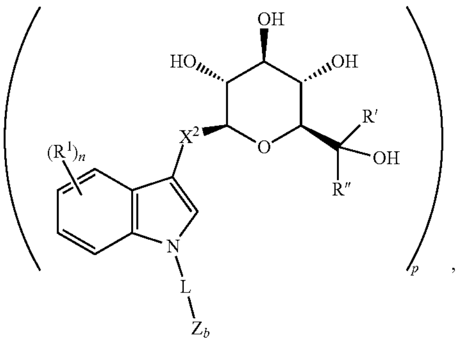

, wherein:

R' and R'' are both hydrogen or together form an oxo;

and Z, L, $R^1$, $R^2$, $X^2$, b, p, and n are each as defined herein.

In some embodiments, R' and R'' in the compound of Formula II' are both hydrogen. In some embodiments, R' and R'' in the compound of Formula II' together form an oxo. In some embodiments, p in the compound of Formula II' is 1, 2, 3, 4, 5, or 6. In some embodiments, b in the compound of Formula II' is 1, 2, 3, 4, 5, or 6.

In some embodiments, $R^1$ in a compound of Formula I or I' may be present at position 4, 5, 6, or 7 of the indole ring and n is an integer of 1, 2, or 3. In some embodiments, $R^1$ in a compound of Formula II or II' may be present at position 4, 5, 6, or 7 of the indole ring and n is an integer of 1, 2, 3, or 4. As one of skill in the art would understand, hydrogen is present at position 4, 5, 6, or 7 of the indole ring (as well as at position 2 of the indole ring), unless another substituent is indicated to be present. In some embodiments, n is 1 in a compound of Formula I, I', II, or II'. In some embodiments, n is 2 in a compound of Formula I, I', II, or II'. In some embodiments, n is 1 in a compound of Formula I, I', II, or II' and $R^1$ is at position 4 or 6 of the indole ring. In some embodiments, n is 2 in a compound of Formula I, I', II, or II' and $R^1$ is at position 4 and 6 of the indole ring. In some embodiments, $R^1$ in the compound of Formula I, I', II, or II' is a halogen (e.g., bromo). In some embodiments, $R^1$ at position 5 and/or 7 of the indole ring in the compound of Formula I, I', II, or II' is alkyl, alkenyl, alkynyl, —OH, alkoxy, acyloxy, carboxy, carboxylic ester, boronate ester, thioalkoxy, or amino.

In some embodiments, a compound of the present invention has a structure of Formula I'' or Formula II''.

I''

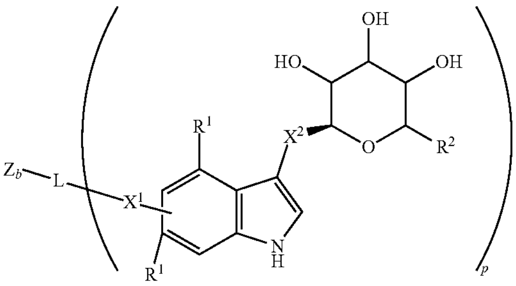

, or

II''

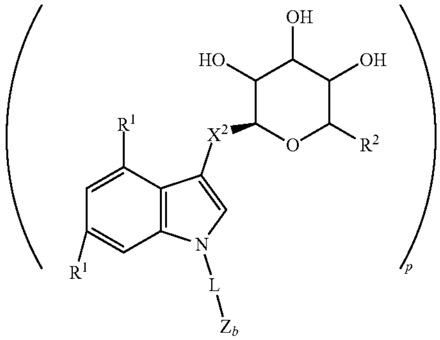

, wherein Z, L, $X^1$, $R^1$, $R^2$, $X^2$, b, p, and n are each as defined herein. In some embodiments, at least one of $R^1$ in the compound of Formula I'' or Formula II'' is a halogen. In some embodiments, both $R^1$ in the compound of Formula I'' or Formula II'' are a halogen. In some embodiments, p in the compound of Formula I'' or Formula II'' is 1, 2, 3, 4, 5, or 6.

In some embodiments, a compound of the present invention has a structure of Formula III:

III

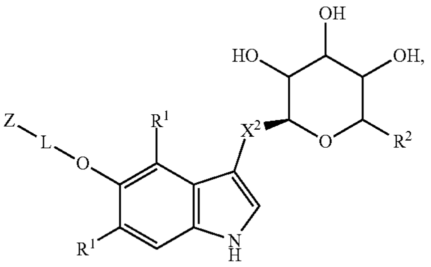

wherein Z, L, $R^1$, $R^2$, $X^2$, and n are each as defined above. In some embodiments, $X^2$ in the compound of Formula III is O and each $R^1$ is a halogen (e.g., bromo). In some embodiments, Z in the compound of Formula III is hydrogen or hydroxyl and L is $-(CH_2CH_2O)_m-$, wherein m is an integer of 1, 5, 10, 25, or 50 to 55, 75, or 100. As one of skill in the art will understand, $-(CH_2CH_2O)_m-$ is attached to the adjacent oxygen of the compound of Formula III (i.e., the oxygen adjacent to L in Formula III above) via a bond to a carbon of $-(CH_2CH_2O)_m-$ and Z is attached to an oxygen of $-(CH_2CH_2O)_m-$.

In some embodiments, $R^2$ in the compound of Formula I, I', I'', II, II', II'', or III is $-CH_2OH$. In some embodiments, $R^2$ in the compound of Formula I, I', I'', II, II', II'', or III is $-C(O)OH$.

In some embodiments, $X^2$ in the compound of Formula I, I', I", II, II', II", or III is O. In some embodiments, $X^2$ in the compound of Formula I, I', I", II, II', II", or III is S. In some embodiments, $X^2$ in the compound of Formula I, I', I", II, II', II", or III is a self-immolative linker that may be joined to the indoxyl and/or glucuronide or glucoside via an O or S of the self-immolative linker.

Exemplary linkers (also referred to herein interchangeably as a linking moiety, "L", "L1", "L2," or "$L_1$") that may be used in a compound of Formula I, I', I", II, II', II", or III include, but are not limited to, an atom (e.g., an oxygen, nitrogen, or sulfur atom that is optionally substituted), a hydrocarbon moiety, a peptoid moiety, an amino acid (e.g., lysine), an oligoethylene glycol group, 1,3,5-triazine, 1,3,5-trisubstituted benzene, self-immolative linkers, and/or a polyethylene glycol (PEG) group, each of which may be optionally substituted and/or attached to another linker. A linker may be selected to provide an attachment to another portion of the compound via a carbon-carbon bond or a carbon-heteroatom (e.g., oxygen, sulfur, or nitrogen) bond. For example, for a compound of Formula II, the linker may be attached to the depicted nitrogen via a carbon-nitrogen bond. In some embodiments, the linker may be a linear or branched hydrocarbon moiety (e.g., an alkyl moiety) and/or a carrier protein. In some embodiments, a linker (e.g., "L" or "L1") in a compound of Formula I, I', I", II, II', II", or III may be substituted with one or more substituents such as, but not limited to, an unsubstituted or substituted aryl, alkylamino, alkoxy, heterocycle, Z as defined herein, a moiety having a structure of Formula Ia as defined herein, a moiety having a structure of Formula IIa, a water solubilizing group, and/or a chromophore. Thus, in some embodiments, a compound of Formula I, I', I", III, II', II", or III may include two or more (e.g., 2, 3, 4, 5, 6, or more) of Z as defined herein, a moiety having a structure of Formula Ia as defined herein, and/or a moiety having a structure of Formula IIa. For example, in some embodiments, R in a compound of Formula I has a structure of Formula Ia and L is substituted with a moiety having a structure of Formula Ia, thereby the compound comprises two moieties having a structure of Formula Ia. In some embodiments, the compound is a compound of Formula I and Z in the compound is a bioconjugatable group and L in the compound is substituted with a bioconjugatable group, thereby the compound comprises two bioconjugatable groups. The linker may be multivalent. In some embodiments, a linker is covalently attached to a targeting agent (e.g., a cancer targeting agent), a circulation enhancing agent, a water-solubilizing group, and/or one or more (e.g., 2, 3, 4, 5, or more) cross-linking moieties as described herein and PG is a protecting group as described herein. Further example linkers are shown in Scheme I.

Scheme I: Example linkers that may be used in a compound of the present invention.

Linear:

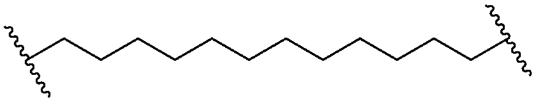

$—(CH_2)_n—$

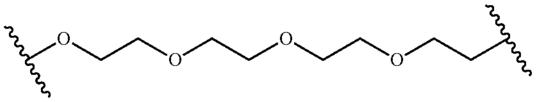

PEG

Branched:

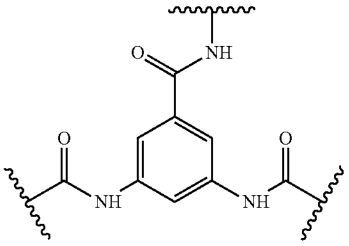

multiply substituted benzene

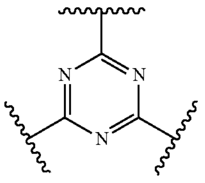

1,3,5-triazine

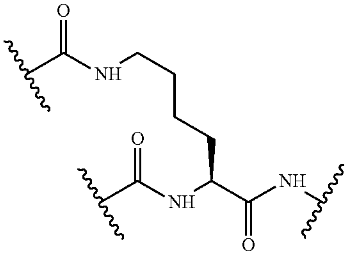

lysine

-continued

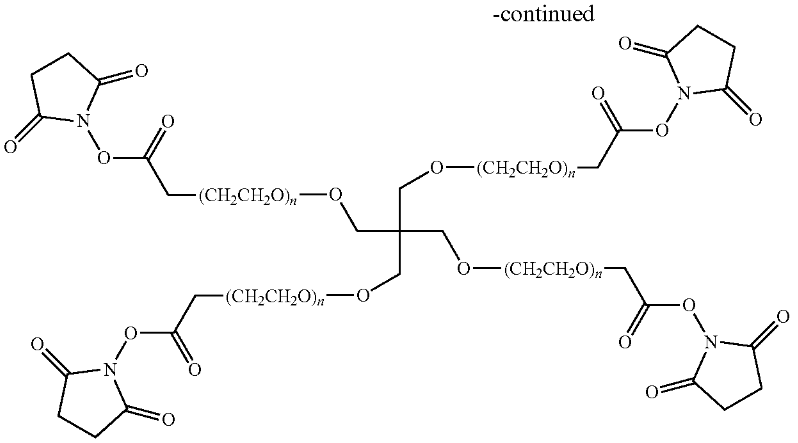

4-am PEG N-hydroxysuccinimidyl ester
8-am PEG N-hydroxysuccinimidyl ester (structure not shown)
4- or 8-am PEG maleimide (structure not shown)

Another exemplary linker has the structure of Formula VIII:

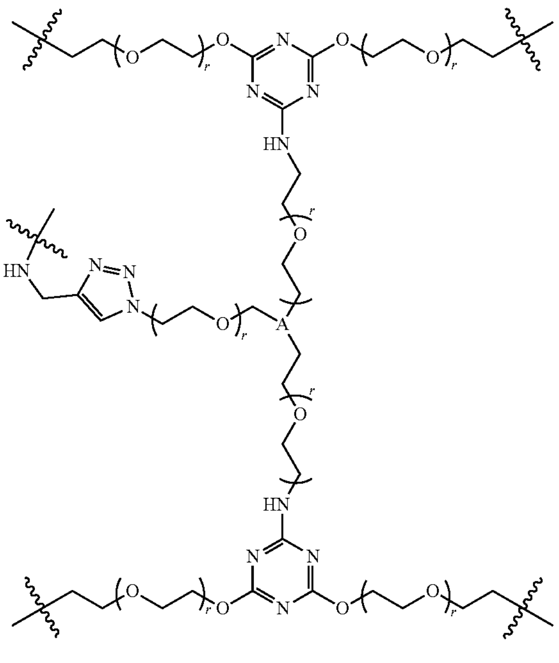

wherein:

A is a linking moiety (e.g., a nitrogen atom, an aryl, or a heteroaryl);

each r is independently an integer of 0 to 10, 20, 30, 40, 50, 60, 70, or 100.

In some embodiments, A in a compound of Formula VIII is a trivalent moiety such as, but not limited to, lysine, aspartic acid, glutamic acid, cysteine, melamine, cyanuric chloride, phloroglucinol, 1,3,5-tricarboxybenzene (trimesic acid), 1,3,5-triaminobenzene, tris(4-hydroxyphenyl)methane, tris(4-carboxyphenyl)methane, tris(4-aminophenyl) methane, and homologues thereof.

In some embodiments, L in the compound of Formula I, I', I", II, II', II", or III comprises a PEG. In some embodiments, L in the compound of Formula I, I', I", II, II', II", or III comprises $-(CH_2CH_2O)_m-$, wherein m is an integer of 1, 5, 10, 25, or 50 to 55, 75, or 100. In some embodiments, L in the compound of Formula I, I', I", II, II', II", or III comprises 1,3,5-triazine. In some embodiments, L in the compound of Formula I, I', I", II, II', II", or III comprises the structure:

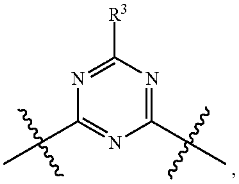

wherein $R^3$ comprises Z as defined herein, a moiety having a structure of Formula Ia as defined herein, a moiety having a structure of Formula IIa as defined herein, or an aryl, alkylamino, alkoxy, or heterocycle, each of which may be substituted or unsubstituted. In some embodiments, $R^3$ comprises a water solubilizing group, bioconjugatable group, and/or chromophore. In some embodiments, $R^3$ comprises a linker as described herein, optionally wherein the linker (e.g., L2) attaches 1,3,5-triazine and Z as defined herein, a moiety having a structure of Formula Ia as defined herein, a moiety having a structure of Formula IIa as defined herein, an aryl, an alkylamino, an alkoxy, or a heterocycle. For example, in some embodiments, L in the compound of Formula I, I', I", II, II', II", or III comprises 1,3,5-triazine and $R^3$ is -L2-Z, wherein L2 is present or absent and is a linker as defined herein and Z is as defined herein.

In some embodiments, L in a compound of Formula I, I', I", II, II', II", or III has the structure:

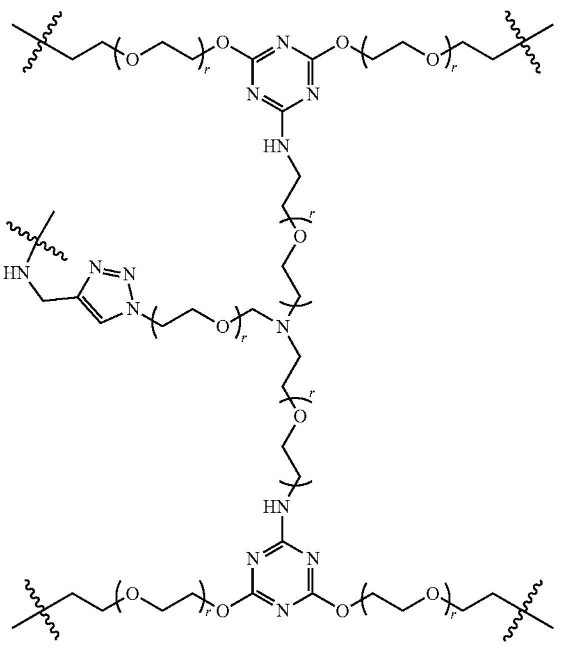

wherein:

each r is independently an integer of 0 to 10, 20, 30, 40, 50, 60, 70, or 100.

Exemplary water-solubilizing groups include, but are not limited to, a phosphoester (phosphate), thiophosphoester (thiophosphate), dithiophosphoester (dithiophosphate), phosphoamidate, thiophosphoamidate, glycoside, glucuronide, and/or peptide.

A "chromophore" as used herein refers to a molecular entity that absorbs light. Exemplary chromophores include, but are not limited to, tetrapyrroles; rylenes such as perylene, terrylene, and quarterrylene; fluoresceins such as TET (Tetramethyl fluorescein), 2',7'-dimethoxy-4',5'-dichloro-6-carboxyfluorescein (JOE), 6-carboxyfluorescein (HEX) and 5-carboxyfluorescein (5-FAM); phycoerythrins; resorufin dyes; coumarin dyes; rhodamine dyes such as 6-carboxy-X-rhodamine (ROX), Texas Red, and N,N,N',N'-tetramethyl-6-carboxyrhodamine (TAMRA); cyanine dyes; phthalocyanines; boron-dipyrromethene (BODIPY) dyes; quinolines; pyrenes; acridine; stilbene; as well as derivatives thereof. In some embodiments, the chromophore is a tetrapyrrole, which includes porphyrins, chlorins, and bacteriochlorins, and derivatives thereof. Exemplary tetrapyrroles include but are not limited to those described in U.S. Pat. Nos. 6,272,038; 6,451,942; 6,420,648; 6,559,374; 6,765,092; 6,407,330; 6,642,376; 6,946,552; 6,603,070; 6,849,730; 7,005,237; 6,916,982; 6,944,047; 7,884,280; 7,332,599; 7,148,361; 7,022,862; 6,924,375; 7,501,507; 7,323,561; 7,153,975; 7,317,108; 7,501,508; 7,378,520; 7,534,807; 7,919,770; 7,799,910; 7,582,751; 8,097,609; 8,187,824; 8,207,329; 7,633,007; 7,745,618; 7,994,312; 8,278,340; 9,303,165; and 9,365,722; and International Application Nos. PCT/US17/47266 and PCT/US17/63251.

In some embodiments, $R^3$ has the structure:

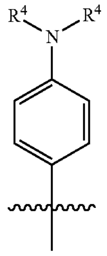

, wherein each $R^4$ is independently a hydrogen or a substituted or unsubstituted alkyl, alkenyl, or alkynyl. In some embodiments, $R^4$ is substituted with a water solubilizing group, bioconjugatable group, and/or chromophore. In some embodiments, each $R^4$ is independently an alkyl substituted with an alkoxy group (e.g., methoxy).

In some embodiments, $R^3$ has the structure:

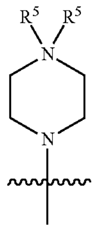

wherein each $R^5$ is independently a hydrogen or a substituted or unsubstituted alkyl, alkenyl, or alkynyl. In some embodiments, $R^5$ is substituted with a water solubilizing group, bioconjugatable group, and/or chromophore. In some embodiments, each $R^5$ is independently an alkyl substituted with a hydroxyl or $—SO_3$.

In some embodiments, L in the compound of Formula I, I', I", II, II', II", or III comprises a structure of Formula IV:

IV

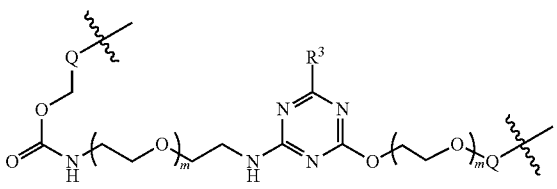

, wherein:

each Q is independently absent or is $—(CH_2)_q—$, alkenyl, alkynyl, aryl, $—C(O)—$, or $—CH_2C(O)—$ each of which may be substituted or unsubstituted, where q is an integer of 2 to 5, 10, or 20;

each m is independently an integer of 1, 5, 10, 25, or 50 to 55, 75, or 100; and $R^3$ is Z as defined herein, a moiety having a structure of Formula Ia as defined herein, a moiety having a structure of Formula IIa as defined herein, or an aryl, alkylamino, alkoxy, or heterocycle each of which may be substituted or unsubstituted. In some embodiments, $R^3$ comprises a water solubilizing entity, bioconjugatable group, and/or chromophore. In some embodiments, $R^3$ in the compound of Formula IV has a structure of:

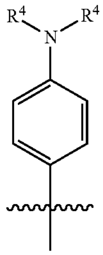
, or
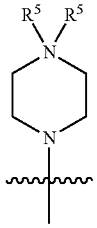
, wherein each $R^4$ is independently a hydrogen or a substituted or unsubstituted alkyl, alkenyl, or alkynyl; and each $R^5$ is independently a hydrogen or a substituted or unsubstituted alkyl, alkenyl, or alkynyl.

In some embodiments, L in the compound of Formula I, I', I", II, II', II", or III comprises a structure of Formula V:

V

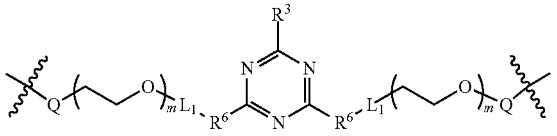
, wherein:

each Q is independently absent or is —$(CH_2)_q$—, alkenyl, alkynyl, aryl, —C(O)—, or —$CH_2C(O)$— each of which may be substituted or unsubstituted, where q is an integer of 2 to 5, 10, or 20;

each m is independently an integer of 1, 5, 10, 25, or 50 to 55, 75, or 100;

$R^3$ is Z as defined herein, a moiety having a structure of Formula Ia as defined herein, a moiety having a structure of Formula IIa as defined herein, or an aryl, alkylamino, alkoxy, or heterocycle, each of which may be substituted or unsubstituted;

each $L_1$ is independently absent or an alkyl, alkenyl, or alkynyl; and each $R^6$ is independently —O— or —NH—.

In some embodiments, $R^3$ comprises a water solubilizing entity, bioconjugatable group, and/or chromophore. In some embodiments, $R^3$ in the compound of Formula V has a structure of:

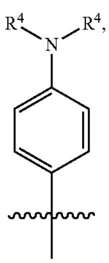
, or
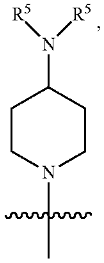
, wherein each $R^4$ is independently a hydrogen or a substituted or unsubstituted alkyl, alkenyl, or alkynyl; and each $R^5$ is independently a hydrogen or a substituted or unsubstituted alkyl, alkenyl, or alkynyl.

In some embodiments, in the compound of Formula IV or V at least one Q is absent. In some embodiments, in the compound of Formula IV or V each Q is independently —$(CH_2)_q$—, alkenyl, alkynyl, aryl, —C(O)—, or —$CH_2C$(O)— each of which may be substituted or unsubstituted, where q is an integer of 2 to 5, 10, or 20.

Exemplarily self-immolative linkers include, but are not limited to, those described in "Self-Immolative Spacers: Kinetic Aspects, Structure-Property Relationships, and Applications," Ahmed Alouane, Raphaël Labruère, Thomas Le Saux, Frédéric Schmidt, and Ludovic Jullien, Angew. Chem. Int. Ed. 2015, 54, 7492-7509 and "Self-immolative Chemistry in Nanomedicine," M. Gisbert-Garzarán, M. Manzano, M. Vallet-Regí, Chem. Eng. J. 2018, 340, 24-31. In some embodiments, a self-immolative linker comprises a moiety having the structure:

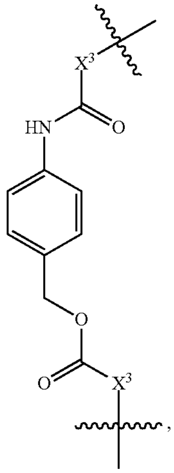
,
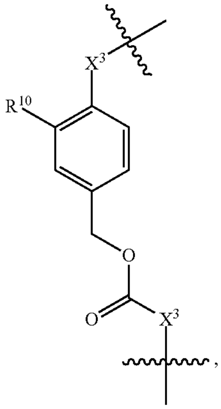
, or
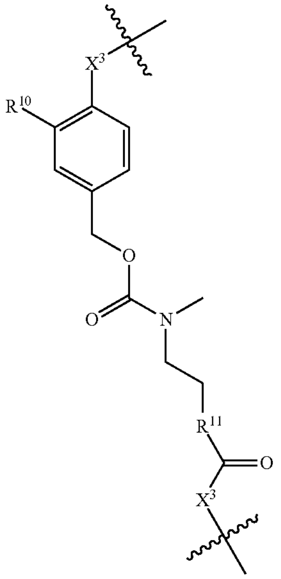

wherein:

$R^{10}$ is H, $NH_2$, $NCH_3$, or $NO_2$; and $R^{11}$ is —O— or —$N(CH_3)$—; and $X^3$ is each independently absent or is —O—, —S—, —$(CH_2)_q$—, alkenyl, alkynyl, aryl, —C(O)—, or —$CH_2C(O)$— each of which may be substituted or unsubstituted, where q is an integer of 2 to 5, 10, or 20.

In some embodiments, the compound of Formula I, I', I", or III comprises a self-immolative linker and each $X^3$ is independently —O— or —S—. In some embodiments, the compound of Formula I, I', I", II, II', II", or III comprises a self-immolative linker and at least one $X^3$ is absent. In some embodiments, the compound of Formula I, I', I", II, II', II", or III comprises a self-immolative linker and each $X^3$ is independently $-(CH_2)_q-$, alkenyl, alkynyl, aryl, —C(O)—, or $-CH_2C(O)-$ each of which may be substituted or unsubstituted, where q is an integer of 2 to 5, 10, or 20.

In some embodiments, Z in the compound of Formula I, I', I", II, II', II", or III is absent. In some embodiments, Z in the compound of Formula I, I', I", II, II', II", or III is hydroxyl or amino. In some embodiments, Z in the compound of Formula I, I', I", II, II', II", or III is hydroxyl. In some embodiments, Z in the compound of Formula I, I', I", II, II', II", or III is amino. In some embodiments, Z in the compound of Formula I, I', I", II, II', II", or III is an enzyme, polyiodide binding matrix, or bioconjugatable group. In some embodiments, Z in the compound of Formula I, I', I", II, II', II", or III is an enzyme. In some embodiments, Z in the compound of Formula I, I', I", II, II', II", or III is a polyiodide binding matrix. In some embodiments, Z in the compound of Formula I, I', I", II, II', II", or III is a bioconjugatable group.

Exemplary enzymes include, but are not limited to, proteins, ribozymes, abzymes, and/or abiological catalysts. In some embodiments, the enzyme may be an enzyme that has activity toward a substrate that is not native in a cell (e.g., a cancer cell). In some embodiments, the enzyme may lack activity toward native substrates in a cell (e.g., a cancer cell) and/or may be heterologous to a subject that the enzyme and/or compound is to be administered to. In some embodiments, the enzyme is an enzyme as described in International Application No. PCT/US19/19090, which is incorporated herein by reference in its entirety.

"Polyiodide binding matrix" as used herein refers to any compound or moiety that binds a polyiodide. "Polyiodide" as used herein includes iodine ($I_2$), $I_n$, wherein n is an integer of 3 to 12 and $I_n$ may or may not carry a charge such as a −1 or −2 negative charge, a radioiodide isotope, and/or a radical thereof (e.g., $I_2$., $I_n$., $I_n.^-$, etc.). In some embodiments, "polyiodide" refers to iodide atoms in a linear chain, for example, in the form of: $I_3^-$, $I_5^-$, $I_7^-$, $I_9^-$, and mixtures of these species. In some embodiments, polyiodide species may be formed in equilibrium upon reaction of $I^-$ and molecular iodine, $I_2$, (e.g., $I^-+I_2 \rightarrow I_3^-$). As one of skill in the art will understand, iodide is simply the monoatomic anion, namely $I^-$, but a mixture of iodine (i.e., $I_2$) and iodide forms multiple species collectively referred to herein as polyiodide, which can be a linear chain of triiodide ($I_3^-$), pentaiodide ($I_5^-$), and/or the like. In some embodiments, a polyiodide binding matrix binds and/or sequesters a radioiodide isotope such as $^{131}I$, $^{123}I$, $^{124}I$, and/or $^{125}I$. In some embodiments, a method of the present invention localizes and/or deposits a compound of the present invention and/or derivative thereof (e.g., the polyiodide binding matrix) in and/or around a tumor, optionally in tumor extracellular space, and provides a bed or matrix for spontaneous sequestration of a radioiodide isotope (e.g., $^{131}I$).

In some embodiments, the polyiodide binding matrix comprises a polysaccharide. The polysaccharide may be a linear polysaccharide and/or a modified polysaccharide. A modified polysaccharide refers to a polysaccharide for which at least one hydrogen or functional group of the native polysaccharide has been substituted. For example, a modified polysaccharide comprises at least one unit (e.g., sugar moiety such as a glucose unit) that comprises a substituent not present in the native polysaccharide. In some embodiments, the polyiodide binding matrix comprises amylose or a derivative thereof, cyclitol, an L-sugar, and/or a non-natural L-sugar. The polyiodide binding matrix (e.g., amylose) may be water-soluble and/or suitable for intravenous injection. In some embodiments, an amylose derivative is a compound in which one or more functional groups have been substituted with a substituent such as an alkyl, alkoxy, acyloxy and/or water-solubilizing group. The polyiodide binding matrix may comprise amylose or a derivative thereof having a 6-turn helix (i.e., 6 glucose units per helical turn). The polyiodide binding matrix may comprise one or more anhydroglucose unit(s). In some embodiments, the polyiodide binding matrix comprises at least one anhydroglucose unit (AGU) comprising a protecting group and cross-linking moiety bound to the AGU via a linker. In some embodiments, an AGU comprises a glucose unit having a structure of:

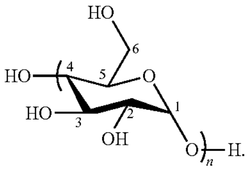

A polyiodide binding matrix may comprise one or more groups that aid in increasing the water solubility of the polyiodide binding matrix. For example, in some embodiments, the polyiodide binding matrix may comprise a water-solubilizing group such as 1, 2, 3, 4, or more water-solubilizing group(s). Example water-solubilizing groups include, but are not limited to, a phosphoester (phosphate), thiophosphoester (thiophosphate), dithiophosphoester (dithiophosphate), phosphoamidate, thiophosphoamidate, glycoside, glucuronide, and/or peptide. In some embodiment, the polyiodide binding matrix comprises a water-solubilizing group that comprises a sulfate, phosphate, PEG, and/or surfactant (e.g., a cationic and/or anionic surfactant) and/or the polyiodide binding matrix has undergone sulfation and/or phosphorylation. In some embodiments, a hydroxy group of the polyiodide binding matrix has been modified to comprise a water-solubilizing group. In some embodiments, a water-solubilizing group may increase water solubility of the compound and/or decrease enzyme (e.g., amylase such as exo-amylases and/or endo-amylases) digestion.

In some embodiments, the polyiodide binding matrix has an average molecular weight from about 5,000 or 10,000 Da to about 25,000, 50,000, 100,000, 150,000, 200,000, 250,000, 300,000, 350,000, 400,000, 450,000, or 500,000 Da. In some embodiments, the polyiodide binding matrix has an average molecular weight of about 5,000, 10,000, 15,000, 25,000, 50,000, 75,000, 100,000, 150,000, 200,000, 250,000, 300,000, 350,000, 400,000, 450,000, or 500,000 Da. In some embodiments, the polyiodide binding matrix has an average molecular weight from about 5,000 or 10,000 Da to about 25,000 or 50,000 Da or about 200,000 or 300,000 Da to about 400,000 or 500,000 Da. In some embodiments, the polyiodide binding matrix is polydisperse.

Figure 2:
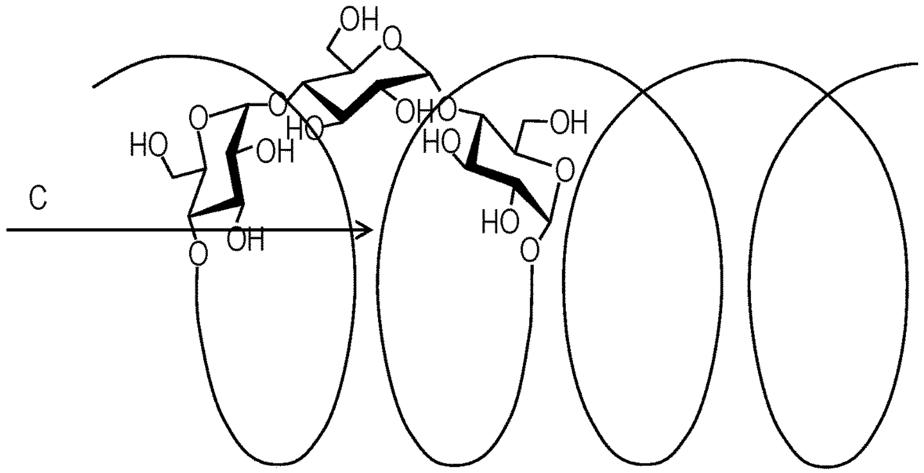
FIG. 2 is an axial view of a polyiodide binding matrix comprising a helical structure.

The polyiodide binding matrix may comprise a helical structure as shown in FIG. 2. The helical structure may have a mass per helical turn from about 900 Da to about 1,200 Da. In some embodiments, the helical structure has a mass per helical turn of about 900, 950, 1,000, 1,050, 1,100, 1,150, or 1,200 Da.

Figure 3:
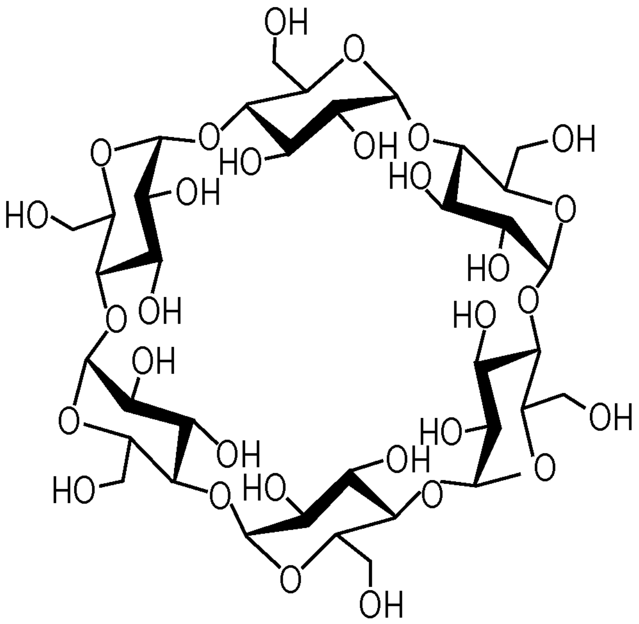
FIG. 3 is a circumferential view of the polyiodide binding matrix of FIG. 2 along the axis C.

The polyiodide binding matrix may have a structure in which it comprises one or more (e.g., 1, 2, 3, 4, 5, 6, 7, 8, 9, 10, or more) helical turn(s). A "helical turn" as used herein refers to a structure that forms a circle as shown in FIG. 3 when viewed down the helix axis in the direction of C as shown in FIG. 2, even though the beginning and end portions of the structure forming the helix turn are not directly attached to each other. As can be seen in FIG. 2, the helix comprises at least 4 helical turns. In some embodiments, the polyiodide binding matrix comprises at least 5, 10, 25, 50, 75, 100, 150, 200, 250, 300, 350, 400, 450, or 500 helical turns. In some embodiments, the polyiodide binding matrix comprises 1, 5, 10, 15, 20, or 25 to 30, 35, 40, 45, 50, 55, 60, 65, 70, 75, 80, 85, 90, 95, 100, 150, 200, 250, 300, 350, 400, 450, or 500 helical turns. In some embodiments, the polyiodide binding matrix comprises 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 helical turns.

The polyiodide binding matrix may have a loading capacity of about 1 iodide atom per helical turn. As one of skill of art will understand, a polyiodide binding matrix comprising at least 7 helical turns may have a loading capacity sufficient for the polyiodide species $I_7$ as each of the 7 iodide atoms in $I_7$ may be encompassed by one of the seven helical turns. In some embodiments, the polyiodide binding matrix has a loading capacity of about 1, 5, 10, 15, 20, or 25 iodide atoms to about 30, 35, 40, 45, 50, 55, 60, 65, 70, 75, 80, 85, 90, 95, 100, 150, 200, 250, 300, 350, 400, 450, or 500 iodide atoms. In some embodiments, the polyiodide binding matrix has a loading capacity of 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 iodide atoms.

Figure 4A:
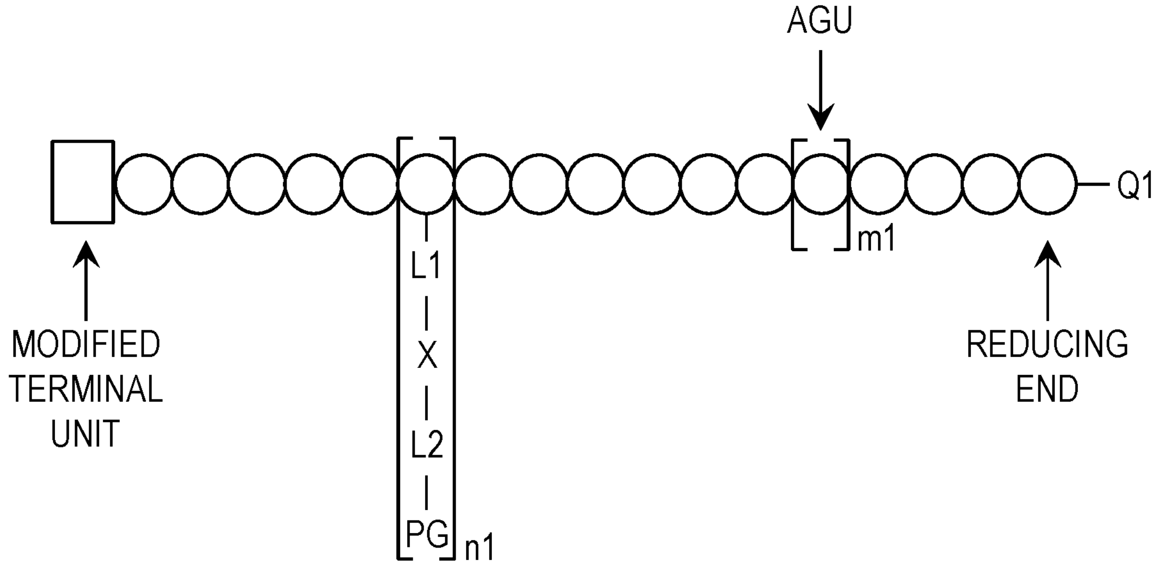
FIG. 4A is an illustration of a polyiodide binding compound according to embodiments of the present invention.

Referring now to FIG. 4A, in some embodiments, a polyiodide binding matrix comprises: one or more unmodified anhydroglucose units (AGUs), wherein the number of unmodified AGUs is ml and ml is an integer of 1 to 20,000; one or more AGUs comprising a —O-L1-X-L2-PG group, wherein L1 is absent or a linker as described herein, X is absent or a cross-linking moiety as described herein, L2 is absent or a linker as described herein, and PG is a protecting group as described herein, wherein the number of AGUs comprising a —O-L 1-X-L2-PG group is n1 and n1 is an integer of 1 to 20,000; a modified terminal unit (e.g., a unit comprising an alkyl, alkoxy, acyloxy at the 2-position of the unit); and Q1 wherein Q1 is a cancer targeting agent and/or a circulation enhancing agent. L1 and L2 may be the same or different, and L1, X, and L2 are each independently present or absent. The unmodified AGUs and AGUs comprising a —O-L1-X-L2-PG group may be in any order and are shown for simplicity in a consecutive sequence in FIG. 4A. Further, as one of skill in the art will readily recognize, the polyiodide binding matrix shown in FIG. 4A is depicted as a linear structure for simplicity, but the polyiodide binding matrix may be branched. For example, amylose may be mostly linear but slightly branched (e.g., about 1% or less branching points) and amylopectin may have a greater number of branching points than amylose.

Figure 4B:
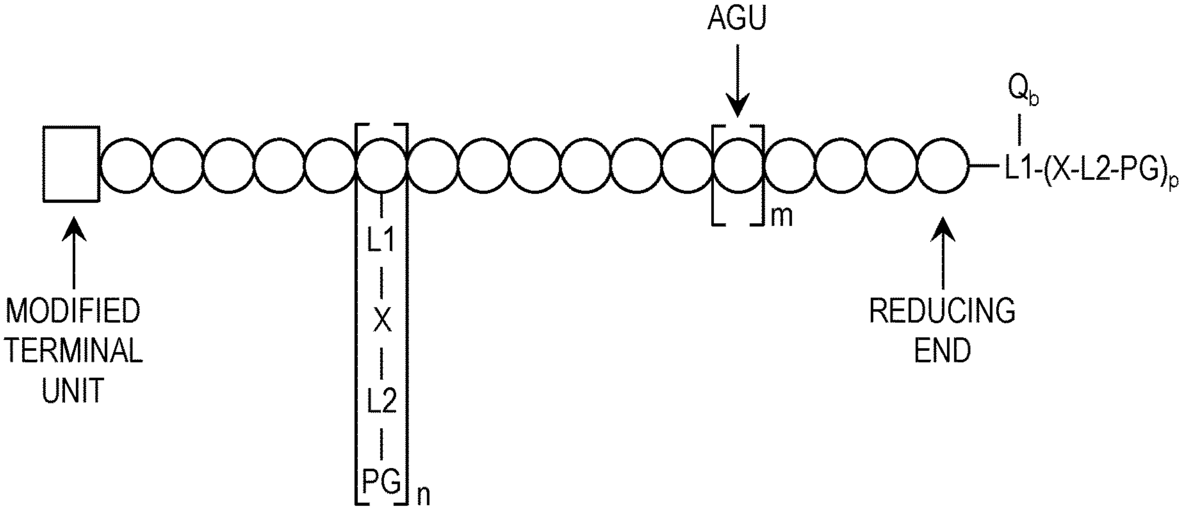
FIG. 4B is an illustration of a polyiodide binding compound according to embodiments of the present invention.

Referring now to FIG. 4B, in some embodiments, a polyiodide binding compound comprises a polyiodide binding matrix that comprises: one or more unmodified AGUs, wherein the number of unmodified AGUs is m and m is an integer of 1 to 20,000; optionally one or more AGUs comprising a —O-L1-X-L2-PG group, wherein L1 is absent or a linker, X is absent or a cross-linking moiety, L2 is absent or a linker, and PG is a protecting group, wherein the number of AGUs comprising a —O-L1-X-L2-PG group is n and n is an integer of 0 to 20,000; a modified terminal unit (e.g., a unit comprising an alkyl, alkoxy, acyloxy at the 2-position of the unit); and at the reducing end of the polyiodide matrix a $-L1(Q)_b(X\text{-}L2\text{-}PG)_p$ group, wherein each Q is independently a targeting agent (e.g., a cancer targeting agent), water-solubilizing group, and/or a circulation enhancing agent, b is an integer of 0 to 6, X is a cross-linking moiety, L2 is absent or a linker, PG is a protecting group, and p is an integer of 0 to 6. L1 and L2 may be the same or different, and L1, X, and L2 are each independently present or absent. The unmodified AGUs and AGUs comprising a —O-L1-X-L2-PG group may be in any order and are shown for simplicity in a consecutive sequence in FIG. 4B. Further, as one of skill in the art will readily recognize, the polyiodide binding matrix shown in FIG. 4B is depicted as a linear structure for simplicity, but the polyiodide binding matrix may be branched. For example, amylose may be mostly linear but slightly branched (e.g., about 1% or less branching points) and amylopectin may have a greater number of branching points than amylose.

"Bioconjugatable group" or "bioconjugate group" and grammatical variations thereof, refer to a moiety and/or functional group that may be used to bind or is bound to a biomolecule (e.g., a protein, peptide, DNA, RNA, polysaccharide, etc.). Thus, "bioconjugatable group" or "bioconjugate group" and grammatical variations thereof do not comprise a biomolecule. However, in some embodiments, a bioconjugatable group is used to bind to a biomolecule, or a bioconjugate group or derivative thereof is bound to a biomolecule (e.g., a protein, peptide, DNA, RNA, polysaccharide, etc.). Exemplary bioconjugatable groups include, but are not limited to, amines (including amine derivatives) such as isocyanates, isothiocyanates, iodoacetamides, azides, diazonium salts, etc.; acids or acid derivatives such as N-hydroxysuccinimide esters (more generally, active esters derived from carboxylic acids, e.g., p-nitrophenyl ester), acid hydrazides, etc.; and other linking groups such as aldehydes, sulfonyl chlorides, sulfonyl hydrazides, epoxides, hydroxyl groups, thiol groups, maleimides, aziridines, acryloyls, halo groups, biotin, 2-iminobiotin, etc. Linking groups such as the foregoing are known and described in U.S. Pat. Nos. 6,728,129; 6,657,884; 6,212,093; and 6,208,553. For example, a compound of the present invention may comprise a bioconjugate group that comprises a carboxylic acid and the carboxylic acid may be used for bioconjugation to a biomolecule (e.g., via carbodiimide-activation and coupling with an amino-substituted biomolecule). In some embodiments, a bioconjugatable group comprises an alkyne (e.g., a strained alkyne and/or a functional group used in click chemistry). Exemplary bioconjugatable groups comprising an alkyne include, but are not limited to, alkyne compounds described in Gröst, C. and Berg T., *Org. Biomol. Chem.,* 2015, 13, 3866-3870. In some embodiments a bioconjugatable group has the structure:

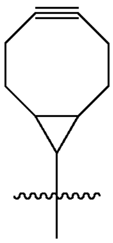
.

Any suitable targeting agent may be used in the present invention. In some embodiments, Z comprises a targeting agent (e.g., a cancer cell targeting agent) that binds to and/or targets an endocytosing receptor or other internalizing unit on a cell (e.g., a cancer cell), and the endocytosing receptor or other internalizing unit may be overexpressed in diseased cells (e.g., cancer cells) relative to normal cells. In some embodiments, the targeting agent is any agent or compound that directs the polyiodide binding compound to a given or target cellular destination such as a cancer cell and/or tumor extracellular space. In some embodiments, the targeting agent directs the polyiodide binding compound from outside a cell (e.g., a cancer cell) across and through the plasma membrane of the cell, into the cytoplasm of the cell, and optionally into a cell organelle (e.g., the lysosome of the cell). In some embodiments, a targeting agent is to a receptor that does not get endocytosized. In some embodiments, a targeting agent binds to and/or targets a receptor on a cell surface such that a compound of the present invention or a portion thereof is bound to the cell surface and/or remains in extracellular space. Example targeting agents include, but are not limited to, polypeptides such as antibodies; viral proteins such as human immunodeficiency virus (HIV) 1 TAT protein or VP22; cell surface ligands; peptides such as peptide hormones; and/or small molecules such as hormones or folic acid. Further example targeting agents include, but are not limited to, those described in U.S. Pat. Nos. 7,807,136 and 7,615,221. In some embodiments, an agent to which a cancer cell targeting agent binds (e.g., a receptor) is expressed on cancer cells at a concentration that is greater than non-cancerous cells such as, for example, at a concentration that is about 2, 3, 4, 5, 6, 7, 8, 9, or 10-fold higher or more.

In some embodiments, a compound of the present invention is a crosslinked compound that comprises an indigo moiety. For example, in some embodiments, a compound of the present invention is a crosslinked compound that has a structure of Formula VI or VI':

VI

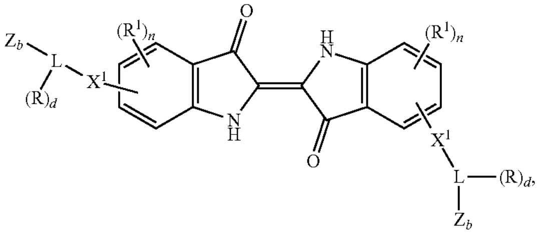

or

VI'

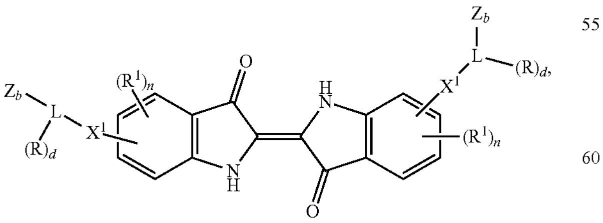

wherein:

each R independently is an indoxyl, a portion of an indigo moiety, or has a structure of Formula Ia or Formula IIa:

Ia

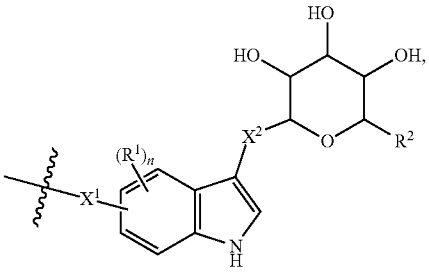

or

IIa

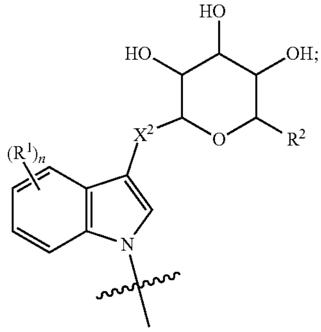

d is an integer of 0 to 5; and

Z, L, $X^1$, $X^2$, $R^1$, $R^2$, b, and n are each as defined herein. In some embodiments, L in the compound of Formula VI or VI' has a structure of Formula IV, Formula V, or Formula VIII.

In some embodiments, a compound of the present invention has a structure of Formula VII or VII':

VII

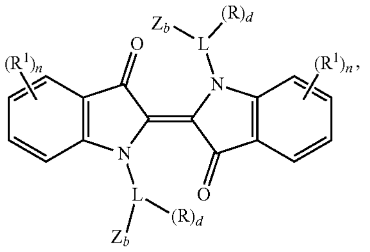

or

VII'

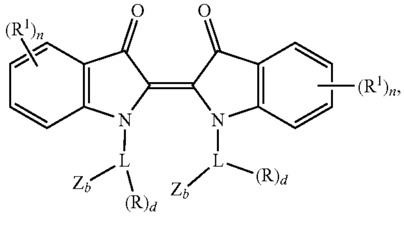

wherein:

each R independently is an indoxyl, a portion of an indigo moiety, or has a structure of Formula Ia or Formula IIa:

Ia

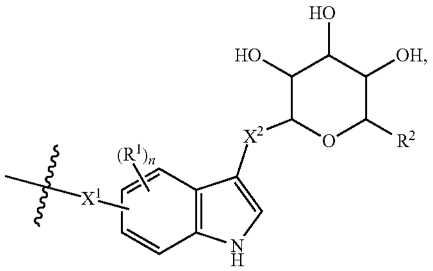

or

-continued

IIa

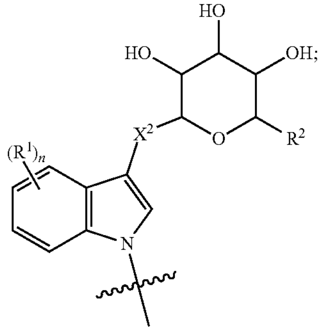

d is an integer of 0 to 5; and

Z, L, $X^1$, $X^2$, $R^1$, $R^2$, b, and n are each as defined herein.

In some embodiments, L in the compound of Formula VII or VII' has a structure of Formula IV, Formula V, or Formula VIII.

In some embodiments, a compound of the present invention has the structure:

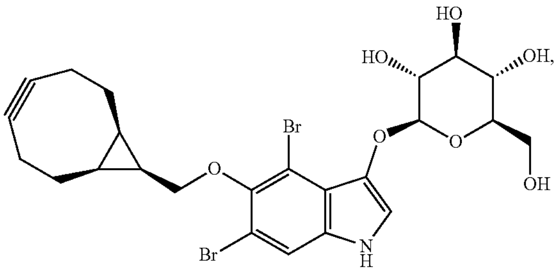

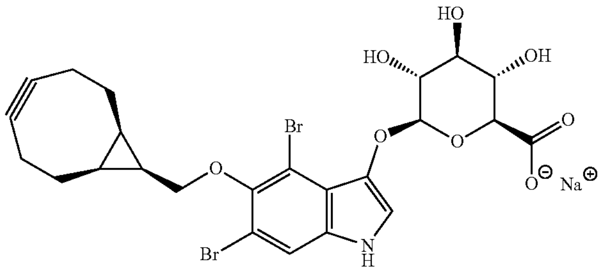

,

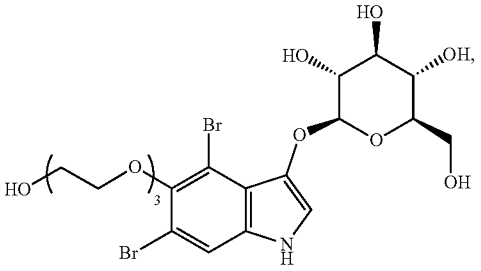

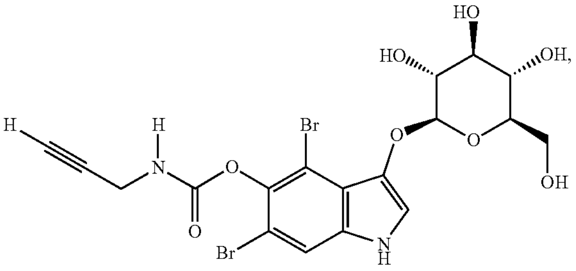

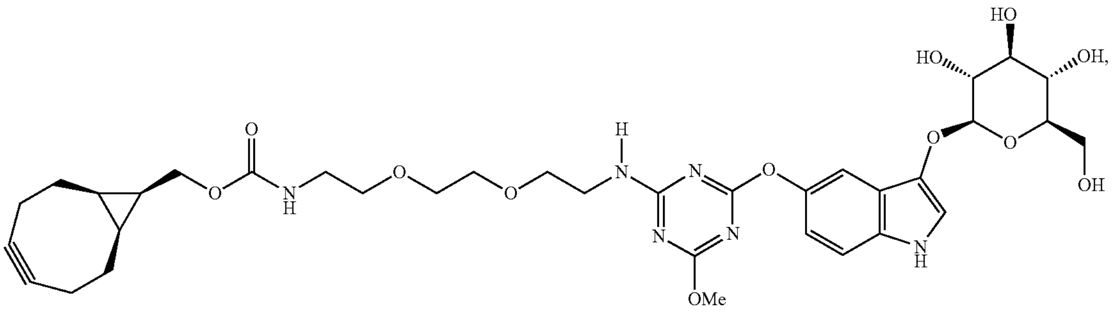

-continued
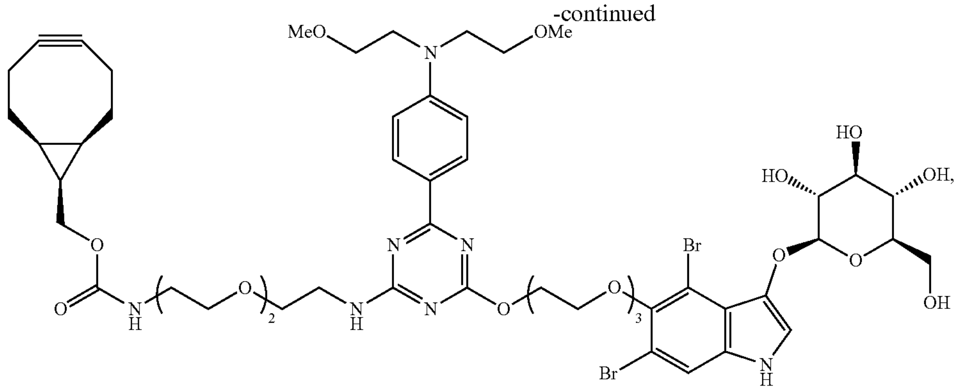
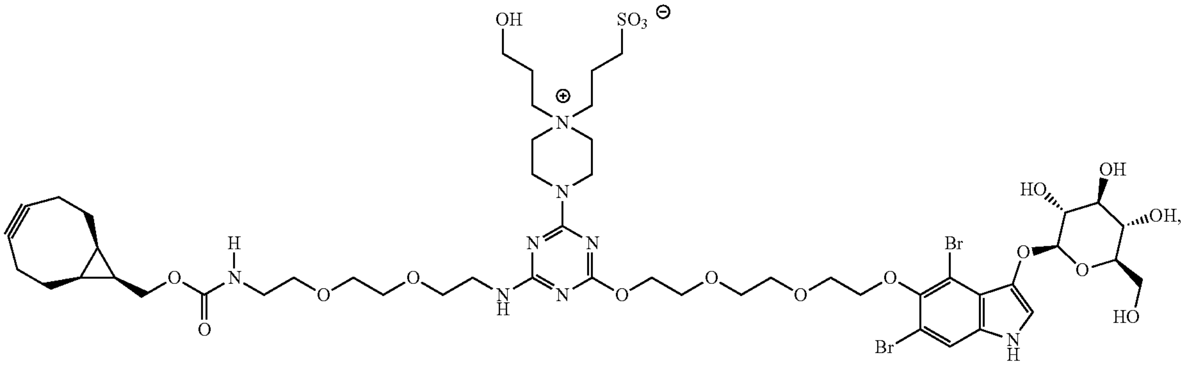
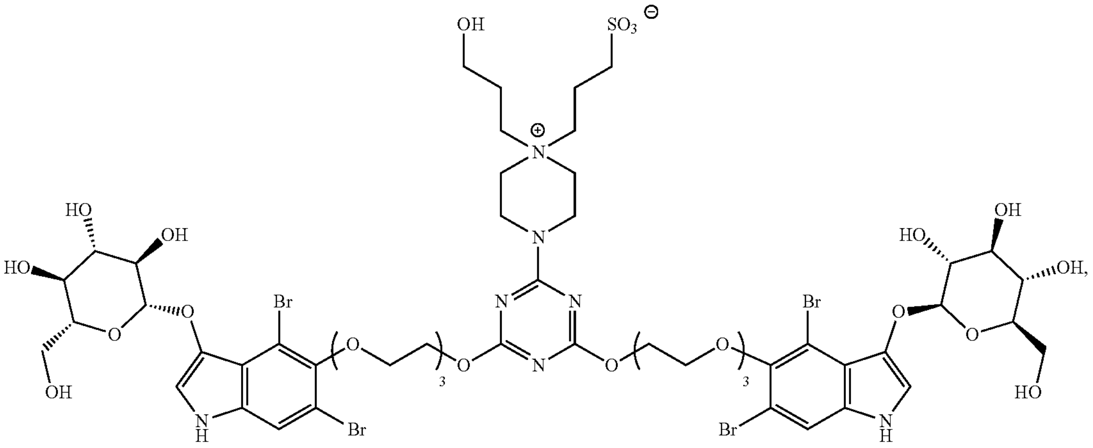
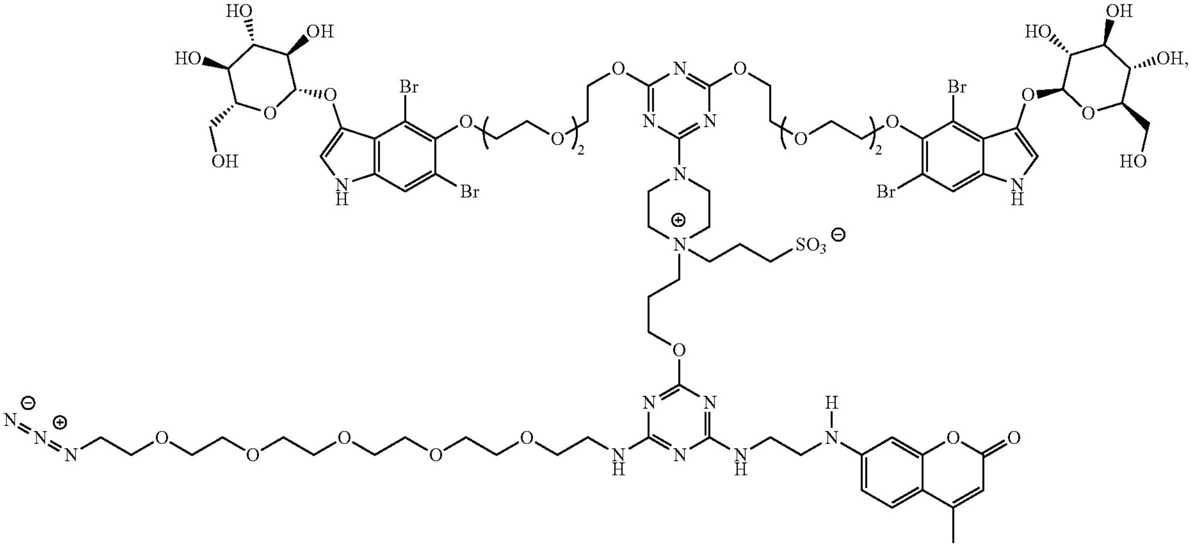

-continued

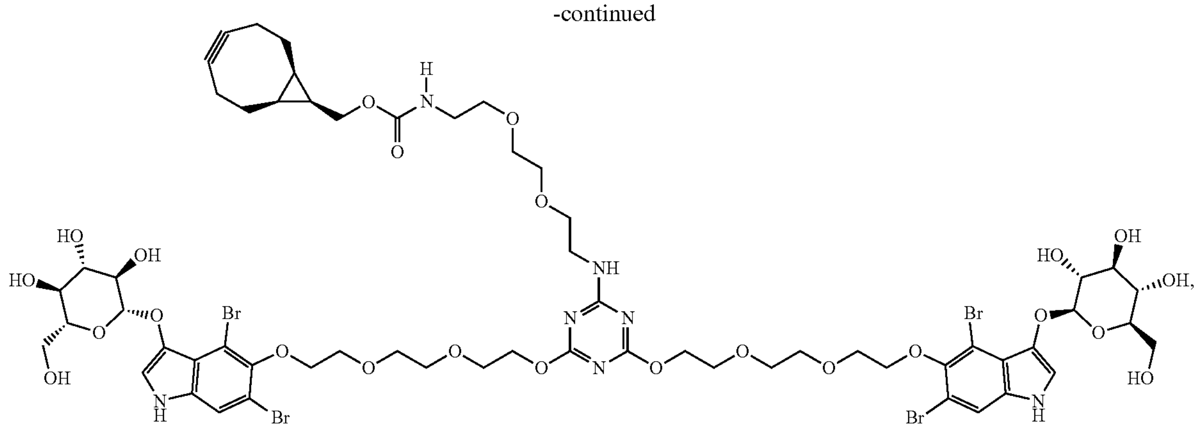

According to some embodiments provided is a method of using a compound of the present invention, optionally to form a cross-linked compound. In some embodiments, a method of using a compound of Formula I or Formula II to form a cross-linked compound is provided. The cross-linked compound may be a cross-linked deposit. The cross-linked compound and/or cross-linked deposit may have a structure of Formula VI of Formula VII. In some embodiments, the cross-linked compound comprises an enzyme, polyiodide binding matrix, or bioconjugatable group.

A compound of the present invention may be contacted with an enzyme that may cleave or remove a protecting group. In some embodiments, a compound of the present invention may be contacted with an enzyme that may cleave or remove a portion of a compound of Formula I or Formula II. The portion of the compound that may be cleaved may be the sugar portion (e.g., the glucuronide or glucoside) and/or a linker (e.g., a self-immolative linker). Enzymes that may cleave and/or remove the sugar portion and/or linker from the compound include, but are not limited to, phosphatases, sulfatases, glucosidases, galactosidases, glucuronidases, and/or glucuronidases. In some embodiments, a glucuronidase (e.g., a β-glucuronidase) may enzymatically cleave a compound of Formula I or Formula II comprising a glucuronide. In some embodiments, a glucosidase (e.g., a β-glucosidase) may enzymatically cleave a compound of Formula I or Formula II comprising a glucoside. In some embodiments, a compound of Formula I or Formula II comprises an enzymatically cleavable group that can be cleaved by an enzyme that is present at a concentration in tumor extracellular space that is greater than the concentration of the enzyme in extracellular space of non-cancerous cells. In some embodiments, a compound of Formula I or Formula II may be enzymatically cleaved by a glucosidase (e.g., a β-glucosidase) and/or a glucuronidase (e.g., a β-glucuronidase).

As used herein "contact", "contacting", "contacted," and grammatical variations thereof, refer to bringing two or more materials (e.g., composition(s), enzyme(s), and/or compound(s), etc.) together in sufficient proximity such that, under suitable conditions, a desired reaction can be carried out (e.g., cross-linking a compound of the present invention). Contacting the two or more materials may be carried out by adding, administering, combining, pouring, spraying, mixing, flowing, injecting, and/or the like the two materials or a portion thereof together. For example, contacting may comprise placing a compound of the present invention in contact with an enzyme, which may cause a compound of the present invention to cross-link and/or form a cross-linked compound. The compound may cross-link with itself (e.g., two or more cross-linking units of the compound may cross-link) and/or the compound may cross-link with another compound of the present invention (e.g., a cross-linking unit of a first compound may cross-link with a cross-linking unit of a second compound). In some embodiments, a compound of the present invention is administered to a subject and a native enzyme aids in cross-linking the compound.

A compound of the present invention may be water-soluble and/or may comprise one or more (e.g., 1, 2, or more) bioconjugatable groups. In some embodiments, a compound of the present invention comprises a 4,6-dibromo-substituted indoxyl unit and may provide an indigoid chromophore. One or more cross-linking units of the present invention may be linked and/or attached using a propargyloxy and/or PEG-O— on the 5-position of the indoxyl unit. A compound of the present invention may comprise a triazine. In some embodiments, a cross-linked compound of the present invention may be enzymatically triggered (e.g., using a glucosidase) and/or may cross-link under physiological conditions. The cross-linking may be bioorthogonal to the two bioconjugatable groups. A biomolecule may be attached before and/or after formation of a cross-linked compound and/or may be attached via standard bioconjugation (including click chemistry). In some embodiments, a compound of the present invention provides a means for creating a stabilized matrix of biomolecules including enzymes and/or recognition motifs including polyiodide binding matrixes.

The present invention is explained in greater detail in the following non-limiting examples.

EXAMPLES

Example 1

Here, an enzymatically triggered "click reaction" has been developed by exploiting the indigo-forming reaction from indoxyl β-glucoside. The covalent cross-linking proceeds in aqueous solution, requires the presence only of an oxidant (e.g., $O_2$), and is readily detectable owing to the blue color of the resulting indigoid dye. To achieve facile indigoid formation in the presence of a bioconjugatable tether, diverse indoxyl β-glucosides were synthesized and studied in enzyme assays. The latter include glucosidases from two sources; tritosomes; and rat liver homogenates.

Altogether 35 new compounds including 17 new glycosyl-indoxyl compounds were prepared and fully characterized in the course of meeting four essential requirements: enzyme triggering, facile indigoid dye formation, bioconjugatability, and synthetic accessibility. The 4,6-dibromo motif in a 5-alkoxy-substituted indoxyl-glucoside was a key design feature for fast and high-yielding indigoid formation. Two attractive molecular designs include (1) an indoxyl-glucoside linked to a bicyclo[6.1.0]nonyl (BCN) group for Cu-free click chemistry, and (2) a bis(indoxyl-glucoside). In both cases the intervening linker between the reactive moieties is composed of a two short PEG groups and a central triazine derivatized with a sulfobetaine for water solubilization. Glucosidase treatment of the bis(indoxyl-glucoside) in aqueous solution gave oligomers that were characterized by absorption, optical, and $^1$H NMR spectroscopy; mass spectrometry; dynamic light-scattering; and HPLC. Key attractions of indigoid dye formation, beyond enzymatic triggering under physiological conditions without exogenous catalysts or reagents, are the chromogenic readout and compatibility with attachment to diverse molecules.

Enzyme-triggered reactions, where a spontaneous chemical reaction follows an enzymatic process, are of great interest in the life sciences particularly for therapeutic and diagnostic applications.[1-4] As a general strategy, a molecule to be released (A) upon action by the target enzyme is protected with a covalently attached enzyme-cleavable ligand PG (A-PG) (FIG. 1). This general description encompasses yet extends far beyond the design of prodrugs (drug-PG) in formats such as antibody-directed enzyme-prodrug therapy (ADEPT), where the drug is released upon contact with a site-localized enzyme. Recently, there is increasing interest in enzyme-triggered construction of nanostructures in living cells, which constitutes an example of synthetic chemistry in vivo. For example, in enzyme-instructed self-assembly (EISA), a peptide cleaved by an enzyme assembles to form a hydrogel due to hydrophobic interactions and hydrogen-bonding [FIG. 1, (i)].[5] The cyanobenzothiazole cysteine (CBT-Cys) click reaction[6,7] relies on enzyme-triggered covalent-bond formation, where covalent coupling occurs between an enzymatically deprotected cysteine (A) and CBT (B) as an acceptor for the cysteine [FIG. 1(*ii*)]. Nanostructures that have been prepared using compounds bearing cysteine and CBT moieties include nanorings formed by oligomerization followed by self-assembly[8] and nanocrystals immobilized by cross-linking.[9] Such enzyme-triggered covalent-bond forming reactions remain rare despite extensive development of click chemistry as a potent means for bioconjugation.[10]

Figure 5:
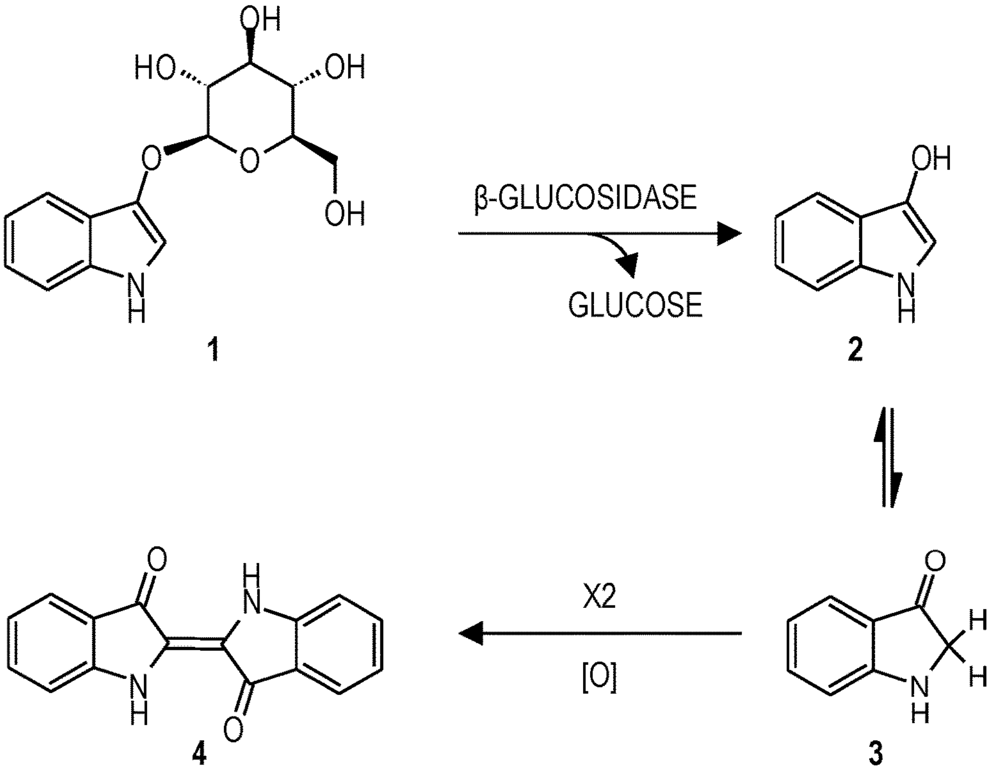
FIG. 5 is a schematic showing formation of indigo (4) from indoxyl β-glucoside (1) via indoxyl (2) and tautomer (3).

Another example of enzyme-triggered covalent bond formation is the natural formation of indigo. Indoxyl-glucoside 1 (also known as indican) upon action of a glycosidase yields indoxyl (2); subsequent enol-keto tautomerism affords indoline (3), which in the presence of air undergoes homo-coupling to give indigo (4) (FIG. 5).[11] Indigo is quite insoluble in water and typically precipitates upon formation. The homo-coupling of two molecules of A to afford indigo (A-A) occurs without an acceptor (B), and is irreversible owing to the oxidation process [FIG. 1, (iii)]. The conversion of indoxyl-glucoside to indigo is accompanied by profound changes in the absorption spectrum, which facilitates quantitative characterization of the products.

The attractive features of indigoid dye formation include enzymatic triggering, chromogenicity, insoluble deposition from aqueous solution at the site of reaction, and reaction under physiological conditions. Histological and bacteriological use has been extended to include indoxyls bearing enzymatically cleavable substituents other than glucosides, including glucuronides, carboxylic esters, phosphoesters, phosphodiesters, and sulfoesters.[14] However, indoxyls have been little explored as cross-linking agents for biomolecules in vitro or in vivo.

Figure 6:
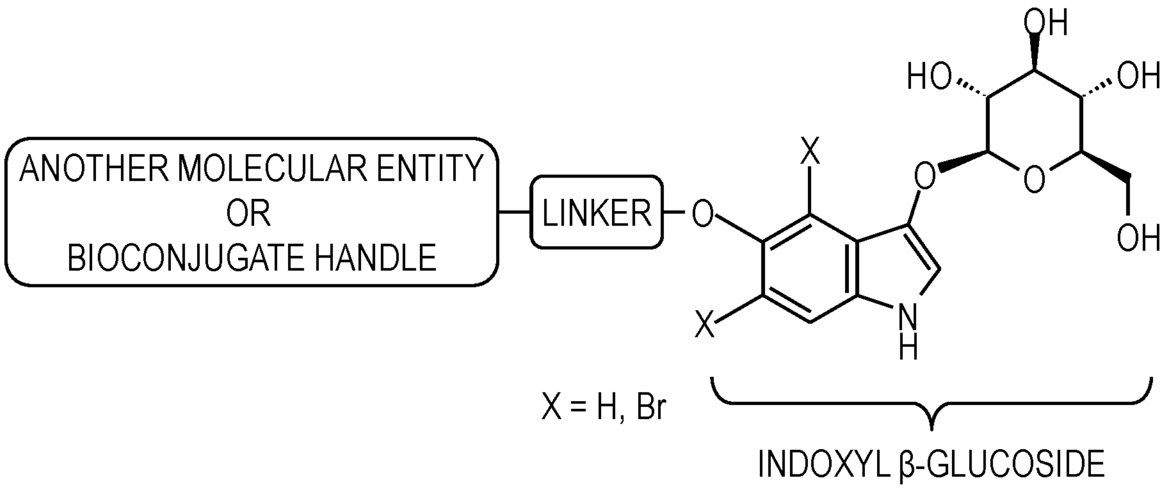
FIG. 6 is a schematic showing a general structure of ii-indoxyl glucosides linked to a chemical/bioconjugatable handle.

Here, we describe results from lengthy studies aimed at developing indoxyl-based chromogenic cross-linking agents of the general design illustrated in FIG. 6. We were surprised to find that the linkers we employed for attaching a bioconjugatable tether thwarted indigoid dye formation upon enzymatic cleavage of the indoxyl-glucoside. Hence, a first set of studies entailed syntheses of diverse indoxyl β-glucosides to identify the structural features compatible with facile indigoid dye formation while bearing a bioconjugatable tether. Next, each structure was examined for indigoid dye formation upon treatment to several enzymatic conditions including β-glucosidases, tritosomes, and rat liver homogenates; from these studies the 5-alkoxy-4,6-dibromoindoxyl nucleus was found to give superior results. Finally, oligomerization via the indigoid dye-forming reaction under physiological conditions was explored to understand the fundamental properties of this cross-linking motif.

1. Synthesis of Indoxyl Species.

The commercially available 5-benzyloxy-3-formylindole (8) provided the sole indole starting material for all 17 new synthetic indoxyl-glucosides described herein. Compound 8 was converted in 3 steps to the fully protected 5-hydroxyindoxyl β-glucoside 9 (Scheme 1) in accord with a patent.[20] Deprotection of the acetyl and benzyl groups of 9 provided 5-hydroxyindoxyl β-glucoside 10 in 89% yield, while debenzylation of 9 afforded acetyl-protected 5-hydroxyindoxyl β-glucoside 11 in 99% yield.

Scheme 1. Synthesis of 5-hydroxyindoxyls 10 and 11.

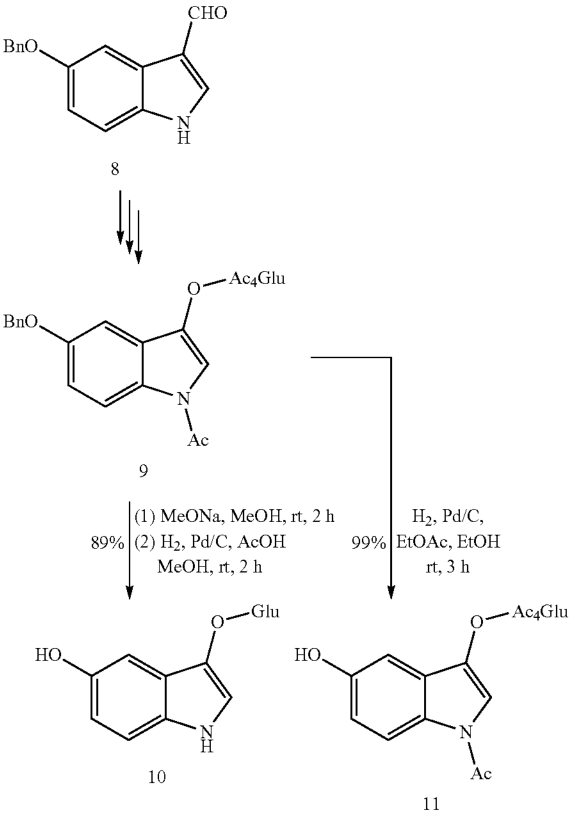

8

9

10

11

-continued

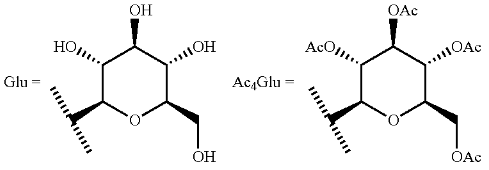

1,3,5-Triazine[26] and carbamate linkers were selected to derivatize the phenolic hydroxy group in 11 (Scheme 2). Thus, treatment of 11 with 2,4-dichloro-6-methoxy-1,3,5-triazine (12) replaced one of the two chlorines to form chlorotriazine 13 in 87% yield. The remaining chloride was substituted upon pilot reaction with morpholine and with the elaborate amine 14 bearing a bicyclo[6.1.0]nonyl (BCN) group[28] for Cu-free click chemistry.[10] Subsequent deprotection of the sugar in the BCN-tethered indoxyl-glucoside gave 15 in 93% yield (Scheme 2). Treatment of 11 with p-nitrophenyl chloroformate afforded a carbonate intermediate, which upon reaction with benzylamine gave the carbamate. Reaction with NaOMe caused removal of the acetyl groups to give carbamate 16 in 53% yield.

Scheme 2. Synthesis of 4,6-unsubstituted indoxyls bearing the triazine or carbamate linker.

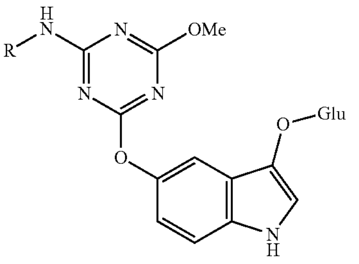

15

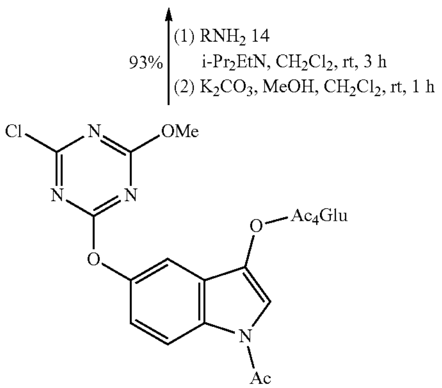

13

-continued

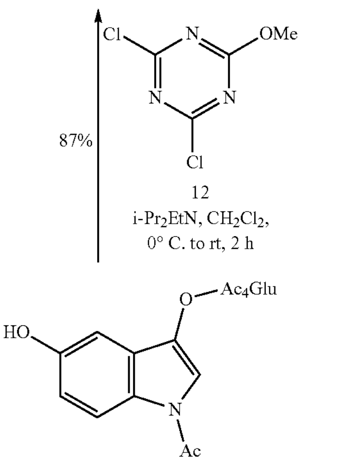

11

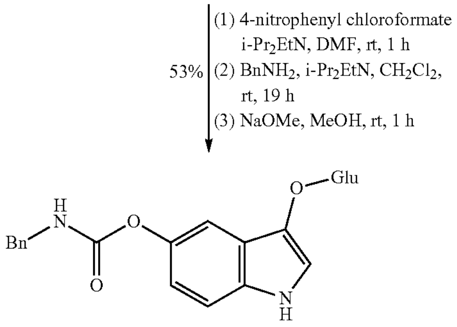

16

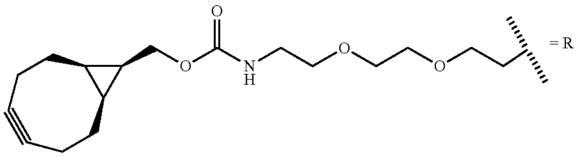

Figure 7:
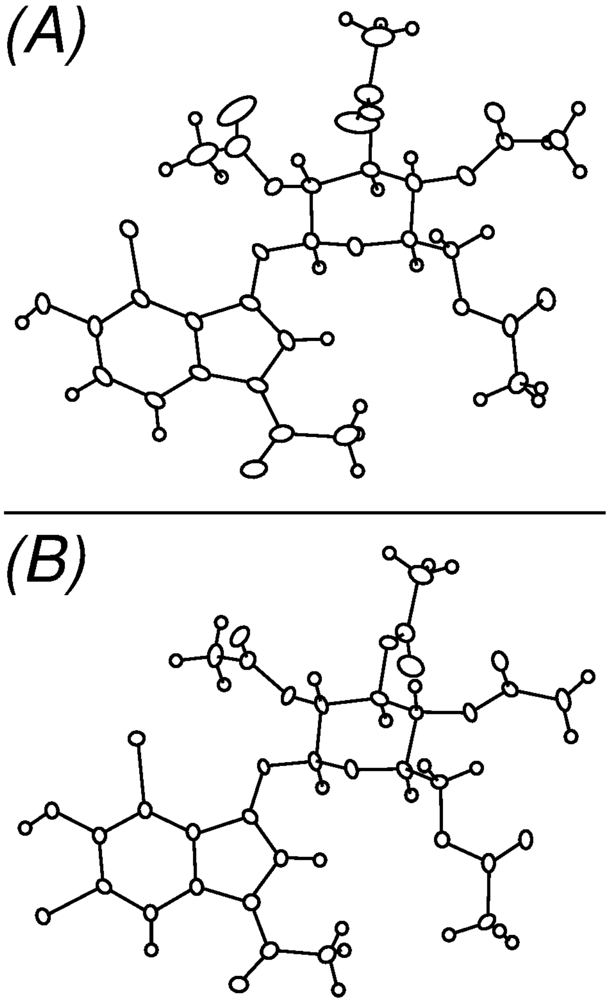
FIG. 7 is an ORTEP drawing of the single-crystal X-ray structures of (A) 17 and (B) 18. All ellipsoids are contoured at the 50% level.

In initial studies with β-glucosidase from almonds, neither 15 nor 16 afforded the corresponding indigoid species in good yield. It appeared that the alkoxy group, necessary for later bioconjugation, inhibited the indigogenic process. Thus, bromine atoms were introduced onto the indole ring to overcome the inhibitory effect of the alkoxy group (Scheme 3). Treatment of 11 with N-bromosuccinimide (NBS, 1.05 equiv) afforded 4-bromoindoxyl 17 in 75% yield, whereas a larger quantity of NBS (2.3 equiv) gave 4,6-dibromoindoxyl 18 in 83% yield. Single-crystal X-ray structures of 17 and 18 confirmed the sugar stereochemistry and the positions of the bromine atoms (FIG. 7).

Scheme 3. Synthesis of 4-bromoindoxyls.

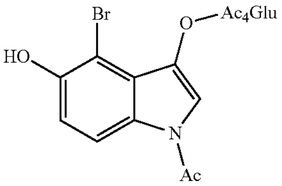

17

-continued

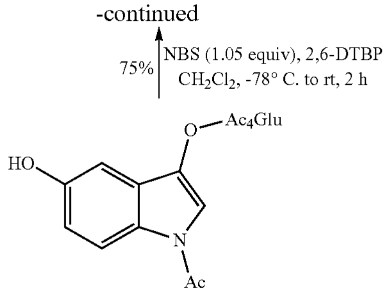

11

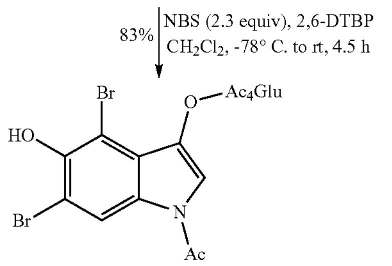

18

The 4,6-unsubstituted indoxyls, the 4-bromoindoxyls, and the 4,6-dibromoindoxyls bearing a linker at the 5-position were prepared from 10, 11, 17, or 18 (Scheme 4). As indoxyls (and the corresponding indigoid dyes) bearing 5-oxy and bromine substituents have not been reported (although each is known separately), we compared the indigogenic reactions among these indoxyls to investigate the effects of the bromine substituents. The triazine linker was introduced into indoxyls 10, 17, and 18 via the successive substitution of the chloro groups in dichlorotriazine 12. 4,6-Unsubstituted indoxyl glucoside 10 was treated with 12 followed by morpholine to afford 19 in 59% yield. 4-Bromoindoxyl 20 bearing the triazine linker was prepared from acetyl-protected 4-bromoindoxyl 17. Treatment of 17 with 12 followed by morpholine and subsequent acetyl deprotection gave 20 in 77% yield. Similarly, 4,6-dibromoindoxyl 21 was prepared from acetyl-protected 18 in 67% yield. Indoxyls 22-26 possess a methoxycarbonyl group, which can function as an amine-reactive linker. This linker was introduced by alkylation of the 5-hydroxy group in 11, 17, and 18 with ethyl bromoacetate in the presence of NaH and subsequent treatment with NaOMe in MeOH. Indoxyl 10 was reacted with propargyl bromide in the presence of $K_2CO_3$ to afford 4,6-unsubstituted indoxyl glucoside 25 in 30% yield, which bears a propargyl group for ensuing click chemistry. Propargylation of acetyl-protected indoxyl 17 and 18 followed by acetyl-deprotection with triethylamine in MeOH provided 4-bromoindoxyl 26 and 4,6-dibromoindoxyl 27 in 71 and 53% yield, respectively.

Scheme 4. Synthesis of 4,6-unsubstituted indoxyls, 4-bromoindoxyls, and 4,6-dibromoindoxyls bearing a linker at the 5-position.

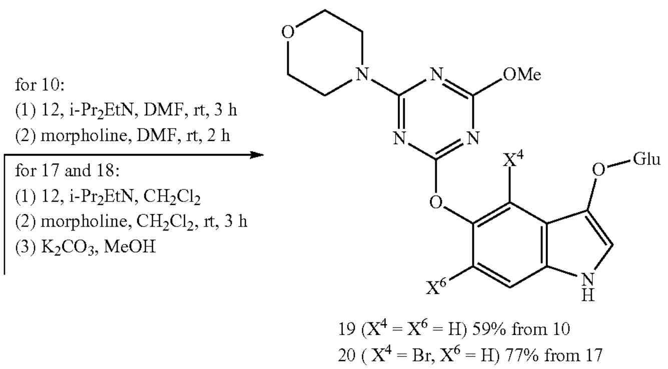

19 ($X^4$ = $X^6$ = H) 59% from 10
20 ( $X^4$ = Br, $X^6$ = H) 77% from 17
21 ($X^4$ = $X^6$ = Br) 67% from 18

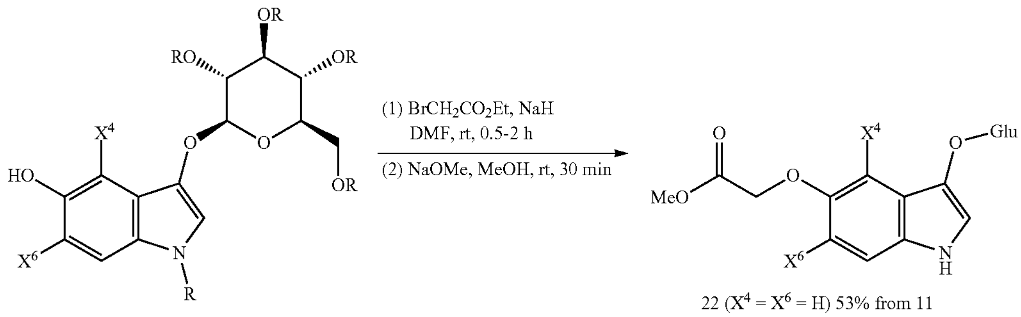

10 (R = $X^4$ = $X^6$ = H)
11 (R = Ac, $X^4$ = $X^6$ = H)
17 (R = Ac, $X^4$ = Br, $X^6$ = H)
18 (R = Ac, $X^4$ = $X^6$ = Br)

22 ($X^4$ = $X^6$ = H) 53% from 11
23 ($X^4$ = Br, $X^6$ = H) 52% from 17
24 ($X^4$ = $X^6$ = Br) 82% from 18

-continued

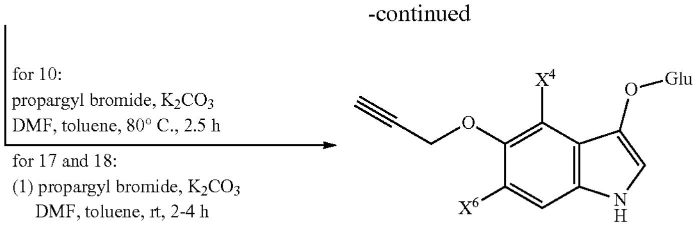

25 ($X^4 = X^6 = H$) 30% from 10
26 ($X^4 = Br$, $X^6 = H$) 71% from 17
27 ($X^4 = X^6 = Br$) 53% from 18

4,6-Dibromoindoxyl 30, which possesses the BCN group instead of the propargyl group in 27, was prepared from 18 (Scheme 5). The Mitsunobu reaction between 18 and commercially available BCN-methanol 28 gave 29 in 63% yield. Deacetylation of 29 with $K_2CO_3$/MeOH afforded 30 in 99% yield. Additionally, 18 was treated with triethylene glycol mononosylate 31 to give 32 in 89% yield, which was deprotected to afford 4,6-dibromoindoxyl 33 bearing a triethylene glycol linker in 94% yield.

Scheme 5. Synthesis of 4,6-dibromoindoxyls bearing the bicyclononyne or triethylene glycol substituent.

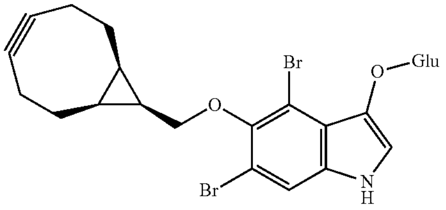

30

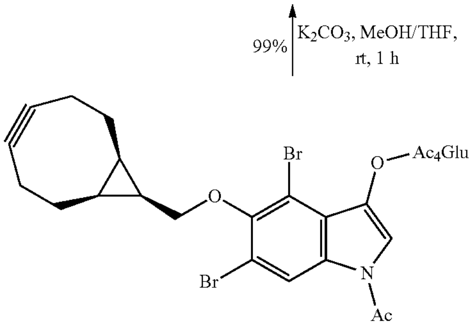

29

-continued

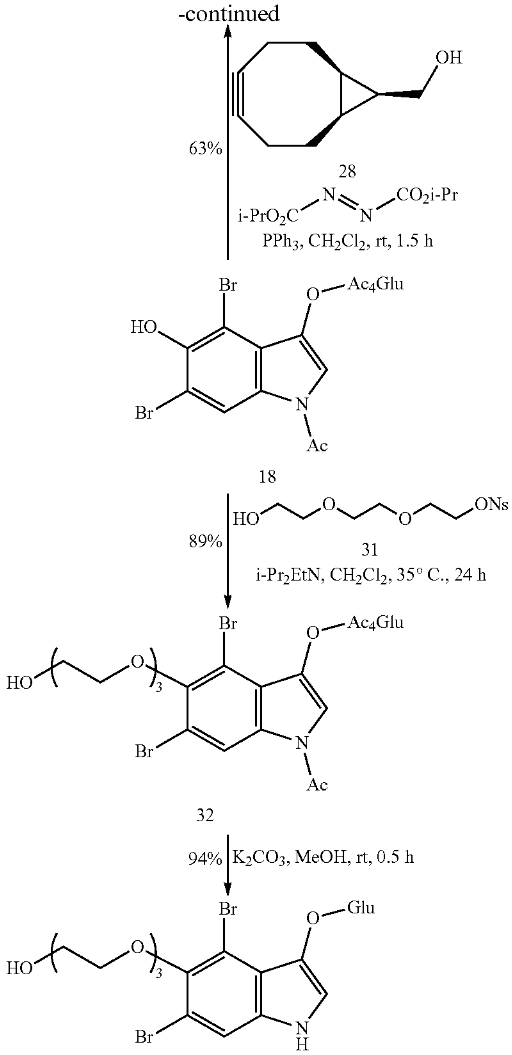

33

Figure 8:
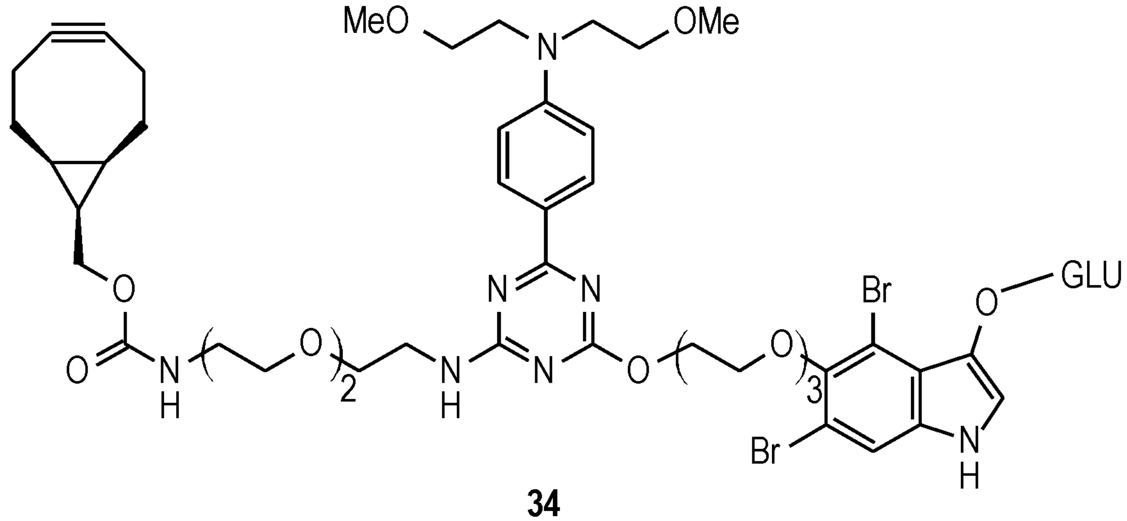
FIG. 8 shows BCN-dibromoindoxyl 34, which has limited solubility in aqueous buffer.

Water solubility of the indoxyl glucoside is important for biological applications. Regardless of the presence of the polar glucosyl group, poor water-solubility of the indoxyl glucoside was observed in some cases. For example, we prepared 4,6-dibromoindoxyl glucoside 34 (FIG. 8), which contains the BCN group along with a fluorescent anilinotriazine moiety;[29,30] however, 34 had limited solubility in aqueous buffers (<10 μM at room temperature). Therefore, this compound is not suitable for bioconjugation. The synthesis of 34 relies on successive substitution of the dichloroanilinotriazine unit (derived from N,N-bis(2-methoxyethyl)aniline[31] and cyanuric chloride) with indoxyl-glucoside-PEG-OH and BCN-PEG-$NH_2$ building blocks.

To improve the water solubility of the indoxyl species, a sulfobetaine unit[32,33] was incorporated as a water-solubilizing group. Sulfobetaines are stable zwitterions over a wide range of pH. Synthesis of an indoxyl bearing a sulfobetaine unit is illustrated in Scheme 6. Boc-piperazine (35) was treated with 1,3-propane sultone to afford 36 in 63% yield. Quaternization of the tertiary nitrogen atom in 36 with 3-bromopropanol gave Boc-protected sulfobetaine 37 in 69% yield. The Boc group was cleaved with trifluoroacetic acid (TFA) to afford piperazine-TFA salt 38 in 97% yield. The N-acetyl group of 32 was selectively deprotected with $NaHCO_3$/MeOH in 84% yield. The product 39, piperazine-TFA salt 38, and BCN-amine 14 were assembled at a triazine ring via one-flask, successive substitution of cyanuric chloride to afford 40 in 51% yield. Cleavage of the acetyl groups of sulfobetaine 40 provided 41 in 98% yield. Owing to the sulfobetaine unit, 41 showed superior solubility (>400 μM at room temperature) versus 34 in a 100 mM phosphate buffer (pH 7.4, containing 100 mM NaCl).

Scheme 6. Synthesis of BCN-dibromoindoxyl 41 containing the water-solubilizing group.

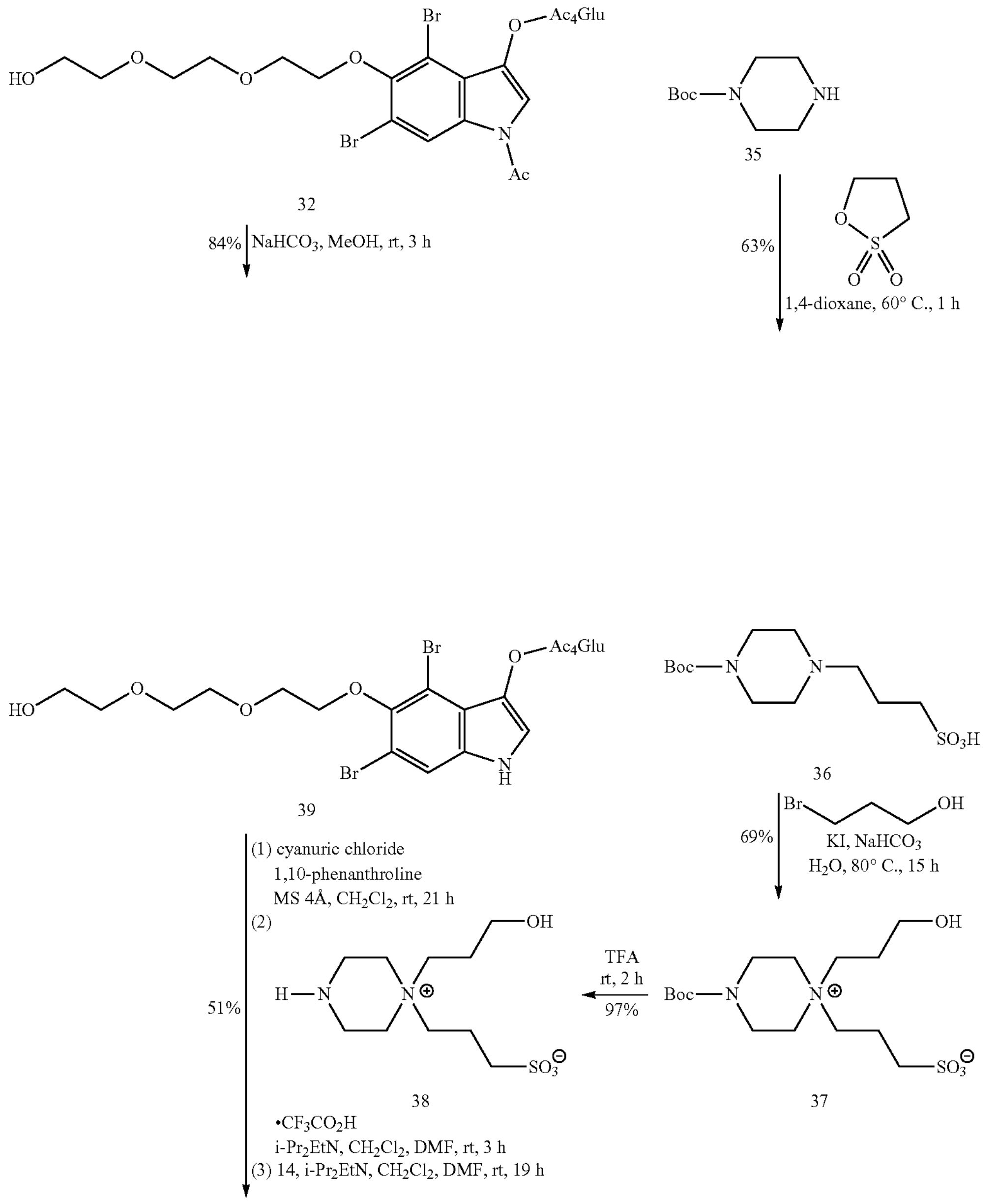

-continued

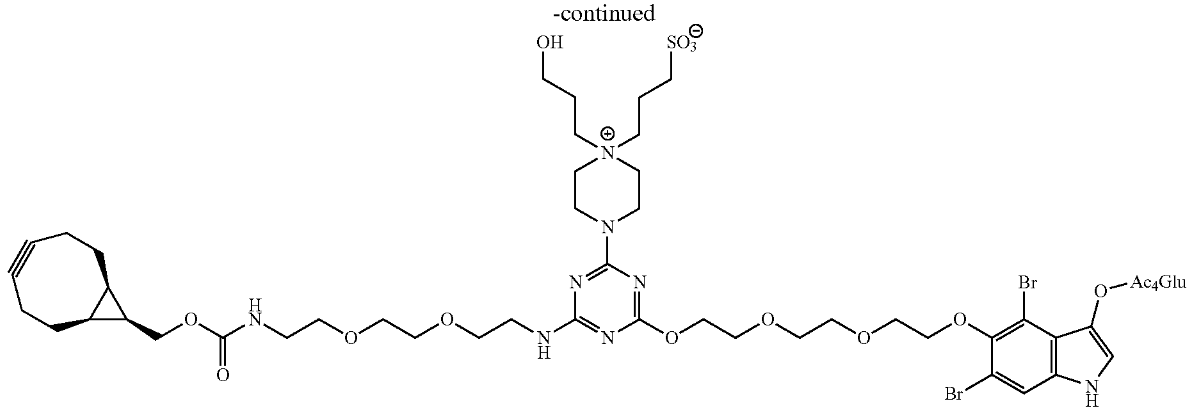

40

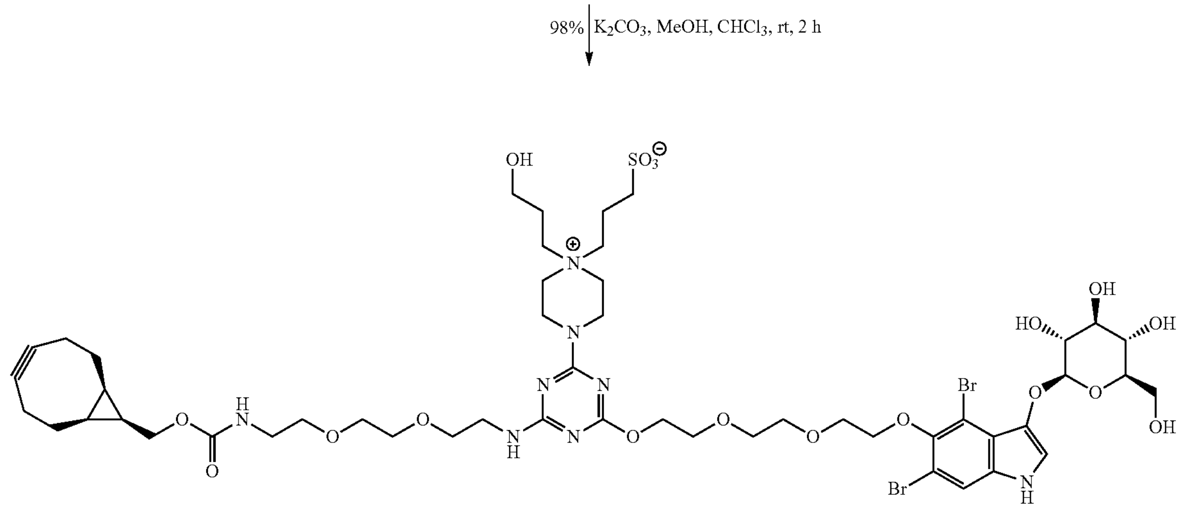

41

2. Indigogenic Studies.

With diverse glucosyl-indoxyl compounds in hand, we carried out a set of studies to examine indigoid-dye formation upon enzymatic cleavage of the glucosyl unit under physiological conditions. Altogether, 14 new (15, 16, 19-27, 30, 33, 41) and 2 known (1, 42) synthetic indoxyl-glucosides (lacking acetyl protecting groups) were examined in an effort to identify suitable combinations of substituents to support both bioconjugation and indigoid dye formation. In initial studies, β-glucosidase from almonds was employed to trigger indigoid dye formation (Table 1). Thus, a mixture of this enzyme (1 unit/mL) and an indoxyl β-glucoside (0.1 μcool, 1 mM) in acetate buffer (pH 5, containing 5% DMF) was incubated at 37° C. for 16-19 h. All indigoid dye was dissolved in each case for quantitative evaluation. The parent indoxyl 1 afforded indigo only in 17% yield under the reaction conditions (entry 1). By contrast, 5-bromo-4-chloroindoxyl β-glucoside (42, also known as X-Glu used in a chromogenic assay for β-glucosides)[14] provided the corresponding indigoid dye in 74% yield (entry 2, yield calculated based on $\varepsilon=2.00\times10^4$ $M^{-1}cm^{-1}$ reported for 5,5'-dibromo-4,4'-dichloroindigo).[34] These results are consistent with Holt's report that a bromo (and chloro) substituent(s) on the indoxyl facilitated indigoid dye formation.

No indigoid dye was detected with 15 (entry 3), whereas 16 formed the corresponding indigoid dye, albeit in low yield (24%, entry 4). We measured the molar absorption coefficient of the parent indigo 4 in DMF/water (2:1) and found the value at $\lambda_{max}$ near 600 nm to be $\varepsilon=1.27\times10^4$ $M^{-1}cm^{-1}$, to be compared with $\varepsilon=1.66\times10^4$ $M^{-1}cm^{-1}$ in a different solvent reported by Holt and Sadler.[34] For consistency, we have used the value in DMF/water (2:1) for all studies here unless noted otherwise.

Indoxyls 19-21 bearing the triazine linker did not form the indigoid dye regardless of the presence or absence of a bromo atom (entries 5-7, respectively). In the case of 5-[(methoxycarbonyl)methoxy]indoxyls 22-24, the yield of indigoid dye was markedly improved as the number of bromine atoms increased (entry 8, 22, <1%; entry 9, 23, 68%; entry 10, 24, 122% yield). The same trend was observed for 5-(propargyloxy)indoxyls 25-27 (entry 11, 25, <5%; entry 12, 26, 56%; entry 13, 27, 105% yield). These results indicated a significant promoting effect of the bromine atoms on indigoid dye formation. No indigo product was detected with BCN-indoxyl 30 (entry 14) whereas $PEG_3$-indoxyl 33 afforded indigoid dye in 52% yield (entry 15). In summary, the structure of the 5-substituent controlled the indigo-forming reaction: indoxyls 20, 21, and 30 did not engender the formation of any indigoid product regardless of the presence of bromine atoms. This may be because these substrates have low affinity for the enzyme due to the presence of the bulky triazine or BCN moiety.

TABLE 1
Indigogenic reactions of indoxyl derivatives.
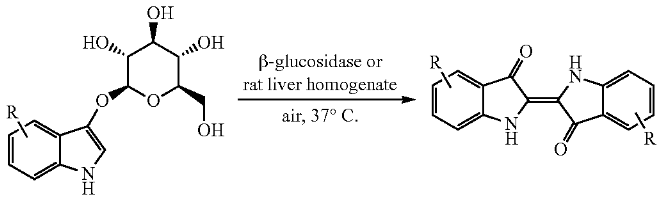
| | | | Yield (%)[a] | | |
|---|---|---|---|---|---|
| Entry | Indoxyl | Structure | β-glucosidase from almonds[b] | β-glucosidase from *Agrobacterium*[c] | rat liver homogenate[d] |
| 1 | 1 | 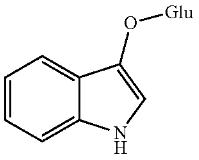 | 17 | 97 ± 5 | 10 |
| 2 | 42 | 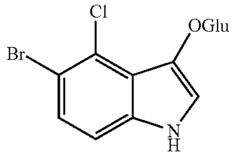 | 74[e] | 116 ± 8[e] | 65 |
| 3 | 15 | 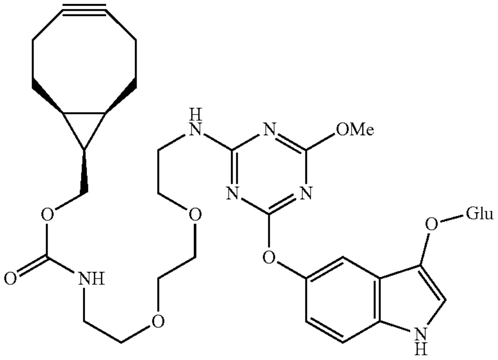 | <1 | —[f] | —[f] |
| 4 | 16 | 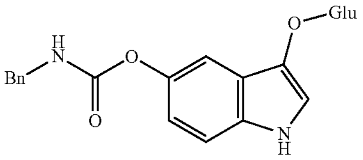 | 24 | —[f] | 9 |
| 5 | 19 | 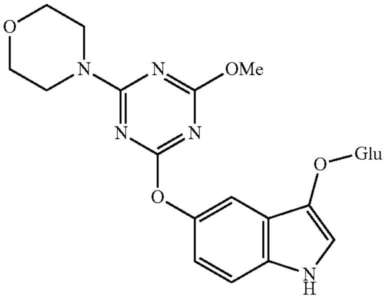 | <1 | 46 ± 5 | <5 |

TABLE 1-continued
Indigogenic reactions of indoxyl derivatives.
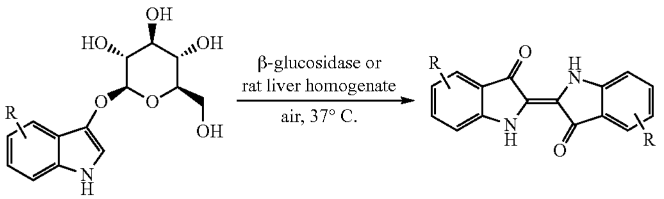
| Entry | Indoxyl | Structure | Yield (%)[a] β-glucosidase from almonds[b] | β-glucosidase from *Agrobacterium*[c] | rat liver homogenate[d] |
|---|---|---|---|---|---|
| 6 | 20 | 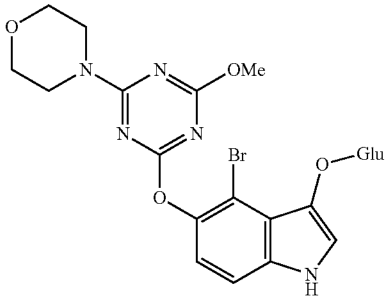 | <1 | 150 ± 3 | <5 |
| 7 | 21 | 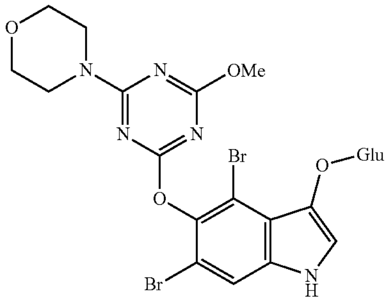 | <1 | 63 ± 4 (31 ± 2)[g] | <5 |
| 8 | 22 | 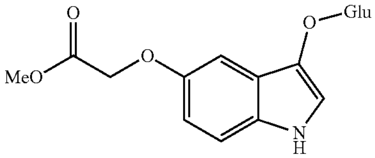 | <1 | 30 ± 6 | <5 |
| 9 | 23 | 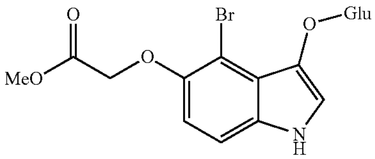 | 68 | 84 ± 4 | <5 |
| 10 | 24 | 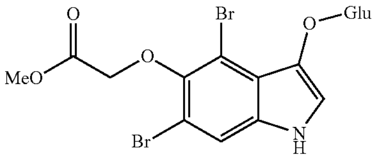 | 122 (59)[g] | 209 ± 6 (102 ± 3)[g] | <5 |

TABLE 1-continued

Indigogenic reactions of indoxyl derivatives.

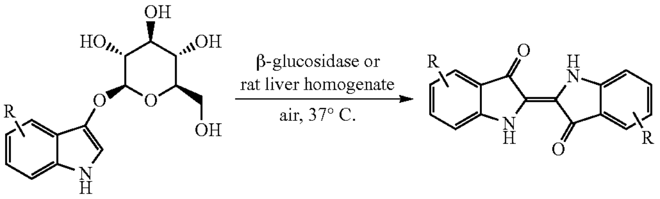

| Entry | Indoxyl | Structure | Yield (%)[a] β-glucosidase from almonds[b] | Yield (%)[a] β-glucosidase from Agrobacterium[c] | Yield (%)[a] rat liver homogenate[d] |
|---|---|---|---|---|---|
| 11 | 25 | 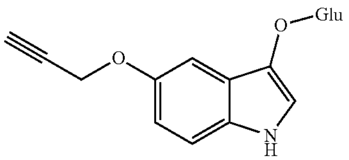 | <5 | 37 ± 2 | 11 |
| 12 | 26 | 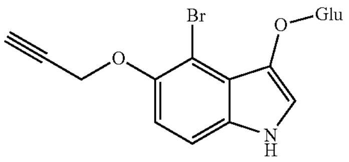 | 56 | 79 ± 1 | 17 |
| 13 | 27 | 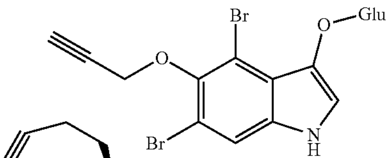 | 105 (51)[g] | 184 ± 3 (89 ± 2)[g] | 50 |
| 14 | 30 | 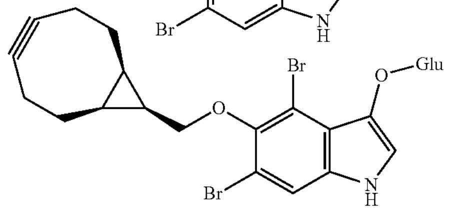 | <1 | 21 ± 1 (10 ± 0.4)[g] | —[f] |
| 15 | 33 | 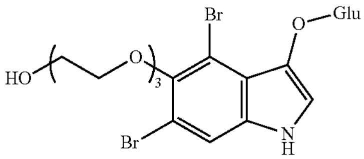 | 52[g] | 99 ± 5[g] | <5[g] 81 ± 5[g,h] |
| 16 | 41 | 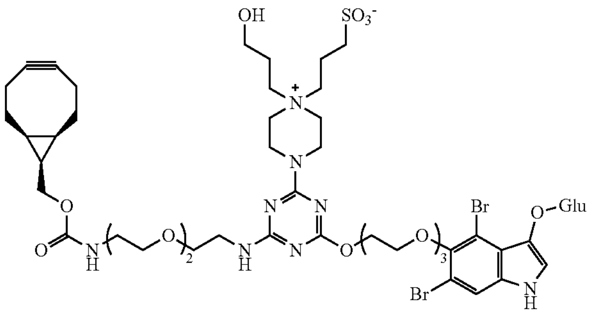 | —[f] | 106 ± 4[g] | —[f] |

[a]The yield was estimated by absorption spectroscopy with ϵ = 1.27 × $10^4$ $M^{-1}$ $cm^{-1}$ (DMF/$H_2O$ = 2:1) measured for 4 (see the ESI) unless otherwise noted.

[b]A mixture of the indoxyl (1 mM) and β-glucosidase from almonds (1 unit/mL) in 0.01M acetate buffer (pH 5, containing 5% DMF) was incubated at 37° C. for 16-19 h.

cA mixture of the indoxyl (100 μM) and β-glucosidase from *Agrobacterium* (200 nM) in 0.05M phosphate buffer (pH 7.0, containing 2% DMF) was incubated at 37° C. for 2 h. The reaction was repeated three times.

TABLE 1-continued

Indigogenic reactions of indoxyl derivatives.

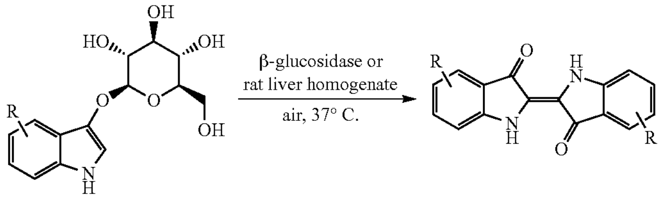

| Entry | Indoxyl | Structure | Yield (%)[a] | | |
|---|---|---|---|---|---|
| | | | β-glucosidase from almonds[b] | β-glucosidase from *Agrobacterium*[c] | rat liver homogenate[d] |

[d]The indoxyl (1 mM) in rat liver homogenate containing 5% DMF was incubated at 37° C. for 24 h.

[e]The yield was estimated from absorption spectroscopy with ε = 2.00 x $10^4$ $M^{-1}$ $cm^{-1}$ reported for 5,5'-dibromo-4,4'-dichloroindigo.[34]

[f]Not conducted.

[g]The yield was estimated from absorption spectroscopy with ε = 2.6 x $10^4$ $M^{-1}$ $cm^{-1}$ (DMF/$H_2O$ = 2:1) measured for 43.

[h]The reaction was carried out with 33 (100 μM) and β-glucosidase from *Agrobacterium* (200 nM) plus rat liver homogenate containing 2% DMF at 37° C. for 4 h.

The results from the glucosidase survey prompted several further experiments. First, a parallel set of studies was carried out with inclusion of several oxidants commonly employed in histochemical studies, given that the indigoid dye forming process requires the presence of an oxidant. No substantial increase in yield was observed for the substrates shown in entries 1-15 of Table 1. Also, the same set of substrates was examined with tritosomes (lysosomes isolated by loading with a non-ionic detergent) but the results were uniformly poor except for a low yield of indigoid dye from 16 and 19. The activity of the β-glucosidase was affected only slightly in the presence of a non-ionic detergent. To verify that the results observed in Table 1 were reliable, a 5-mg scale reaction of 33 was carried out to isolate indigo 43, which was obtained in 66% yield (Scheme 7). The 66% isolated yield corresponded well with the enzymatic yield of 52% (Table 1, entry 15).

Scheme 7. Isolation of indigo 43 from a 5-mg scale reaction with 33.

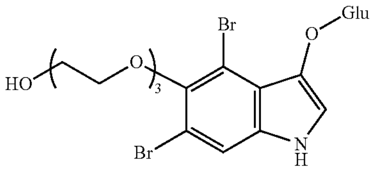

33
(5 mg, 1 mM)

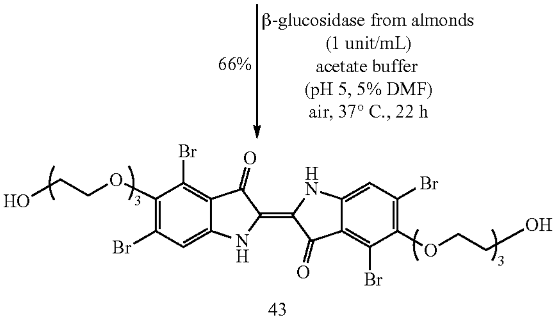

43

Figure 9A:
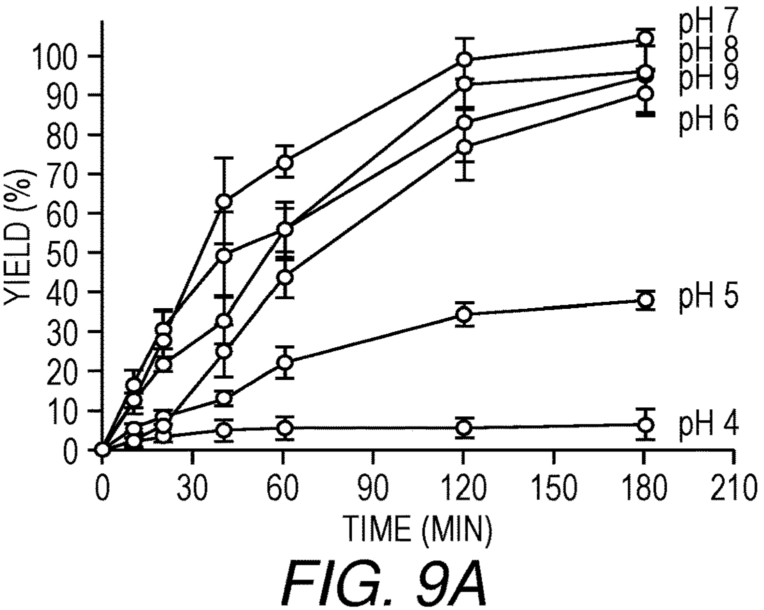
FIGS. 9A-9C show the results from a study of reaction conditions for the indigoid-forming reaction from 33 with β-glucosidase from *Agrobacterium*.
Figure 9B:
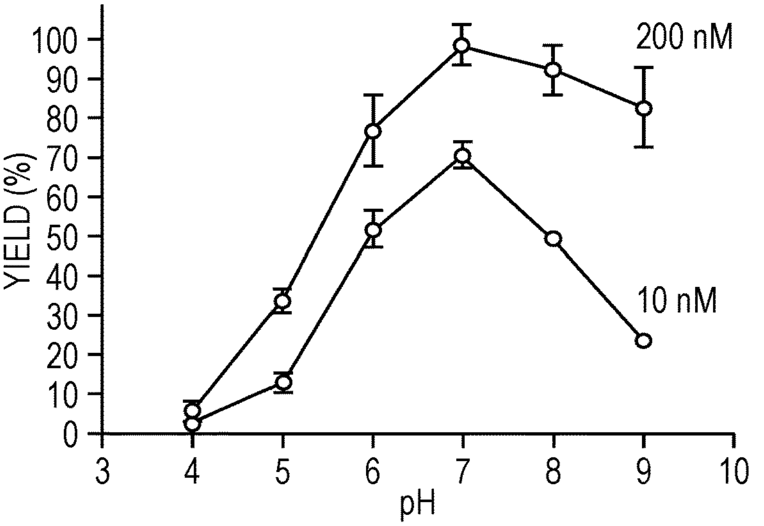
Figure 9C:
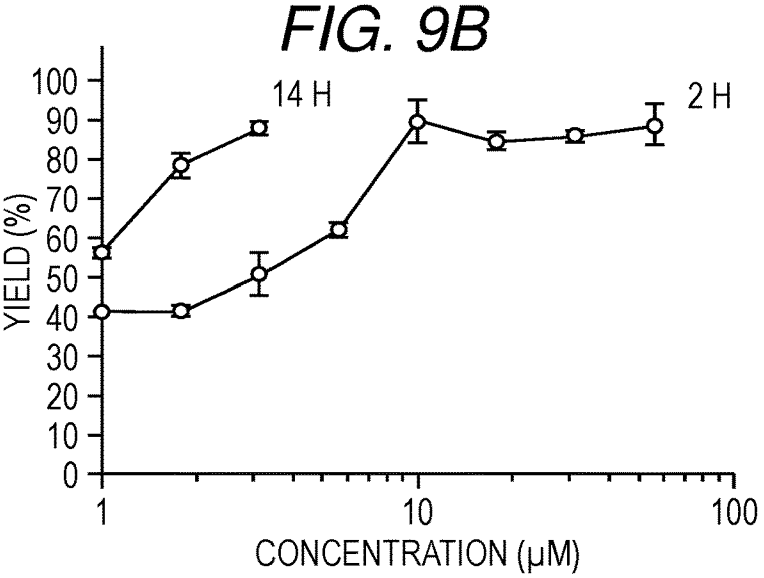

Next, the β-glucosidase from *Agrobacterium* sp. was investigated as the trigger enzyme for indigoid dye formation. In contrast to β-glucosidase from almonds, which works chiefly under acidic conditions[35] (optimum pH 5.6),[36] β-glucosidase from *Agrobacterium* has a neutral pH optimum and maintains partial activity under acidic (pH 4-5) and basic (pH 8-9) conditions as determined by measurement of the rate of hydrolysis of 4-nitrophenyl β-D-glucopyranoside.[37] Given that the indigoid dye-forming reaction is reported to be faster at a basic rather than an acidic pH,[16,38] the pH effect on the indigoid dye-forming reaction was studied with β-glucosidase from *Agrobacterium*. The reaction was carried out using the enzyme (200 nM) and indoxyl-glucoside 33 (100 μM) in phosphate buffer (pH 4-9, containing 2% DMF) at 37° C. The progress of indigoid dye formation as a function of pH is illustrated in FIG. 9A. High to quantitative yields were attained in 3 h at pH 6-9; within this range, pH 7 provided the best result. The reactions at pH 4 and 5 were also nearly complete in 3 h, although the yields were lower (6% and 38% at pH 4 and 5, respectively). The yields with different enzyme concentrations (200 versus 10 nM) at 2 h are shown in FIG. 9B. Good yields (50-71%) obtained at pH 6-8 with 10 nM enzyme suggested that indigoid dye formation from the indolinone intermediate was not very fast compared to the enzymatic cleavage of the sugar of 33. A relatively large decrease in the yield at pH 9 with 10 nM enzyme may be attributed to the importance of the enzymatic activity under the conditions. The effect of concentration of 33 on the indigo-forming reaction at pH 7.0 is illustrated in FIG. 9C. High yields were maintained when the concentration was >10 μM (89, 86, 85, and 90% at 56, 32, 18, and 10 μM, respectively), while lower yields were obtained at lower concentrations (62, 51, 42, and 41% at 5.6, 3.2, 1.8, and 1.0 μM, respectively). Lengthening the reaction time from 2 h to 14 h improved the yields (88, 79, and 57% at 3.2, 1.8, and 1.0 μM, respectively). Note that with 200 nM enzyme and 100 μM substrate, complete reaction requires 500 turnovers of each enzyme. Given that reaction was still observed at 10 nM enzyme, such a modest turnover appears reasonable. In other words, the cases where incomplete reaction was observed likely were not due to limiting enzyme concentration.

With the results in hand for indoxyl-glucoside 33, the 15 other indoxyl compounds shown in Table 1 (100 μM) were similarly treated with β-glucosidase from *Agrobacterium* (200 nM) in phosphate buffer (pH 7) at 37° C. for 2 h. Unsubstituted indoxyl 1 and the 4-chloro-5-bromo derivative 42 provided good yields (97 and 116%, entries 3 and 4, respectively). In contrast to β-glucosidase from almonds, the enzyme from *Agrobacterium* cleaved the glucoside in indoxyls containing the triazine linker to give indigoid dye (entry 5 or 6, 46 or 150% yield). In the reactions of 22-27, the order of the yield was unsubstituted indoxyl<4-bromoindoxyl<4, 6-dibromoindoxyl as observed with β-glucosidase from almonds (entries 8-13). Indoxyl 30 again resulted in low yield (10%, entry 14), suggesting severe steric hindrance of the BCN group in the molecule. The indigoid dye was quantitatively formed from indoxyls 33 and 41 (entries 15 and 16, 99 and 106% yield, respectively).

Finally, indigoid-dye formation was carried out in rat liver homogenate (Table 1, rightmost column). Good yields were obtained in the case of 42 (65%, entry 4) and 27 (50%, entry 13). Indoxyl 33 did not form an indigo product in rat liver homogenate (<5%, entry 15). However, when β-glucosidase from *Agrobacterium* (200 nM) was present in rat liver homogenate, the indigoid dye was obtained in 81% yield (entry 15).

3. Oligomerization Study

We sought to carry out an enzyme-triggered oligomerization using a bis(glucosyl-indoxyl) species bearing a water-solubilization motif. The synthesis of the monomer for oligomerization is shown in Scheme 8. Treatment of acetyl-protected dibromoindoxyl-glucoside 32 (two molar equiv) with cyanuric chloride resulted in substitution of two of the three chloro groups in the latter to give chlorotriazine 44 in 53% yield. After removal of the N-acetyl groups of 44 by treatment with basic methanol, the reaction with 38 installed the water-solubilizing group to afford 45 in 55% yield. Deprotection of the glucosyl O-acetyl groups provided the target bis(glucosyl-indoxyl) species 46 in 77% yield.

Scheme 8. Synthesis of di-indoxyl derivative 46.

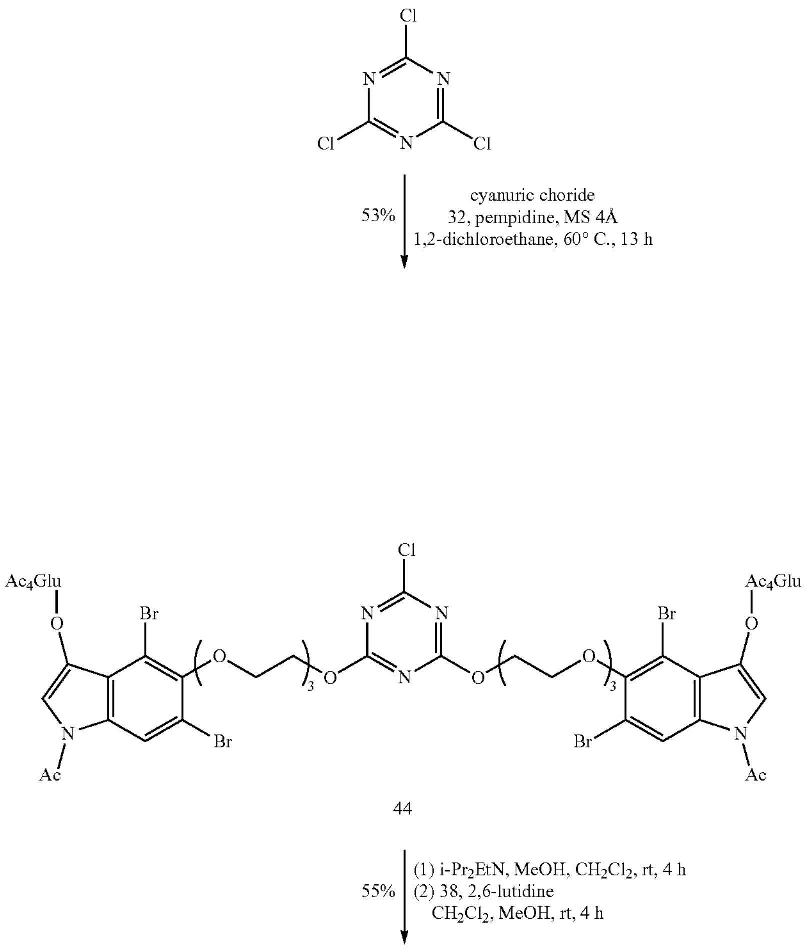

44

-continued
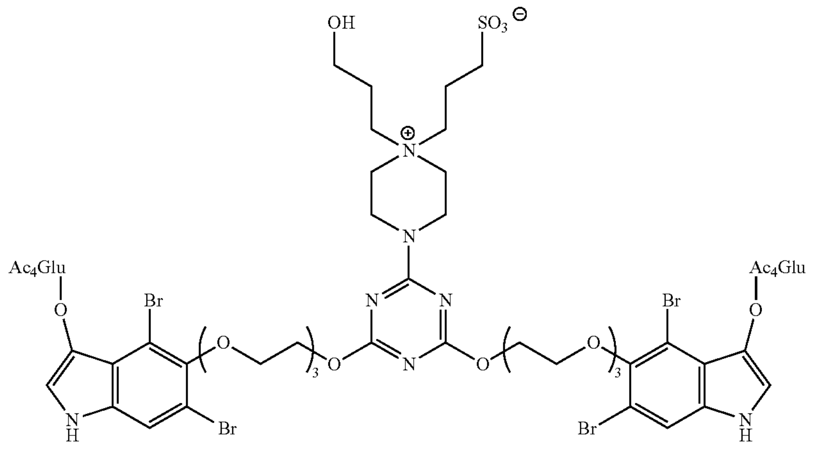
45
77%
$K_2CO_3$, $CH_2Cl_2$, MeOH, $H_2O$
rt, 3 h
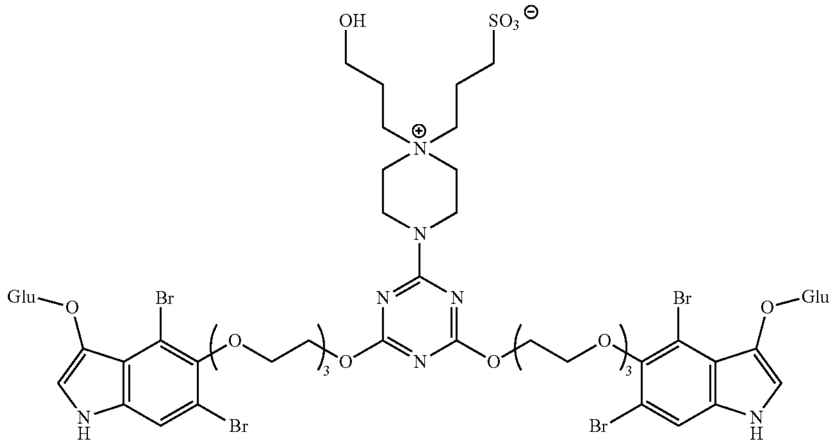
46
Oligomerization of 46 was carried out by treatment with β-glucosidase from *Agrobacterium* (200 nM) in 10 mM phosphate buffer (pH 7) at 37° C. for 2-4 h (Scheme 9). Precipitation occurred during the reaction. After centrifugation, the precipitate was separated from the supernatant, washed with $H_2O$, and dried to afford a blue solid.

Scheme 9. Oligomerization of indigogenic 46.

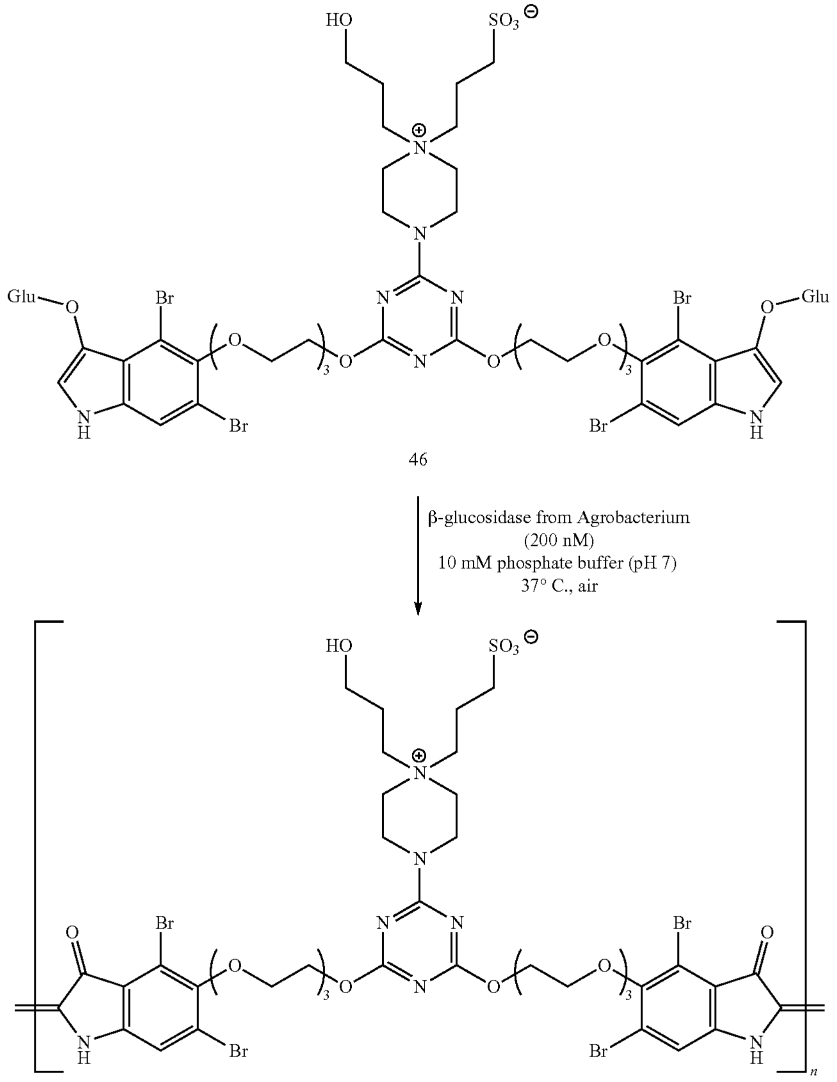

46

The efficacy of the indigogenic oligomerization was examined under a variety of conditions. As shown in entries 1-4 in Table 2, the yield of indigoid dye in the supernatant versus precipitate reversed as the concentration of 46 was decreased from 300 to 10 μM, although the total yields were in the range 17-29%. While the reactions in entries 1-4 were carried out in phosphate buffer containing NaCl (0.05 M), those of entries 5 and 6 (with 300 and 50 μM of 46, respectively) were conducted in NaCl-free phosphate buffer. The use of NaCl-free phosphate buffer facilitated extraction of the indigoid dye in the supernatant for analysis.

TABLE 2

Study of the oligomerization of bis(indoxyl-glucoside) species 46.

| Entry | [46], μM | Time, h | Yield of indigoid dye (%)[a] | |
|---|---|---|---|---|
| | | | supernatant | precipitate |
| 1[b] | 300 | 2 | 6 | 11 |
| 2[b] | 100 | 3 | 10 | 14 |

TABLE 2-continued

Study of the oligomerization of bis(indoxyl-glucoside) species 46.

| Entry | [46], μM | Time, h | Yield of indigoid dye (%)[a] | |
|---|---|---|---|---|
| | | | supernatant | precipitate |
| 3[b] | 50 | 2 | 13 ± 0.4[c] | 16 ± 0.6[c] |
| 4[b] | 10 | 4 | 22 | 6 |
| 5[d] | 300 | 3 | 13 | 13 |
| 6[d] | 50 | 3 | 19 | 8 |

[a]The yield was calculated from absorption spectroscopy with $\varepsilon = 2.6 \times 10^4\ M^{-1}cm^{-1}$.
[b]The reaction was carried out in phosphate buffer containing NaCl (0.05M).
[c]The reaction was repeated three times.
[d]The reaction was carried out in phosphate buffer containing DMF (0.1-0.6%).

Figure 10A:
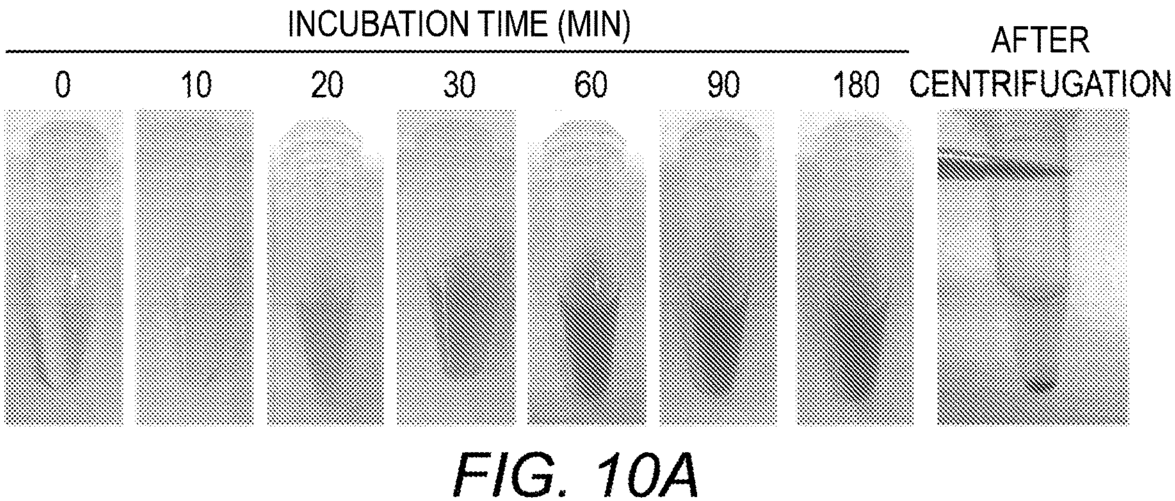
FIG. 10A shows time course of oligomerization with 46 under reaction conditions listed in entry 5 of Table 2.
Figure 10B:
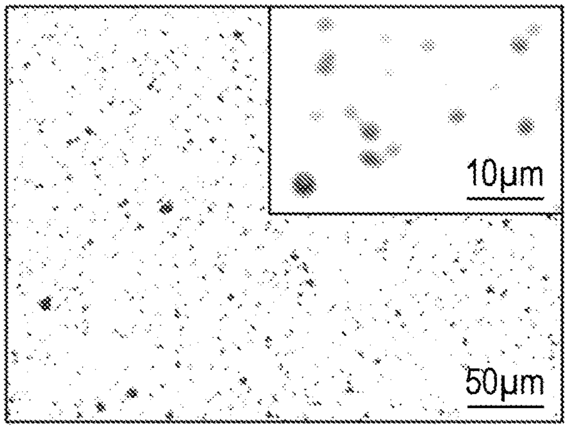
FIG. 10B is an optical microscopic image (×40) of the precipitate suspended in $H_2O$.
Figure 10C:
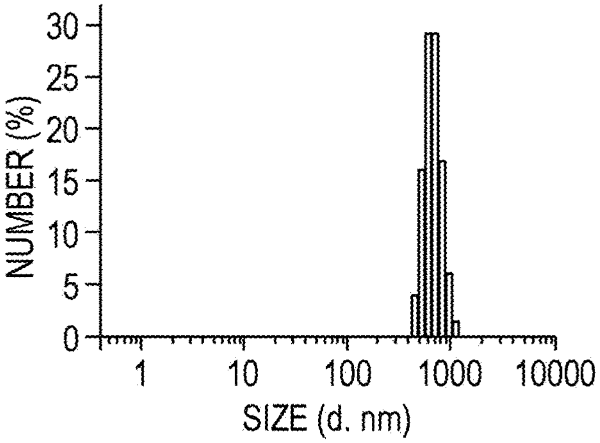
FIG. 10C shows the DLS analysis of the precipitate suspended in $H_2O$.
Figure 10D:
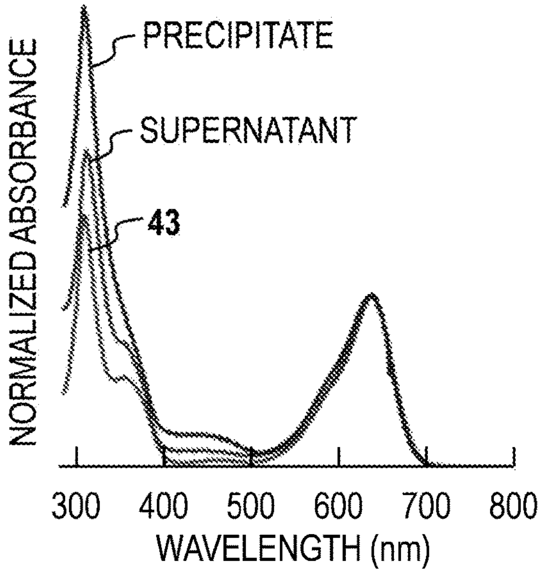
FIG. 10D shows the absorption spectra (normalized at 637 nm) of the precipitate in DMF/DMSO (9:1) (blue), the extracted supernatant in DMF (red), and 43 in DMF (magenta).
Figure 10E:
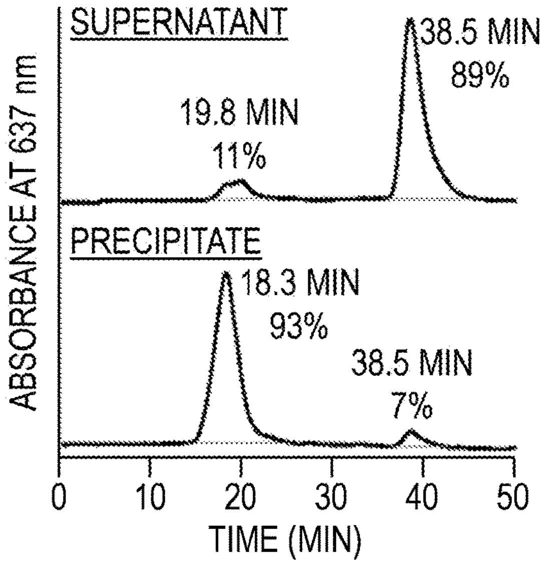
FIG. 10E shows the analytical SEC traces for the supernatant and precipitate samples from 300 μM of 46.

The time course of the oligomerization was examined under the reaction conditions listed in entry 5 of Table 2, with 300 μM of 46. The visible course of the reaction is shown in FIG. 10A. Noticeable changes include observation of blue clouding and color deepening at 20 min. Centrifugation enabled isolation of the precipitate. Optical microscopic analysis of the precipitate suspended in $H_2O$ showed small particles of up to several micron dimensions (FIG. 10B). Dynamic light scattering (DLS) analysis indicated that the particle size was ~680 nm (number mean, FIG. 10C). The absorption spectrum of the precipitate was examined in DMF/DMSO (9:1) and compared with that of the extracted supernatant (in DMF) and 43 (in DMF) (FIG. 10D). All three samples showed a characteristic indigogenic peak in the range 550-700 nm. The greater absorbance at ca. 300 nm in the precipitate and supernatant extract versus that of 43 suggested contamination of impurities composed of indole derivatives. Size-exclusion chromatography (SEC) [DMF/DMSO (9:1) as eluent] was applied to the precipitate and to the supernatant extract prepared from 300 μM of 46 (FIG. 10E). The first peak appeared at 18-20 min, and then the second peak at 38.5 min. The ratio of peak areas in the supernatant extract was 11:89, whereas that in the precipitate was 93:7. On the basis of a calibration curve prepared with poly(2-vinylpyridine) standards, the molecular size for the first and second peaks was expected to be >265 and <1 kDa, respectively. The large molecular size indicated for the first peak likely implies aggregation or assembly of the oligomers. The chromatograms for the samples prepared with 50 μM of 46 gave similar results but with higher purity compared with those at higher concentration.

Figure 11A:
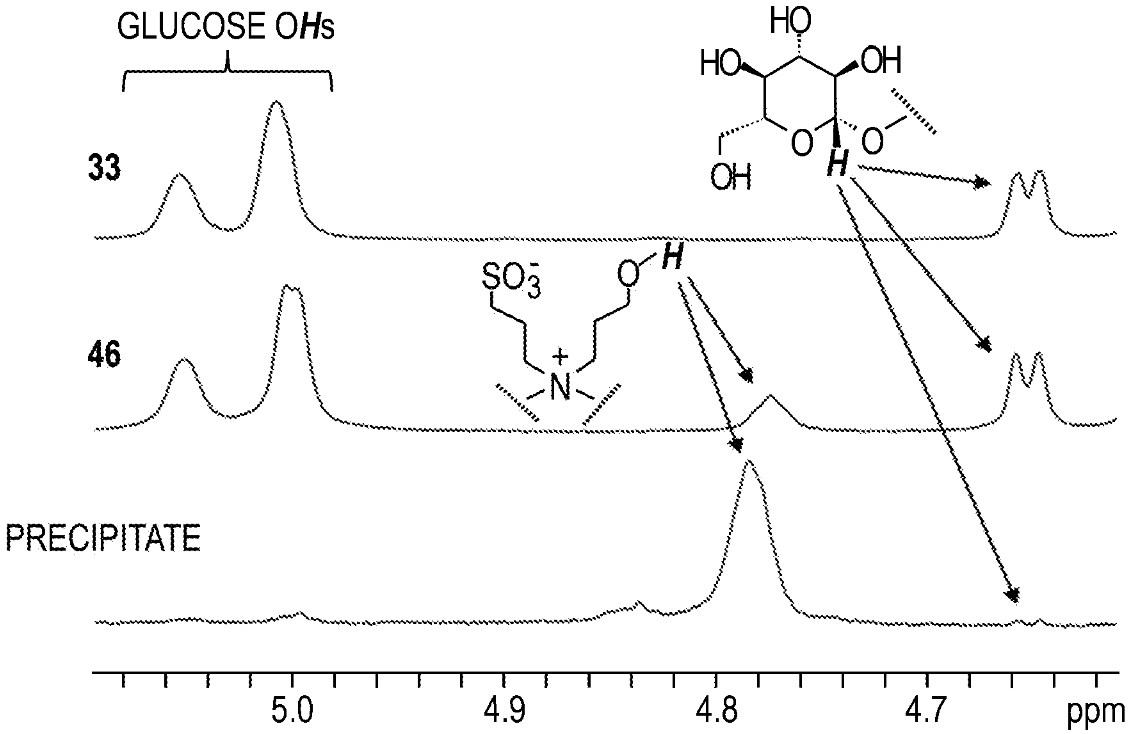
FIGS. 11A-11B show a comparison of $^1H$ NMR spectra (in DMSO-$d_6$) with FIG. 11A being the spectra of 33, 46, and the precipitate, and FIG. 11B being the spectra of 46, 43, and the precipitate.
Figure 11B:
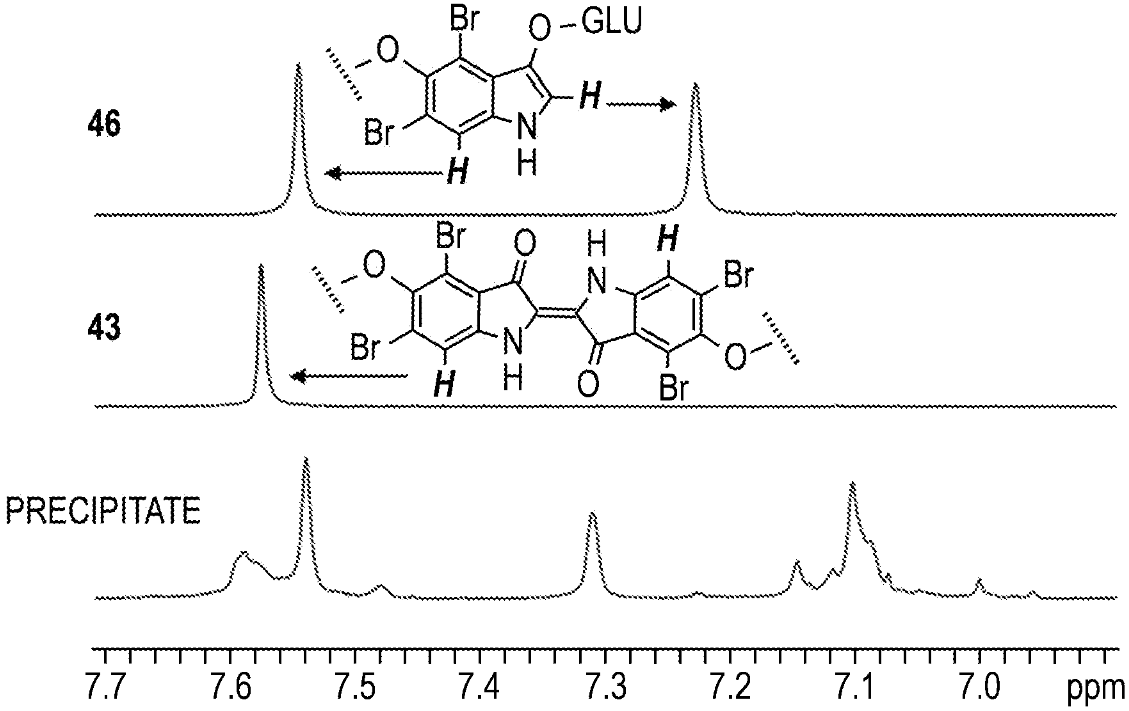

The $^1H$ NMR spectra of 33, 46, and the precipitate dissolved in DMSO-$d_6$ are shown in FIG. 11A. The lack of signals from the glucosyl group (hydroxyl protons ~5.0 ppm; the anomeric proton at 4.65 ppm) in the spectrum of the precipitate is consistent with smooth enzymatic cleavage of the sugar moiety. On the other hand, the signals in the aromatic region of the precipitate were complicated (FIG. 11B). One interpretation is that the precipitate includes the indigoid dye in distinct environments and/or unknown indole derivatives other than the indigoid dye and indoxyl β-glucoside.

Finally, the oligomerization of 46 was carried out on a larger scale (7.87 mg) under the same reaction conditions as those of entry 5 in Table 2. As a result, 3.01 mg of the precipitate was obtained, which corresponds to 49% yield based on the monomer formula weight.

We attempted to use mass spectrometry to gain information about the composition of the oligomeric indigoid products formed upon enzymatic treatment of 46. Analysis of the supernatant by ESI-MS revealed negative ion peaks at m/z 1214.0 and 2428.9, consistent with monomer cyclization (n=1) and cyclodimerization (n=2), respectively. Analysis of the supernatant by MALDI-MS revealed a progression of broad peaks extending to m/z >10,000 with m/z 1210-1250 increment. Although the progression implies a mixture of oligomers, the observed m/z values did not match the calculated values. Incomplete purification, decomposition by laser irradiation (especially the bromoheteroarene units), or complicated isotopic distribution caused by multiple bromine atoms may contribute to the broad peaks. Attempts to use MALDI-MS to analyze the precipitate, which was very insoluble, were unfruitful.

Experimental Section

General methods. 1H NMR and $^{13}C$ NMR spectra were collected at room temperature in $CDCl_3$ unless noted otherwise. Chemical shifts for $^1H$ NMR spectra are reported in parts per million (δ) relative to tetramethylsilane or solvent signal ($CD_3OD$, δ=3.31 ppm). Chemical shifts for $^{13}C$ NMR spectra are reported in parts per million (δ), and spectra were calibrated by using solvent signals [$CDCl_3$, δ=77.16 ppm; $(CD_3)_2SO$, δ=39.52 ppm; $CD_3OD$, δ=49.00 ppm]. Silica (40 μm), diol-functionalized silica (40-63 μm), and reverse phase silica (C18, 40-63 μm) were used for column chromatography. Preparative TLC separations were carried out on Merck analytical plates precoated with silica 60 $F_{254}$. All solvents were reagent grade and were used as received unless noted otherwise. Commercial compounds were used as received. The known compounds 9,[21] 12[27] and N,N-bis(2-methoxyethyl)aniline[31] were prepared generally following procedures described in the literature. Microscopic analysis was performed on a Zeiss Axio Imager M.2. DLS analysis was performed on a Zetasizer Nano ZS. Centrifugation was carried out at 20,000 G at 4° C.

5-Hydroxy-1H-indol-3-yl β-D-glucopyranoside (10). A suspension of 9 (917.4 mg, 1.50 mmol), having >99% stereochemical purity at the anomeric carbon, in MeOH (7.50 mL) at room temperature was treated with sodium methoxide (25 wt % solution in MeOH, 648 μL, 3.0 mmol). After 2 h, acetic acid (229 μL, 6.00 mmol) and palladium on carbon (10 wt %, 79.8 mg, 0.075 mmol) were added. The reaction mixture was stirred for 2 h under hydrogen atmosphere (balloon) at room temperature and then filtered through Celite. The filtrate was concentrated and chromatographed [silica, $CH_2Cl_2$/MeOH (7:3)] to afford a pale yellow solid (417.6 mg, 89%): $^1H$ NMR [400 MHz, $(CD_3)_2SO$] δ 3.09-3.29 (m, 4H), 3.42-3.53 (m, 1H), 3.65-3.76 (m, 1H), 4.47-4.55 (m, 1H), 4.59 (br s, 1H), 5.07 (br s, 1H), 5.15 (br s, 1H), 5.38 (br s, 1H), 6.58 (dd, J=2.6, 8.6 Hz, 1H), 6.89 (d, J=2.0 Hz, 1H), 6.98 (d, J=2.6 Hz, 1H), 7.06 (d, J=8.6 Hz, 1H), 8.68 (br s, 1H), 10.21 (s, 1H); $^{13}C$ NMR (100 MHz, $CD_3OD$) δ 62.6, 71.5, 75.0, 78.02, 78.04, 102.5, 105.8, 112.9, 113.1, 113.5, 121.9, 130.4, 138.4, 160.0; ESI-MS obsd 334.0894, calcd 334.0897 $[(M+H)^+$, M=$C_{14}H_{17}NO_7]$.

1-Acetyl-5-hydroxy-1H-indol-3-yl 2,3,4,6-tetra-O-acetyl-β-D-glucopyranoside (11).[21] Following a reported debenzylation procedure,[21] a suspension of 9 (6.911 g, 11.3 mmol) and Pd/C (10 w/w %, 360.8 mg, 0.339 mmol) in ethyl acetate/EtOH (4:1, 113 mL) was stirred for 3 h at room temperature under $H_2$ atmosphere (balloon). The reaction mixture was filtered through Celite. The filtrate was concentrated and chromatographed [silica, $CH_2Cl_2$/ethyl acetate (10:1)] to afford a pale yellow solid (5.85 g, 99%): mp 88-90° C.; $^1H$ NMR (400 MHz, $CDCl_3$) δ 2.05 (s, 3H), 2.06 (s, 3H), 2.09 (s, 3H), 2.12 (s, 3H), 2.56 (s, 3H), 3.77-3.88 (m, 1H), 4.23 (dd, J=5.0, 12.4 Hz, 1H), 3.34 (d, J=12.4 Hz), 4.93-5.03 (m, 1H), 5.11-5.23 (m, 1H), 5.23-5.34 (m, 2H), 5.82-6.02 (m, 1H), 6.85-6.96 (m, 2H), 7.10 (br s, 1H), 8.22 (br s, 1H); $^{13}C$ NMR (100 MHz, $CDCl_3$) δ 20.63, 20.66, 20.73, 20.8, 23.7, 62.1, 68.3, 71.1, 72.4, 72.6, 101.0, 103.2, 110.9, 115.1, 117.7, 125.4, 128.3, 141.3, 153.0, 168.2, 169.58, 169.63, 170.4, 171.0; ESI-MS obsd 544.1430, calcd 544.1426 $[(M+Na)^+$, M=$C_{24}H_{27}NO_{12}]$.

1-Acetyl-5-[(4-chloro-6-methoxy-1,3,5-triazin-2-yl)oxy]-1H-indole-3-yl 2,3,4,6-tetra-O-acetyl-β-D-glucopyranoside (13). A sample of i-$Pr_2$EtN (65.3 μL, 0.375 mmol) was added dropwise over 5 min to a suspension of 11 (130.4 mg, 0.250 mmol) and 12 (58.5 mg, 0.325 mmol) in $CH_2Cl_2$ (1.25 mL) at 0° C. The reaction mixture was allowed to warm to room temperature and stirred for 2 h. The reaction mixture was washed with aqueous citric acid (10%, 1 mL) followed by brine (1 mL), dried ($Na_2SO_4$), and filtered. The filtrate was concentrated and chromatographed [silica, hexanes/ethyl acetate (2:3)] to afford a white solid (188.3 mg, 87%): $^1H$ NMR (300 MHz, $CDCl_3$) δ 2.05 (s, 3H), 2.06 (s, 3H), 2.09 (s, 3H), 2.10 (s, 3H), 2.62 (s, 3H), 3.80-3.95 (m, 1H), 4.02 (s, 3H), 4.14-4.38 (m, 2H), 4.97-5.09 (m, 1H), 5.09-5.40 (m, 3H), 7.10-7.36 (m, 3H), 8.44 (br s, 1H); $^{13}C$ NMR (175 MHz, $CDCl_3$) δ 20.6, 20.68, 20.71, 23.8, 56.3, 61.9, 68.2, 70.9, 72.37, 72.43, 100.7, 110.2, 111.1, 117.7, 119.7, 124.8, 131.4, 141.0, 147.6, 168.1, 169.2, 169.4, 170.2, 170.5, 172.5, 172.8, 173.2; ESI-MS obsd 665.1499, calcd 665.1492 [$(M+H)^+$, M=$C_{28}H_{29}ClN_4O_{13}$].

5-{[4-({1-[(1R,8S,9s)-Bicyclo[6.1.0]non-4-yn-9-yl]-3-oxo-2,7,10-trioxa-4-azadodecan-12-yl}amino)-6-methoxy-1,3,5-triazin-2-yl]oxy}-1H-indole-3-yl β-D-glucopyranoside (15). A sample of 13 (20.3 mg, 0.0305 mmol) was added to a solution of (1R,8S,9s)-bicyclo[6.1.0]non-4-yn-9-yl-methanol (10.4 mg, 0.0321 mmol) and i-$Pr_2$EtN (6.7 μL, 0.038 mmol) in $CH_2Cl_2$ (150 μL) at room temperature. After 3 h, MeOH (750 μL) and $K_2CO_3$ (13.3 mg, 0.096 mmol) were added. After 1 h, the reaction mixture was quenched by the addition of acetic acid (9.2 μL) and then filtered. The filtrate was concentrated and chromatographed [silica, $CH_2Cl_2$/MeOH (3:1)] to afford a pale yellow solid (21.0 mg, 93%): $^1$H NMR (700 MHz, $CD_3OD$, ~1:1 mixture of rotamers) δ 0.85-0.98 (m, 2H), 1.25-1.40 (m, 1H), 1.49-1.65 (m, 2H), 2.09-2.30 (m, 6H), 3.10-3.18 (m, 1H), 3.23-3.28 (m, 1H), 3.29-3.63 (m, 14H), 3.716 (dd, J=5.6, 11.9 Hz, 0.5H), 3.719 (dd, J=5.7, 11.9 Hz, 0.5H), 3.87-3.93 (m, 2.5H), 3.94 (s, 1.5H), 4.10 (d, J=8.1 Hz, 0.5H), 4.12 (d, J=8.2 Hz, 0.5H), 4.68 (d, J=8.1 Hz, 0.5H), 4.70 (d, J=8.1 Hz, 0.5H), 6.67-6.73 (m, 0.5H), 6.78-6.84 (m, 0.5H), 6.87 (dd, J=2.3, 8.7 Hz, 1H), 6.90 (dd, J=2.3, 8.7 Hz, 1H), 7.17 (s, 1H), 7.28 (d, J=8.7 Hz, 0.5H), 7.29 (d, J=8.7 Hz, 0.5H), 7.47 (d, J=2.3 Hz, 0.5H), 7.48 (d, J=2.3 Hz, 0.5H); $^{13}$C NMR (175 MHz, $CD_3OD$) δ 18.9, 21.4, 21.9, 30.1, 41.2, 41.5, 41.6, 41.7, 41.9, 55.2, 55.3, 62.6, 63.70, 63.74, 70.0, 70.3, 70.8, 70.88, 70.91, 71.16, 71.22, 71.5, 75.0, 78.0, 78.16, 78.19, 99.5, 105.9, 106.0, 110.8, 111.0, 112.7, 112.9, 114.0, 114.2, 117.3, 117.5, 121.4, 121.5, 132.9, 133.0, 139.18, 139.24, 146.4, 146.6, 159.2, 159.2, 169.3, 169.5, 173.4, 173.7, 173.9, 174.1; ESI-MS obsd 743.3249, calcd 743.3247 [$(M+H)^+$, M=$C_{35}H_{46}N_6O_{12}$].

5-[(Benzylcarbamoyl)oxy)]-1H-indole-3-yl β-D-glucopyranoside (16). Samples of p-nitrophenyl chloroformate (6.0 mg, 0.029 mmol) and i-$Pr_2$EtN (6 μL, 0.03 mmol) were added to a solution of 11 (13.0 mg, 0.025 mmol) in $CH_2Cl_2$ (1 mL) at room temperature. After 1 h, the reaction mixture was quenched by the addition of saturated aqueous $NH_4Cl$ (2 mL) and stirred for 30 min at room temperature. After $H_2O$ (2 mL) was added, the mixture was extracted with $Et_2O$ (3×2 mL). The combined organic layer was washed with $H_2O$ (2 mL), brine (2 mL), dried ($Na_2SO_4$), and filtered. The filtrate was concentrated under reduced pressure. The residue was dissolved in $CH_2Cl_2$ (1 mL). Benzylamine (3 μL, 0.03 mmol) was added to the solution at room temperature. After 20 h, the reaction mixture was concentrated under reduced pressure. The residue was dissolved in MeOH (1 mL). NaOMe (25% in MeOH, 5 μL, 0.02 mmol) was added to the solution at room temperature. After 45 min, the reaction mixture was quenched with ion exchange resin (DOWEX 50WX8-200), stirred for 20 min at room temperature, and filtered. The filtrate was concentrated under reduced pressure. Column chromatography [silica, $CH_2Cl_2$/MeOH (5:1)] afforded a colorless oil (5.9 mg, 53%): $^1$H NMR (700 MHz, $CD_3OD$) δ 3.32-3.36 (m, 1H), 3.40 (t, J=9.0 Hz, 1H), 3.43 (t, J=9.0 Hz, 1H), 3.48 (dd, J=9.0, 8.0 Hz, 1H), 3.71 (dd, J=12.0, 6.0 Hz, 1H), 3.90 (dd, J=12.0, 2.0 Hz, 1H), 4.37 (s, 2H), 4.67 (d, J=8.0 Hz, 1H), 6.85 (dd, J=8.0, 2.0 Hz, 1H), 7.14 (s, 1H), 7.24-7.28 (m, 2H), 7.31-7.40 (m, 4H), 7.43 (d, J=2.0 Hz, 1H); $^{13}$C NMR (175 MHz, $CD_3OD$) δ 45.7, 62.6, 71.5, 75.0, 78.0, 78.2, 106.0, 111.0, 112.7, 114.2, 117.5, 121.5, 128.2, 128.4, 129.6, 132.9, 139.0, 140.4, 145.4, 158.6; ESI-MS obsd 467.1419, calcd 467.1425 [$(M+Na)^+$, M=$C_{22}H_{23}N_2NaO_8$].

1-Acetyl-4-bromo-5-hydroxy-1H-indol-3-yl 2,3,4,6-tetra-O-acetyl-β-D-glucopyranoside (17). A solution of N-bromosuccinimide in $CH_2Cl_2$ (100 mM, 4.20 mL) was added dropwise over 5 min to a solution of 11 (208.6 mg, 0.400 mmol) and 2,6-di-tert-butylpyridine (88 μL, 0.40 mmol) in $CH_2Cl_2$ (5.80 mL) at −78° C. After 1.5 h, the reaction mixture was allowed to warm to room temperature and stirred for 30 min. The reaction mixture was washed with saturated aqueous $Na_2S_2O_3$ (3 mL) and brine (5 mL), dried ($Na_2SO_4$), and concentrated under reduced pressure. Column chromatography [silica, hexanes/$CH_2Cl_2$/MeCN (2:1:1)] afforded a white solid (180.6 mg, 75%): mp 130° C. (dec.); $^1$H NMR (400 MHz, $CDCl_3$) δ 2.05 (s, 3H), 2.08 (s, 3H), 2.10 (s, 3H), 2.10 (s, 3H), 3.86-3.96 (m, 1H), 4.22 (dd, J=5.4, 12.3 Hz, 1H), 4.36 (dd, J=2.0, 12.3 Hz, 1H), 5.06 (d, J=7.8 Hz, 1H), 5.21 (dd, J=9.2, 9.2 Hz, 1H), 5.31 (dd, J=9.2, 9.2 Hz, 1H), 5.40 (dd, J=7.8, 9.2 Hz, 1H), 5.74 (s, 1H), 7.05 (d, J=8.8 Hz, 1H), 7.22 (br s, 1H), 8.29 (br s, 1H); $^{13}$C NMR (75 MHz, $CDCl_3$) δ 20.8, 20.9, 21.0, 23.9, 62.1, 68.3, 71.0, 72.6, 72.8, 98.6, 100.3, 111.2, 114.7, 117.1, 122.6, 129.0, 140.5, 149.4, 167.9, 169.4, 169.5, 170.4, 170.6; ESI-MS obsd 600.0712, calcd 600.0711 [$(M+H)^+$, M=$C_{24}H_{26}BrNO_{12}$]. Suitable crystals for X-ray analysis were obtained by recrystallization from cyclohexane/$CHCl_3$.

1-Acetyl-4,6-dibromo-5-hydroxy-1H-indol-3-yl 2,3,4,6-tetra-O-acetyl-β-D-glucopyranoside (18). A solution of N-bromosuccinimide (3.987 g, 22.4 mmol) in $CH_2Cl_2$ (240 mL) was added dropwise over 1 h to a solution of 11 (5.841 g, 11.2 mmol) and 2,6-di-tert-butylpyridine (2.47 mL, 11.2 mmol) in $CH_2Cl_2$ (160 mL) at −78° C. The reaction mixture was allowed to warm to room temperature and stirred for 3.5 h. N-Bromosuccinimide (598 mg, 3.36 mmol) was added. After 1 h, the reaction mixture was washed with aqueous $Na_2S_2O_3$ (10%, 50 mL) and brine (50 mL), dried ($Na_2SO_4$), and filtered. The filtrate was concentrated under reduced pressure. Column chromatography [silica, hexanes/ethyl acetate (1:1)] followed by recrystallization from $CH_2Cl_2$/MeOH afforded a white solid (6.32 g, 83%): mp 102-103° C.; $^1$H NMR (700 MHz, $CDCl_3$) δ 2.05 (s, 3H), 2.07 (s, 3H), 2.10 (s, 3H), 2.10 (s, 3H), 2.59 (s, 3H), 3.91 (ddd, J=2.4, 5.2, 9.9 Hz, 1H), 4.22 (dd, J=5.2, 12.5 Hz, 1H), 4.37 (dd, J=2.4, 12.5 Hz, 1H), 5.05 (d, J=7.6 Hz, 1H), 5.21 (dd, J=9.5, 9.9 Hz, 1H), 5.31 (dd, J=9.3, 9.5 Hz, 1H), 5.38 (dd, J=7.6, 9.3 Hz, 1H), 6.02 (s, 1H), 7.22 (br s, 1H), 8.63 (br s, 1H); $^{13}$C NMR (100 MHz, $CDCl_3$) δ 20.7, 20.9, 21.0, 23.7, 62.1, 68.4, 71.0, 72.7, 72.8, 98.4, 100.3, 108.6, 112.0, 120.0, 122.6, 128.7, 140.2, 146.3, 167.8, 169.4, 169.5, 170.3, 170.6; ESI-MS obsd 699.9645, calcd 699.9636 [$(M+Na)^+$, M=$C_{24}H_{25}Br_2NO_{12}$]. Suitable crystals for X-ray analysis were obtained by recrystallization from cyclohexane/acetone.

5-[(4-Methoxy-6-morpholino-1,3,5-triazin-2-yl)oxy]-1H-indole-3-yl β-D-glucopyranoside (19). A sample of i-$Pr_2$EtN (13.1 μL, 0.075 mmol) was added to a solution of 10 (15.6 mg, 0.050 mmol) and 12 (9.9 mg, 0.055 mmol) in DMF (125 μL) at room temperature. After 3 h, morpholine (8.6 μL, 0.10 mmol) was added. After 2 h, the reaction mixture was passed through silica. The resulting solution was concentrated under reduced pressure. Column chromatography [silica, $CHCl_3$/MeOH (4:1)] afforded a white solid (15.0 mg, 59%): $^1$H NMR (300 MHz, $CD_3OD$) δ 3.25-3.93 (m, 14H), 3.92 (s, 3H), 4.67 (d, J=7.2 Hz, 1H), 6.87 (dd, J=8.7, 1.8 Hz, 1H), 7.16 (s, 1H), 7.27 (d, J=8.7 Hz, 1H), 7.46 (d, J=1.8 Hz, 1H); $^{13}$C NMR (75 MHz, $CD_3OD$) δ 45.2, 55.3, 62.6, 67.5, 71.5, 75.0, 78.0, 78.2, 106.0, 110.7, 112.7, 114.1, 117.3, 121.4, 132.9, 139.2, 146.5, 167.9, 173.8, 174.0; ESI-MS obsd 506.1883, calcd 506.1880 [$(M+H)^+$, $M=C_{22}H_{27}N_5O_9$].

1-Acetyl-4-bromo-5-[(4-methoxy-6-morpholino-1,3,5-triazin-2-yl)oxy]-1H-indole-3-yl 2,3,4,6-tetra-O-acetyl-β-D-glucopyranoside (pre-20). A sample of i-$Pr_2EtN$ (10.5 μL, 0.060 mmol) was added to a solution of 17 (24.0 mg, 0.040 mmol) and 12 (7.9 mg, 0.044 mmol) in $CH_2Cl_2$ (200 μL) at room temperature. After 30 min, morpholine (6.9 μL, 0.080 mmol) was added. After 3 h, the reaction mixture was quenched with acetic acid (2.2 μL) and then passed through silica (ethyl acetate as an eluent). The eluent was concentrated under reduced pressure. Column chromatography [silica, hexanes/ethyl acetate (1:2)]afforded a white solid (27.6 mg, 87%): $^1H$ NMR (400 MHz, $CDCl_3$) δ 3.60-3.76 (m, 6H), 3.78-3.94 (m, 6H), 4.20 (dd, J=5.2, 12.5 Hz, 1H), 4.37 (dd, J=2.2, 12.5 Hz, 1H), 5.06 (d, J=7.6 Hz, 1H), 5.19 (dd, J=9.3, 9.3 Hz, 1H), 5.29 (dd, J=9.3, 9.3 Hz, 1H), 5.37 (dd, J=7.6, 9.3 Hz, 1H), 7.17 (d, J=8.8 Hz, 1H), 7.30 (br s, 1H), 8.30-8.50 (m, 1H); $^{13}C$ NMR (175 MHz, $CDCl_3$) δ 20.7, 20.9, 21.0, 24.0, 44.06, 44.11, 54.8, 62.0, 66.6, 66.7, 68.3, 70.8, 72.6, 72.7, 100.3, 106.4, 112.1, 116.3, 121.5, 123.5, 132.1, 140.8, 146.2, 166.9, 168.1, 169.3, 169.5, 170.3, 170.6, 171.9, 172.6; ESI-MS obsd 816.1321, calcd 816.1334 [$(M+Na)^+$, $M=C_{32}H_{36}BrN_5O_{14}$].

4-Bromo-5-[(4-methoxy-6-morpholino-1,3,5-triazin-2-yl)oxy]-1H-indole-3-yl β-D-glucopyranoside (20). A suspension of pre-20 (15.9 mg, 0.020 mmol) and $K_2CO_3$ (2.8 mg, 0.020 mmol) in MeOH was stirred at room temperature for 20 min. The reaction mixture was quenched with acetic acid (2.9 μL) and concentrated under reduced pressure. Column chromatography [silica, $CH_2Cl_2$/MeOH (1:2)] afforded a white solid (10.4 mg, 89%): 1H NMR (300 MHz, $CD_3OD$) δ 3.34-4.00 (m, 17H), 4.76 (d, J=7.8 Hz, 1H), 7.21-7.34 (m, 2H); $^{13}C$ NMR (175 MHz, $CD_3OD$) δ 45.1, 45.3, 55.29, 55.34, 62.65, 62.69, 67.5, 71.6, 75.3, 78.1, 78.3, 105.2, 106.1, 112.2, 114.7, 118.3, 119.8, 133.6, 139.2, 143.8, 167.9, 173.4, 173.8; ESI-MS obsd 584.0986, calcd 584.0987 [$(M+H)^+$, $M=C_{22}H_{26}BrN_5O_9$].

4,6-Dibromo-5-[(4-methoxy-6-morpholino-1,3,5-triazin-2-yl)oxy]-1H-indole-3-yl β-D-glucopyranoside (21). A sample of i-$Pr_2EtN$ (7.3 μL, 0.042 mmol) was added to a solution of 18 (19.0 mg, 0.028 mmol) and 2,4-dichloro-6-methoxy-1,3,5-triazine (5.54 mg, 0.031 mmol) in $CH_2Cl_2$ (140 μL) at 0° C. The reaction mixture was allowed to warm to room temperature and stirred for 1 h. Morpholine (4.8 μL, 0.056 mmol) was added. After 3 h, MeOH (560 μL) and $K_2CO_3$ (19.3 mg, 0.14 mmol) were added. The reaction mixture was heated at 35° C. for 1 h and cooled to room temperature. The reaction mixture was quenched by the addition of acetic acid (16 μL) and filtered. The filtrate was concentrated under reduced pressure. Column chromatography [silica, $CH_2Cl_2$/MeOH (6:1)] afforded a white solid (12.5 mg, 67%): $^1H$ NMR (300 MHz, $CD_3OD$) δ 3.34-4.02 (m, 17H), 4.77 (d, J=7.2 Hz, 1H), 7.30 (s, 1H), 7.56 (s, 1H); $^{13}C$ NMR (175 MHz, $CD_3OD$) δ 45.1, 45.3, 55.4, 55.5, 62.6, 67.4, 71.5, 75.2, 78.1, 78.3, 105.00, 105.02, 107.6, 111.2, 115.2, 115.7, 119.5, 133.6, 139.2, 140.6, 167.9, 172.6, 173.9; ESI-MS obsd 662.0098, calcd 662.0092 [$(M+H)^+$, $M=C_{22}H_{25}Br_2N_5O_9$].

5-(Methoxycarbonyl)methoxy-1H-indol-3-yl β-D-glucopyranoside (22). Ethyl bromoacetate (5.0 μL, 45 μmol) and NaH (2.0 mg, 83 μmol) were added to a solution of 11 (10.0 mg, 0.019 mmol) in DMF (1 mL) at room temperature. After 1 h, the reaction mixture was quenched with saturated aqueous $NH_4Cl$ (2 mL) and stirred for 10 min at room temperature. After $H_2O$ (2 mL) was added, the mixture was extracted with $Et_2O$ (3×2 mL). The combined organic layer was washed with $H_2O$ (2 mL), brine (2 mL), dried ($Na_2SO_4$), and filtered. The filtrate was concentrated under reduced pressure. The residue was dissolved in MeOH (1 mL). NaOMe (25% in MeOH, 5 μL, 0.02 mmol) was added to the solution at room temperature. After 45 min, the reaction mixture was quenched with ion exchange resin (DOWEX 50WX8-200), stirred for 20 min at room temperature, and filtered. The filtrate was concentrated and chromatographed [silica, $CH_2Cl_2$/MeOH (5:1)] to afford a colorless oil (3.9 mg, 53%): $^1H$ NMR (300 MHz, $CD_3OD$) δ 3.34-3.56 (m, 4H), 3.72 (dd, J=12.0, 5.0 Hz, 1H), 3.80 (s, 3H), 3.91 (dd, J=12.0, 2.0 Hz, 1H), 4.66 (d, J=7.5 Hz, 1H), 4.71 (s, 2H), 6.82 (dd, J=9.0, 2.5 Hz, 1H), 7.09 (s, 1H), 7.16-7.22 (m, 2H); $^{13}C$ NMR (75 MHz, $CD_3OD$) δ 52.5, 62.7, 67.0, 71.5, 75.1, 78.0, 78.2, 101.5, 106.0, 113.3, 113.7, 113.9, 153.1, 172.1; ESI-MS obsd 406.1109, calcd 406.1109 [$(M+Na)^+$, $M=C_{17}H_{21}NO_9$].

4-Bromo-5-(methoxycarbonyl)methoxy-1H-indol-3-yl β-D-glucopyranoside (23). Ethyl bromoacetate (4.0 μL, 36 μmol) and NaH (1.0 mg, 42 μmol) were added to a solution of 17 (15 mg, 0.025 mmol) in DMF (0.5 mL) at room temperature. After 1 h, the reaction mixture was quenched with saturated aqueous $NH_4Cl$ (2 mL) and stirred for 10 min at room temperature. After $H_2O$ (2 mL) was added, the mixture was extracted with $Et_2O$ (3×2 mL). The combined organic layer was washed with $H_2O$ (2 mL), brine (2 mL), dried ($Na_2SO_4$), and filtered. The filtrate was concentrated under reduced pressure. The residue was dissolved in MeOH (0.5 mL). NaOMe (25% in MeOH, 5 μL, 0.02 mmol) was added to the solution at room temperature. After 45 min, the reaction mixture was quenched with ion exchange resin (DOWEX 50WX8-200), stirred for 20 min at room temperature, and filtered. The filtrate was concentrated and chromatographed [silica, $CH_2Cl_2$/MeOH (5:1)] to afford a colorless oil (5.4 mg, 52%): $^1H$ NMR (300 MHz, $CD_3OD$) δ 3.34-3.56 (m, 4H), 3.72 (dd, J=12.0, 5.0 Hz, 1H), 3.80 (s, 3H), 3.92 (d, J=12.0 Hz, 1H), 4.66 (s, 2H), 4.75 (d, J=7.0 Hz, 1H), 6.91 (dd, J=9.0, 1.0 Hz, 1H), 7.20 (dd, J=9.0, 1.0 Hz, 1H), 7.24 (s, 2H); $^{13}C$ NMR (175 MHz, $CD_3OD$) δ 52.5, 69.7, 69.8, 71.6, 75.4, 78.3, 103.3, 105.3, 112.2, 113.9, 115.0, 120.3, 132.5, 138.9, 149.7, 171.7; ESI-MS obsd 484.0205, calcd 484.0214 [$(M+Na)^+$, $M=C_{17}H_{20}BrNO_9$].

4,6-Dibromo-5-(methoxycarbonyl)methoxy-1H-indol-3-yl β-D-glucopyranoside (24). Ethyl bromoacetate (3.0 μL, 27 μmol) and NaH (1.0 mg, 42 μmol) were added to a solution of 18 (12.7 mg, 0.019 mmol) in DMF (1 mL) at room temperature. After 1 h, the reaction mixture was quenched with saturated aqueous $NH_4Cl$ (2 mL) and stirred for 20 min at room temperature. After $H_2O$ (2 mL) was added, the mixture was extracted with $Et_2O$ (3×2 mL). The combined organic layer was washed with $H_2O$ (2 mL), brine (2 mL), dried ($Na_2SO_4$), and filtered. The filtrate was concentrated under reduced pressure. The residue was dissolved in MeOH (1 mL). NaOMe (25% in MeOH, 5 μL, 0.02 mmol) was added to the solution at room temperature. After 45 min, the reaction mixture was quenched with ion exchange resin (DOWEX 50WX8-200), stirred for 20 min at room temperature, and filtered. The filtrate was concentrated and chromatographed [silica, $CH_2Cl_2$/MeOH (5:1)] to afford a colorless oil (8.3 mg, 82%): $^1H$ NMR (700 MHz, $CD_3OD$) δ 3.37-3.41 (m, 2H), 3.45 (t, J=9.0 Hz, 1H), 3.53 (dd, J=9.0, 8.0 Hz, 1H), 3.70 (dd, J=12.0, 5.0 Hz, 1H), 3.84 (s, 3H), 3.92 (d, J=12 Hz, 1H), 4.61 (s, 2H), 4.74 (d, J=8.0 Hz, 1H), 7.27 (s, 1H), 7.51 (s, 1H); $^{13}C$ NMR (175 MHz, $CD_3OD$) δ 52.6, 62.7, 70.3, 71.6, 75.3, 78.2, 78.3, 105.1, 107.6, 111.6, 115.4, 116.1, 119.9, 133.2, 139.1, 145.6, 170.6; ESI-MS obsd 561.9310, calcd 561.9319 [$(M+Na)^+$, $M=C_{17}H_{19}Br_2NO_9$].

5-Propargyloxy-1H-indol-3-yl β-D-glucopyranoside (25). A suspension of 10 (15.6 mg, 0.050 mmol), propargyl bromide (18.6 μL, 80% in toluene, 0.125 mmol), and $K_2CO_3$ (17.2 mg, 0.124 mmol) in DMF (125 μL) was heated to 80° C. for 2.5 h. The reaction mixture was allowed to cool to room temperature and then passed through silica ($CH_2Cl_2$/MeOH=1:1 as an eluent). The eluent was concentrated under reduced pressure. Preparative thin layer chromatography [silica, 0.25 mm, 20×20 cm, $CHCl_3$/MeOH (4:1)] afforded a brown solid (5.3 mg, 30%): $^1$H NMR (400 MHz, $CD_3OD$) δ 2.88 (t, J=2.4 Hz, 1H), 3.32-3.54 (m, 4H), 3.73 (dd, J=5.0, 11.8 Hz, 1H), 3.92 (dd, J=2.2, 11.8 Hz, 1H), 4.69 (d, J=7.6 Hz, 1H), 4.71 (d, J=2.4 Hz, 2H), 6.79 (dd, J=2.4, 8.8 Hz, 1H), 7.09 (s, 1H), 7.18 (d, J=8.8 Hz, 1H), 7.28 (d, J=2.4 1H); $^{13}$C NMR (100 MHz, $CD_3OD$) δ 57.6, 62.7, 71.5, 75.1, 76.1, 78.0, 78.2, 80.5, 102.2, 105.9, 113.1, 113.5, 114.1, 121.4, 131.0, 139.0, 152.8; ESI-MS obsd 372.1055, calcd 372.1054 $[(M+Na)^+$, $M=C_{17}H_{19}NO_7]$.

4-Bromo-5-propargyloxy-1H-indol-3-yl β-D-glucopyranoside (26). Propargyl bromide (8.9 μL, 80% in toluene, 0.060 mmol) was added to a suspension of 17 (30.0 mg, 0.050 mmol) and $K_2CO_3$ (8.3 mg, 0.060 mmol) in DMF (200 μL) at room temperature. After 4.5 h, triethylamine (20.9 μL, 0.15 mmol) and MeOH (100 μL) were added. After 2 h, NaOMe (21.6 μL, 25% in MeOH, 0.10 mmol) was added. After 30 min, the reaction mixture was quenched by the addition of acetic acid (20 μL) and concentrated under reduced pressure. Column chromatography [silica ($CH_2Cl_2$/MeOH=8:1) followed by diol-functionalized silica (acetone)] afforded a white solid (15.3 mg, 71%): $^1$H NMR (400 MHz, $CD_3OD$) δ 2.90 (t, J=2.4 Hz, 1H), 3.34-3.52 (m, 3H), 3.55 (dd, J=8.2, 8.2 Hz, 1H), 3.65-3.7 (m, 1H), 3.92 (dd, J=1.2, 11.8 Hz, 1H), 4.71 (d, J=2.4 Hz, 2H), 4.74 (d, J=8.0 Hz, 1H), 7.01 (d, J=8.8 Hz, 1H), 7.20 (d, J=8.8 Hz, 1H), 7.23 (s, 1H); $^{13}$C NMR (100 MHz, $CD_3OD$) δ 60.2, 62.7, 71.5, 75.3, 76.7, 78.0, 78.2, 80.2, 103.6, 105.2, 112.0, 114.5, 114.9, 120.2, 132.5, 138.8, 149.2; ESI-MS obsd 450.0155, calcd 450.0159 $[(M+Na)^+$, $M=C_{17}H_{19}BrNO_7]$.

4,6-Dibromo-5-propargyloxy-1H-indol-3-yl β-D-glucopyranoside (27). Propargyl bromide (1.8 μL, 80% in toluene, 0.012 mmol) was added to a suspension of 18 (6.8 mg, 0.010 mmol) and $K_2CO_3$ (1.7 mg, 0.012 mmol) in DMF (80 μL) at room temperature. After 2 h, triethylamine (4.2 μL, 0.30 mmol) and MeOH (40 μL) were added. After 4.5 h, NaOMe (4.3 μL, 25% in MeOH, 0.020 mmol) was added. After 30 min, the reaction mixture was quenched by the addition of acetic acid (4 μL) and concentrated under reduced pressure. Column chromatography [silica ($CH_2Cl_2$/MeOH=4:1) followed by diol-functionalized silica (acetone)] afforded a white solid (2.7 mg, 53%): $^1$H NMR (700 MHz, $CD_3OD$) δ 2.94 (t, J=2.6 Hz, 1H), 3.37-3.42 (m, 2H), 3.42-3.49 (m, 1H), 3.54 (dd, J=7.9, 9.1 Hz, 1H), 3.68-3.74 (m, 1H), 3.92 (dd, J=1.5, 11.9 Hz, 1H), 4.68 (d, J=2.6 Hz, 2H), 4.75 (d, J=7.8 Hz, 1H), 7.25 (s, 1H), 7.50 (s, 1H); $^{13}$C NMR (175 MHz, $CD_3OD$) δ 61.6, 62.7, 71.6, 75.3, 76.8, 78.1, 78.3, 79.5, 105.1, 108.1, 112.3, 115.2, 115.9, 119.8, 133.1, 139.1, 145.8, ESI-MS obsd 527.9260, calcd 527.9264 $[(M+Na)^+$, $M=C_{17}H_{17}Br_2NO_7]$.

1-Acetyl-5-{[(1R,8S,9s)-bicyclo[6.1.0]non-4-yn-9-yl]methoxy}-4,6-dibromo-1H-indole-3-yl 2,3,4,6-tetra-O-acetyl-β-D-glucopyranoside (29). Diisopropyl azodicarboxylate (39.4 μL, 0.20 mmol) was added to a solution of 18 (67.9 mg, 0.10 mmol), 28 (16.5 mg, 0.11 mmol), and $PPh_3$ (52.5 mg, 0.20 mmol) in $CH_2Cl_2$ (0.50 mL) at room temperature. After 1.5 h, the reaction mixture was passed through silica (ethyl acetate as an eluent). The eluent was concentrated and again chromatographed [silica, hexanes/acetone (2:1) followed by hexanes/ethyl acetate (1:1)] to afford a white solid (51.1 mg, 63%): $^1$H NMR (400 MHz, $CDCl_3$) δ 1.09-1.1 (m, 2H), 1.60-1.82 (m, 3H), 2.05 (s, 3H), 2.07 (s, 3H), 2.09 (s, 3H), 2.11 (s, 3H), 2.18-2.40 (m, 6H), 2.60 (s, 3H), 3.89 (ddd, J=2.3, 5.1, 9.7 Hz, 1H), 4.10 (d, J=7.2 Hz, 2H), 4.20 (dd, J=5.1, 12.5 Hz, 1H), 4.38 (dd, J=2.3, 12.5 Hz, 1H), 5.06 (d, J=7.6 Hz, 1H), 5.21 (dd, J=9.2, 9.7 Hz, 1H), 5.31 (dd, J=9.2, 9.2 Hz, 1H), 5.39 (dd, J=7.6, 9.2 Hz, 1H), 7.25 (s, 1H), 8.70 (br s, 1H); $^{13}$C NMR (175 MHz, $CDCl_3$) δ 19.2, 20.7, 20.8, 20.9, 21.1, 21.7, 23.9, 29.5, 62.0, 68.3, 70.9, 72.0, 72.6, 72.7, 99.1, 100.3, 107.9, 112.0, 116.6, 120.4, 123.2, 131.0, 140.5, 150.1, 168.0, 169.4, 169.6, 170.4, 170.6; ESI-MS obsd 810.0761, calcd 810.0755 $[(M+H)^+$, $M=C_{34}H_{37}Br_2NO_{12}]$.

5-{[(1R,8S,9s)-Bicyclo[6.1.0]non-4-yn-9-yl]methoxy}-4,6-dibromo-1H-indole-3-yl β-D-glucopyranoside (30). $K_2CO_3$ (2.8 mg, 0.020 mmol) was added to a solution of 29 (16.2 mg, 0.020 mmol) in MeOH/THF (4:1, 200 μL) at room temperature. After 1 h, the reaction mixture was diluted with $CH_2Cl_2$ and passed through silica [$CH_2Cl_2$/MeOH (2:1) as an eluent] to afford a white solid (11.9 mg, 99%): $^1$H NMR (700 MHz, $CD_3OD$) δ 0.97-1.06 (m, 2H), 1.65-1.77 (m, 3H), 2.14-2.21 (m, 2H), 2.21-2.34 (m, 4H), 3.37-3.44 (m, 2H), 3.44-3.52 (m, 1H), 3.55 (dd, J=8.1, 8.9 Hz, 1H), 3.68-3.75 (m, 1H), 3.92 (d, J=11.8 Hz, 1H), 4.08 (d, J=7.8 Hz, 2H), 4.74 (d, J=7.7 Hz, 1H), 7.24 (s, 1H), 7.49 (s, 1H); $^{13}$C NMR (175 MHz, $CD_3OD$) δ 20.1, 21.7, 22.0, 30.6, 62.7, 71.5, 72.8, 75.3, 78.1, 78.3, 99.6, 105.2, 107.9, 112.5, 115.2, 116.0, 119.9, 132.8, 139.0, 146.9; ESI-MS obsd 600.0238, calcd 600.0227 $[(M+H)^+$, $M=C_{24}H_{28}Br_2NO_7]$.

2-[2-(2-Hydroxyethoxy)ethoxy]ethyl 2-nitrobenzenesulfonate (31). Triethylamine (1.53 mL, 11.0 mL) was added to a suspension of 2-nitrobenzenesulfonic chloride (2.216 g, 10.0 mmol) in triethylene glycol (26.7 mL, 200 mmol) at 0° C. The reaction mixture was warmed to room temperature. After 30 min, the reaction mixture was diluted with $CH_2Cl_2$ (50 mL), washed with aqueous citric acid (10%, 100 mL) and brine (50 mL), dried ($Na_2SO_4$), and filtered. The filtrate was concentrated and chromatographed [silica, hexanes/acetone (2:3)] to afford a clear pale yellow oil (2.929 g, 87%): $^1$H NMR (700 MHz, $CDCl_3$) δ 2.41 (br s, 1H), 3.54-3.59 (m, 2H), 3.59-3.66 (m, 4H), 3.66-3.75 (m, 2H), 3.76-3.83 (m, 2H), 4.38-4.47 (m, 2H), 7.74-7.79 (m, 1H), 7.79-7.85 (m, 2H), 8.13-8.20 (m, 1H); $^{13}$C NMR (175 MHz, $CDCl_3$) δ 61.9, 68.7, 70.4, 70.9, 71.2, 72.5, 125.0, 129.9, 131.5, 132.5, 134.9, 148.4; ESI-MS obsd 336.0735, calcd 336.0748 $[(M+H)^+$, $M=C_{12}H_{17}NO_8S]$.

1-Acetyl-4,6-dibromo-5-[1-hydroxy-3,6,9-trioxanon-9-yl]-1H-indol-3-yl 2,3,4,6-tetra-O-acetyl-β-D-glucopyranoside (32). A sample of i-$Pr_2$EtN (66 μL, 0.38 mmol) was added to a suspension of 18 (172.0 mg, 0.253 mmol) and 31 (110.4 mg, 0.329 mmol) in $CH_2Cl_2$ (253 μL) at room temperature. The reaction mixture was heated to 35° C. for 24 h and then allowed to cool to room temperature. The reaction mixture was diluted with ethyl acetate (2 mL), washed with aqueous HCl (1 M, 2 mL) and brine (2 mL), dried ($Na_2SO_4$), and filtered. The filtrate was concentrated and chromatographed (silica, ethyl acetate as an eluent) to afford a white solid (182.7 mg, 89%): $^1$H NMR (700 MHz, $CDCl_3$) δ 2.05 (s, 3H), 2.07 (s, 3H), 2.09 (s, 3H), 2.10 (s, 3H), 2.44 (br s, 1H), 2.60 (s, 3H), 3.64 (t, 2H), 3.71-3.78 (m, 4H), 3.78-3.84 (m, 2H), 3.89 (ddd, J=2.5, 5.2, 9.9 Hz, 1H), 4.17-4.23 (m, 2H), 3.97 (t, 2H), 4.20 (dd, J=5.2, 12.4 Hz, 1H), 4.38 (dd, J=2.5, 12.4 Hz, 1H), 5.05 (d, J=7.6 Hz, 1H), 5.20 (dd, J=9.6, 9.9 Hz, 1H), 5.30 (dd, J=9.4, 9.6 Hz, 1H), 5.38 (dd, J=7.6, 9.4 Hz, 1H), 7.25 (s, 1H), 8.69 (br s, 1H); $^{13}$C NMR (175 MHz, $CDCl_3$) δ 20.7, 20.9, 21.1, 23.9, 61.9, 62.0, 68.3, 70.3, 70.6, 70.9, 71.0, 72.6, 72.7, 100.3, 107.7, 112.1, 116.3, 120.4, 123.2, 131.1, 140.5, 149.8, 168.0, 169.4, 169.5, 170.3, 170.6; ESI-MS obsd 832.0399, calcd 832.0422 [$(M+Na)^+$, M=$C_{30}H_{37}Br_2NO_{15}$].

4,6-Dibromo-5-[1-hydroxy-3,6,9-trioxanon-9-yl]-1H-indol-3-yl β-D-glucopyranoside (33). A suspension of 32 (10.2 mg, 0.013 mmol) and $K_2CO_3$ (0.4 mg, 0.003 mmol) in MeOH (250 μL) was stirred for 30 min at room temperature. The reaction mixture was quenched with AcOH (0.4 μL), diluted with $CH_2Cl_2$, and then passed through silica gel [$CH_2Cl_2$/MeOH (2:1) as an eluent]. The eluent was concentrated under reduced pressure. The residue was triturated with MeOH/ethyl acetate/hexanes to afford a white solid (7.1 mg, 94%): $^1$H NMR (700 MHz, $CD_3OD$) δ7.49 (s, 1H), 7.25 (s, 1H), 4.74 (d, J=7.7 Hz, 1H), 4.14 (t, J=4.9 Hz, 2H), 3.95 (t, J=4.9 Hz, 2H), 3.92 (d, J=11.8 Hz, 1H), 3.82-3.77 (m, 2H), 3.74-3.65 (m, 5H), 3.59 (t, J=4.8 Hz, 2H), 3.54 (dd, J=7.8, 9.2 Hz, 1H), 3.50-3.43 (m, 1H), 3.43-3.37 (m, 2H); $^{13}$C NMR (175 MHz, $CD_3OD$) δ146.8, 139.0, 132.9, 119.9, 116.0, 115.2, 112.2, 107.7, 105.1, 78.3, 78.1, 75.3, 73.7, 73.6, 71.7, 71.54, 71.50, 71.3, 62.7, 62.3; HRMS (ESI-TOF) m/z: $[M+Na]^+$ Calcd for $C_{20}H_{27}Br_2NNaO_{10}$ 621.9894; found 621.9891.

3-[14-(tert-Butoxycarbonyl)piperazin-1-yl]propane-1-sulfonic acid (36). A sample of 1-(tert-butoxycarbonyl) piperazine (35, 2.011 g, 10.8 mmol) was added to a solution of 1,3-propane sultone (1.319 g, 10.8 mmol) in 1,4-dioxane (5.40 mL) at room temperature. The reaction mixture was heated to 60° C. for 1 h, and then allowed to cool to room temperature. The precipitate was filtered and washed with ethyl acetate to afford a white solid (2.106 g, 63%): $^1$H NMR (700 MHz, $D_2O$) δ 1.47 (s, 9H), 2.17-2.28 (m, 2H), 3.02 (t, J=7.3 Hz, 2H), 3.20-3.39 (m, 2H), 2.65-3.91 (m, 6H), 4.23 (br s, 2H); $^{13}$C NMR (175 MHz, $D_2O$) δ 20.3, 28.5, 41.5, 48.7, 52.5, 56.4, 83.8, 156.5; ESI-MS obsd 309.1474, calcd 309.1479 [$(M+H)^+$, M=$C_{12}H_{24}N_2O_5S$].

3-(4-(tert-Butoxycarbonyl)-1-(3-hydroxypropyl)piperazin-1-ium-1-yl)propane-1-sulfonate (37). 3-Bromopropanol (2.17 mL, 24 mmol) was added to a mixture of 36 (1.234 g, 4.00 mmol), $NaHCO_3$ (2.688 g, 32.0 mmol), KI (132.8 mg, 0.80 mmol) in $H_2O$ (1.09 mL) at room temperature. The reaction mixture was heated to 80° C. for 15 h, allowed to cool to room temperature, and washed with $Et_2O$ (20 mL). The residue was suspended in $CH_2Cl_2$/MeOH (4:1, 25 mL) and filtered. The filtrate was concentrated and chromatographed [silica, $CH_2Cl_2$/MeOH (4:6)] to afford a white solid (1.011 g, 69%): $^1$H NMR (700 MHz, $CD_3OD$) δ 1.48 (s, 9H), 1.95-2.03 (m, 2H), 2.14-2.24 (m, 2H), 2.90 (t, J=6.6 Hz, 2H), 3.46-3.60 (m, 6H), 3.64-3.72 (m, 4H), 3.81 (br s, 4H); $^{13}$C NMR (175 MHz, $CD_3OD$) δ 18.7, 25.5, 28.5, 37.8, 39.0, 48.4, 57.4, 57.7, 59.3, 82.4, 155.5, ESI-MS obsd 367.1896, calcd 367.1897 [$(M+H)^+$, M=$C_{15}H_{30}N_2O_6S$].

3-(1-(3-Hydroxypropyl)piperazin-1-ium-1-yl)propane-1-sulfonate trifluoroacetic acid salt (38). A sample of 37 (980.2 mg, 2.67 mmol) was dissolved in trifluoroacetic acid (1.78 mL) at room temperature. After 2 h, the reaction mixture was concentrated under reduced pressure. The residue was triturated with EtOH/$Et_2O$ to afford a pale yellow solid (985.4 mg, 97%): $^1$H NMR (700 MHz, $CD_3OD$) δ 0.75-0.85 (m, 2H), 0.96-1.07 (m, 2H), 1.75 (t, J=6.5 Hz, 2H), 2.40-2.73 (m, 14H); $^{13}$C NMR (175 MHz, $CD_3OD$) δ 18.9, 25.6, 38.8, 48.2, 58.3 (br s), 58.8 (br s), 59.1, 163.1 (q, J=34.5 Hz), ESI-MS obsd 267.1371, calcd 267.1373 [$(M-CF_3CO_2H+H)^+$, M=$C_{12}H_{23}F_3N_2O_6S$].

4,6-Dibromo-5-[1-hydroxy-3,6,9-trioxanon-9-yl]-1H-indol-3-yl 2,3,4,6-tetra-O-acetyl-β-D-glucopyranoside (39). A suspension of 32 (811.4 mg, 1.00 mmol) and $NaHCO_3$ (8.4 mg, 0.0.10 mmol) in MeOH (5.00 mL) was stirred for 3.5 h at room temperature. The reaction mixture was concentrated under reduced pressure. The residue was suspended in ethyl acetate. The suspension was passed through silica (ethyl acetate as an eluent). The eluent was concentrated under reduced pressure to afford a white solid (650.1 mg, 84%): $^1$H NMR (700 MHz, $CDCl_3$) δ 2.04 (s, 3H), 2.05 (s, 3H), 2.096 (s, 3H), 2.103 (s, 3H), 2.50 (br s, 1H), 3.62-3.68 (m, 2H), 3.71-3.78 (m, 4H), 3.78-3.84 (m, 3H), 3.94-4.00 (m, 2H), 4.13-4.20 (m, 2H), 4.24 (dd, J=4.8, 12.3 Hz, 1H), 4.27 (dd, J=2.8, 12.3 Hz, 1H), 4.97 (d, J=7.8 Hz, 1H), 5.19 (dd, J=9.5, 9.6 Hz, 1H), 5.29 (dd, J=9.3, 9.5 Hz, 1H), 5.37 (dd, J=7.8, 9.6 Hz, 1H), 7.07 (d, J=2.7 Hz, 1H), 7.45 (s, 1H), 7.94 (br s, 1H); $^{13}$C NMR (175 MHz, $CDCl_3$) δ 20.6, 20.7, 20.8, 21.1, 61.7, 61.9, 68.4, 70.2, 70.4, 70.7, 71.0, 71.9, 72.4, 72.5, 72.9, 101.0, 106.6, 112.0, 114.5, 115.2, 118.7, 131.3, 136.7, 145.9, 169.5, 169.6, 170.3, 170.7; ESI-MS obsd 768.0494, calcd 768.0497 [$(M+H)^+$, M=$C_{28}H_{35}Br_2NO_{14}$].

4-({1-[(1R,8S,9s)-Bicyclo[6.1.0]non-4-yn-9-yl]-3-oxo-2,7,10-trioxa-4-azadodecan-12-yl)amino}-6-[14-(3-hydroxypropyl)-4-(3-sulfopropyl)piperazin-1-yl])-2-{10-[1-acetyl-3-(2,3,4,6-tetra-O-acetyl-β-D-glucopyranosyloxy)-4,6-dibromo-1H-indol-5-yl]-1,4,7,10-tetraoxadec-1-yl}-1,3,5-triazine (40). Cyanuric chloride (20.3 mg, 0.11 mmol) was added to a mixture of 39 (76.9 mg, 0.10 mmol), 1,10-phenanthroline (36.0 mg, 0.20 mmol), and powdered molecular sieves 4 Å (50.0 mg) in $CH_2Cl_2$ (0.50 mL) at room temperature. After 16 h, 38 (49.4 mg, 0.13 mmol) in DMF (0.50 mL) and $^i$Pr$_2$EtN (70 μL, 0.40 mmol) were added. After 3 h, 14 (35.7 mg, 0.11 mmol) in $CH_2Cl_2$ (300 μL) and $^i$Pr$_2$EtN (35 μL, 0.20 mmol) were added. After 4 h, $^i$Pr$_2$EtN (35 μL, 0.20 mmol) was added. After 15 h, the reaction mixture was diluted with $CH_2Cl_2$ (3 mL) and filtered. The filtrate was washed with aqueous citric acid (10%, 3 mL) and brine (3 mL), dried ($Na_2SO_4$), and filtered. The filtrate was concentrated under reduced pressure. Column chromatography [diol-functionalized silica (ethyl acetate/MeOH=19:1 to $CH_2Cl_2$/MeOH=5:1) followed by silica ($CH_2Cl_2$/MeOH=5:1)] afforded a white solid (72.5 mg, 51%): $^1$H NMR (700 MHz, $CDCl_3$, mixture of rotamers) δ 0.91 (m, 2H), 1.26-1.38 (m, 1H), 1.54 (br s, 2H), 1.80-2.00 (m, 2H), 2.01 (s, 3H), 2.04 (s, 3H), 2.07 (s, 3H), 2.08 (s, 3H), 2.11-2.33 (m, 9H), 2.90 (br s, 2H), 3.15-4.47 (m, 42H), 4.75 (br s, 1H), 4.92 (s, 1H), 5.16 (t, J=9.1 Hz, 1H), 5.21-5.36 (m, 2H), 5.43 (s, 0.5H), 5.53 (s, 0.5H), 5.81 (br s, 0.5H), 6.05 (br s, 0.5H), 7.13 (s, 1H), 7.62 (s, 1H), 10.3 (s, 1H); $^{13}$C NMR (175 MHz, $CDCl_3$, mixture of rotamers) δ 17.8, 17.9, 20.1, 20.7, 20.9, 21.1, 21.5, 24.6, 29.1, 36.8, 40.5, 40.7, 40.8, 41.5, 47.4, 53.5, 56.4, 57.0, 58.3, 61.9, 62.7, 66.0, 66.1, 68.4, 69.3, 69.4, 69.7, 69.8, 70.1, 70.20, 70.23, 70.7, 70.8, 71.1, 71.9, 72.5, 73.0, 98.9, 101.1, 106.2, 111.6, 114.7, 115.7, 118.3, 131.5, 136.5, 145.6, 156.9, 165.6, 165.8, 166.7, 167.2, 169.5, 169.6, 170.2, 170.4, 170.8; ESI-MS obsd 717.1884, calcd 717.1888 [$(M+2H)^{2+}$, M=$C_{58}H_{82}Br_2N_8O_{22}S$].

4-({1-[(1R,8S,9s)-Bicyclo[6.1.0]non-4-yn-9-yl]-3-oxo-2,7,10-trioxa-4-azadodecan-12-yl)amino}-6-[4-(3-hydroxypropyl)-4-(3-sulfopropyl)piperazin-1-yl])-2-{10-[β-D-glucopyranosyloxy)-4,6-dibromo-1H-indol-5-yl]-1,4,7,10-tetraoxadec-1-yl}-1,3,5-triazine (41). $K_2CO_3$ (0.3 mg, 2 μmol) was added to a solution of 40 in MeOH/$CH_2Cl_2$ (25:6, 310 μL) at room temperature. After 2 h, the reaction mixture was passed through diol-functionalized silica [$CH_2Cl_2$/MeOH (2:1) as an eluent]. The eluent was concentrated under reduced pressure to afford a white solid (12.5 mg, 98%): $^1$H NMR (700 MHz, $CD_3OD$, mixture of rotamers) δ 0.85-0.97 (m, 2H), 1.28-1.41 (m, 1H), 1.50-1.63 (m, 2H), 1.88-1.99 (m, 2H), 2.07-2.29 (m, 8H), 2.79-2.91 (m, 2H), 3.24-3.33 (m, 2H), 3.37-4.25 (m, 44H), 4.42-4.61 (m, 2H), 4.78 (d, J=8.3 Hz, 1H), 7.27 (d, J=6.8 Hz, 1H), 7.53 (s, 1H); $^{13}$C NMR (175 MHz, $CD_3OD$, mixture of rotamers) δ 18.7, 19.0, 21.4, 21.9, 22.0, 25.5, 30.2, 37.9, 38.0, 41.5, 41.7, 48.3, 49.5, 54.8, 55.1, 57.6, 57.7, 59.3, 59.46, 59.52, 62.56, 62.62, 63.7, 67.2, 67.3, 70.6, 70.7, 71.0, 71.1, 71.3, 71.4, 71.50, 71.55, 71.85, 71.88, 73.8, 75.3, 78.2, 78.30, 78.32, 99.6, 105.1, 105.2, 107.7, 112.4, 116.2, 132.9, 139.0, 146.8, 159.2, 166.9, 167.2, 168.2, 168.6, 171.8, 172.2; ESI-MS obsd 633.1670, calcd 633.1677 [$(M+2H)^{2+}$, $M=C_{50}H_{74}Br_2N_8O_{18}S$].

4,4',6,6'-Tetrabromo-5,5'-bis[1-hydroxy-3,6,9-trioxanon-9-yl]indigo (43). Samples of 33 (4.98 mg, 8.28 μmol) in DMF (414 μL), β-glucosidase in water (10 units/mL, 828 μL), and acetate buffer (pH 5.0, 7038 μL) were mixed at room temperature. The reaction mixture was incubated at 37° C. under air for 22 h and then allowed to cool to room temperature. The reaction mixture was diluted with $H_2O$ (20 mL) and extracted with $CH_2Cl_2$ (20 mL). The organic layer was washed with brine (10 mL), dried ($Na_2SO_4$), and filtered. The filtrate was concentrated under reduced pressure. Preparative thin layer chromatography [silica, 0.25 mm, $CHCl_3$/MeOH (12:1)] afforded an indigo-blue solid (2.4 mg, 66%): $^1$H NMR (700 MHz, $CDCl_3/CD_3OD$=9:1) δ 3.60-3.66 (m, 4H), 3.69-3.76 (m, 8H), 3.79-3.84 (m, 4H), 3.94-4.00 (m, 4H), 4.16-4.21 (m, 4H), 7.31 (s, 1H); $^{13}$C NMR (175 MHz, $CDCl_3/CD_3OD$=9:1) δ 61.6, 70.2, 70.4, 70.9, 72.78, 72.79, 115.3, 116.0, 118.1, 122.3, 127.4, 147.9, 149.6, 185.7; ESI-MS obsd 870.8692, calcd 870.8707 [$(M+H)^+$, $M=C_{28}H_{30}Br_4N_2O_{10}$]. To measure the molar absorption coefficient, the title compound (1.6 mg) was dissolved in $CHCl_3$/MeOH (2:1, 2.93 mL). Then an aliquot (64.0 μL) was withdrawn from this solution and concentrated under reduced pressure. The residue was dissolved in DMF/$H_2O$ (2:1, 1000 μL) to prepare a 40 μM solution. The absorption spectrum was recorded at room temperature: $\varepsilon_{631\ nm}=2.6\times10^4\ M^{-1}\ cm^{-1}$.

2,4-Bis{10-[1-acetyl-3-(2,3,4,6-tetra-O-acetyl-β-D-glucopyranosyloxy)-4,6-dibromo-1H-indol-5-yl]-1,4,7,10-tetraoxadec-1-yl]}-6-chloro-1,3,5-triazine (44). Pempidine (38.1 μL, 0.21 mmol) was added to a mixture of cyanuric chloride (11.1 mg, 0.060 mmol), 32 (102.6 mg, 0.13 mmol), and powdered molecular sieves 4 Å (12.0 mg) in 1,2-dichloroethane (120 μL) at room temperature. The reaction mixture was heated to 60° C. for 13 h, cooled to room temperature, and passed through a silica pad (ethyl acetate as an eluent). The eluent was concentrated under reduced pressure. Preparative thin layer chromatography [silica, 1.0 mm, 20×20 cm, hexanes/acetone (6:4)] afforded a white solid (55.7 mg, 53%): $^1$H NMR (700 MHz, $CDCl_3$) δ 2.04 (s, 6H), 2.07 (s, 6H), 2.091 (s, 6H), 2.093 (s, 6H), 2.60 (s, 6H), 3.70-3.73 (m, 4H), 3.73-3.82 (m, 4H), 3.83-3.94 (m, 6H), 3.94-3.97 (m, 4H), 4.13-4.23 (m, 6H), 4.38 (dd, J=1.5, 12.3 Hz, 2H), 4.55-4.62 (m, 4H), 5.05, (d, J=7.6 Hz, 2H), 5.17-5.23 (m, 2H), 5.30 (dd, J=9.3, 9.3 Hz, 2H), 5.34-5.41 (m, 2H), 7.25 (s, 2H), 8.68 (br s, 2H); $^{13}$C NMR (175 MHz, $CDCl_3$) δ 20.7, 20.9, 21.1, 23.8, 62.0, 68.4, 68.5, 68.9, 70.3, 70.9, 71.0, 72.6, 72.7, 100.3, 107.7, 112.2, 116.3, 120.3, 123.1, 131.0, 140.5, 149.8, 167.9, 169.4, 169.5, 170.3, 170.6, 172.5, 172.7; ESI-MS obsd 1730.0752, calcd 1730.0757 [$(M+H)^+$, $M=C_{63}H_{72}Br_4ClN_5O_{30}$].

2,4-Bis{10-[3-(2,3,4,6-tetra-O-acetyl-β-D-glucopyranosyloxy)-4,6-dibromo-1H-indol-5-yl]-1,4,7,10-tetraoxadec-1-yl]}-6-[4-(3-hydroxypropyl)-4-(3-sulfopropyl)piperazin-1-yl]-1,3,5-triazine (45). i-$Pr_2$EtN (19.2 μL, 0.11 mmol) was added to a solution of 44 (190.8 mg, 0.11 mmol) in $CH_2Cl_2$/MeOH (5:1, 0.84 mL) at room temperature. After 4 h, 38 (46.0 mg, 0.12 mmol) in MeOH (0.70 mL) and 2,6-lutidine (25.5 μL, 0.22 mmol) was added. After 4 h, the reaction mixture was quenched with acetic acid (12.6 μL, 0.22 mmol) and concentrated under reduced pressure. Column chromatography [silica, $CH_2Cl_2$/MeOH (7:1 to 5:1)] followed by trituration with $H_2O$ afforded a pale yellow solid (114.7 mg, 55%): $^1$H NMR (700 MHz, $CDCl_3$) δ 1.78 (br s, 2H), 1.96-2.16 (m, 26H), 2.88 (br s, 2H), 3.15 (br s, 2H), 3.23 (br s, 2H), 3.36 (br s, 2H), 3.54 (br s, 4H), 3.68-3.99 (m, 22H), 4.04 (br s, 4H), 4.16-4.52 (m, 9H), 4.89 (d, J=7.3 Hz, 2H), 5.16 (dd, J=9.4, 9.4 Hz, 2H), 5.22-5.33 (m, 4H), 7.13 (s, 2H), 7.59 (s, 1H), 7.59 (s, 1H), 9.96 (s, 1H), 9.99 (s, 1H); $^{13}$C NMR (175 MHz, $CDCl_3$) δ 17.9, 20.7, 20.9, 21.2, 24.6, 37.0, 47.4, 56.4, 56.8, 58.0, 58.2, 61.9, 67.0, 68.4, 69.2, 70.2, 70.6, 70.7, 71.1, 71.8, 72.4, 73.0, 101.2, 0106.2, 111.6, 114.9, 115.7, 118.3, 131.4, 136.5, 145.5, 166.4, 169.6, 169.6, 170.2, 170.8, 171.6; ESI-MS obsd 1876.2076, calcd 1876.2079 [$(M+H)^+$, $M=C_{69}H_{89}Br_4N_7O_{32}S$].

2,4-Bis{10-[3-β-D-glucopyranosyloxy)-4,6-dibromo-1H-indol-5-yl]-1,4,7,10-tetraoxadec-1-yl]}-6-[4-(3-hydroxypropyl)-4-(3-sulfopropyl)piperazin-1-yl]-1,3,5-triazine (46). $K_2CO_3$ (0.6 mg, 4 μmol) was added to a solution of 45 (39.3 mg, 0.020 mmol) in MeOH/$CH_2Cl_2$ (5:1, 600 μL) at room temperature. After 15 min, $H_2O$ (50 μL) was added. After 2 h, $H_2O$ (150 μL) and $K_2CO_3$ (2.2 mg, 16 μmol) were added. After 1 h, reverse phase silica (320 mg) was added. The mixture was dried under reduced pressure. The residue was purified by column chromatography [reverse phase silica, $H_2O$ to MeOH/$H_2O$ (4:1)] afforded a pale yellow solid (23.9 mg, 77%): $^1$H NMR [700 MHz, $(CD_3)_2SO$] δ 1.78-1.87 (m, 2H), 1.93-2.02 (m, 2H), 2.47-2.56 (m, 2H), 3.15 (t, J=9.1 Hz, 2H), 3.22-3.36 (m, 6H), 3.38-3.55 (m, 11H), 3.55-3.69 (m, 11H), 3.69-3.78 (m, 6H), 3.78-3.86 (m, 4H), 3.93-4.05 (m, 6H), 4.05-4.15 (m, 2H), 4.36-4.45 (m, 4H), 4.56-4.64 (m, 2H), 4.65 (d, J=7.6 Hz, 2H), 4.78 (br s, 1H), 4.95-5.14 (m, 6H), 7.23 (s, 2H), 7.55 (s, 2H), 10.92 (s, 2H); $^{13}$C NMR [175 MHz, $(CD_3)_2SO$] δ 17.7, 24.1, 36.8, 47.3, 56.9, 57.6, 60.9, 66.4, 68.4, 69.4, 69.8, 69.9, 70.0, 72.4, 73.5, 76.8, 77.2, 99.5, 103.3, 106.1, 110.4, 113.3, 114.9, 117.9, 131.0, 137.4, 144.8, 166.4, 171.5; ESI-MS obsd 770.5642, calcd 770.5653 [$(M+2H)^{2+}$, $M=C_{53}H_{73}Br_4N_7O_{24}S$].

Procedure for ε determination for unsubstituted indigo. Indigo (13.1 mg, 50 μmol) was dissolved in DMF (200 mL) to prepare a 250 μM solution. An aliquot (320 μL) was withdrawn from the solution and diluted with DMF/$H_2O$ (1680:1000, 2680 μL) to prepare a 40.0 μM solution. The absorption spectrum was recorded at room temperature. The averages of two runs were calculated.

Procedure for ε determination for 43. Indigo 43 (1.6 mg, 1.8 μmol) was dissolved in $CHCl_3$/MeOH (2:1, 2.93 mL). An aliquot (64.0 μL) was withdrawn from the solution and concentrated under reduced pressure. The residue was dissolved in DMF/$H_2O$ (2:1, 1000 μL) to prepare a 40 μM solution. The absorption spectrum was recorded at room temperature. $\varepsilon_{631\ nm}=2.6\times10^4 M^{-1}cm^{-1}$.

Procedures for Indigogenic Reactions in Table 1

General methods. β-Glucosidase from almonds (lyophilized powder, ≥2 units/mg solid) and peroxidase from horseradish were purchased from Sigma-Aldrich. β-Glucosidase from *Agrobacterium* sp. (recombinant, suspension in 3.2 M $(NH_4)_2SO_4$) was purchased from Megazyme; the concentration in solution was determined by absorption spectroscopy with $E^{0.1\%}=2.20\ cm^{-1}$ at 280 nm.[37] Tritosomes were purchased from XenoTech. Rat liver homogenate was purchased from MP Biomedicals.

Reactions with β-glucosidase from almonds. An indoxyl compound in DMF (5 μL, 20 mM) and β-glucosidase from almonds in $H_2O$ (10 μL, 10 units/mL) were mixed with acetate buffer (85 μL, 50 mM, pH 5.0). The reaction mixture was incubated at 37° C. for 16-19 h and then allowed to cool to room temperature. DMF (300 μL for the reactions of 15, 16, 1, 19, 22, and 25; or 900 μL for the reactions of 42, 20, 21, 23, 24, 26, 27, 30, and 31, respectively) was added to dissolve any indigoid precipitate. The resulting solution was analyzed by absorption spectroscopy.

Reactions with β-glucosidase from *Agrobacterium*. An indoxyl compound in DMF (2 μL, 5 mM) and β-glucosidase from *Agrobacterium* in 10 mM phosphate buffer [2 μL, 10 μM, pH 7.0, containing 50 mM NaCl and 0.6 M $(NH_4)_2SO_4$] were mixed with 50 mM phosphate buffer (96 μL, pH 7.0). The reaction mixture was incubated at 37° C. for 2 h and then centrifuged for 3 min. Any precipitate was separated from the supernatant and dissolved in DMF (200 μL). The resulting solution was analyzed by absorption spectroscopy. The experiment was repeated three times.

Reactions in rat liver homogenate. An indoxyl compound in DMF (5 μL, 20 mM) was mixed with rat liver homogenate (95 μL). The reaction mixture was incubated at 37° C. for 24 h. After allowing to cool to room temperature, the reaction mixture was diluted with DMF (900 μL). The mixture was heated at 70° C. for 2 min and then centrifuged for 2 min. The supernatant was separated from any precipitate. This extraction procedure was repeated two or three times with DMF (100-500 μL). The combined supernatant (1500-1800 μL) was analyzed by absorption spectroscopy.

Reaction of 33 with β-glucosidase from *Agrobacterium* in rat liver homogenate. A DMF solution of 33 (2 μL, 5 mM) and β-glucosidase from *Agrobacterium* in 10 mM phosphate buffer [2 μL, 10 μM, pH 7.0, containing 50 mM NaCl and 0.6 M $(NH_4)_2SO_4$] were mixed with rat liver homogenate (96 μL). The reaction mixture was incubated at 37° C. for 4 h and then centrifuged for 3 min. Any precipitate was separated from the supernatant and then suspended in DMF (200 μL). The suspension was centrifuged for 3 min. The supernatant was analyzed by absorption spectroscopy.

REFERENCES (1) Y.-H. Yang, H. Aloysius, D. Inoyama, Y. Chen and L.-Q. Hu, *Acta Pharm. Sin. B,* 2011, 1, 143-159. "Enzyme-Mediated Hydrolytic Activation of Prodrugs."

(2) R. de la Rica, D. Aili and M. M. Stevens, *Adv. Drug Deliv. Rev.,* 2012, 64, 967-978. "Enzyme-Responsive Nanoparticles for Drug Release and Diagnostics."

(3) Q. Hu, P. S. Katti and Z. Gu, *Nanoscale,* 2014, 6, 12273-12286. "Enzyme-Responsive Nanomaterials for Controlled Drug Delivery."

(4) J. Mu, J. Lin, P. Huang and X. Chen, *Chem. Soc. Rev.,* 2018, 47, 5554-5573. "Development of Endogenous Enzyme-Responsive Nanomaterials for Theranostics."

(5) C. S. McKay and M. G. Finn, *Chem. Biol.,* 2014, 21, 1075-1101. "Click Chemistry in Complex Mixtures: Bioorthogonal Bioconjugation."

(6) G. Liang, H. Ren and J. Rao, *Nat. Chem.,* 2010, 2, 54-60. "A Biocompatible Condensation Reaction for Controlled Assembly of Nanostructures in Living Cells."

(7) M. Zhang and G. Liang, *Sci. China Chem.,* 2018, 61, 1088-1098. "Applications of CBT-Cys Click Reaction: Past, Present, and Future."

(8) Y. Yuan, J. Zhang, M. Wang, B. Mei, Y. Guan and G. Liang, *Anal. Chem.,* 2013, 85, 1280-1284. "Detection of Glutathione in Vitro and in Cells by the Controlled Self-Assembly of Nanorings."

(9) X. Ai, C. J. H. Ho, J. Aw, A. B. E. Attia, J. Mu, Y. Wang, X. Wang, Y. Wang, X. Liu, H. Chen, M. Gao, X. Chen, E. K. L. Yeow, G. Liu, M. Olivo and B. Xing, *Nat. Commun.,* 2016, 7, 10432. "In Vivo Covalent Cross-Linking of Photon-Converted Rare-Earth Nanostructures for Tumour Localization and Theranostics."

(10) P. Thirumurugan, D. Matosiuk and K. Jozwiak, *Chem. Rev.,* 2013, 113, 4905-4979. "Click Chemistry for Drug Development and Diverse Chemical-Biology Applications."

(11) G. A. Russell and G. Kaupp, *J. Am. Chem. Soc.,* 1969, 91, 3851-3859. "Oxidation of Carbanions. N. Oxidation of Indoxyl to Indigo in Basic Solution."

(12) E. S. B. Ferreira, A. N. Hulme, H. McNab and A. Quye, *Chem. Soc. Rev.,* 2004, 33, 329-336. "The Natural Constituents of Historical Textile Dyes."

(13) N. R. Krishnaswamy and C. N. Sundaresan, *Reson.,* 2012, 17, 1022-1033. "Fascinating Organic Molecules from Nature. 2. The Blue of Blue Jeans and Royal Purple."

(14) J. A. Kiernan, *Biotech. Histochem.,* 2007, 82, 73-103. "Indigogenic Substrates for Detection and Localization of Enzymes."

(15) S. Trifonov, Y. Yamashita, M. Kase, M. Maruyama and T. Sugimoto, *Anat. Sci. Int.,* 2016, 91, 56-67. "Overview and Assessment of the Histochemical Methods and Reagents for the Detection of β-Galactosidase Activity in Transgenic Animals."

(16) S. Cotson and S. J. Holt, *Proc. R. Soc. Lond. B,* 1958, 148, 506-519. "Studies in Enzyme Cytochemistry. N. Kinetics of Aerial Oxidation of Indoxyl and Some of Its Halogen Derivatives."

(17) C. J. Cooksey, *Molecules,* 2001, 6, 736-769. "Tynan Purple: 6,6'-Dibromoindigo and Related Compounds."

(18) S. Rose, U.S. Pat. No. 5,816,259, 1998.

(19) S. Rose, U.S. Pat. No. 6,080,383, 2000.

(20) S. Rose, U.S. Pat. No. 6,468,503 B2, 2002.

(21) G. L. Mayers, D. Lee and H.-L. Chin, U.S. Pat. No. 7,615,221 B2, 2009.

(22) G. L. Mayers, S. Rose and L. Rose, U.S. Pat. No. 7,807,136 B2, 2010.

(23) G. L. Mayers, S. Rose and D. Rose, US 2011/0142756 A1, 2011.

(24) G. L. Mayers, *Drug. Dev. Res.,* 2006, 67, 94-106. "Targeted Molecular Brachytherapy."

(25) S. Rose, *J. Theor. Biol.,* 1998, 195, 111-128. "A Proposal for a New Direction to Treat Cancer."

(26) G. Blotny, *Tetrahedron,* 2006, 62, 9507-9522. "Recent Applications of 2,4,6-Trichloro-1,3,5-Triazine and Its Derivatives in Organic Synthesis."

(27) H. Tanaka, A. Wada, M. Shiro, K. Hioki, D. Morisaki and M. Kunishima, *Heterocycles,* 2009, 79, 609-616. "Synthesis of Aza-Bridged Calix(4-Methoxy)Triazines toward Flattened π-Conjugated Macrocycles."

(28) J. Dommerholt, S. Schmidt, R. Temming, L. J. A. Hendriks, F. P. J. T. Rutjes, J. C. M. van Hest, D. J. Lefeber, P. Friedl and F. L. van Delft, *Angew. Chem. Int. Ed.*, 2010, 49, 9422-9425. "Readily Accessible Bicyclononynes for Bioorthogonal Labeling and Three-Dimensional Imaging of Living Cells."

(29) D. J. Cowley, E. O'Kane and R. S. J. Todd, *J. Chem. Soc. Perkin Trans.* 2, 1991, 1495-1500. "Triazinylaniline Derivatives as Fluorescence Probes. Part 1. Absorption and Fluorescence in Organic Solvents and in Aqueous Media in Relation to Twisted Intramolecular Charge-Transfer State Formation, Hydrogen Bonding, and Protic Equilibria."

(30) V. S. Padalkar, V. S. Patil, R. D. Telore and N. Sekar, *Heterocycl. Commun.*, 2012, 18, 127-134. "Synthesis of Novel Fluorescent 1,3,5-Trisubstituted Triazine Derivatives and Photophysical Property Evaluation of Fluorophores and Their BSA Conjugates."

(31) R. Gotor, P. Ashokkumar, M. Hecht, K. Keil and K. Rurack, *Anal. Chem.*, 2017, 89, 8437-8444. "Optical pH Sensor Covering the Range from PH 0-14 Compatible with Mobile-Device Readout and Based on a Set of Rationally Designed Indicator Dyes."

(32) S.-L. Niu, G. Ulrich, P. Retailleau, J. Harrowfield and R. Ziessel, *Tetrahedron Lett.*, 2009, 50, 3840-3844. "New Insights into the Solubilization of Bodipy Dyes."

(33) A. Natrajan, D. Sharpe and D. Wen, *Org. Biomol. Chem.*, 2012, 10, 1883-1895. "Zwitterionic Reagents for Labeling, Cross-Linking and Improving the Performance of Chemiluminescent Immunoassays."

(34) S. J. Holt and P. W. Sadler, *Proc. R. Soc. Lond. B*, 1958, 148, 495-505. "Studies in Enzyme Cytochemistry. III. Relationships between Solubility, Molecular Association and Structure in Indigoid Dyes."

(35) E. M. Bowers, L. O. Ragland and L. D. Byers, *Biochim. Biophys. Acta*, 2007, 1774, 1500-1507. "Salt Effects on β-Glucosidase: pH-Profile Narrowing."

(36) M. P. Dale, H. E. Ensley, K. Kern, K. A. R. Sastry and L. D. Byers, *Biochemistry*, 1985, 24, 3530-3539. "Reversible Inhibitors of β-Glucosidase."

(37) J. B. Kempton and S. G. Withers, *Biochemistry*, 1992, 31, 9961-9969. "Mechanism of *Agrobacterium* β-Glucosidase: Kinetic Studies."

(38) D. J. Rabiger, M. Y. Chang, S. Matsukawa and K. C. Tsou, *J. Heterocycl. Chem.*, 1970, 7, 307-311. "Synthesis of 5-Iodo- and 5-Nitro-3-Indolyl Phosphates as Cytochemical Substrates for Acid Phosphatase."

(39) C. Gröst and T. Berg, *Org. Biomol. Chem.*, 2015, 13, 3866-3870. "PYRROC: The First Functionalized Cycloalkyne that Facilitates Isomer-Free Generation of Organic Molecules by SPAAC."

(40) S. Fräbel, B. Wagner, M. Krischke, V. Schmidts, C. M. Thiele, A. Staniek and H. Warzecha, *Metab. Eng.*, 2018, 46, 20-27. "Engineering of New-to-Nature Halogenated Indigo Precursors in Plants."

Example 2

Treatment of an indoxyl β-glucoside with β-glucosidase affords the free indoxyl in situ, which dimerizes to the corresponding indigo. An indoxyl has been examined that bears 4,6-dibromo groups for efficient indigo formation and a linker at the 5-position for further derivatization. Although only β-glucosidase was employed, other enzymes can trigger the cross-linking if the indoxyl bears an appropriate ligand instead of the β-glucoside. We herein describe indoxyl β-glucuronides as the chromogenic cross-linking agents triggered by the enzyme β-glucuronidase. β-Glucuronide was selected as the enzymatically cleavable moiety for the indoxyl for the following reasons: (1) β-glucuronide and β-glucoside are structurally (and thus synthetically) related, (2) 5-bromo-4-chloroindoxyl β-glucuronide has been successfully used for histochemistry,[Pear,Kie] (3) the carboxy group in β-glucuronide is expected to afford higher solubility in aqueous solution compared to that of the β-glucoside, and (4) β-glucuronidase is an important target enzyme in cancer therapy.[Gra,Tra]

1. Conversion of an Indoxyl β-Glucoside to the Corresponding Indoxyl 11-Glucuronide.

Methyl α-glucoside or phenyl β-glucoside is known to be converted into the corresponding glucuronide by selective oxidation of the primary hydroxy group at the 6-position with 2,2,6,6-tetramethyl-1-piperidinyloxy free radical (TEMPO) and a co-oxidizing agent such as $PhI(OAc)_2$ or t-BuOCl.[Lu,Mel] Therefore, direct conversion of indoxyl β-glucosides into the corresponding indoxyl β-glucuronides was investigated. Oxidation of indoxyl β-glucosides with TEMPO/$PhI(OAc)_2$ in the presence of a free indole nitrogen or a free hydroxy group at the indole 5-position was unsuccessful (see the Appendix), which prompted conversion of 1 with use of protecting groups (Scheme 10). The acetyl group of the primary hydroxy group in 1 was selectively deprotected with $[t\text{-BuSnOH(Cl)}]_2$ in MeOH to afford 2 in 61% yield.[Ori] The phenolic hydroxy group in 2 was protected with t-butyldimethylsilyl (TBS) group to give 3 in 65% yield. Subsequently, the primary hydroxy group in 3 was oxidized with TEMPO/$PhI(OAc)_2$. After methylation of the resulting carboxylate and deprotection of the TBS group, protected indoxyl β-glucuronide 4 was obtained in 33% yield from 3. Introduction of (1R,8S,9s)-bicyclo[6.1.0]non-4-yn-9-yl (BCN) group for copper-free click chemistry via the Mitsunobu reaction followed by removal of the acetyl groups afforded 5 in 44% yield. As the BCN group did not survive under the oxidation conditions with TEMPO/PhI $(OAc)_2$ (see the Appendix), this group was introduced after the oxidation. Hydrolysis of methyl ester 5 gave BCN-indoxyl β-glucuronide sodium salt 6 in 86% yield. Although the conversion of 1 to 6 was achieved, the overall yield (~5%) was unsatisfactory.

Scheme 10. Synthesis of BCN-indoxyl β-glucuronide 6 form indoxyl β-glucoside 1.

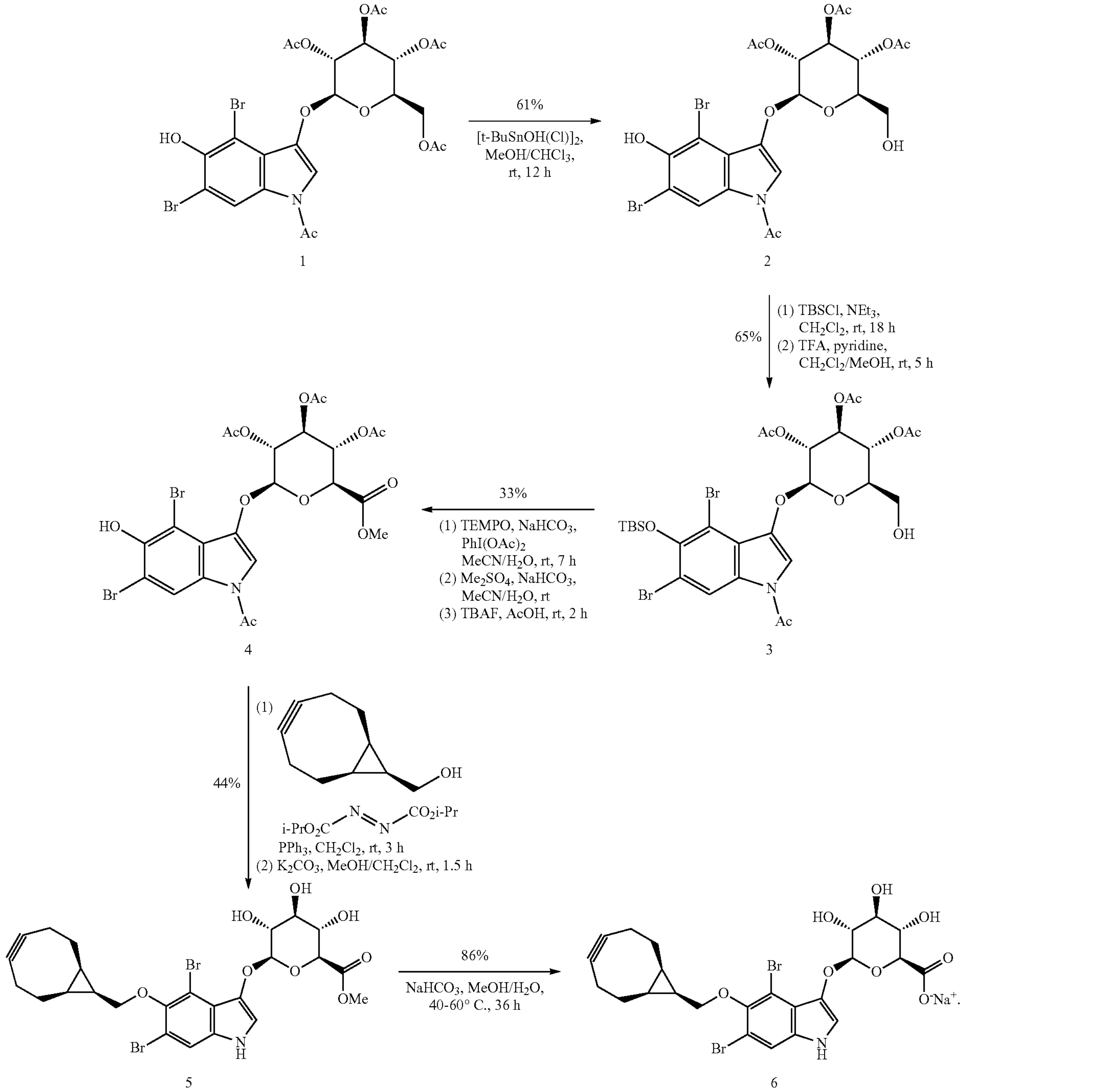

1, 2, 3, 4, 5, 6

2. Direct Synthesis of indoxyl β-glucuronides.

In an alternative route, a solution of 7 in toluene/nitromethane was treated with methyl acetobromo-α-D-glucuronate (8) in the presence of $HgBr_2$, HgO and molecular sieves 4 Å at 40° C. to give 9 in 52% yield (Scheme 11). Debenzylation of 9 was then carried out in tetrahydrofuran/$CH_2Cl_2$/ethanol containing Pd/C under an atmosphere of $H_2$ to give 10 following recrystallization in 75% yield. Even though the starting material 9 was the pure β-isomer, a small amount of α-10 (2-3% on the basis of $^1$H NMR spectroscopy) was obtained after deprotection. This epimer byproduct was readily removed by recrystallization of the mixture in hexanes/$CH_2Cl_2$. The solution of 10 (in $CH_2Cl_2$) was then treated with NBS (in $CH_2Cl_2$) at −78° C. to give 10 in 64% yield. Following the similar procedure as the previous synthetic route (Scheme 10), the BCN group was introduced via a Mitsunobu reaction to afford 11 in 69% yield. Removal of the acetyl groups and hydrolysis of the methyl ester were conducted (as for 6 in Scheme 10) to give the same final product 6. The overall yield of this route is around 11%, which is slightly better than that in Scheme 10.

Scheme 11. Alternative route to compound 6.

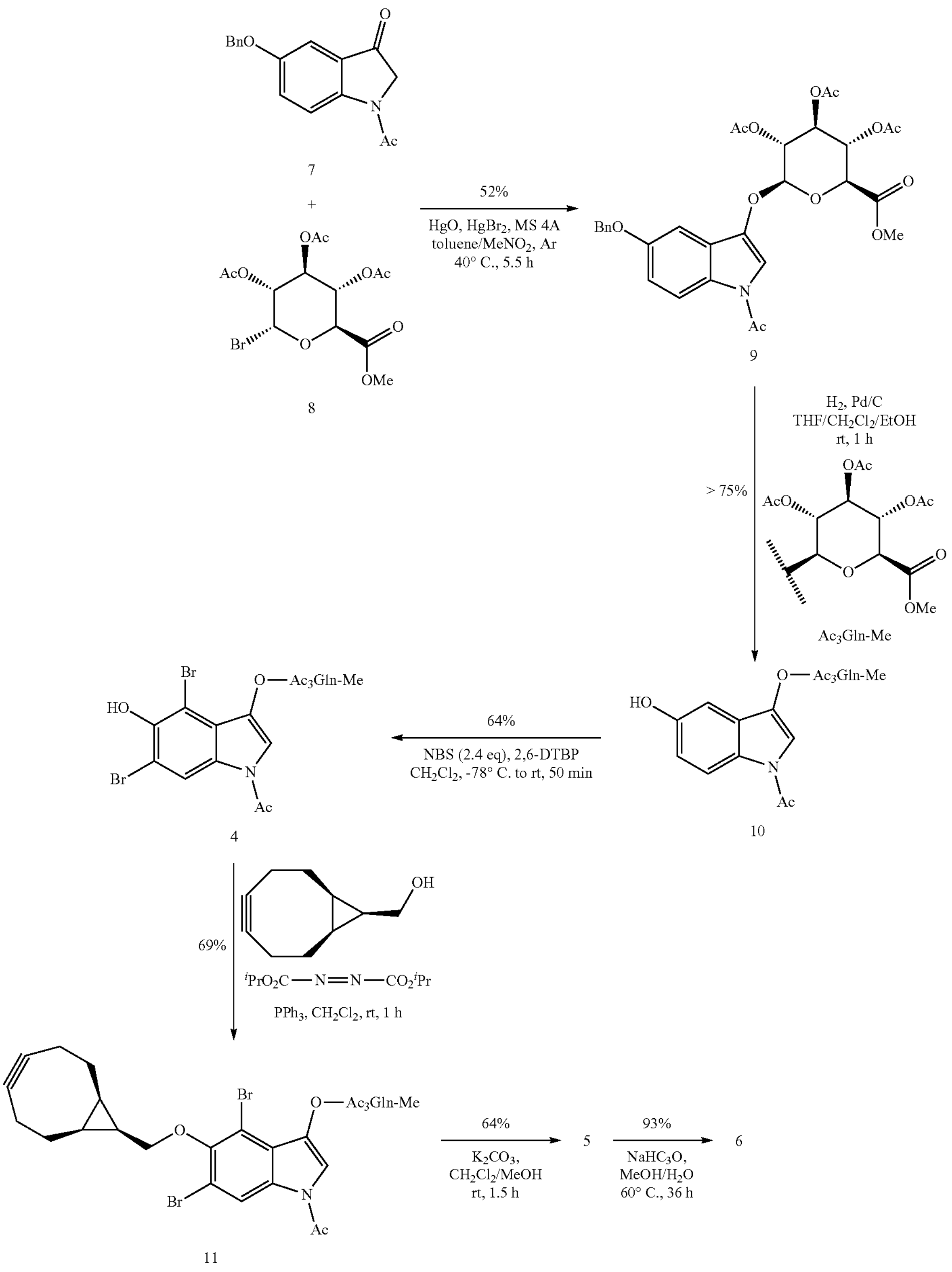

3. Introduction of PEG Tether Between Indoxyl and BCN Group.

A PEGylated chain was introduced with the aim to avoid steric hindrance for the enzymatic cleavage (Scheme 12). Compound 4 was treated with 2-(2-(2-hydroxyethoxy)ethoxy)ethyl 4-nitrobenzenesulfonate and N,N-diisopropylethylamine (DIPEA) to give the PEGylated indoxyl 12 in 79% yield. Following the same manner for the synthesis of 6, treatment of 12 to a two-step deprotection process afforded PEG-Ind-Gln (14).

Scheme 12. Synthesis of PEG-Ind-Gln (14).
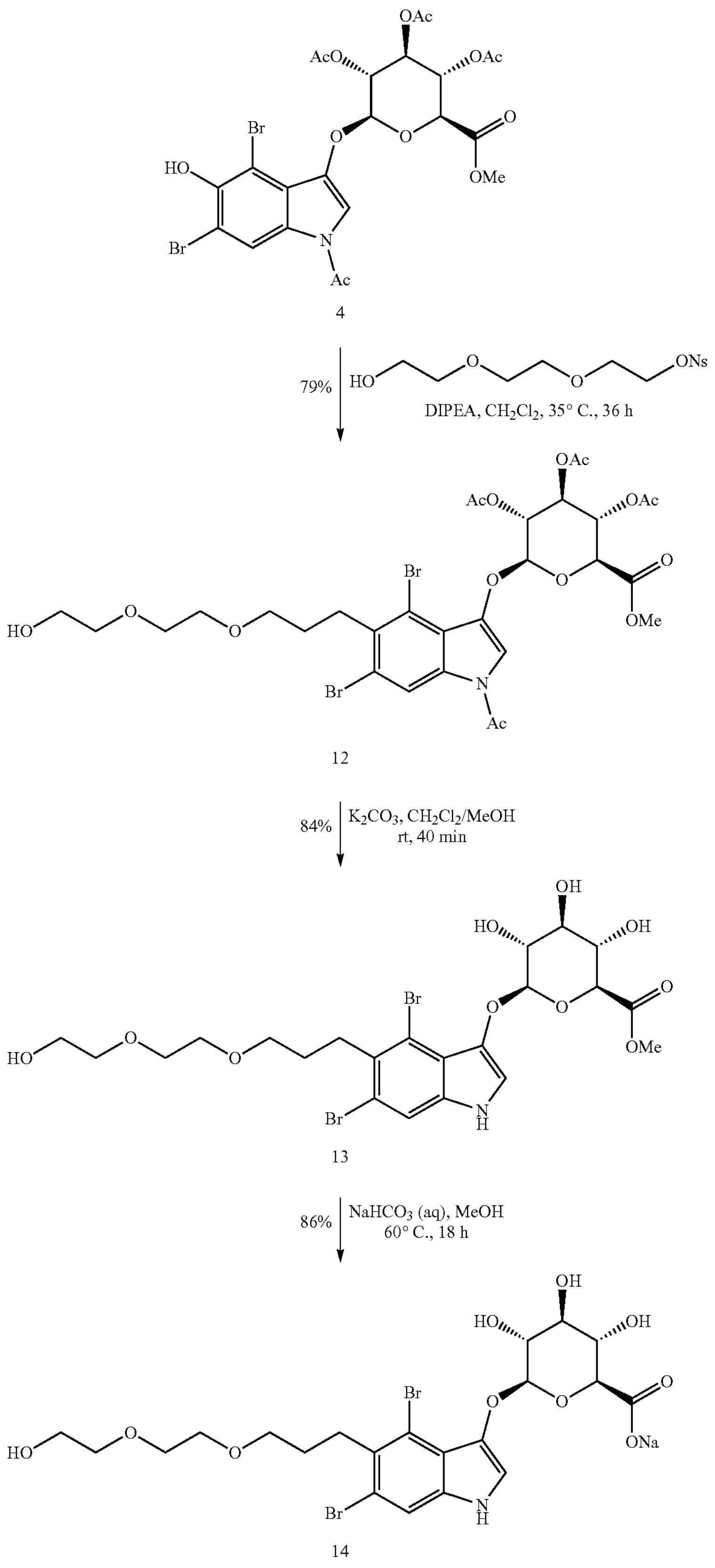

Compound 12 also was treated with 4-nitrophenyl carbonochloridate in the presence of pyridine to give the activated carbonate 15 in 97% yield (Scheme 13). Subsequent reaction with the commercially available building block 16 in the presence of DIPEA gave compound 17. A similar procedure of deprotection was then conducted to give the desired product BCN-PEG-Ind-Gln (19).

Scheme 13. Synthesis of BCN-PEG-Ind-Gln (19).

12

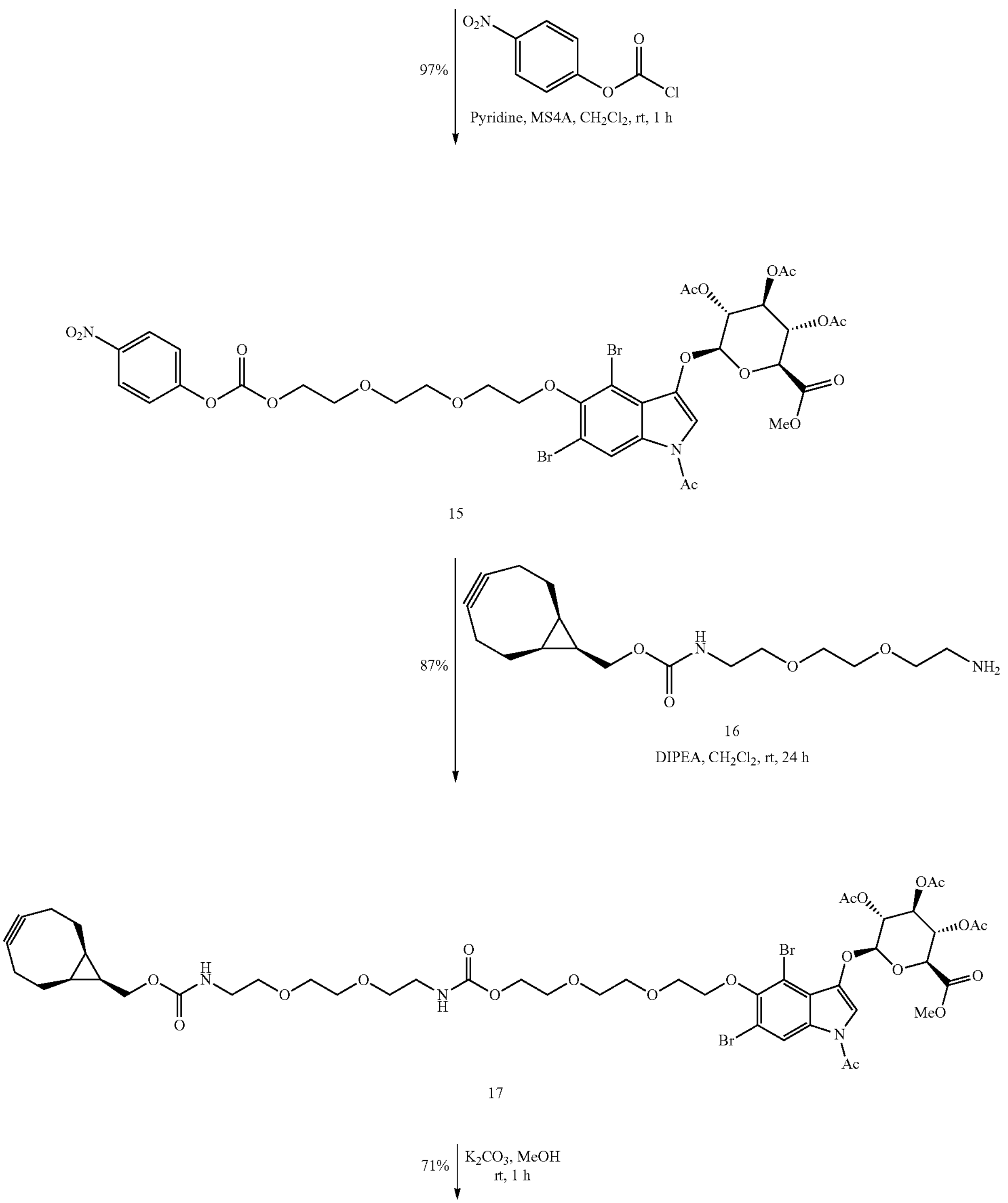

-continued

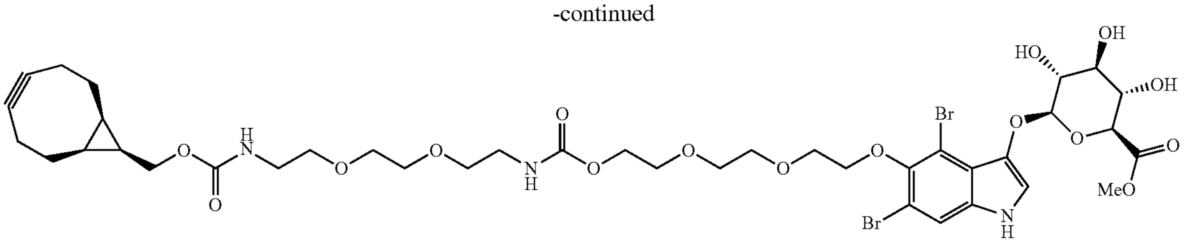

18

81%
NaHCO3 (aq), MeOH
60°C ., 18 h

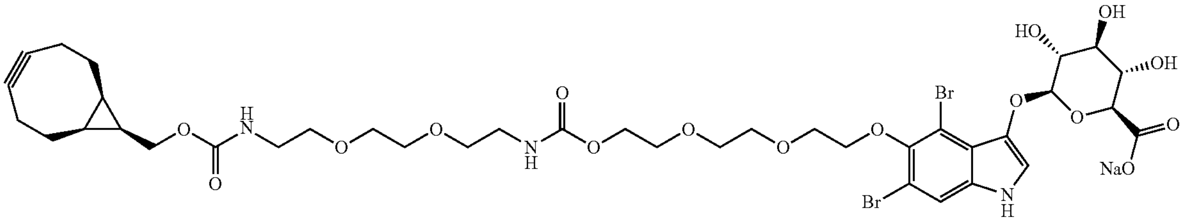

19

4. Installation of a Self-Immolative Spacer Between Indoxyl and Glucuronide.

Based on a well-established strategy in the design of many prodrugs, several potential structures were proposed as shown in Chart 1. We here proposed general synthetic routes (shown in Scheme 14), where solid lines represent reported reactions and dashed lines are unknown steps. A more specific route toward to the targets with a shorter spacer is shown in Scheme 15. Due to the deprotection step of the benzyl group, the amino group is accessible via the reductive condition.

Chart 1. Structure containing a self-immolative spacer.

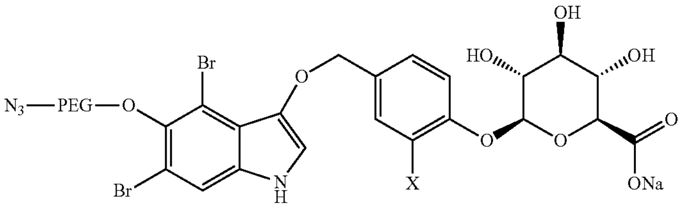

X = $NO_2$ or $NH_2$

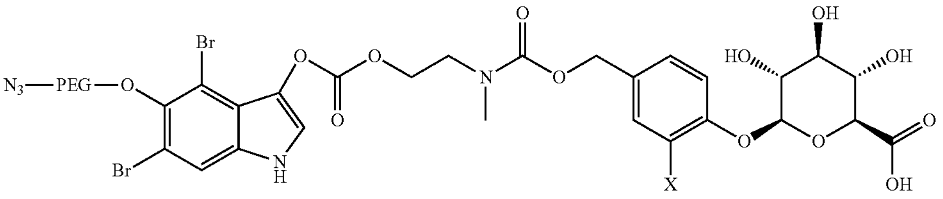

X = $NO_2$ or $NH_2$

Scheme 14. Synthetic route to designs with a self-immolative linker.
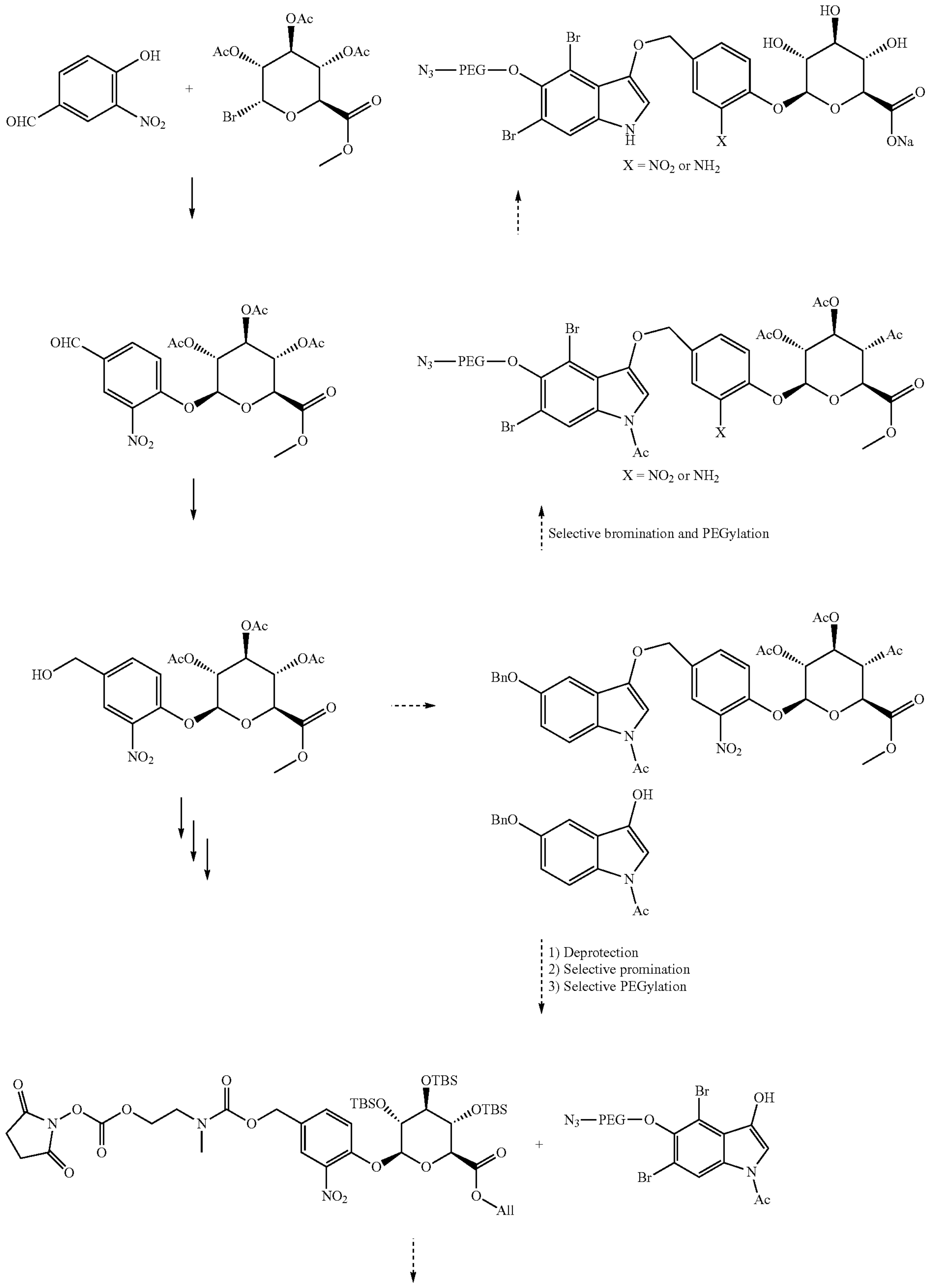

-continued
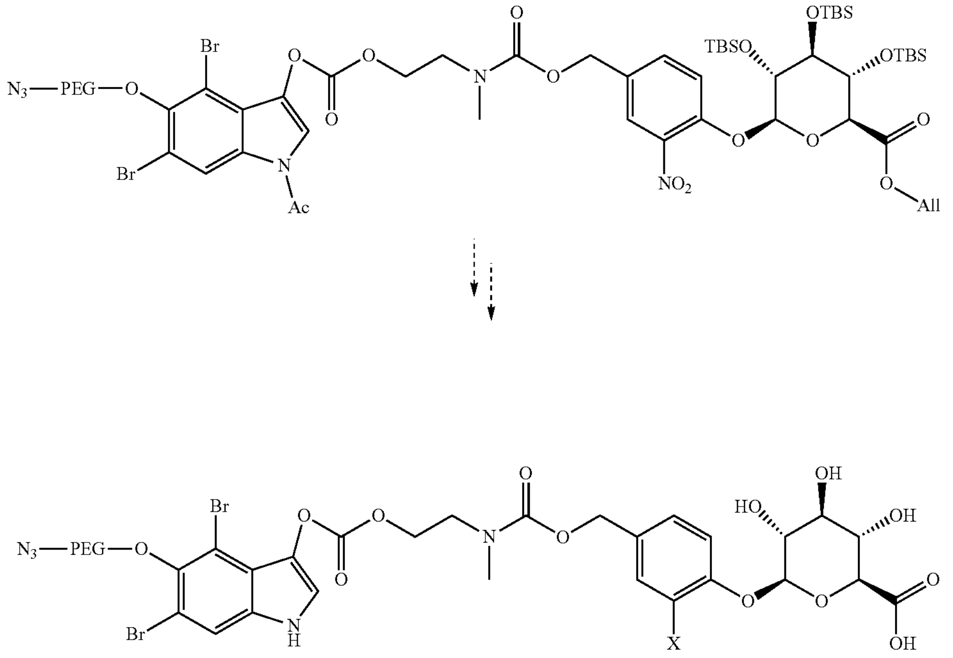
X = $NO_2$ or $NH_2$
Scheme 15. Synthetic route to desings with a self-immolative linker.
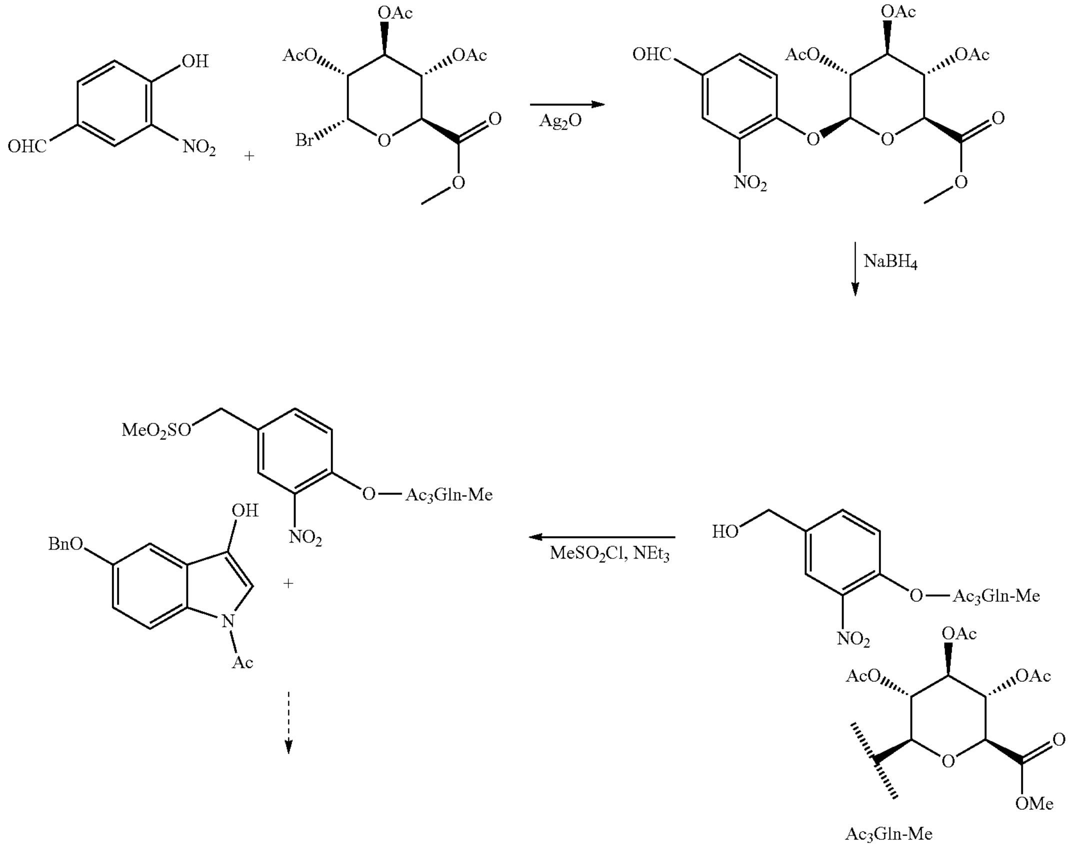

-continued

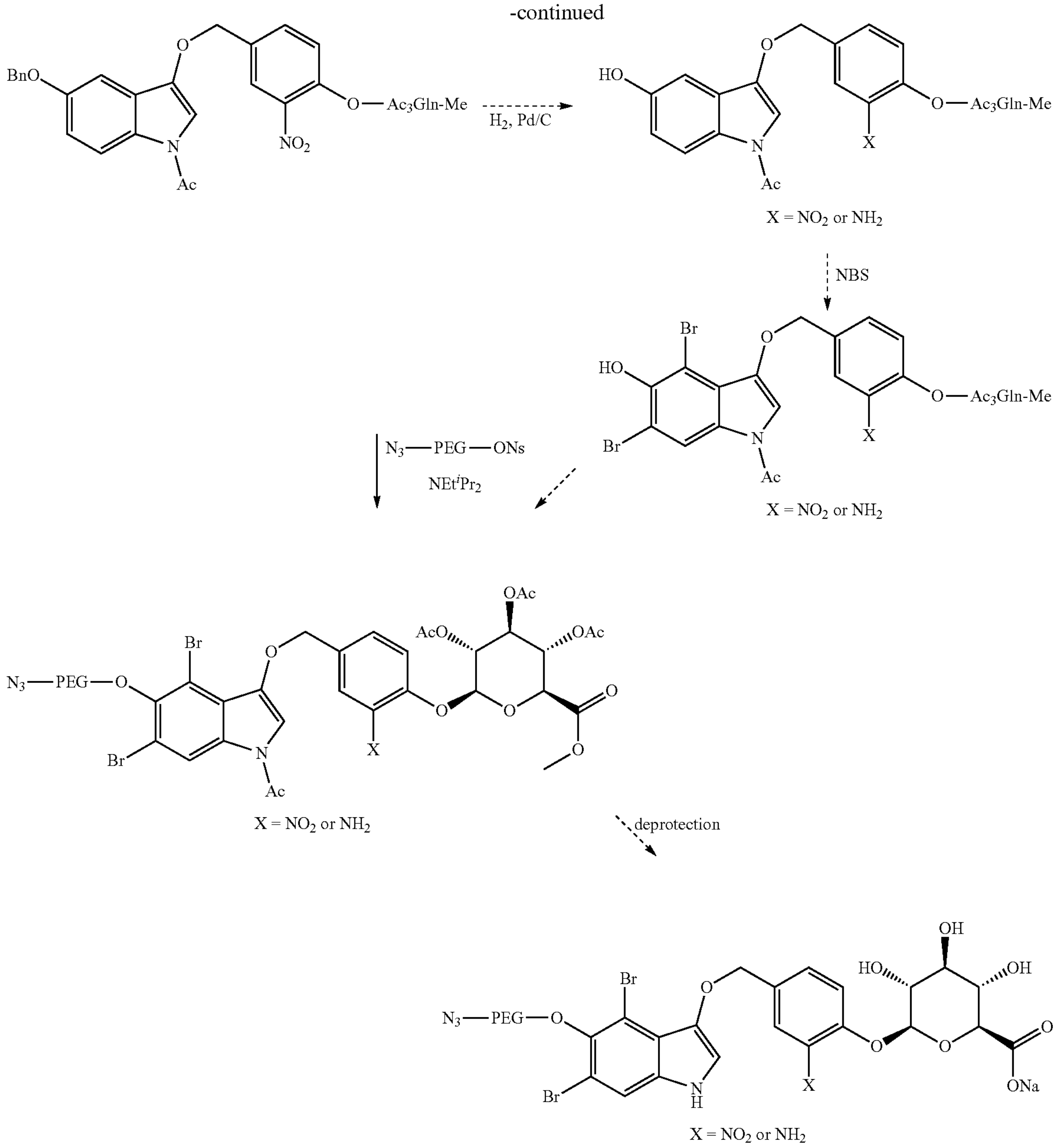

Experimental Section

General methods. $^1$H NMR (700 MHz) and $^{13}$C NMR (175 MHz) spectra were collected at room temperature in $CDCl_3$ unless noted otherwise. Chemical shifts for $^1$H NMR spectra are reported in parts per million (δ) relative to tetramethylsilane (or by use of the solvent signal for $CD_3OD$, δ=3.31 ppm). Chemical shifts for $^{13}$C NMR spectra are reported in parts per million (δ), and spectra were calibrated by using solvent signals [$CDCl_3$, δ=77.16 ppm; $(CD_3)_2SO$, δ=39.52 ppm; $CD_3OD$, δ=49.00 ppm]. Silica gel (40 μm) was used for column chromatography. Preparative TLC separations were carried out on Merck analytical plates precoated with silica gel 60 F. All solvents were reagent grade and were used as received unless noted otherwise. Commercial compounds were used as received.

1-Acetyl-4,6-dibromo-5-hydroxy-1H-indol-3-yl 2,3,4-tri-O-acetyl-β-D-glucopyranoside (2)

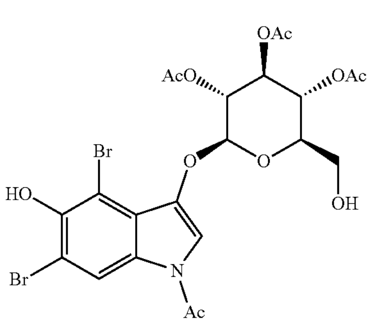 [SMILES: CC(=O)O[C@@H]1[C@@H](OC(C)=O)[C@H](Oc2cn(C(C)=O)c3cc(Br)c(O)c(Br)c23)O[C@H](CO)[C@H]1OC(C)=O]

Following a general procedure[Ori] with slight modification, dichlorotetrakis(1,1-dimethylethyl)di-μ-hydroxyditin[Dri] (6.8 mg, 0.012 mmol) was added to a solution of 1-acetyl-4,6-dibromo-5-hydroxy-1H-indol-3-yl 2,3,4,6-tetra-O-acetyl-β-D-glucopyranoside (81.5 mg, 0.12 mmol) in MeOH/$CHCl_3$ (0.80 mL, 5:3) at room temperature. After 12 h, the reaction mixture was diluted with ethyl acetate and passed through silica gel (ethyl acetate as eluent). The eluent was concentrated under reduced pressure. Column chromatography [silica gel, hexanes/acetone (2:1)] followed by trituration with hexanes/acetone afforded a white solid (46.7 mg, 61%): $^1$H NMR (700 MHz, $CD_3OD$) δ 2.00 (s, 3H), 2.07 (s, 3H), 2.08 (s, 3H), 2.55 (s, 3H), 3.65 (dd, J=6.9, 12.1 Hz, 1H), 3.75 (dd, J=1.5, 12.1 Hz, 1H), 3.90-3.97 (m, 1H), 5.08 (dd, J=9.5, 9.7 Hz, 1H), 5.22 (d, J=8.3 Hz, 1H), 5.32 (dd, J=8.3, 9.0 Hz, 1H), 5.38 (dd, J=9.0, 9.5 Hz, 1H), 7.50 (s, 1H), 8.54 (s, 1H); $^{13}$C NMR (175 MHz, $CD_3OD$) δ 20.57, 20.58, 21.0, 23.6, 61.9, 70.3, 72.5, 74.6, 76.3, 100.8, 101.4, 110.9, 112.9, 120.8, 123.9, 129.6, 141.8, 148.9, 170.4, 171.2, 171.3, 171.7; ESI-MS obsd 659.9532, calcd 659.9530 $[(M+Na)^+$, $M=C_{22}H_{23}Br_2NO_{11}]$.

1-Acetyl-4,6-dibromo-5-(tert-butyldimethylsilyl)oxy-1H-indol-3-yl 2,3,4-tri-O-acetyl-β-D-glucopyranoside (3)

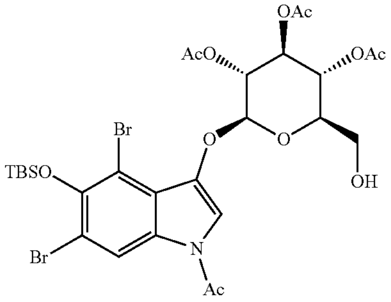 [SMILES: CC(=O)O[C@@H]1[C@@H](OC(C)=O)[C@H](Oc2cn(C(C)=O)c3cc(Br)c(O[Si](C)(C)C(C)(C)C)c(Br)c23)O[C@H](CO)[C@H]1OC(C)=O]

$Et_3N$ (14.9 μL, 0.107 mmol) was added to a suspension of 1-acetyl-4,6-dibromo-5-hydroxy-1H-indol-3-yl 2,3,4-tri-O-acetyl-β-D-glucopyranoside (34.1 mg, 0.0535 mmol) and tert-butylchlorodimethylsilane (16.1 mg, 0.107 mmol) in $CH_2Cl_2$ (535 μL) at room temperature. After 18 h, 2,2,2-trifluoroacetic acid (16.4 μL, 0.214 mmol), pyridine (4.3 μL, 0.53 mmol), and MeOH (535 μL) were added. After 5 h, the reaction mixture was diluted with ethyl acetate and passed through silica gel (ethyl acetate as eluent). The eluent was concentrated under reduced pressure. Column chromatography [silica gel, hexanes/ethyl acetate (2:3)] afforded a white solid (26.3 mg, 65%): $^1$H NMR (700 MHz, $CDCl_3$) δ 0.35 (s, 3H), 0.36 (s, 3H), 1.05 (s, 9H), 2.05 (s, 3H), 2.07 (s, 3H), 2.08 (s, 3H), 2.52 (s, 3H), 2.67 (br s, 1H), 3.71-3.85 (m, 3H), 4.99 (d, J=7.8 Hz, 1H), 5.15 (dd, J=9.3, 9.3 Hz, 1H), 5.32 (dd, J=8.6, 9.3 Hz, 1H), 5.37 (dd, J=8.6, 9.3 Hz, 1H), 7.22 (s, 1H), 8.57 (br s, 1H); $^{13}$C NMR (175 MHz, $CDCl_3$) δ 19.2, 20.8, 21.0, 23.7, 26.4, 29.8, 61.5, 68.8, 70.9, 72.8, 75.1, 100.7, 104.6, 111.0, 114.5, 120.5, 123.0, 129.2, 141.0, 147.1, 168.0, 169.7, 170.1, 170.4; ESI-MS obsd 750.0581, calcd 750.0575 $[(M+H)^+$, $M=C_{28}H_{37}Br_2NO_{11}Si]$.

1-Acetyl-4,6-dibromo-5-hydroxy-1H-indol-3-yl 2,3,4-tri-O-acetyl-β-D-glucopyranosiduronic acid methyl ester (4, route A)

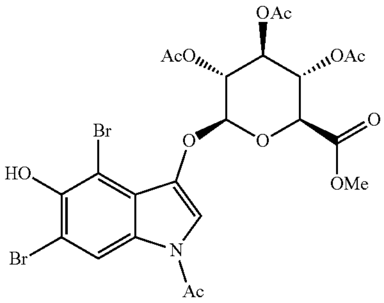 [SMILES: COC(=O)[C@H]1O[C@@H](Oc2cn(C(C)=O)c3cc(Br)c(O)c(Br)c23)[C@H](OC(C)=O)[C@@H](OC(C)=O)[C@@H]1OC(C)=O]

Following a reported procedure[Lu] with modification, (diacetoxyiodo)benzene (26.4 mg, 0.082 mmol) was added to a suspension of 1-acetyl-4,6-dibromo-5-(tert-butyldimethylsilyl)oxy-1H-indol-3-yl 2,3,4-tri-O-acetyl-β-D-glucopyranoside (28.0 mg, 0.037 mmol), 2,2,6,6-tetramethylpiperidine 1-oxyl (1.7 mg, 0.011 mmol), and $NaHCO_3$ (3.1 mg, 0.037 mmol) in $MeCN/H_2O$ (3:1, 273 μL) at room temperature. After 3 h, $NaHCO_3$ (6.2 mg, 0.074 mmol) was added. After 2 h, 2,2,6,6-tetramethylpiperidine 1-oxyl (1.2 mg, 0.0077 mmol) was added. After 1.5 h, (diacetoxyiodo)benzene (12.0 mg, 0.037 mmol) was added. After 30 min, $NaHCO_3$ (15.7 mg, 0.19 mmol) and dimethyl sulfate (28.3 μL, 0.30 mmol) were added. After 4 h, the reaction mixture was diluted with ethyl acetate and passed through silica gel (ethyl acetate as eluent). The eluent was concentrated under reduced pressure. The residue was dissolved in THF (317 μL). AcOH (4.3 μL, 0.075 mmol) and tetra-n-butylammonium fluoride (1.0 M in THF, 56 μL, 0.056 mmol) were added at room temperature. After 2 h, the reaction mixture was diluted with ethyl acetate and passed through silica gel (ethyl acetate as eluent). The eluent was concentrated under reduced pressure. Column chromatography [silica gel, hexanes/acetone (3:2)] afforded a pale brown solid (8.2 mg, 33%): mp 202-204° C.; $^1$H NMR (400 MHz, $CDCl_3$) δ 2.07 (s, 3H), 2.07 (s, 3H), 2.10 (s, 3H), 2.57 (s, 3H), 3.78 (s, 3H), 4.26 (d, J=9.2 Hz, 1H), 5.13 (d, J=6.8 Hz, 1H), 5.28-5.48 (m, 3H), 6.00 (br s, 1H), 7.32 (s, 1H), 8.67 (br s, 1H); $^{13}$C NMR (175 MHz, $CDCl_3$) δ 20.7, 20.8, 21.0, 23.7, 53.3, 68.9, 70.7, 72.0, 72.6, 98.4, 100.3, 108.6, 112.3, 120.1, 122.6, 128.7, 139.9, 146.3, 167.0, 168.0, 169.3, 169.5, 170.2; ESI-MS obsd 685.9469, calcd 685.9479 $[(M+Na)^+$, $M=C_{23}H_{23}Br_2NO_{12}]$.

5-{[(1R,8S,9s)-Bicyclo[6.1.0]non-4-yn-9-yl]methoxy}-4,6-dibromo-1H-indole-3-yl β-D-glucopyranosiduronic acid methyl ester (5, route A)

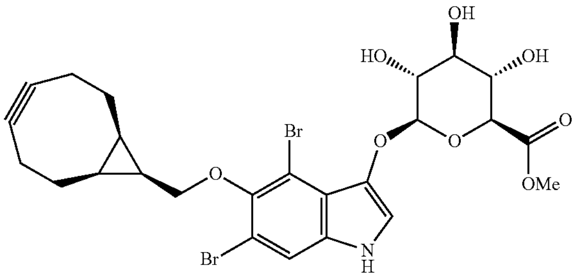 [SMILES: COC(=O)[C@H]1O[C@@H](Oc2c[nH]c3cc(Br)c(OC[C@@H]4[C@@H]5CCC#CCC[C@@H]54)c(Br)c23)[C@H](O)[C@@H](O)[C@@H]1O]

Diisopropyl azodicarboxylate (3.5 μL, 0.018 mmol) was added to a solution of 1-acetyl-4,6-dibromo-5-hydroxy-1H-indol-3-yl 2,3,4-tri-O-acetyl-β-D-glucopyranosiduronic acid methyl ester (7.0 mg, 0.11 mmol), (1R,8S,9s)-bicyclo[6.1.0]non-4-yn-9-ylmethanol (1.9 mg, 0.013 mmol), and $PPh_3$ (4.7 mg, 0.018 mmol) in $CH_2Cl_2$ (105 μL) at room temperature. After 3 h, MeOH (420 μL) and $K_2CO_3$ (1.5 mg) were added. After 1.5 h, the reaction mixture was passed through silica gel [$CH_2Cl_2$/MeOH (2:1) as eluent]. The eluent was concentrated under reduced pressure. Preparative thin layer chromatography [silica gel, 0.25 mm, $CHCl_3$/MeOH (10:1)] afforded a white solid (2.9 mg, 44%): $^1$H NMR (700 MHz, $CD_3OD$) δ 0.98-1.09 (m, 2H), 1.64-1.80 (m, 3H), 2.13-2.23 (m, 2H), 2.23-2.38 (m, 4H), 3.49 (dd, J=8.8, 9.4 Hz, 1H), 3.59 (dd, J=8.0, 8.8 Hz, 1H), 3.66 (dd, J=9.4, 9.6 Hz, 1H), 3.78 (s, 3H), 3.96 (d, J=9.6 Hz, 1H), 4.09 (d, J=7.8 Hz, 2H), 4.83 (d, J=8.0 Hz, 1H), 7.12 (s, 1H), 7.50 (s, 1H); $^{13}$C NMR (175 MHz, $CD_3OD$) δ 20.2, 21.7, 22.0, 30.6, 52.9, 72.8, 73.0, 75.0, 76.8, 77.3, 99.6, 105.3, 107.9, 112.6, 115.4, 116.0, 120.1, 132.9, 138.5, 147.0, 171.1; ESI-MS obsd 650.0000, calcd 649.9996 [$(M+Na)^+$, $M=C_{25}H_{27}Br_2NO_8$].

Sodium 5-{[(1R,8S,9s)-bicyclo[6.1.0]non-4-yn-9-yl]methoxy}-4,6-dibromo-1H-indole-3-yl β-D-glucopyranosiduronate (6, route A)

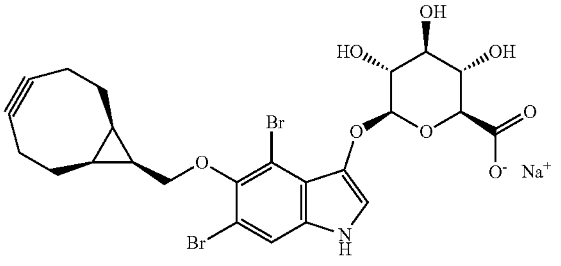 [SMILES: O=C([O-])[C@H]1O[C@@H](Oc2c[nH]c3cc(Br)c(OC[C@@H]4[C@@H]5CCC#CCC[C@@H]54)c(Br)c23)[C@H](O)[C@@H](O)[C@@H]1O ; [Na+]]

Aqueous $NaHCO_3$ (100 mM, 46 μL) was added to a solution of 5-(((1R,8S,9s)-bicyclo[6.1.0]non-4-yn-9-yl)methoxy)-4,6-dibromo-1H-indole-3-yl β-D-glucopyranosiduronic acid methyl ester (2.9 mg, 0.0046 mmol) in MeOH (184 μL) at room temperature. The reaction mixture was heated to 40° C. for 13 h and then 60° C. for 23 h. The reaction mixture was allowed to cool to room temperature and then concentrated under reduced pressure to afford a white solid (2.5 mg, 86%): $^1$H NMR (700 MHz, $CD_3OD$) δ 0.98-1.08 (m, 2H), 1.65-1.80 (m, 3H), 2.13-2.22 (m, 2H), 2.22-2.36 (m, 4H), 3.51 (dd, J=8.8, 9.2 Hz, 1H), 3.56 (dd, J=9.2, 9.5 Hz, 1H), 3.59 (dd, J=8.1, 8.8 Hz, 1H), 3.68 (d, J=9.5 Hz, 1H), 4.09 (d, J=7.8 Hz, 2H), 4.73 (d, J=8.1 Hz, 1H), 7.35 (s, 1H), 7.49 (s, 1H); $^{13}$C NMR (175 MHz, $CD_3OD$) δ 20.1, 21.7, 22.0, 30.6, 72.8, 73.7, 75.1, 76.6, 77.9, 99.6, 105.2, 107.8, 112.3, 115.9, 116.2, 120.0, 132.8, 138.7, 146.8, 176.6; ESI-MS obsd 635.9840, calcd 635.9839 [$(M+Na)^+$, $M=C_{24}H_{25}Br_2NO_8$].

1-Acetyl-5-(benzyl)oxy-1H-indol-3-yl 2,3,4-tri-O-acetyl-β-D-glucopyranosiduronic acid methyl ester (9)

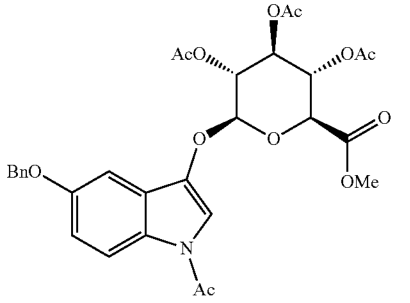 [SMILES: COC(=O)[C@H]1O[C@@H](Oc2cn(C(C)=O)c3ccc(OCc4ccccc4)cc23)[C@H](OC(C)=O)[C@@H](OC(C)=O)[C@@H]1OC(C)=O]

Activated molecular sieves 4 Å (250 mg), 1-acetyl-5-(benzyloxy)indolin-3-one (7) (28 mg, 0.10 mmol), acetobromo-α-D-glucuronic acid methyl ester (8) (124 mg, 0.31 mmol) and HgO (34 mg, 0.16 mmol) were placed in a flask and treated with toluene/$MeNO_2$ (4:1, 1.0 mL). The orange suspension was then treated with $HgBr_2$ (7.0 mg, 19 μmol), heated to 40° C. and stirred for 5.5 h. The reaction was quenched by the addition of pyridine (200 μL) and filtered through a silica pad (2 cm×2 cm, acetone). The filtrate was concentrated to give a crude mixture. Column chromatography [silica gel, hexanes/acetone (7:3)] followed by recrystallization in hexanes/$CH_2Cl_2$ afforded a white solid (31 mg, 52%): mp 189-191° C.; 1H NMR (600 MHz, $CDCl_3$) δ 8.31 (b, 1H), 7.46 (d, J=7.0 Hz, 2H), 7.39 (t, J=7.7 Hz, 2H), 7.35-7.30 (m, 1H), 7.15 (b, 1H), 7.07-7.01 (m, 2H), 5.40-5.31 (m, 3H), 5.11 (s, 2H), 5.08 (d, J=7.0 Hz, 1H), 4.19 (d, J=8.9 Hz, 1H), 3.74 (s, 3H), 2.55 (s, 3H), 2.08 (s, 3H), 2.07 (s, 3H), 2.05 (s, 3H); $^{13}$C NMR (150 MHz, $CDCl_3$) δ 170.1, 169.4, 169.2, 168.0, 166.8, 155.6, 141.1, 137.0, 128.6, 128.0, 127.6, 124.7, 117.7, 115.7, 110.6, 101.5, 100.8, 72.7, 71.8, 71.0, 70.5, 69.0, 53.1, 23.7, 20.7, 20.6, 20.5.

1-Acetyl-5-hydroxy-1H-indol-3-yl 2,3,4-tri-O-acetyl-β-D-glucuronic acid methyl ester (10)

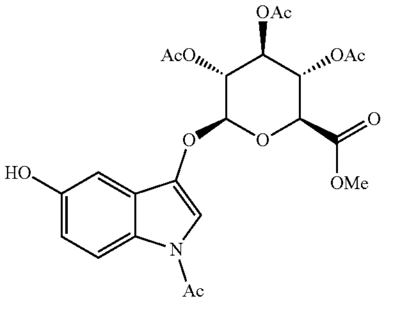 [SMILES: COC(=O)[C@H]1O[C@@H](Oc2cn(C(C)=O)c3ccc(O)cc23)[C@H](OC(C)=O)[C@@H](OC(C)=O)[C@@H]1OC(C)=O]

A suspension of 9 (170 mg, 0.28 mmol) and Pd/C (10 wt %, 30 mg, 28 μmol) in THF/$CH_2Cl_2$/EtOH (5:4:1, 11 mL) was stirred under an atmosphere of $H_2$ (1 atm) for 1 h. The reaction mixture was filtered through a silica pad (2 cm×2 cm, acetone). The filtrate was concentrated and recrystallized (hexanes/$CH_2Cl_2$) to afford a white solid (106 mg, 75%): mp 200-202° C.; $^1$H NMR (600 MHz, $CDCl_3$) δ 8.24 (b, 1H), 7.10 (b, 1H), 6.92 (d, J=2.5 Hz, 1H), 6.89 (dd, J=8.9, 2.5 Hz, 1H), 6.13 (s, 1H), 5.41-5.32 (m, 3H), 5.09-5.05 (m, 1H), 4.23-4.19 (m, 1H), 3.76 (s, 3H), 2.54 (s, 3H), 2.10 (s, 3H), 2.07 (s, 3H), 2.06 (s, 3H); $^{13}$C NMR (150 MHz, $CDCl_3$) δ 170.4, 169.7, 169.5-168.3, 167.1, 152.8, 141.1, 128.4, 125.1, 117.8, 115.2, 110.8, 103.0, 100.8, 72.7, 71.9, 71.0, 69.1, 53.3, 23.7, 20.79, 20.75, 20.6.

1-Acetyl-4,6-dibromo-5-hydroxy-1H-indol-3-yl 2,3,4-tri-O-acetyl-β-D-glucopyranosiduronic acid methyl ester (4, route B)

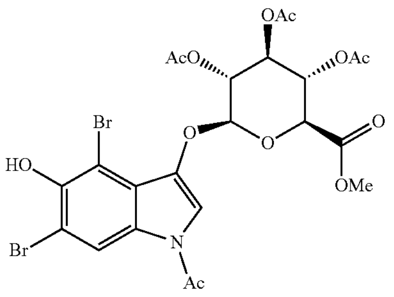 [SMILES: COC(=O)[C@H]1O[C@@H](Oc2cn(C(C)=O)c3cc(Br)c(O)c(Br)c23)[C@H](OC(C)=O)[C@@H](OC(C)=O)[C@@H]1OC(C)=O]

A solution of NBS (156 mg, 0.88 mmol) in $CH_2Cl_2$ (10.0 mL) was added dropwise over 30 min to a solution of 10 (215 mg, 0.42 mmol) and 2,6-di-tert-butylpyridine (92 μL, 0.42 mmol) in $CH_2Cl_2$ (6.0 mL) at −78° C. The reaction mixture was allowed to warm to rom temperature, stirred for 2.5 h, and quenched by the addition of 10% aqueous $Na_2S_2O_3$. The organic layer was washed with brine, dried ($Na_2SO_4$), and concentrated. Column chromatography (silica, $CH_2Cl_2$ with 1% to 4% acetone) afforded a white solid (242 mg, 87%): the characterization data ($^1$H NMR) were consistent with the product from route A.

1-Acetyl-5-{[(1R,8S,9s)-bicyclo[6.1.0]non-4-yn-9-yl]methoxy}-4,6-dibromo-5-hydroxy-1H-indol-3-yl 2,3,4-tri-O-acetyl-β-D-glucopyranosiduronic acid methyl ester (11)

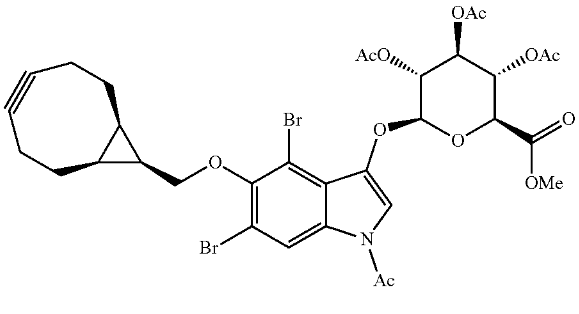 [SMILES: COC(=O)[C@H]1O[C@@H](Oc2cn(C(C)=O)c3cc(Br)c(OC[C@@H]4[C@@H]5CCC#CCC[C@@H]54)c(Br)c23)[C@H](OC(C)=O)[C@@H](OC(C)=O)[C@@H]1OC(C)=O]

Diisopropyl azodicarboxylate (13 μL, 63 μmol) was added to a solution containing 4 (34 mg, 51 μmol), (1R,8S,9s)-bicyclo[6.1.0]non-4-yn-9-ylmethanol (9.3 mg, 62 μmol), and $PPh_3$ (17 mg, 65 μmol) in $CH_2Cl_2$ (0.51 mL) at room temperature. The reaction mixture was stirred for 1 h and then quenched by the addition of $H_2O$. The organic layer was washed with brine, dried ($Na_2SO_4$), and concentrated. Column chromatography (silica, hexanes with 0% to 4% acetone) afforded a white solid (28 mg, 69%): $^1$H NMR (500 MHz, $CDCl_3$) δ 8.71 (s, 1H), 7.35 (s, 1H), 5.47-5.31 (m, 3H), 5.14 (d, J=7.0 Hz, 1H), 4.27 (d, J=9.6 Hz, 1H), 4.10 (d, J=7.8 Hz, 2H), 3.78 (s, 3H), 2.58 (s, 3H), 2.37-2.28 (m, 4H), 2.28-2.20 (m, 2H), 2.11 (s, 3H), 2.07 (s, 3H), 2.06 (s, 3H), 1.79-1.68 (m, 2H), 1.06 (dd, J=11.4, 8.5 Hz, 2H).

5-{[(1R,8S,9s)-Bicyclo[6.1.0]non-4-yn-9-yl]methoxy}-4,6-dibromo-1H-indole-3-yl β-D-glucopyranosiduronic acid methyl ester (5, route B)

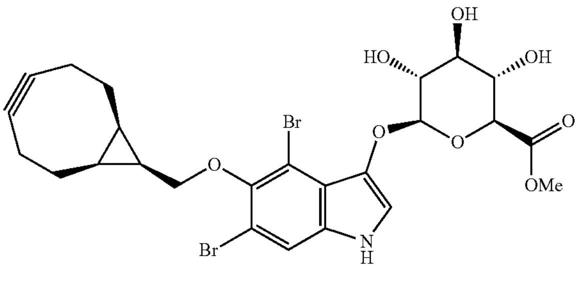 [SMILES: COC(=O)[C@H]1O[C@@H](Oc2c[nH]c3cc(Br)c(OC[C@@H]4[C@@H]5CCC#CCC[C@@H]54)c(Br)c23)[C@H](O)[C@@H](O)[C@@H]1O]

A suspension of 11 (28 mg, 35 μmol) and $K_2CO_3$ (4.8 mg, 35 μmol) in $CH_2Cl_2$/MeOH (1:4, 1.8 mL) was stirred at room temperature for 1.5 h and then quenched by the addition of acetic acid (7.0 μL, 0.12 mmol). The crude mixture was filtered through a silica pad (2 cm×2 cm, methanol). The filtrate was concentrated and chromatographed [silica, $CH_2Cl_2$/MeOH (9:1)] to afford a pale-yellow solid (14 mg, 64%): the characterization data ($^1$H NMR) were consistent with the product from route A.

Sodium 5-{[(1R,8S,9s)-bicyclo[6.1.0]non-4-yn-9-yl]methoxy}-4,6-dibromo-1H-indole-3-yl β-D-glucopyranosiduronate (6, route B)

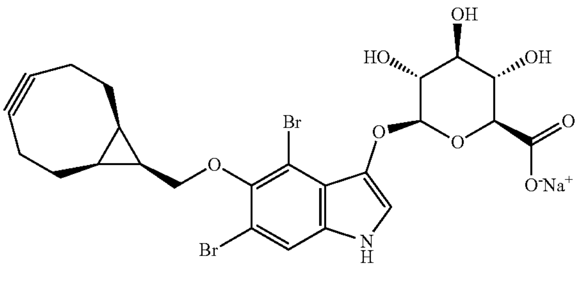

A solution of 5 (14 mg, 22 μmol) in MeOH (0.88 mL) was treated with aqueous $NaHCO_3$ (100 mM, 0.22 mL) at room temperature and stirred at 60° C. for 32 h. The reaction mixture was allowed to cool to room temperature and then concentrated. The residue was washed with hexanes (3.0 mL×3) and $CH_2Cl_2$ (3.0 mL×3) to give the title compound as a pale-brown solid (13 mg, 93%): the characterization data ($^1$H NMR) were consistent with the product from route A.

Compound 12

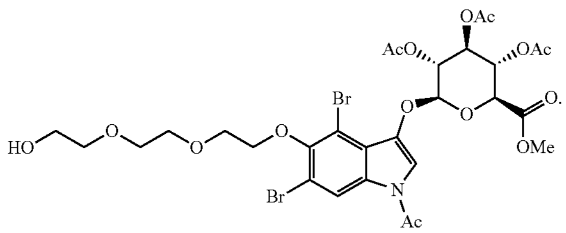

N,N-Diisopropylethylamine (DIPEA, 64 μL, 0.37 mmol) was added to a solution containing 4 (122 mg, 0.18 mmol) and 2-(2-(2-hydroxyethoxy)ethoxy)ethyl 4-nitrobenzene-sulfonate (100 mg, 0.30 mmol) in $CH_2Cl_2$ (1.0 mL) at room temperature. The reaction mixture was stirred for 36 h and then concentrated. Column chromatography (silica, $CH_2Cl_2$ with 0% to 70% ethyl acetate) afforded a white amorphous non-crystalline solid (116 mg, 79%): $^1$H NMR (600 MHz, $CDCl_3$) δ 8.71 (s, 1H), 7.35 (s, 1H), 5.47-5.37 (m, 2H), 5.34 (t, J=8.9 Hz, 1H), 5.13 (d, J=7.0 Hz, 1H), 4.26 (d, J=9.7 Hz, 1H), 4.22-4.16 (m, 2H), 4.00-3.94 (m, 2H), 3.84-3.78 (m, 2H), 3.78 (s, 3H), 3.77-3.70 (m, 4H), 3.67-3.60 (m, 2H), 2.57 (s, 3H), 2.10 (s, 3H), 2.06 (s, 3H), 2.06 (s, 3H); $^{13}$C NMR (150 MHz, $CDCl_3$) δ 170.1, 169.3, 169.2, 167.9, 166.8, 149.7 140.1, 131.0, 123.0, 120.3, 116.2, 112.4, 107.5, 100.2, 72.53, 72.50, 72.4, 71.9, 70.9, 70.61, 70.5, 70.2, 68.8, 61.8, 53.1, 23.7, 20.9, 20.64, 20.55].

Compound 13

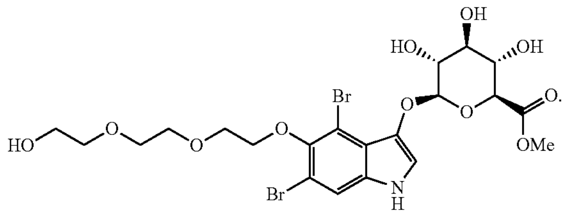

A suspension of 12 (15 mg, 19 μmot) and $K_2CO_3$ (2.7 mg, 19 μmot) in $CH_2Cl_2$/MeOH (1:4, 0.95 mL) was stirred at room temperature for 40 min and then quenched by the addition of acetic acid (3.0 μL, 52 μmol). The crude mixture was filtered through a silica pad (2 cm×2 cm, methanol). The filtrate was concentrated and chromatographed [silica, $CH_2Cl_2$/MeOH (9:1)] to afford a pale-yellow amorphous solid (10 mg, 84%): 1H NMR (600 MHz, $CD_3OD$) δ 7.49 (s, 1H), 7.12 (s, 1H), 4.82 (d, J=7.6 Hz, 1H), 4.14 (t, J=4.9 Hz, 2H), 3.98-3.91 (m, 3H), 3.81-3.75 (m, 5H), 3.70-3.63 (m, 5H), 3.61-3.55 (m, 3H), 3.48 (t, J=9.1 Hz, 1H).

Compound 14

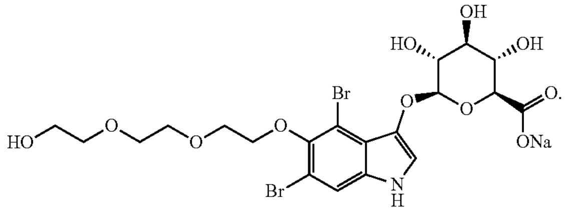

A solution of 13 (10 mg, 16 μmot) in MeOH (0.64 mL) was treated with aqueous $NaHCO_3$ (100 mM, 0.16 mL) at room temperature and then stirred at 60° C. for 18 h. The reaction mixture was allowed to cool to room temperature and then concentrated. Column chromatography [silica, $CH_2Cl_2$/MeOH (4:1 to 1:4)] afforded a white solid (8.8 mg, 86%): 1H NMR (600 MHz, $CD_3OD$) δ 7.48 (s, 1H), 7.34 (s, 1H), 4.72 (d, J=7.7 Hz, 1H), 4.14 (t, J=4.8 Hz, 2H), 3.94 (t, J=4.8 Hz, 2H), 3.82-3.77 (m, 2H), 3.71-3.64 (m, 5H), 3.61-3.53 (m, 4H), 3.50 (t, J=9.0 Hz, 1H); $^{13}$C NMR (150 MHz, $CD_3OD$) δ 175.2, 145.3, 137.4, 131.6, 118.6, 114.8, 114.6, 110.6, 106.2, 103.7, 76.5, 75.2, 73.7, 72.32, 72.27, 72.2, 70.3, 70.1, 69.9, 60.8.

Compound 15

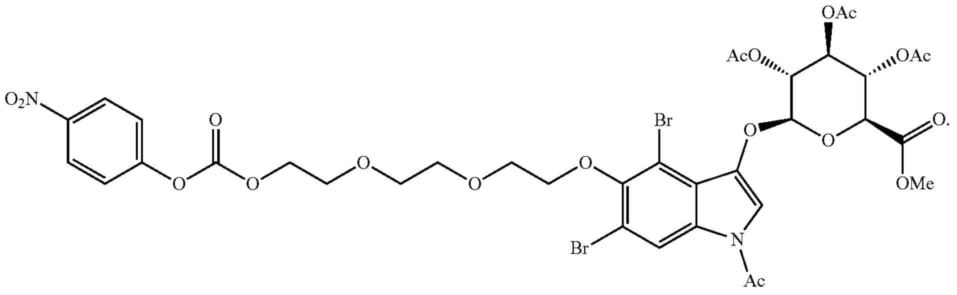

A suspension of 12 (60 mg, 75 μmol), 4-nitrophenyl carbonochloridate (24 mg, 119 μmol), and activated molecular sieves 4 Å (150 mg) in anhydrous $CH_2Cl_2$ (3.0 mL) was treated with pyridine (12 μL, 150 μmol) and stirred at room temperature for 6 h. The crude mixture was filtered through a silica pad (2 cm×2 cm, ethyl acetate). The filtrate was concentrated and chromatographed (silica, $CH_2Cl_2$ with 0% to 20% ethyl acetate) to afford a white amorphous non-crystalline solid (70 mg, 97%); $^1$H NMR (600 MHz, $CDCl_3$) δ 8.69 (s, 1H), 8.26-8.20 (m, 2H), 7.39-7.36 (m, 2H), 7.35 (s, 1H), 5.47-5.31 (m, 3H), 5.13 (d, J=6.9 Hz, 1H), 4.48-4.43 (m, 2H), 4.27 (d, J=9.7 Hz, 1H), 4.23-4.14 (m, 2H), 4.00-3.94 (m, 2H), 3.88-3.83 (m, 3H), 3.85-3.80 (m, 3H), 3.80-3.74 (m, 6H), 2.57 (s, 3H), 2.10 (s, 3H), 2.06 (s, 6H).

Compound 17

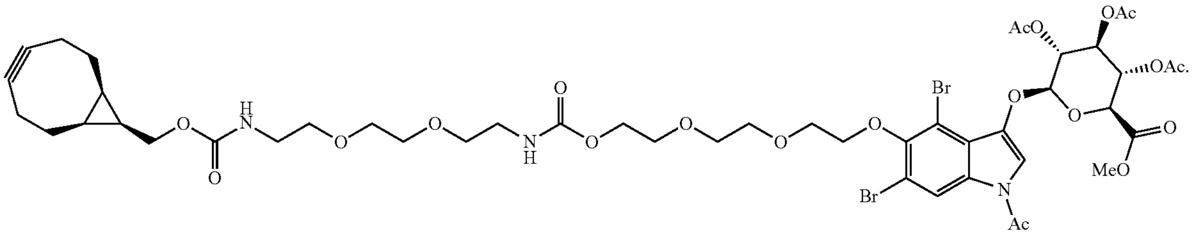

A solution of 13 (5.4 mg, 5.6 μmol) and 16 (3.8 mg, 12 μmol) in anhydrous $CH_2Cl_2$ (0.50 mL) was treated with DIPEA (2.0 μL, 11 μmol) and stirred at room temperature for 24 h. The crude mixture was concentrated and chromatographed (silica, $CH_2Cl_2$ to ethyl acetate) to afford a pale-yellow amorphous solid (5.6 mg, 87%): $^1$H NMR (700 MHz, $CDCl_3$) δ 8.72 (s, 1H), 7.36 (s, 1H), 5.45-5.38 (m, 2H), 5.36-5.30 (m, 2H), 5.14 (d, J=7.1 Hz, 1H), 4.26 (d, J=9.7 Hz, 1H), 4.25-4.21 (m, 2H), 4.19-4.13 (m, 4H), 3.96 (t, J=5.0 Hz, 2H), 3.81-3.76 (m, 5H), 3.74-3.68 (m, 4H), 3.61-3.59 (m, 4H), 3.58-3.54 (m, 4H), 3.41-3.36 (m, 4H), 2.58-3H), 2.32-2.18 (m, 6H), 2.10 (s, 3H), 2.06 (s, 3H), 2.06 (s, 3H), 1.60-1.56 (m, 2H), 0.94 J=9.8 Hz, 2H).

Compound 18

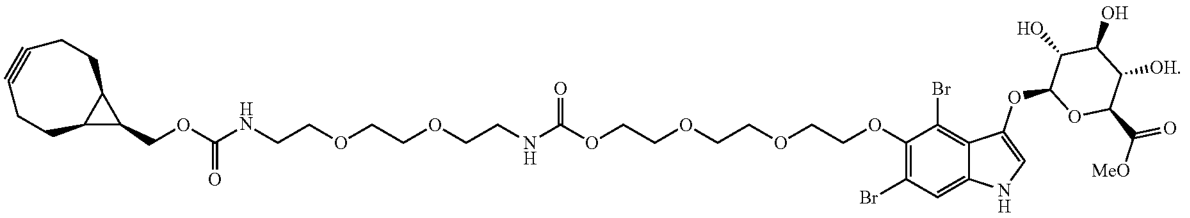

A suspension of 17 (5.6 mg, 4.9 μmol) and $K_2CO_3$ (1.3 mg, 9.4 μmol) in MeOH (1.0 mL) was stirred at room temperature for 1 h and then quenched by the addition of acetic acid (2.0 μL, 34 μmol). The crude mixture was concentrated and chromatographed [silica, $CHCl_3$/MeOH (9:1)] to afford a pale-yellow amorphous solid (3.4 mg, 71%): $^1$H NMR (700 MHz, $CD_3OD$) δ 7.52 (s, 1H), 7.14 (s, 1H), 4.85 (d, J=7.7 Hz, 1H), 4.21-4.11 (m, 6H), 3.98 (d, J=9.8 Hz, 1H), 3.96 (t, J=4.9 Hz, 2H), 3.81-3.76 (m, 5H), 3.74-3.66 (m, 5H), 3.62-3.57 (m, 5H), 3.55-3.49 (m, 6H), 3.32-3.27 (m, 4H), 2.27-2.13 (m, 6H), 1.64-1.51 (m, 2H), 0.96-0.85 (m, 2H).

Compound 19

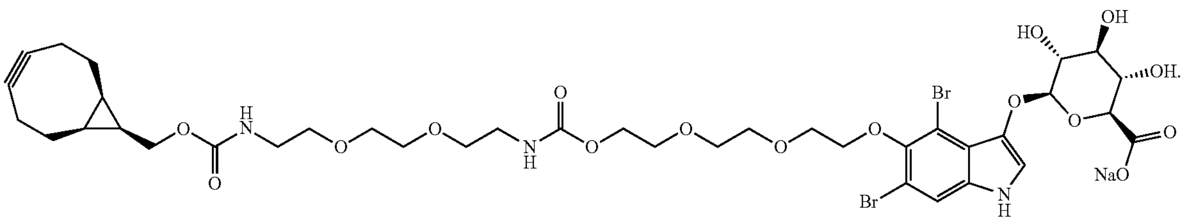

A solution of 18 (3.4 mg, 3.5 μmol) in MeOH (0.25 mL) was treated with aqueous $NaHCO_3$ (100 mM, 50 μL) at room temperature and then stirred at 60° C. for 18 h. The reaction mixture was allowed to cool to room temperature and then concentrated. Column chromatography [silica, $CH_2Cl_2$/MeOH (4:1 to 1:4)] afforded a white solid (2.8 mg, 81%).

APPENDIX

Attempted reactions toward indoxyl β-glucuronides are shown in Scheme 16.

Scheme 16. Attempted reactions toward indoxyl β-glucoronides. (A) Oxidation in the presence of a free indole nitrogen. (B) Oxidation in the presence of a free phenolic HO group at the indole 5-position. (C) Treatment of BCN-indoxyl S2 wtih [t-$Bu_2SnOH(Cl)]_2$.

(A)

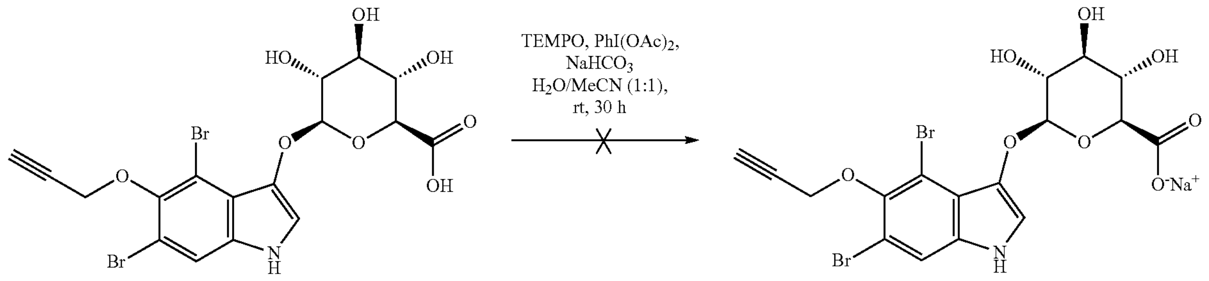

S1

(B)

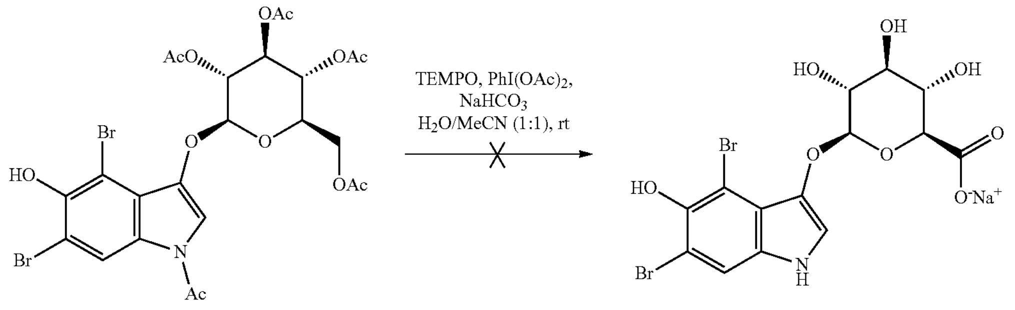

2

-continued (C)

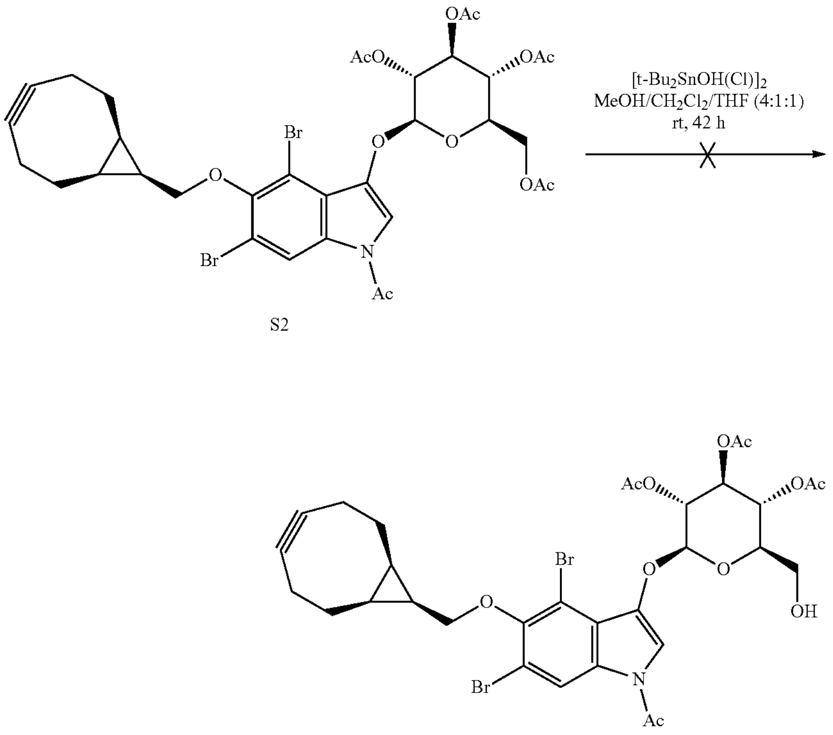

S2

REFERENCES (Pea) Pearson, B.; Standen, A. C.; Esterly, J. R. Histochemical β-Glucuronidase Distribution in Mammalian Tissue as Detected by 5-Bromo-4-Chloroindol-3-yl-β-D-glucopyruroniside. *Lab. Investig.* 1967, 17, 217-224.

(Kie) Kiernan, J. A. Indigogenic Substrates for Detection and Localization of Enzymes. *Biotech. Histochem.* 2007, 82, 73-103.

(Gra) Graaf, M.; Boven, E.; Scheeren, H.; Haisma, H.; Pinedo, H. Beta-Glucuronidase-Mediated Drug Release. *Curr. Pharm. Des.* 2002, 8, 1391-1403.

(Tra) Tranoy-Opalinski, I.; Legigan, T.; Barat, R.; Clarhaut, J.; Thomas, M.; Renoux, B.; Papot, S. β-Glucuronidase-Responsive Prodrugs for Selective Cancer Chemotherapy: An Update. *Eur. J. Med. Chem.* 2014, 74, 302-313.

(Ori) Orita, A.; Hamada, Y.; Nakano, T.; Toyoshima, S.; Otera, J. Highly Efficient Deacetylation by Use of the Neutral Organotin Catalyst [$tBu_2SnOH(Cl)]_2$. *Chem. Eur. J.* 2001, 7, 3321-3327.

(Dri) Driguez, P.-A. Dichlorotetrakis(1,1-Dimethylethyl)Di-μ-Hydroxyditin. In *Encyclopedia of Reagents for Organic Synthesis*; John Wiley & Sons, Ltd: Chichester, UK, 2012; pp 1-3.

(Lu) Lu, H.; Drelich, A.; Omri, M.; Pezron, I.; Wadouachi, A.; Pourceau, G. Catalytic Synthesis of a New Series of Alkyl Uronates and Evaluation of Their Physicochemical Properties. *Molecules* 2016, 21, 1301.

(Mel) Melvin, F.; McNeill, A.; Henderson, P. J. F.; Herbert, R. B. The Improved Synthesis of β-D-Glucuronides Using TEMPO and t-Butyl Hypochlorite. *Tetrahedron Len.* 1999, 40, 1201-1202.

Example 3

Enzymatic studies of β-glucuronidase enzymes from *E. coli* and bovine liver have been reported by Antunes, I. F., et al. “Synthesis and Evaluation of [18F]-FEAnGA as a PET Tracer for β-Glucuronidase Activity,” *Bioconjug. Chem.* 2010, 21, 911-920. Compounds of the present invention can be tested with a β-glucuronidase enzyme from *E. coli* or bovine liver. Both enzymes are readily available for studies. Enzymatic cleavage of a glucuronide releases a nitrophenol, the absorption of which is readily detected by absorption spectroscopy.

Example 4

An $A_2BC$-functionalized molecule (V) (i.e., a molecule that includes two scaffold cross-linking units ($A_2$), a bioconjugatable handle (B), and a molecular entity (C) such as a dye, docking group, reactive handle, or biomolecule) has been prepared that contains a pair of alkoxyamino-substituted triazines for branching, two dibromoindoxyl β-glucosides ($A_2$), an azide (B), and an aminocoumarin dye (C). Compound V additionally bears a sulfobetaine moiety to impart greater water solubility. The rationale for the dibromoindoxyl moieties stems from systematic studies of various indoxyl-glucoside substrates with β-glucosidase enzymes to identify molecular designs that (1) are compatible with enzymatic cleavage, (2) undergo facile indigoid dye formation, (3) are synthetically accessible, and (4) support incorporation into larger architectures via bioconjugation chemistry.

V

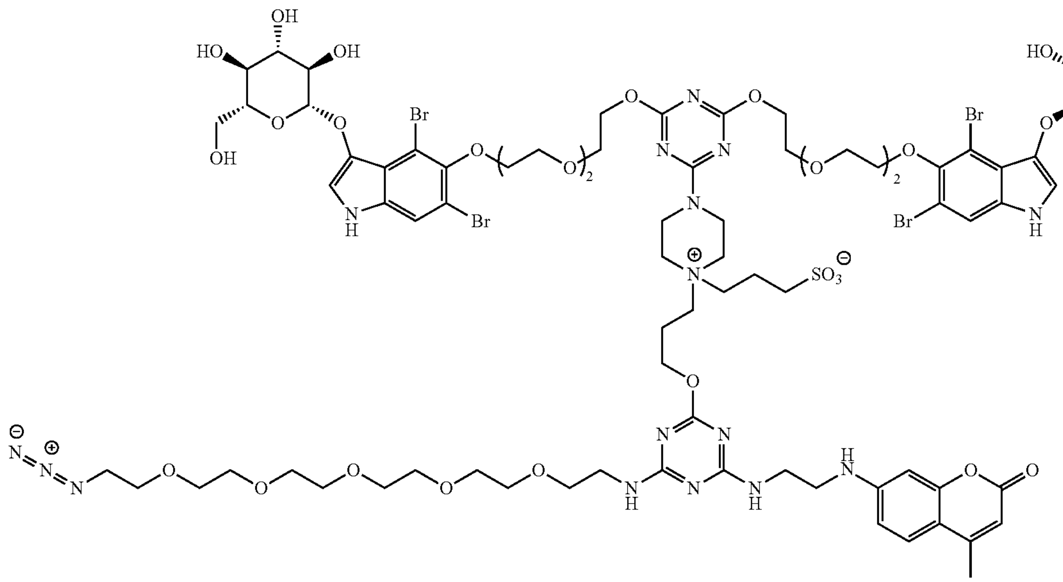

double triazines with piperazine-sulfobetaine

Figure 12:
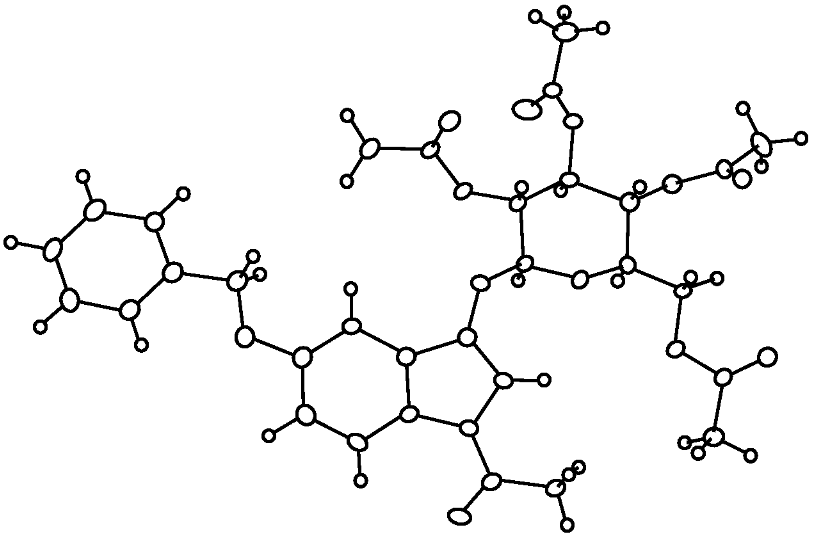
FIG. 12 is an ORTEP drawing of the single-crystal X-ray structure of F-5. All ellipsoids are contoured at the 50% level.

Refined synthesis of indoxyl species. A refined synthesis of the fully protected 5-hydroxyindoxyl-glucoside F-6 was developed (Scheme 16) to avoid a mixture of β/α epimers. Indole F-1 was acetylated using acetic anhydride and triethylamine in the presence of a catalytic amount of 4-dimethylaminopyridine (DMAP) to afford the N-acetylated indole F-2.[cmpdO-2] The Baeyer-Villiger oxidation[Bour] to convert F-2 to F-3 was carried out in toluene (rather than dichloromethane), affording a low yield (32%) but the starting material F-2 was recovered in 42% yield and recycled. The glucosidation of F-3 with acetobromo-α-D-glucose (F-4) was carried out in a mixture of toluene and nitromethane, affording stereoselective formation of β-glucoside F-5. $^1$H NMR investigation of F-5 showed >99% stereochemical purity at the anomeric carbon. A single-crystal X-ray structure determination (recrystallization from hexanes/$CH_2Cl_2$) also showed the β anomer (FIG. 12). Deprotection of the acetyl and benzyl groups of F-5 provided 5-hydroxyindoxyl-glucoside F-7 in 89% yield, while debenzylation of F-5 afforded acetyl-protected 5-hydroxyindoxyl-glucoside F-6 in 99% yield (see Example 1 where F-1 is compound 8, F-5 is compound 9, and F-7 is compound 10).

Scheme 16. Synthesis of 5-hydroxyindoxyls bearing glucosyl groups.

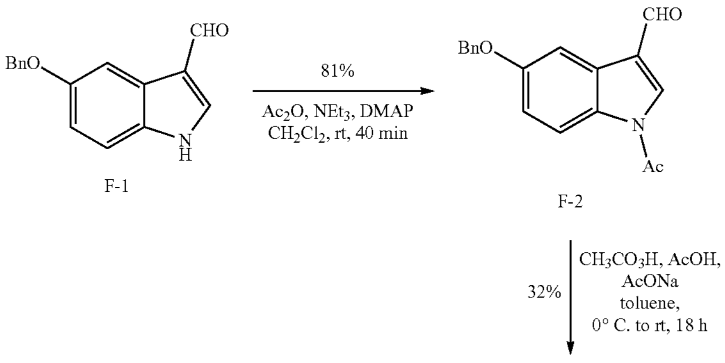

F-1 F-2

-continued

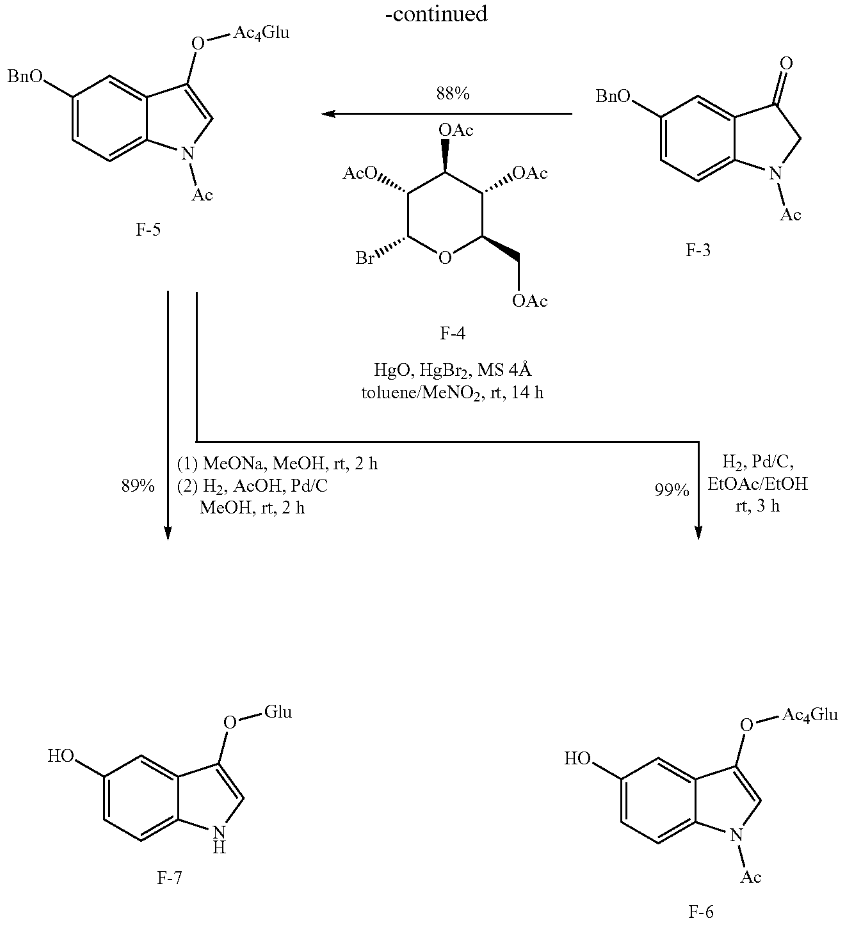

Glu = 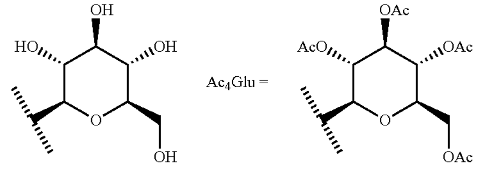 $Ac_4Glu$ =

Triazine-based $A_2BC$ architectures. Cyanuric chloride (F-8) was treated with 2 equiv of F-7 followed by tyramine to afford F-9 in 56% yield (Scheme 17). The two indoxyl moieties in F-9 showed distinguishable signals in NMR spectroscopy owing to slow rotation of the C—N bond between the triazine ring and the tyramine unit. Treatment of N-(6-hydroxyhexyl)maleimide (F-10) (K. A. Keller, et al., *Tetrahedron Lett.*, 2005, 46, 1181-1184. "A Thermally-Cleavable Linker for Solid-Phase Synthesis") with cyanuric chloride (F-8) followed by F-9 in the presence of bases gave F-11 in 77% yield. Ultimately we found that F-9 did not form the corresponding indigoid dye upon treatment with β-glucosidase, while treatment with tritosomes gave the indigoid dye albeit in low yield (ca. 4%). While F-9 and F-11 were attractive from a synthetic standpoint given the ability to derivatize the 5-hydroxy group of the indoxyl unit without protection of the four hydroxy groups of the glucosyl unit, the reaction with a β-glucosidase was sine qua non in the molecular design. Accordingly, we moved to the design of a more suitable architecture.

Scheme 17. Protecting group free synthesis of an $A_2B$-construct.

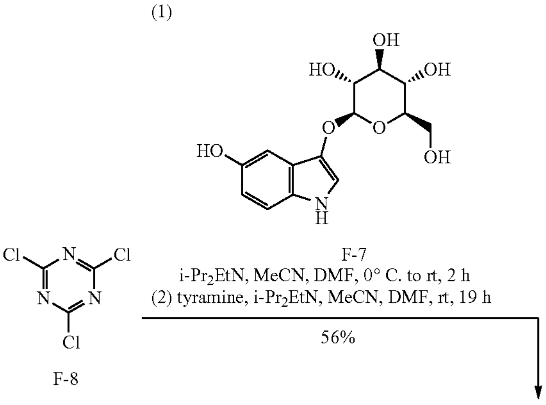

-continued

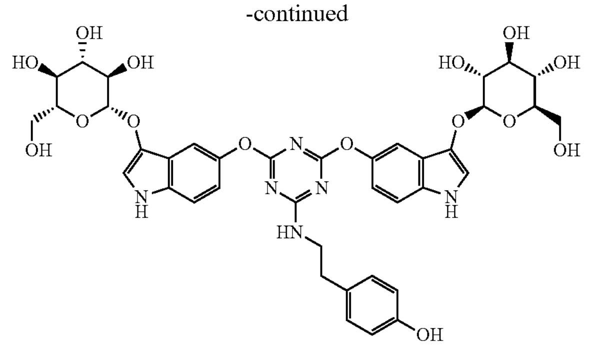

F-9

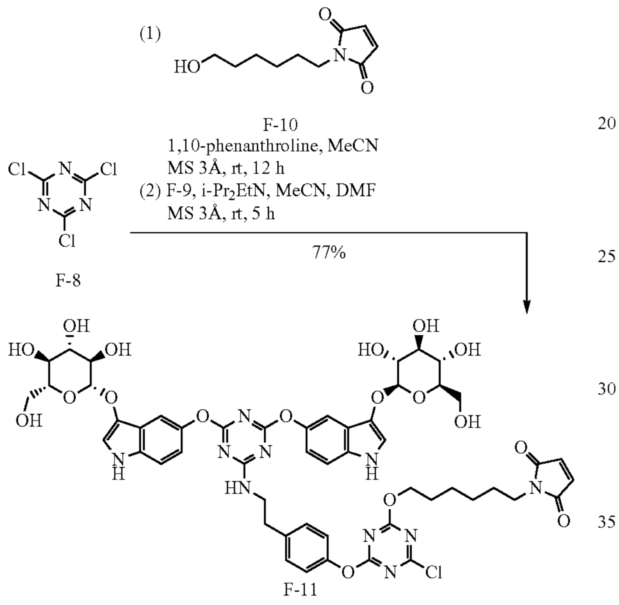

Compound V was designed for preparation through selective and successive substitution of cyanuric chloride (F-8) (C. Afonso, N. Lourenco and A. Rosatella, Molecules, 2006, 11, 81-102; M. B. Steffensen, et al., J. Polym. Sci. Part A Polym. Chem., 2006, 44, 3411-3433; A. E. Enciso, et al., Polym. Chem., 2014, 5, 4635-4640). The assembly relied on two protected indoxyl-glucoside units (F-12) and a sulfobetaine-amino alcohol (F-13). Indoxyl F-12 emerged from a lengthy study of the interplay of substituents that enable attachment of a bioconjugatable tether and facile formation of the corresponding indigoid dye (see Example 1). Sulfobetaine F-13 emerged from studies of bis(indoxyl-glucoside) molecules wherein the intervening linker imparts water solubility (see Example 1 where F-12 is compound 32 and F-13 is compound 38). The assembly of protected indoxyl F-12 (two units) and sulfobetaine-amino alcohol F-13 onto a triazine ring afforded F-14 in 29% yield in 2 steps from F-8, as described previously (see Example 1 where F-14 is compound 45). Selective substitution (M. Kunishima, et al., J. Fluorine Chem., 2016, 190, 68-74) of one of three chlorines in cyanuric chloride F-8 by alcohol F-14 was carried out with 1,10-phenanthroline as a base at room temperature (Scheme 18). Subsequently, azide-PEG$_5$-amine F-15 was added to the reaction mixture to replace the second chlorine. After the solvent was changed to DMF, the third substitution for chlorotriazine intermediate F-16 (used without isolation) with coumarin-amine F-17 (Y. Shiraishi, et al., *Org. Biomol. Chem.* 2010, 8, 1310-1314) afforded F-18 in 39% yield from F-14. Treatment of F-18 with basic methanol caused removal of the acetyl groups and gave V in quantitative yield.

Scheme 18. Synthesis of V bearing indoxyl-glucosides, coumarin, and azide functionalities.

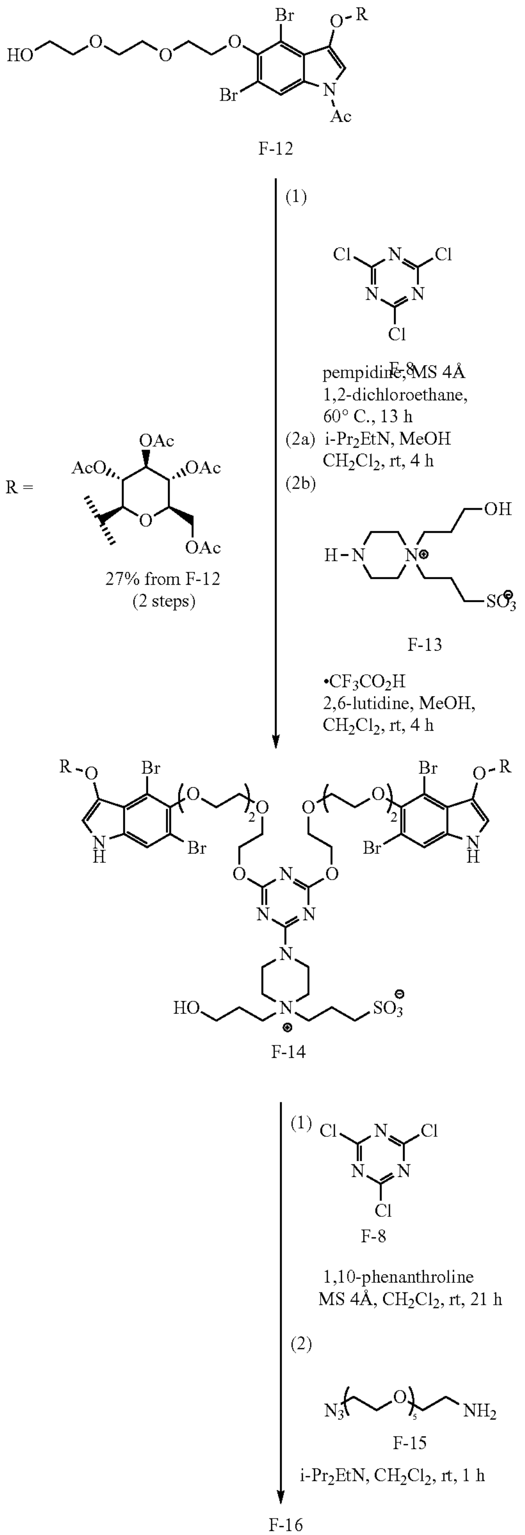

-continued

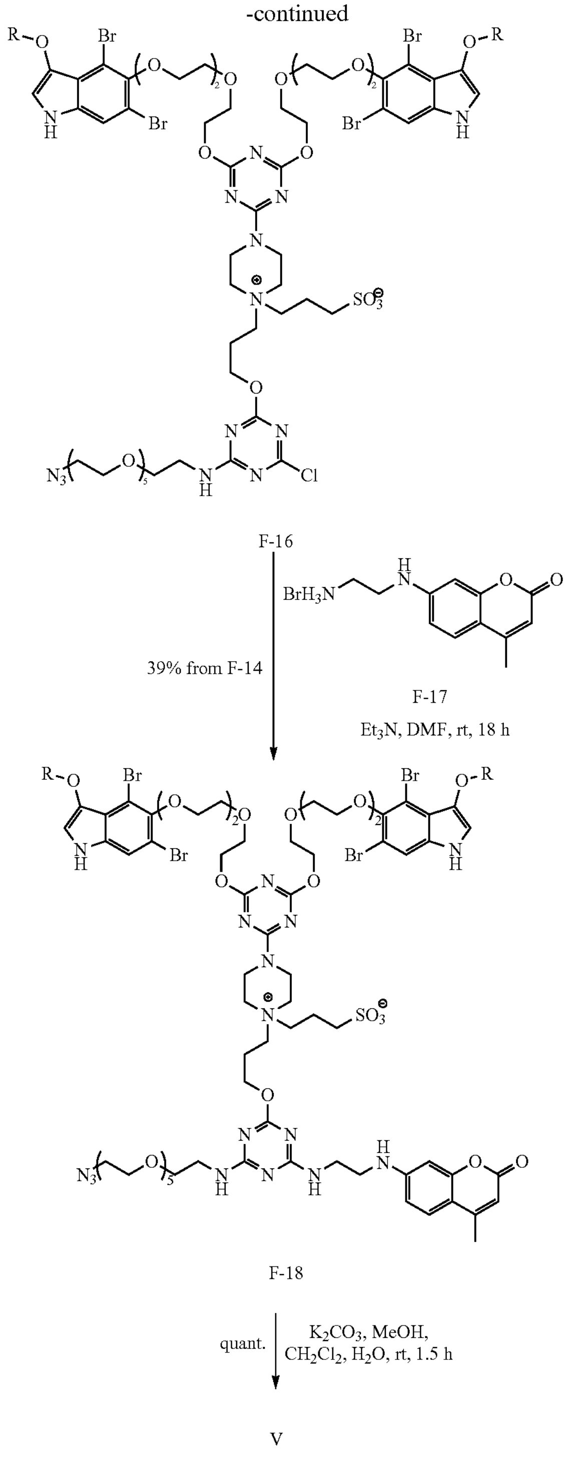

F-16

F-17

F-18

V

Oligomers of the Triazine-Based $A_2BC$ Construct.

Figure 13:
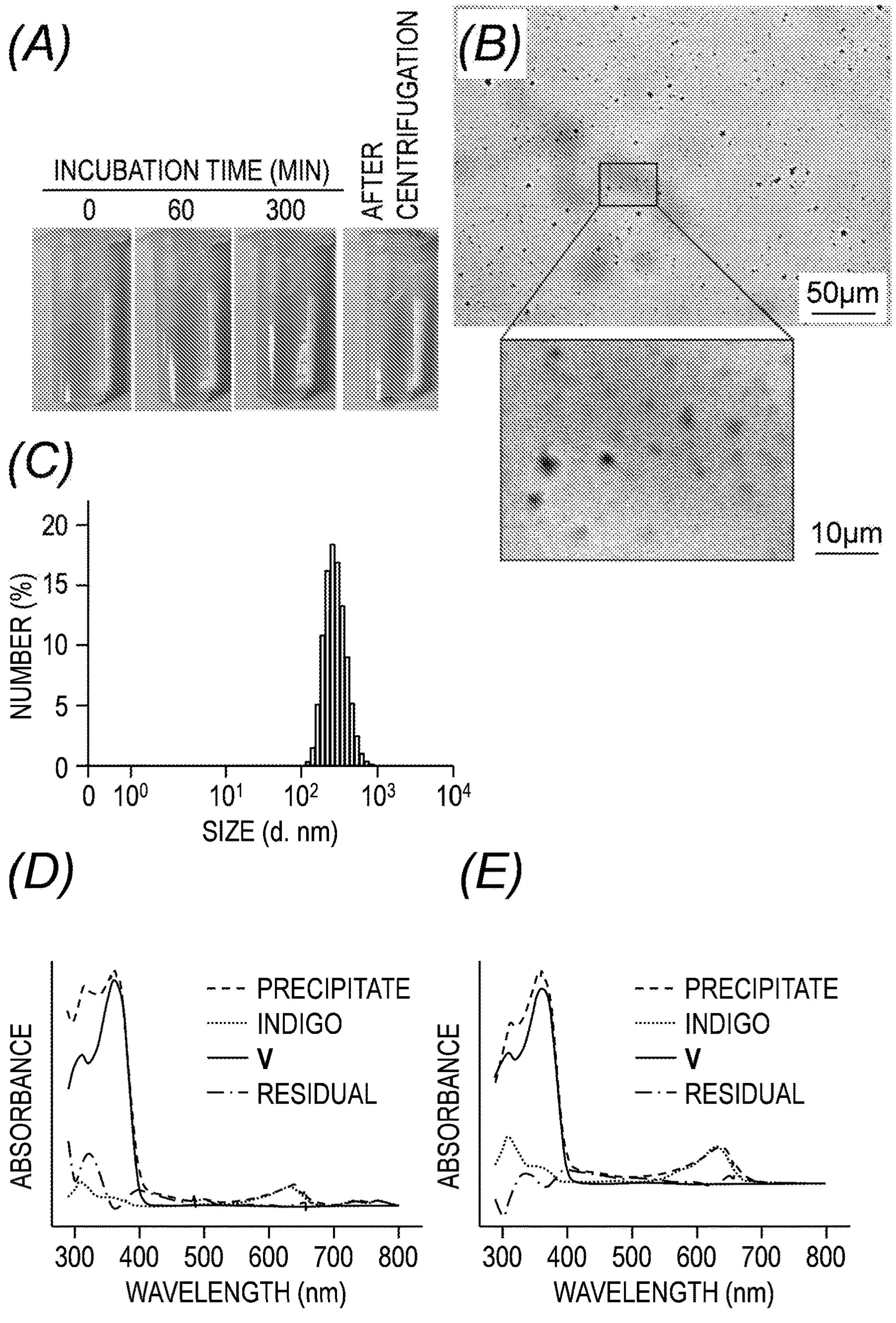
FIG. 13 shows images relating to the oligomerization of compound V upon enzymatic digestion with β-glucosidase. (A) Photographs of the reaction samples in a 300-min time course. (B) Optical microscopic image (×40) of the precipitate suspended in $H_2O$. (C) DLS analysis of the precipitate suspended in $H_2O$. (D) Absorption spectral MCA of the precipitate. (E) Absorption spectral MCA of the supernatant.
Figure 14:
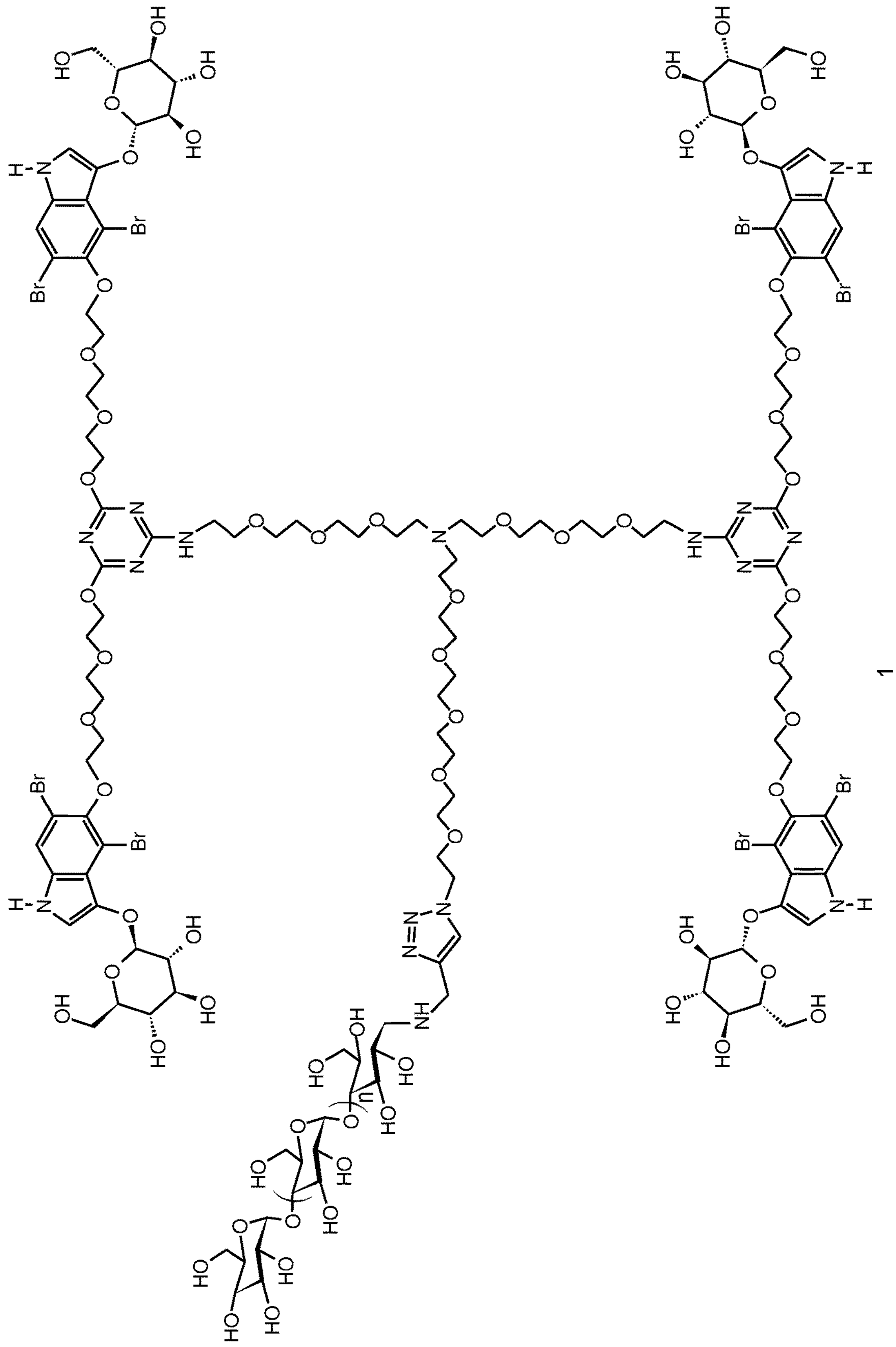
FIG. 14 shows the structure of tetrakis(indoxyl)amylose 1.

The oligomerization of compound V was examined by treatment with the enzyme □-glucosidase. The reaction mixture contained 50 μM of compound V and 200 nM of β-glucosidase (250-fold ratio). The reaction mixture was only faintly blue but upon centrifugation after 5 h of incubation, a blue precipitate was obtained. According to the colors of samples (FIG. 13, panel A), the yield of precipitate is low by comparison with our previously reported enzyme-substrate pairs (see Example 1). Multiple additions of enzyme (4×0.20 μM of enzyme stock, every 2 h) and longer incubation times (10 h or 24 h) were also tested but no increase in solution intensity or precipitate was observed. For the samples after 300 min of incubation, the precipitates suspended in $H_2O$ were screened by optical microscopy (FIG. 13, panel B) and DLS (FIG. 13, panel C). The size of aggregates is between 100 and 1000 nm as measured by DLS, which is consistent with the images obtained by optical microscopy (~1 μm).

Quantitation of the indigogenic compounds in the precipitate and supernatant was carried out by absorption spectroscopy and multicomponent analysis (MCA) (M. Taniguchi, et al., Photochem. Photobiol., 2018, 94, 277-289) (FIG. 13, panels D and E). MCA analysis is essential due to the overlaid spectra of indigo and coumarin at 362 nm, the peak wavelength for the coumarin. Spectral deconvolution relied on knowledge of the molar absorption coefficient at 362 nm of coumarin ($\varepsilon_{cou362}$=2.0×10$^4$ M$^{-1}$ cm$^{-1}$ measured in DMF) and indigo model compound F19 (see Example 1 where F-19 is compound 43) shown in Chart 2 ($\varepsilon_{ind362}$=0.81×10$^4$ M$^{-1}$ cm$^{-1}$ measured in DMSO/$H_2O$, v/v=2/1); and the molar absorption coefficient of F19 at 630 nm ($\varepsilon_{ind630}$=2.6×10$^4$ M$^a$ cm$^{-1}$, measured in DMSO/$H_2O$, v/v=2/1). The residual upon MCA was smaller than any of the components, as required for accurate analysis (Y. Mang, et al., Phytochem. Anal., 2018, 29, 205-216). In this manner, the precipitate is composed of 51.6 nmol of coumarin and 2.8 nmol of indigoid dye; the supernatant is composed of 11.1 nmol of coumarin and 0.3 nmol of indigoid dye.

The results obtained from the above analysis are as follows: (1) the total quantity of indigoid dye (3.1 nmol) corresponds to a yield of 3.1%; (2) the indigoid dye in the precipitate (2.8 nmol) is 10 times greater than that in the supernatant (0.3 nmol), hence aggregation ensued following the indigogenic reaction; (3) the total quantity of compound V added (100 nmol) exceeds the total amount of coumarin calculated by MCA (62.7 nmol) may stem from experimental error, loss on handling, and/or alteration of the molar absorption coefficients of the indigoid dye in DMF employed in the MCA method. Regardless, the extent of oligomerization was low, which may stem from toxicity of the substrate to the β-glucosidase or aggregation of compound V prior to or during the course of enzymatic action. Further studies are required to better understand the origin of this result.

Chart 2. Indigoid dye model compound (see Example 1).

F-19

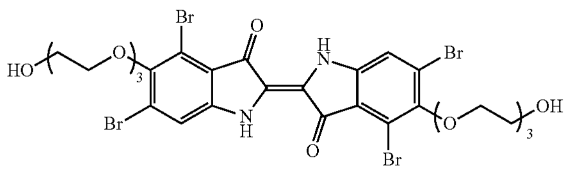

Experimental Section

Oligomerization of Compound V.

Materials. DMF (HPLC grade) was purchased from Alfa Aesar. $H_2O$ (molecular biology grade) for buffer preparation was purchased from Millipore Sigma. Compound V (5.6 mg) was dissolved in DMF (26 μL) to prepare 100 mM stock solution. Pi buffer was prepared freshly at 10 mM, pH 7. The enzyme β-glucosidase from *Agrobacterium* sp. was purchased from MegaZyme and was dissolved in Pi buffer at 10 μM to prepare the stock solution.

The stock solution of compound V was 1000-fold and 2000-fold diluted with DMF for absorption screening, by which the molar absorption coefficients were estimated: $\varepsilon_{310}$ nm=$1.37\times10^4$ $M^{-1}cm^{-1}$, $\varepsilon_{362}$ nm=$2\times10^4$ $M^{-1}cm^{-1}$. The absorption coefficient of compound V in Pi buffers (containing 1-5% DMF with 1% DMSO) was not obtained due to aggregation.

To screen the oligomerization procedure of compound V, samples of Pi buffer (1859 μL), DMF (100 μL), β-glucosidase stock (40 μL) and compound V stock (1 μL) were mixed in a 2-mL Eppendorf tube. The resulting mixed sample (2.0 mL) contains 50 μM of compound V as the substrate and 0.20 μM of β-glucosidase as the enzyme. Three identical samples were prepared for different assays. For a control sample, 40 μL of Pi buffer was added as a replacement for the β-glucosidase stock solution. The tubes were incubated at 37° C. for 5 h, and pictures of the tubes were captured at 0, 15, 30, 60, 120, 180 and 300 min. After 300 min, the tubes were centrifuged at 20,000×g for 10 min to isolate any precipitate from the supernatant. No precipitate formed in the control sample.

Three samples were treated differently for three assays: (1) for sample 1, the precipitate was dissolved in 100 μL of DMF for absorption screening; (2) for sample 2, the precipitate was suspended in 100 μL of $H_2O$ for microscopic imaging; and (3) for sample 3, the precipitate was suspended in 1000 μL of $H_2O$ for dynamic light scattering (DLS) assay. The supernatant of sample 1 was freeze-dried under high vacuum and afterwards dissolved in 100 μL of DMF for absorption screening. The absorption spectra of the precipitates and supernatants were employed for quantitation of indigo and coumarin.

Microscopic imaging of the suspended aggregates was carried out using a Zeiss Axio Observer Z1 inverted microscope with 40× objective lens in the phase contrast mode. DLS assay was carried out with a Malvern Zetasizer Nano. Multicomponent analysis (MCA) was carried out using the software PhotoChemCAD 3 (M. Taniguchi, et al., *Photochem. Photobiol.,* 2018, 94, 277-289) with the following parameters: Range: 290-700 nm, Selected points: 362, 576 and 631 nm.

General. $^1H$ NMR (400 MHz) and $^{13}C$ NMR (175 MHz) spectra were collected at room temperature unless noted otherwise. Silica (40 μm) was used for column chromatography. All solvents were reagent grade and were used as received unless noted otherwise. Commercial compounds were used as received. Known compounds (F-12-F-14 (see Example 1), F-7 (see Example 1), F-10 (K. A. Keller, et al., Tetrahedron Lett., 2005, 46, 1181-1184), and F-17 (Y. Shiraishi, et al., Org. Biomol. Chem. 2010, 8, 1310-1314)) were prepared as described in the literature. Cyanuric chloride (F-8) was recrystallized from hexanes/$CH_2Cl_2$ before use. Silica gel (40 μm) and Diol-functionalized silica gel (40-63 μm) were used for column chromatography. Preparative TLC separations were carried out on Merck analytical plates precoated with silica gel 60 $F_{254}$.

1-Acetyl-5-(benzyloxy)-1H-indole-3-carbaldehyde (F-2) (A. Andreani, et al., J. Med. Chem., 2001, 44, 4011-4014). 4-Dimethylaminopyridine (104.9 mg, 0.86 mmol) was added to a suspension of 5-(benzyloxy)-1H-indole-3-carbaldehyde (F-1, 21.57 g, 85.8 mmol), triethylamine (23.9 mL, 171 mmol), and $Ac_2O$ (16.2 mL, 171 mmol) in $CH_2Cl_2$ (215 mL) at room temperature. After 40 min, the reaction mixture was washed with aqueous HCl (2 M, 200 mL), saturated aqueous $NaHCO_3$ (100 mL), and brine (100 mL). The organic layer was dried ($Na_2SO_4$) and filtered. The filtrate was concentrated and chromatographed [silica, $CH_2Cl_2$/ethyl acetate (40:1)] to afford a pale brown solid (20.44 g, 81%): mp 120-121° C.; 1H NMR (400 MHz, $CDCl_3$) δ 2.58 (s, 3H), 5.08 (s, 2H), 7.04 (d, J=8.0 Hz, 1H), 7.20-7.60 (m, 5H), 7.75 (s, 1H), 7.82 (s, 1H), 8.19 (d, J=8.0 Hz, 1H), 9.99 (s, 1H); $^{13}C$ NMR (100 MHz, $CDCl_3$) δ 23.5, 70.4, 105.1, 116.3, 117.2, 122.2, 127.0, 127.7, 128.0, 128.6, 130.9, 135.6, 136.9, 156.8, 168.3, 185.6; ESI-MS obsd 294.1126, calcd 294.1125 [(M+H)$^+$, M=$C_{18}H_{15}NO_3$].

1-Acetyl-5-(benzyloxy)indolin-3-one (F-3) (C. D. Nenitzescu and D. Râileanu, Chem. Ber., 1958, 91, 1141-1145). Peracetic acid (32 wt % solution in acetic acid, 17.4 mL, 73.3 mmol) was added to a suspension of F-2 (21.5 g, 73.3 mmol) and sodium acetate (12.0 g, 146 mmol) in toluene (293 mL) at 0° C. The reaction mixture was stirred at 0° C. for 30 min followed by room temperature for 18 h. The reaction mixture was quenched by the addition of aqueous $Na_2S_2O_3$ (10%, 100 mL) and filtered through Celite. The filtrate was washed with saturated aqueous $NaHCO_3$ (200 mL) and brine (100 mL), dried ($Na_2SO_4$), and filtered. The filtrate was concentrated and chromatographed [silica, $CH_2Cl_2$/ethyl acetate (25:1)] to afford recovered F-2 (8.94 g, 42%) and the title compound as a pale yellow solid (6.61 g, 32%): mp 163-164° C.; $^1H$ NMR (300 MHz, $CDCl_3$) δ 2.26 (s, 3H), 4.24 (s, 2H), 5.04 (s, 2H), 7.17 (d, J=2.1 Hz, 1H), 7.26-7.46 (m, 6H), 8.46 (d, J=9.3 Hz, 1H); $^{13}C$ NMR (75 MHz, $CDCl_3$) δ 24.0, 56.6, 70.5, 105.8, 119.8, 125.7, 126.8, 127.6, 128.3, 128.7, 136.2, 148.8, 155.6, 167.6, 194.5; ESI-MS obsd 282.1125, calcd 282.1125 [(M+H)$^+$, M=$C_{17}H_{15}NO_3$].

1-Acetyl-5-benzyloxy-1H-indol-3-yl 2,3,4,6-tetra-O-acetyl-β-D-glucopyranoside (F-5). A sample of $HgBr_2$ (0.937 g, 0.65 mmol) was added to a mixture of F-3 (3.657 g, 13.0 mmol), acetobromo-α-D-glucose (F-4, 10.69 g, 26.0 mmol), HgO (2.816 g, 13.0 mmol), powdered molecular sieves 4 Å (26.0 g), and toluene/$MeNO_2$ (2:1, 130 mL) at room temperature. After 11 h, acetobromo-α-D-glucose (2.673 g, 6.5 mmol) was added. After 3 h, the reaction mixture was treated with pyridine (3.1 mL, 39 mmol) and filtered. The filtrate was concentrated and chromatographed [silica, hexanes/acetone (7:3)] to afford a white solid (6.98 g, 88%): mp 146-149° C.; $^1H$ NMR (700 MHz, $CDCl_3$) δ 2.05 (s, 3H), 2.06 (s, 3H), 2.07 (s, 3H), 2.08 (s, 3H), 2.58 (s, 3H), 3.83-3.89 (m, 1H), 4.22-4.30 (m, 2H), 5.01 (d, J=6.0 Hz, 1H), 5.07-5.15 (m, 2H), 5.15-5.22 (m, 1H), 5.28-5.35 (m, 2H), 7.01 (s, 1H), 7.06 (d, J=9.0 Hz, 1H), 7.11 (br s, 1H), 7.30-7.36 (m, 1H), 7.36-7.43 (m, 2H), 7.43-7.48 (m, 2H), 8.33 (br s, 1H); $^{13}C$ NMR (100 MHz, $CDCl_3$) δ 20.65, 20.68, 20.8, 23.8, 62.1, 68.3, 70.6, 71.2, 72.5, 72.6, 100.8, 101.7, 110.4, 115.7, 117.7, 125.0, 127.6, 128.1, 128.5, 128.7, 137.0, 141.4, 155.7, 167.9, 169.3, 169.5, 170.2, 170.6; ESI-MS obsd 612.2071, calcd 612.2076 [(M+H)$^+$, M=$C_{31}H_{33}NO_{12}$]. Suitable crystals for X-ray analysis were obtained by recrystallization (hexanes/$CH_2Cl_2$).

2,4-Bis[3-(β-D-glucopyranosyloxy)-1H-indol-5-yloxy]-6-[2-(4-hydroxyphenyl)ethylamino]-1,3,5-triazine (F-9). Ethyldiisopropylamine (87.1 μL, 0.500 mmol) was added to a suspension of cyanuric chloride (F-8, 36.9 mg, 0.200 mmol) and F-7 (130.7 mg, 0.420 mmol) in MeCN (1.00 mL) at 0° C. After 10 min, DMF (0.40 mL) was added at 0° C. Then the reaction mixture was allowed to warm to rt and stirred for additional 2 h. Tyramine (30.2 mg, 0.220 mmol) and ethyldiisopropylamine (69.7 μL, 0.400 mmol) was added. After 19 h, the reaction mixture was treated with AcOH (23 μL, 0.40 mmol) and concentrated under reduced pressure. Column chromatography [diol-functionalized silica gel, $CH_2Cl_2$/MeOH (6:4)] followed by washing with $H_2O$ afforded a pale yellow solid (94.1 mg, 56%): $^1$H NMR [400 MHz, $CD_3OD$] δ 2.31-2.52 (m, 2H), 3.06 (t, J=7.8 Hz, 2H), 3.05-3.17 (m, 1H), 3.24-3.56 (m, 7H), 3.62-3.78 (m, 2H), 3.78-3.96 (m, 2H), 4.64 (d, J=8.0 Hz, 1H), 4.68 (d, J=7.6 Hz, 1H), 6.35-6.48 (m, 4H), 6.90 (dd, J=2.0, 8.8 Hz, 1H), 6.94 (dd, J=2.0, 8.8 Hz, 1H), 7.18 (s, 1H), 7.24 (s, 1H), 7.29 (d, J=8.8 Hz, 1H), 7.34 (d, J=8.8 Hz, 1H), 7.51 (d, J=2.0 Hz, 1H), 7.56 (d, J=2.0 Hz, 1H); $^{13}$C NMR (100 MHz, $CD_3OD$) δ 35.6, 44.4, 62.5, 62.6, 70.0, 71.3, 71.5, 75.0, 77.9, 78.0, 78.2, 106.1, 111.0, 112.9, 114.4, 115.0, 116.1, 117.3, 117.5, 121.6, 121.7, 130.7, 131.0, 133.05, 133.15, 139.18, 139.21, 146.5, 146.8, 156.4, 169.3, 174.1, 174.6, ESI-MS obsd 835.2756, calcd 835.2781 $[(M+H)^+$, $M=C_{39}H_{42}N_6O_{15}]$ 2,4-Bis[3-(β-D-glucopyranosyloxy)-1H-indol-5-yloxy]-6-[2-(4-(2-(6-maleimidohexyloxy)-6-chloro-1,3,5-triazin-4-yloxy)phenyl)ethylamino]-1,3,5-triazine (F-11). Cyanuric chloride (F-8, 16.6 mg, 0.0900 mmol) was added to a suspension of N-(6-hydroxyhexyl)maleimide (F-10, 21.3 mg, 0.108 mmol), 1,10-phenanthroline (27.0 mg, 0.150 mmol), and molecular sieves 3 Å (45.0 mg) in MeCN (450 μL) at rt. After 12 h, F-9 (50.1 mg, 0.0600 mmol), DMF (180 μL), and ethyldiisopropylamine (31.4 μL, 0.180 mmol) were added. After additional 5 h, the reaction mixture was directly chromatographed [diol-functionalized silica gel, $CH_2Cl_2$/MeOH (17:3)] to afford a yellow solid (53.0 mg, 77%): 1H NMR [400 MHz, $CD_3OD$] δ 1.18-1.40 (m, 4H), 1.44-1.59 (m, 2H), 1.60-1.74 (m, 2H), 2.47-2.66 (m, 2H), 3.08-3.53 (m, 12H), 3.66 (dd, J=5.2, 12.0 Hz, 1H), 3.72 (dd, J=5.2, 12.0 Hz, 1H), 3.81 (dd, J=2.4, 12.0 Hz, 1H), 3.90 (dd, J=2.4, 12.0 Hz, 1H), 4.30 (t, J=6.8 Hz, 2H), 4.57 (d, J=7.2 Hz, 1H), 4.68 (d, J=7.2 Hz, 1H), 6.66 (d, J=8.4 Hz, 2H), 6.76 (s, 2H), 6.82 (d, J=8.4 Hz, 2H), 6.91 (dd, J=2.0, 8.8 Hz, 1H), 6.97 (dd, J=2.0, 8.8 Hz, 1H), 7.18 (s, 1H), 7.21 (s, 1H), 7.30 (d, J=8.8 Hz, 1H), 7.34 (d, J=8.8 Hz, 1H), 7.51 (d, J=2.0 Hz, 1H), 7.57 (d, J=2.0 Hz, 1H); $^{13}$C NMR (100 MHz, $CD_3OD$/$CD_3CN$) δ 26.0, 27.1, 29.1, 29.2, 35.6, 38.4, 43.8, 62.5, 62.6, 70.6, 71.2, 71.3, 74.8, 74.9, 77.76, 77.80, 77.9, 78.0, 105.77, 105.80, 110.8, 110.9, 113.0, 114.1, 114.4, 117.4, 117.7, 118.3, 138.5, 139.0, 139.1, 146.4, 146.7, 151.2, 169.4, 172.6, 173.5, 173.6, 173.7, 174.0, 174.5; ESI-MS obsd 1143.3450, calcd 1143.3457 $[(M+H)^+$, $M=C_{52}H_{55}ClN_{10}O_{18}]$ 2,4-Bis[1-(3-(2,3,4,6-tetra-O-acetyl-β-D-glucopyranosyloxy)-4,6-dibromo-1H-indol-5-yl)-1,4,7,10-tetraoxadec-10-yl]-6-[14-(3-(2-(1-azido-3,6,9,12,15-pentaoxoheptadecylamino)-4-[2-((4-methyl-2H-chromen-2-one-7-yl)amino) ethylamino]-1,3,5-triazin-6-yloxy)propyl)-4-(3-sulfopropyl)piperazin-1-yl]-1,3,5-triazine (F-18). A sample of F-8 (4.4 mg, 0.024 mmol) was added to a suspension of F-14 (37.6 mg, 0.020 mmol), 1,10-phenanthroline (9.0 mg, 0.050 mmol), and molecular sieves 4 Å (10 mg) in $CH_2Cl_2$ (100 μL) at room temperature. After 21 h, F-15 (7.8 μL, 0.028 mmol) and i-$Pr_2$EtN (10.5 μL, 0.060 mmol) were added. After 22 h, the reaction mixture was diluted with $CH_2Cl_2$ (2 mL), filtered, washed with aqueous citric acid (10%, 2 mL) and brine (2 mL), dried ($Na_2SO_4$), and filtered. The filtrate was concentrated under reduced pressure to afford the crude F-16 (2,4-bis[1-(3-(2,3,4,6-tetra-O-acetyl-β-D-glucopyranosyloxy)-4,6-dibromo-1H-indol-5-yl)-1,4,7,10-tetraoxadec-10-yl]-6-[4-(3-(2-(1-azido-3,6,9,12,15-pentaoxoheptadecylamino)-4-chloro-1,3,5-triazin-6-yloxy) propyl)-4-(3-sulfopropyl)piperazin-1-yl]-1,3,5-triazine), which was used as is in the next step. A sample of F-17 (12.0 mg, 0.040 mmol), DMF (100 μL), and $Et_3N$ (22 μL, 0.16 mmol) were added to the residue at room temperature. After 18 h, the reaction mixture was diluted with $CH_2Cl_2$ (2 mL) and filtered. The filtrate was washed with aqueous citric acid (10%, 2 mL) and brine (2 mL), dried ($Na_2SO_4$), and filtered. The filtrate was concentrated under reduced pressure. Column chromatography [silica, $CH_2Cl_2$/MeOH (15:1 to 9:1] afforded a pale brown solid (19.4 mg, 39%): $^1$H NMR ($CDCl_3$, 400 MHz, mixture of rotamers) δ 1.70-1.90 (m, 2H), 1.95-2.17 (m, 26H), 2.29 (s, 3H), 2.93 (br s, 2H), 3.10-4.60 (m, 73H), 4.81-4.98 (m, 2H), 5.05-5.40 (m, 6H), 5.73-6.05 (m, 3H), 6.38-6.65 (m, 2H), 6.88 (br s, 1H), 7.14 (s, 2H), 7.50-7.68 (m, 2H), 10.13 (br s, 2H); $^{13}$C NMR ($CDCl_3$, 175 MHz, mixture of rotamers) δ 18.2, 18.7, 20.8, 21.2, 21.4, 36.9, 39.6, 39.8, 40.6, 40.7, 40.8, 43.0, 43.2, 43.3, 47.26, 47.32, 47.5, 50.8, 53.6, 56.4, 58.3, 62.0, 62.7, 67.1, 68.5, 69.2, 69.8, 70.1, 70.4, 70.6, 70.66, 70.71, 70.73, 70.9, 71.1, 72.0, 72.5, 73.1, 97.5, 101.3, 106.4, 108.48, 108.55, 109.9, 110.5, 111.8, 115.1, 115.7, 118.4, 125.6, 131.5, 136.5, 145.7, 152.1, 152.3, 153.7, 153.8, 156.0, 162.3, 166.4, 166.6, 166.8, 167.0, 167.2, 169.6, 169.7, 169.9, 170.3, 170.8, 171.7; ESI-MS obsd 1238.2465, calcd 1238.2484 $[(M+2H)^{2+}$, $M=C_{96}H_{126}Br_4N_{16}O_{39}S]$.

2,4-Bis[1-(3-(β-D-glucopyranosyloxy)-4,6-dibromo-1H-indol-5-yl)-1,4,7,10-tetraoxadec-10-yl]-6-[14-(3-(2-(1-azido-3,6,9,12,15-pentaoxoheptadecylamino)-4-[12-((4-methyl-2H-chromen-2-one-7-yl)amino)ethylamino]-1,3,5-triazin-6-yloxy)propyl)-4-(3-sulfopropyl)piperazin-1-yl]-1,3,5-triazine (V). $K_2CO_3$ (0.9 mg, 7 μmol) was added to a solution of F-18 (15.9 mg, 6.4 μmol) in MeOH/$CHCl_3$ (4:1, 916 μL) at room temperature. After 30 min, $H_2O$ (366 μL) was added. After 1.5 h, the reaction mixture was diluted with $CH_2Cl_2$ (2 mL), dried ($Na_2SO_4$), and passed through a silica pad [diol-functionalized silica, $CH_2Cl_2$/MeOH (2:1) as an eluent]. The eluent was concentrated under reduced pressure to afford a pale yellow solid (13.7 mg, 100%): $^1$H NMR ($CDCl_3$, 400 MHz) δ 2.09 (br s, 2H), 2.15 (br s, 2H), 2.25-2.33 (m, 3H), 2.54-2.63 (m, 2H), 3.14 (t, J=9.1 Hz, 2H), 3.18-4.43 (m, 76H), 4.64 (d J=7.3 Hz, 2H), 5.85-5.95 (m, 1H), 6.40-6.66 (m, 2H), 7.21 (s, 2H), 7.36-7.47 (m, 1H), 7.55 (s, 2H); $^{13}$C NMR (DMSO-$d_6$, 175 MHz, mixture of rotamers) δ 17.9, 18.1, 20.8, 36.9, 47.3, 47.4, 48.6, 50.0, 52.9, 57.1, 57.2, 61.0, 66.5, 68.5, 68.8, 68.9, 69.3, 69.48, 69.54, 69.59, 69.64, 69.7, 69.8, 69.9, 70.0, 70.1, 72.4, 73.6, 76.9, 77.2, 103.4, 106.2, 107.5, 108.9, 110.5, 113.3, 114.9, 117.9, 126.0, 131.0, 137.4, 144.8, 152.4, 153.8, 153.86, 153.91, 155.7, 155.76, 155.80, 160.8, 160.9, 166.4, 166.7, 167.1, 169.8, 171.5; ESI-MS obsd 1070.2073, calcd 1070.2061 $[(M+2H)^{2+}$, $M=C_{80}H_{110}Br_4N_{16}O_{31}S]$.

Example 5

A compound, tetrakis(indoxyl)amylose (FIG. 12), including four glucose units as the protecting groups, four 4,6-dibromoindoxyls as the cross-linking groups, a three-arm PEG and two triazines as the core molecular junction, and an amylose for binding iodine was prepared. The compound numbers referred to in this example are specific for the compounds described in this example and do not refer to those in another example, unless indicated otherwise.

Synthesis of tetrakis(indoxyl)amylose started with the synthesis of a monochlorotriazine bearing two cross-linking units 4 as shown in Scheme 17.

Scheme 17. Synthesis of monochlorotriazine bearing two cross-linking units 4.

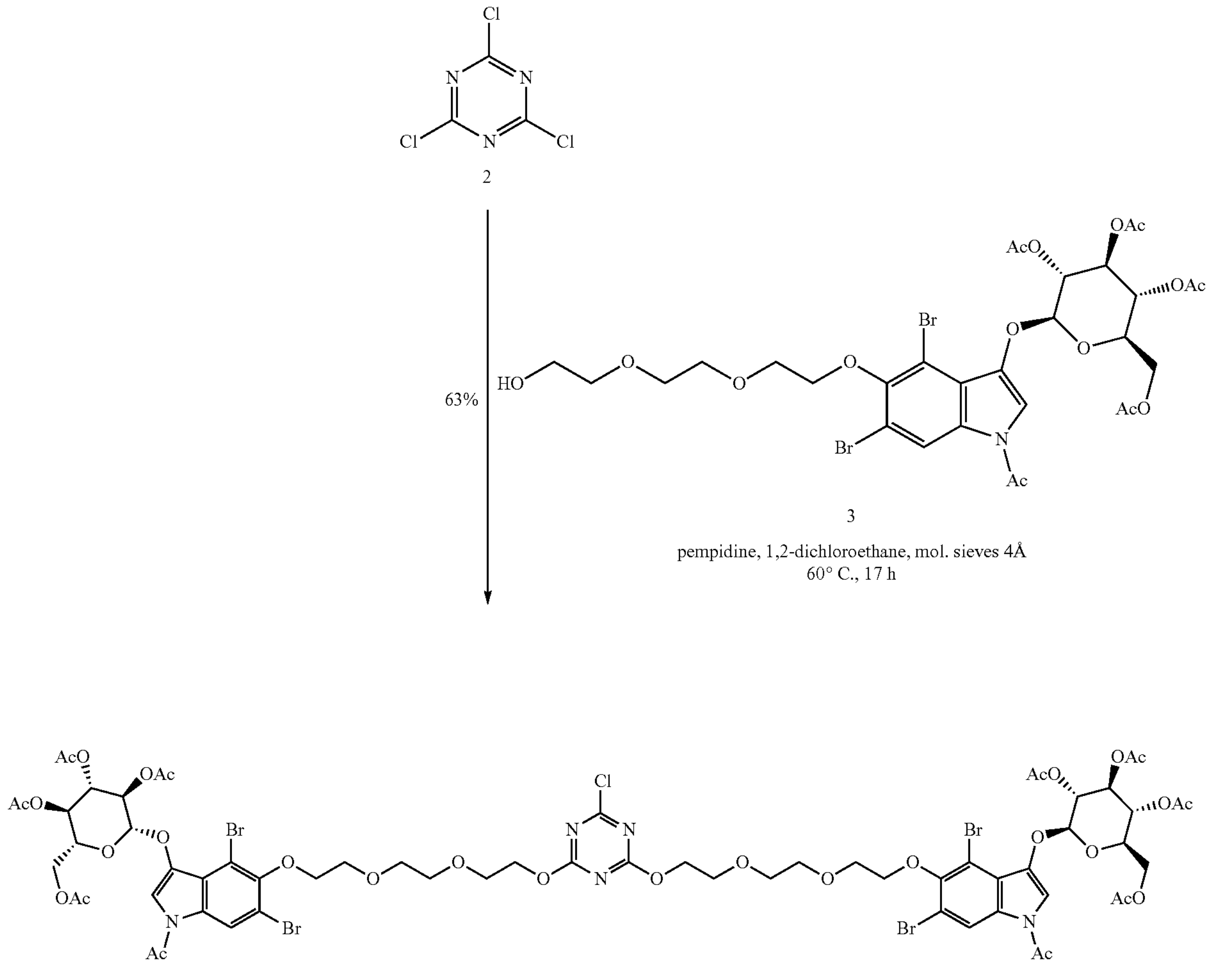

2

3

4

A solution of commercially available cyanuric chloride (2) in 1,2-dichloroethane was treated with 3 in the presence of pempidine (Fujita, H., et al., *New J. Chem.* 2020, 44, 719-743) and powdered molecular sieves 4 Å at 60° C. to give chlorotriazine 4 in 63% yield (Scheme 17).

Derivatization of the reducing terminus of amylose is established (Noga, M., et al., *J. Control. Release* 2012, 159, 92-103; Rachmawati, R., et al., *Macromol. Chem. Phys.* 2015, 216, 1091-1102). A sample of amylose (5) was dissolved in 1 M NaOH, and then treated with 1 M HCl to generate neutral solution. After addition of 100 mM acetate buffer (pH 5.0) (Schatz, C., et al., *Angew. Chem. Int. Ed. Engl.* 2009, 48, 2572-2575), the solution was treated with propargylamine and $NaBH_3CN$ to obtain reductively aminated amylose 6 in 71% yield Scheme 18. Synthesis of clickable alkyne amylose 6.

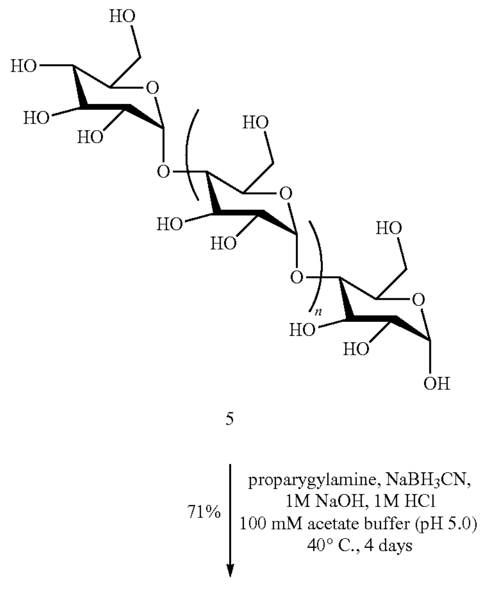

5

-continued

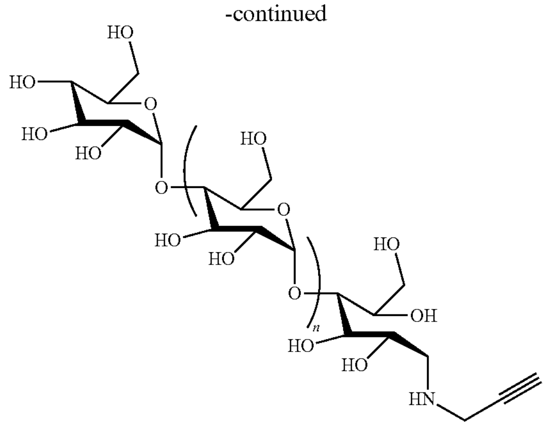

6

The two anomeric proton peaks of 5 were not present in the $^1$H NMR spectrum of 6, which indicated that the reductive amination was successful since the doublet of the amylose anomeric protons (alpha and beta forms) is lost upon reductive amination.

The commercially available NH-bis($PEG_3$-Boc) (7) was treated with bromo-$PEG_5$-azide (8) in the presence of $Et_3N$ to obtain the Boc-protected three-arm PEG core 9 in 31% yield (Scheme 19). After deprotection of the Boc groups of 9 with 4 M hydrogen chloride in dioxane, the resulting diamine was treated with 4 in the presence of DIEA to provide fully protected tetrakis(indoxyl-glycosides) 10 in 31% yield.

Scheme 19. Synthesis of fully protected tetrakis(indoxyl-glycosides) 10.

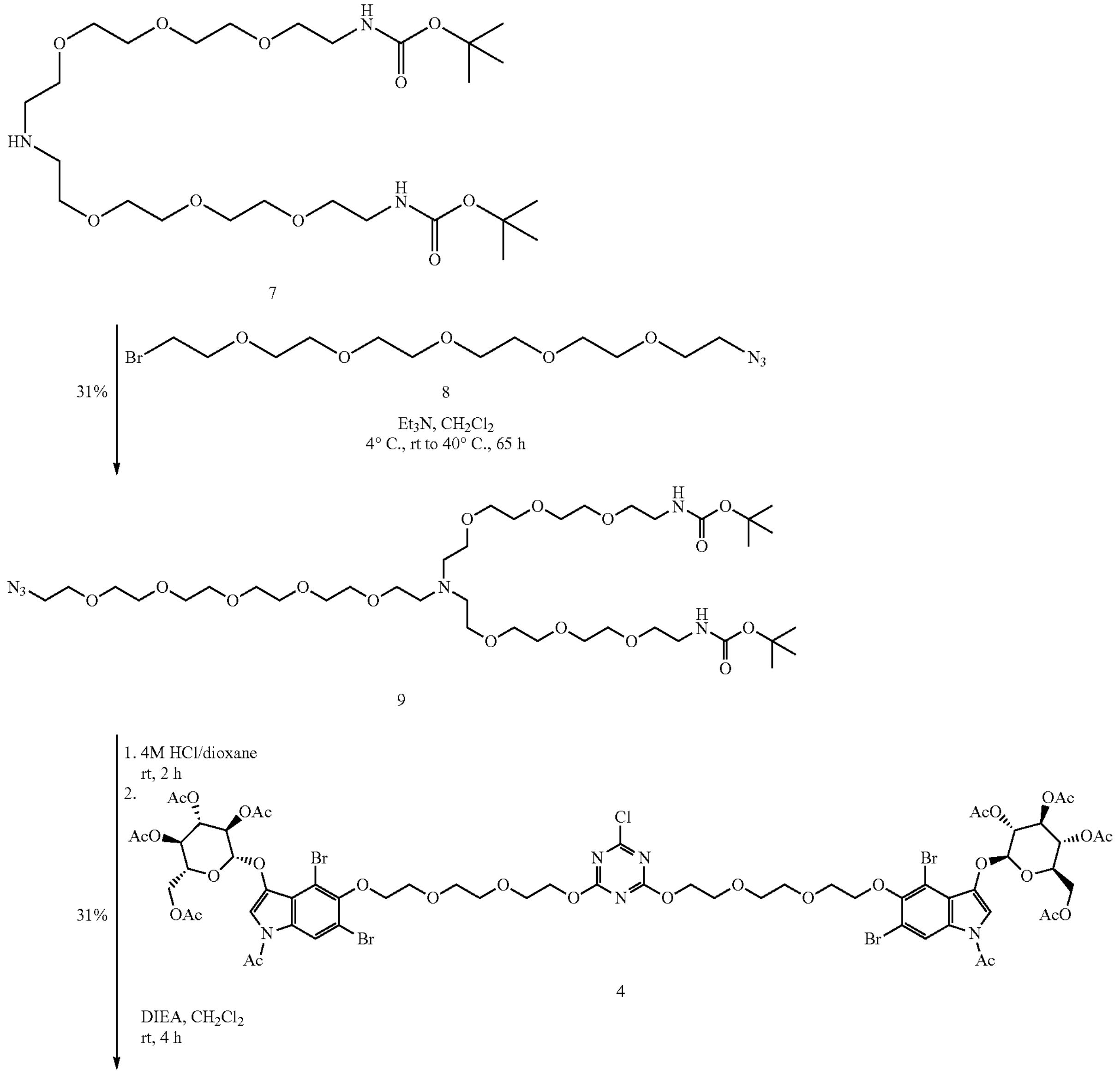

-continued
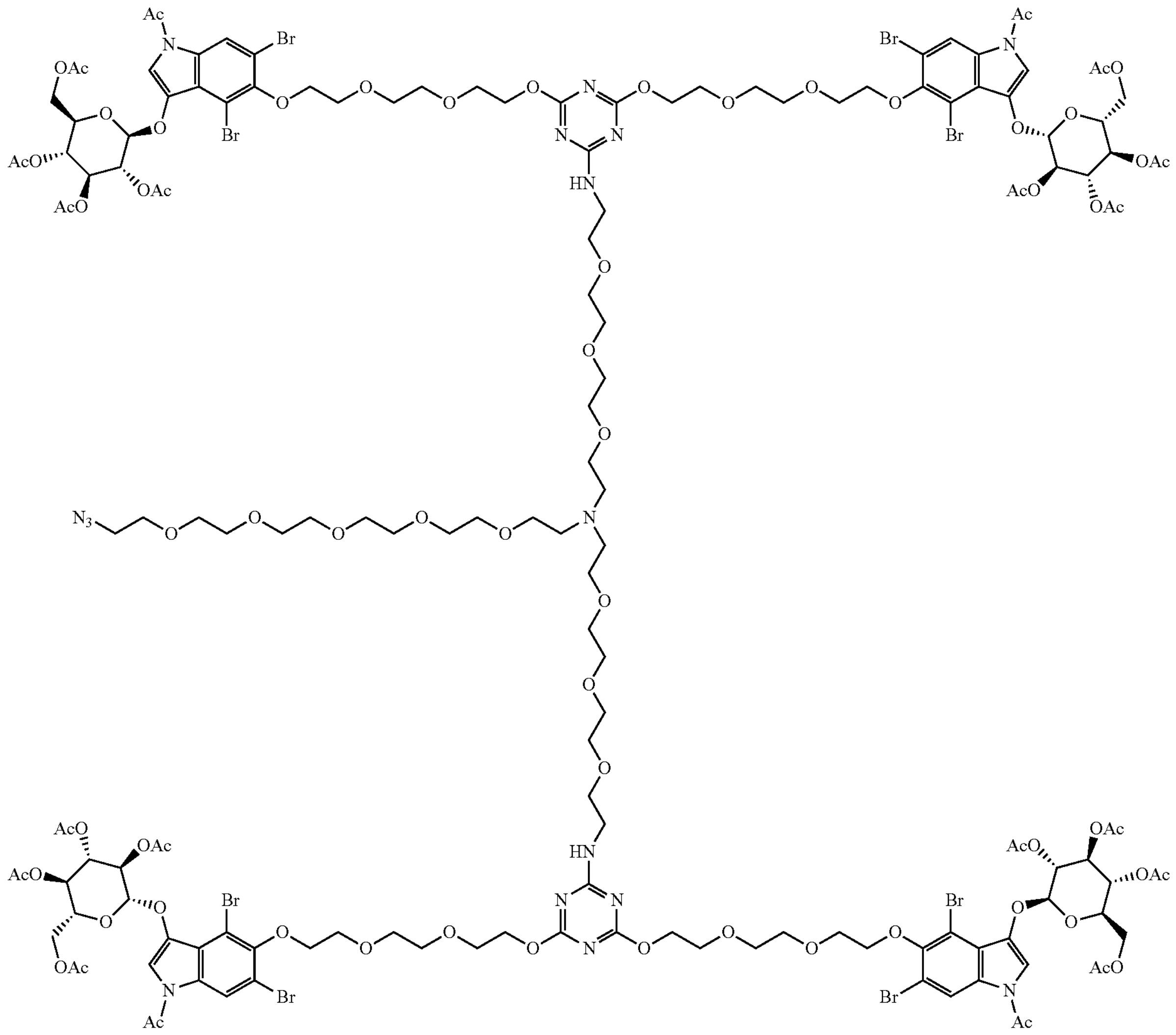
10

Deprotection of all acetyl groups of 10 by $Et_3N$ afforded free tetrakis(indoxyl-glycosides) 11 in quantitative yield (Scheme 20).
Scheme 20. Deacetylation of fully protected tetrakis(indoxyl-glycosides) 10.
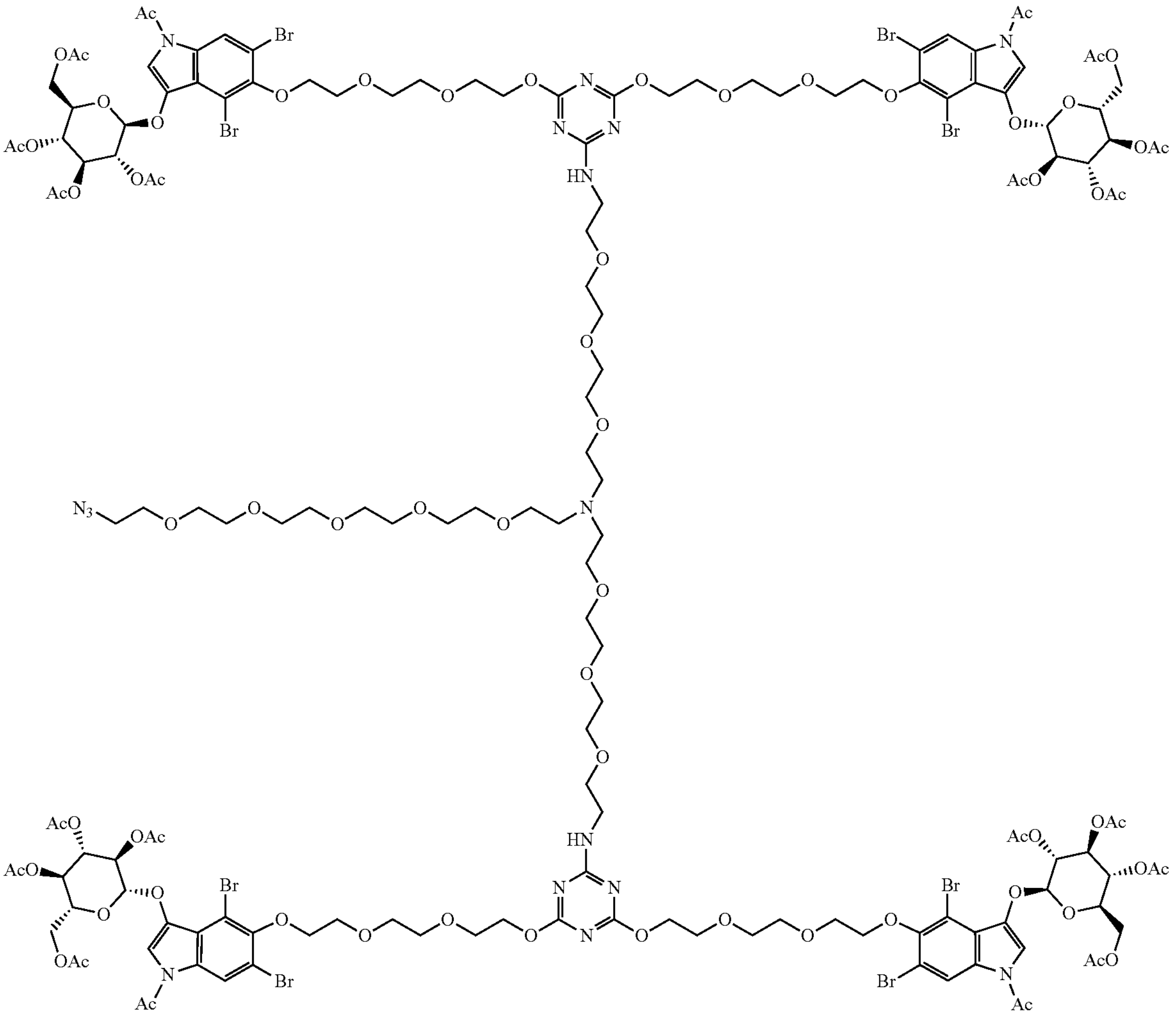
10
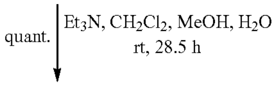

-continued
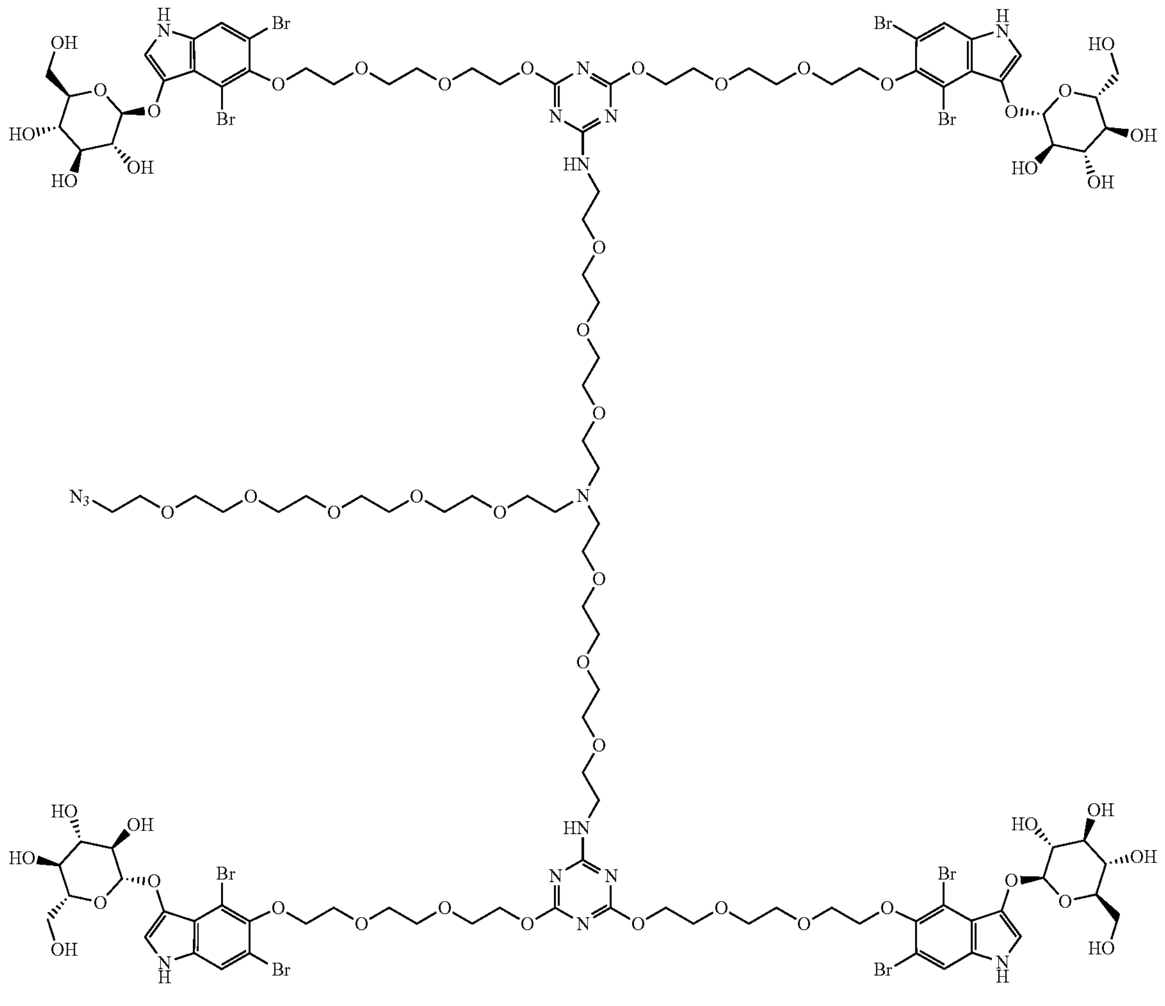
11

Finally, alkyne amylose 6 was conjugated to the tetrakis (indoxyl-glycosides) 11 via click chemistry to obtain tetrakis (indoxyl)amylose 1 (Scheme 21).
Scheme 21. Conjugation of alkyne amylose 6 to enzymatically triggered cross-linking unit 11.
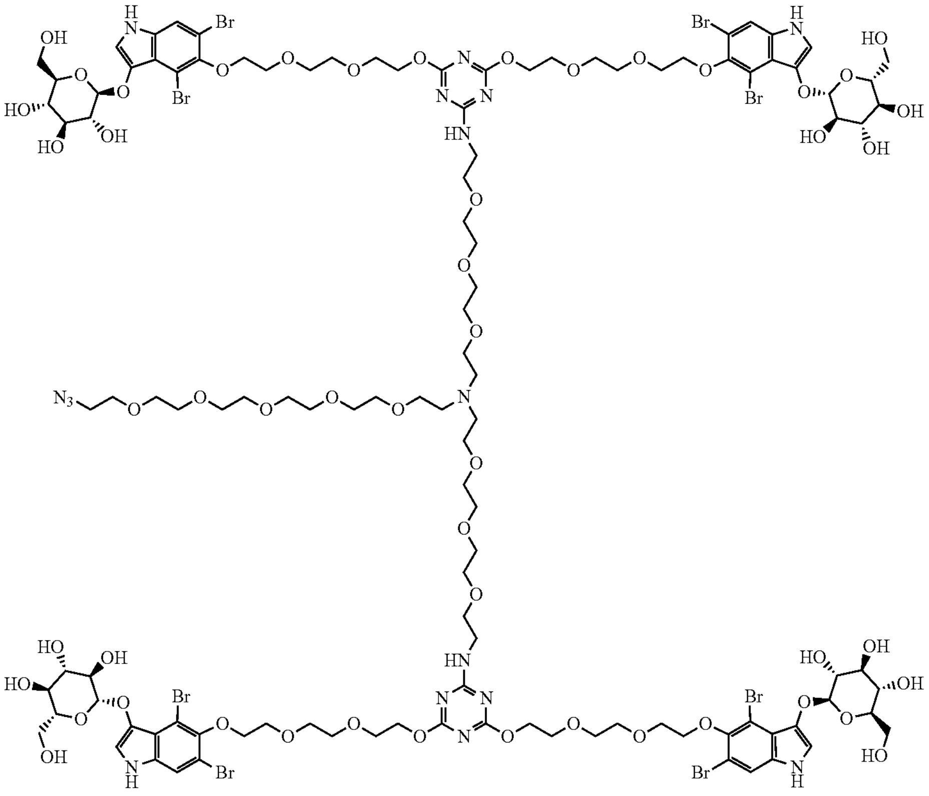
11
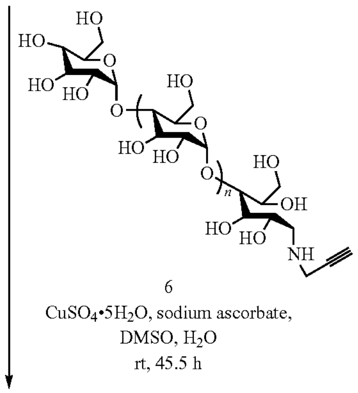
6
CuSO$_4$•5H$_2$O, sodium ascorbate, DMSO, H$_2$O
rt, 45.5 h -continued

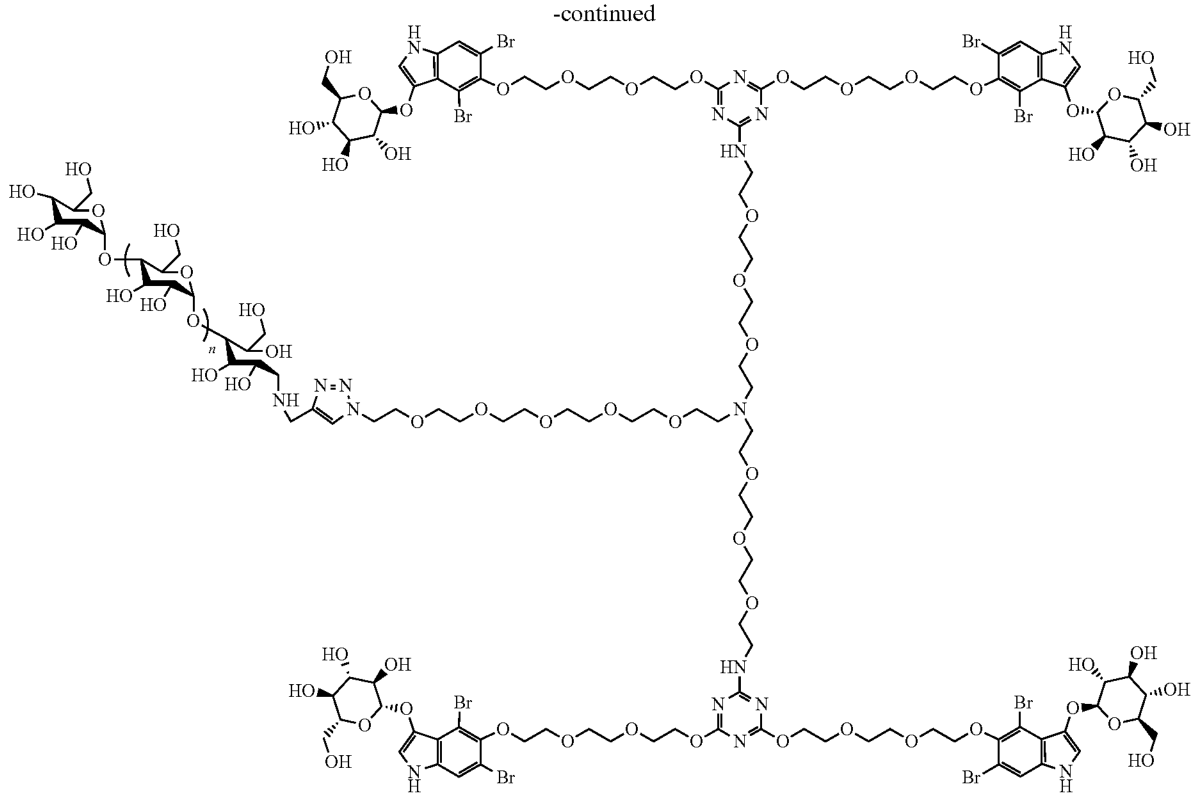

1

General methods. $^{1}H$ NMR (600 MHz) and $^{13}C$ NMR (150 MHz) spectra were collected at room temperature in $CDCl_3$ unless noted otherwise. Chemical shifts for $^{1}H$ NMR spectra are reported in parts per million (δ) relative to tetramethylsilane. Chemical shifts for $^{13}C$ NMR spectra are reported in parts per million (δ), and spectra were calibrated by using tetramethylsilane signal. Silica (40 μm) was used for column chromatography. All solvents were reagent grade and were used as received unless noted otherwise. $CHCl_3$ was stabilized with EtOH. Commercial compounds were used as received unless noted otherwise. Cyanuric chloride was recrystallized from $CH_2Cl_2$ and hexanes before use. Known compound (3) (Fujita, H., et al., *New J. Chem.* 2020, 44, 719-743) was prepared generally following procedure described in the literature.

Synthesis of 2,4-Bis{10-[[1-acetyl-3-(2,3,4,6-tetra-O-acetyl-β-D-glucopyranosyloxy)-4,6-dibromo-1H-indol-5-yl]-1,4,7,10-tetraoxadec-1-yl]}-6-chloro-1,3,5-triazine (4). Following a previously reported procedure (Fujita, H., et al., *New J. Chem.* 2020, 44, 719-743) with some modifications, a sample of pempidine (95.0 μL, 525 μmol, 3.5 equiv) was added to a mixture of cyanuric chloride (2, 27.7 mg, 150 μmol, 1.0 equiv), 3 (256 mg, 315 μmol, 2.1 equiv), and powdered molecular sieves 4 Å (40 mg) in 1,2-dichloroethane (0.50 mL). The reaction mixture was stirred at 60° C. for 17 h. The reaction mixture was concentrated in vacuo, and the resulting yellow oil was purified by column chromatography (silica, $CH_2Cl_2$:acetone=90:10 to 85:15) to obtain a pale yellow foam (163 mg, 94.0 μmol, 63%): 1H NMR (600 MHz, $CDCl_3$) δ 8.66 (br s, 2H), 7.25 (s, 2H), 5.40-5.34 (m, 2H), 5.33-5.27 (m, 2H), 5.20 (t, J=9.6 Hz, 2H), 5.05 (d, J=7.6 Hz, 2H), 4.61-4.54 (m, 4H), 4.38 (dd, J=2.2, 12.4 Hz, 2H) 4.24-4.11 (m, 6H), 3.95 (t, J=5.0 Hz, 4H), 3.92-3.84 (m, 6H), 3.81-3.77 (m, 4H), 3.76-3.71 (m, 4H), 2.60 (s, 6H), 2.09 (s, 12H), 2.07 (s, 6H), 2.05 (s, 6H); $^{13}C$ NMR (150 MHz, $CDCl_3$) δ 172.6, 172.0, 170.5, 170.2, 169.4, 169.2, 167.8, 149.7, 140.3, 130.9, 123.0, 120.2, 116.2, 112.0, 107.5, 100.2, 72.6, 72.5, 70.9, 70.7, 70.2, 69.5, 68.7, 68.4, 68.2, 61.9, 23.7, 20.9, 20.8, 20.6.

Synthesis of alkyne amylose (6). Following a previously reported reductive amination procedure (Schatz, C., et al., *Angew. Chem. Int. Ed. Engl.* 2009, 48, 2572-2575) with some modifications, a sample of amylose (5, 12000-16000 g/mol, 86 AGU, 350 mg, 25.0 μmol amylose, 1.0 equiv) was dissolved in 1 M NaOH (1.5 mL), and then treated with an equivalent amount of acid, 1 M HCl (1.5 mL) to generate neutral solution. After addition of 100 mM acetate buffer (pH 5.0, 6.0 mL), the solution was treated with propargylamine (160 μL, 2.50 mmol, 100 equiv) and $NaBH_3CN$ (39.3 mg, 625 μmol, 25 equiv). The reaction mixture was stirred at 50° C. for 4 days with a daily addition of 25 equiv of $NaBH_3CN$. The solution was directly purified by dialysis (Spectra/Por3, Standard RC, Mw cut off=3,500) against deionized water (1.0 L) at room temperature for 5 days. Deionized water was exchanged 4 times per a day. Resulting solution was lyophilized to obtain a white cotton-like solid (248 mg, 17.7 μmol amylose, 71%).

Synthesis of Di-tert-butyl (12-(17-azido-3,6,9,12,15-pentaoxaheptadecyl)-3,6,9,15,18,21-hexaoxa-12-azatricosane-1,23-diyl)dicarbamate (9). A solution of 7 (114 mg, 200 μmol, 1.0 equiv) in $CH_2Cl_2$ (0.50 mL) was treated with 8 (88.8 mg, 240 μmol, 1.2 equiv) and $Et_3N$ (61.3 μL, 440 μmol, 2.2 equiv) at 4° C. The reaction mixture was stirred at 4° C. to room temperature for 19 h. The reaction mixture was heated at 40° C. and stirred for 46 h. After evaporation of the solvent, 10% aqueous citric acid (2.0 mL) was added. The aqueous solution was washed with ethyl acetate (1.0 mL×3). A sample of $NaHCO_3$ was added to the water layer to generate neutral solution, and the product was extracted with ethyl acetate (2.0 mL×3). The organic layers were combined and washed with brine (5.0 mL×2). The organic layer was dried over anhydrous $Na_2SO_4$. After removal of $Na_2SO_4$ by filtration, the solution was concentrated in vacuo. The residual yellow oil was purified by column chromatography (silica, $CHCl_3$ (containing approx. 0.75% EtOH as preservative):MeOH=93:7) to obtain a pale yellow oil (52.7 mg, 61.5 μcool, 31%): $^1$H NMR (600 MHz, $CDCl_3$) δ 5.07 (br, 2H), 3.70-3.57 (m, 34H), 3.57-3.50 (m, 10H), 3.39 (t, J=5.1 Hz, 2H), 3.35-3.25 (m, 4H), 2.79 (t, J=5.8 Hz, 6H), 1.44 (s, 18H); $^{13}$C NMR (150 MHz, $CDCl_3$) δ 156.0, 79.1, 70.7, 70.6, 70.5, 70.4, 70.2, 70.0, 69.8, 54.6, 54.5, 50.7, 40.4, 28.4.

Synthesis of fully protected tetrakis(indoxyl-glycosides) (10). A solution of 9 (28.6 mg, 29.5 μcool, 1.0 equiv) in 4 M hydrogen chloride in dioxane (1.0 mL) was stirred at room temperature for 2 h. The solution was concentrated and dried under reduced pressure. A solution of the resulting oil (21.7 mg, 29.5 μcool, 1.0 equiv) in $CH_2Cl_2$ (1.0 mL) was treated with 4 (102 mg, 59.0 μcool, 2.0 equiv) and DIEA (15.4 μL, 88.5 μcool, 3.0 equiv), and the reaction mixture was stirred at room temperature for 4 h. After quenching by addition of AcOH (1.69 μL, 29.5 μcool, 1.0 equiv), the solution was concentrated in vacuo. The residual yellow oil was purified by column chromatography (silica, $CHCl_3$ (containing approx. 0.75% EtOH as preservative):MeOH:$CH_3CN$=74:6:20 and $CHCl_3$ (containing approx. 0.75% EtOH as preservative):MeOH:$CH_3CN$=70:10:20) to obtain a colorless oil (36.6 mg, 9.03 μcool, 31%): $^1$H NMR (600 MHz, $CDCl_3$) δ 8.66 (br s, 4H), 7.25 (s, 4H), 5.98 (br, 2H), 5.41-5.33 (m, 4H), 5.33-5.26 (m, 4H), 5.20 (t, J=9.6 Hz, 4H), 5.06 (d, J=7.6 Hz, 4H), 4.49 (t, J=5.0 Hz, 4H), 4.45 (t, J=4.9 Hz, 4H), 4.38 (dd, J=2.2, 12.4 Hz, 4H), 4.25-4.10 (m, 12H), 4.05-3.42 (m, 96H), 3.38 (t, J=5.0 Hz, 2H), 2.60 (s, 12H), 2.09 (s, 24H), 2.07 (s, 12H), 2.04 (s, 12H); $^{13}$C NMR (150 MHz, $CDCl_3$) δ 172.0, 171.5, 170.5, 170.2, 169.4, 169.3, 168.0, 167.8, 149.7, 140.4, 130.9, 123.0, 120.2, 116.2, 112.1, 107.6, 100.2, 72.6, 72.5, 70.8, 70.7, 70.6, 70.4, 70.1, 70.0, 69.6, 69.2, 69.1, 68.2, 66.6, 66.5, 61.9, 54.6, 54.5, 50.7, 40.8, 29.7, 23.7, 21.0, 20.8, 20.6; ESI-MS obsd 1349.87384, calcd 1349.87774 [$(M+3H)^{3+}$, M=$C_{154}H_{202}Br_8N_{16}O_{71}$].

Synthesis of deacetylated tetrakis(indoxyl-glycosides) (11). A sample of $Et_3N$ (0.347 mL, 2.49 mmol, 1000 equiv) was added to a solution of 10 (10.1 mg, 2.49 μmol, 1.0 equiv) in $CH_2Cl_2$/MeOH/$H_2O$ (2:2:1, 1.0 mL), and the reaction mixture was stirred at room temperature for 25 h. After addition of $Et_3N$ (0.174 mL, 12.5 mmol, 500 equiv), the reaction mixture was stirred at room temperature for 3.5 h. The reaction mixture was concentrated in vacuo, and the residue was washed with $CH_3CN$ (2.0 mL×3) to obtain a pale yellow solid (9.20 mg, 2.49 μmol, 100%): $^1$H NMR (600 MHz, $CDCl_3$: $CD_3OD$=1:1) δ 7.48 (s, 4H), 7.17 (d, J=3.0 Hz, 4H), 4.72 (dd, J=0.7, 7.7 Hz, 4H), 4.49 (t, J=4.8 Hz, 4H), 4.45 (t, J=4.7 Hz, 4H), 4.14 (t, J=4.8 Hz, 8H), 4.00-3.89 (m, 16H), 3.89-3.70 (m, 30H), 3.70-3.38 (m, 74H); $^{13}$C NMR (150 MHz, $CDCl_3$: $CD_3OD$=1:1) δ 172.1, 171.6, 168.0, 145.9, 137.7, 131.8, 118.8, 115.5, 114.5, 114.4, 111.8, 106.8, 104.4, 104.3, 76.9, 76.6, 74.2, 72.8, 71.0, 70.8, 70.7, 70.6, 70.5, 70.3, 69.8, 69.5, 69.4, 69.3, 67.0, 66.8, 62.0, 54.4, 52.8, 50.9, 46.2, 41.0; ESI-MS obsd 1069.80731, calcd 1069.80364 [$(M+3H)^{3+}$, M=$C_{114}H_{162}Br_8N_{16}O_{51}$].

Synthesis of tetrakis(indoxyl)amylose (1). A sample of 6 (22.0 mg, 1.83 μmol, 1.0 equiv) was dissolved in DMSO (0.50 mL) at 40° C., and the solution was added to the solution of 11 (7.03 mg, 2.19 μmol, 1.2 equiv), $CuSO_4.5H_2O$ (0.457 mg, 1.83 μmol, 1.0 equiv), and sodium ascorbate (0.725 mg, 3.66 μmol, 2.0 equiv) in $H_2O$ (60 μL). The reaction mixture was stirred at room temperature for 25 h. After addition of $CuSO_4.5H_2O$ (0.457 mg, 1.83 μmol, 1.0 equiv) and sodium ascorbate (0.725 mg, 3.66 μmol, 2.0 equiv) in $H_2O$ (60 μL), and the reaction mixture was stirred at room temperature for 20.5 h. The solution was concentrated in vacuo, and the product was precipitated by $CH_2Cl_2$:MeOH (1:1, 10 mL). The green and white solid was collected by filtration, and dried under reduced pressure. The collected solid was dissolved in $H_2O$ (1.0 mL) and purified by dialysis (Spectra/Por3, Standard RC, Mw cut off=3,500) against deionized water (1.0 L) at room temperature for 2 days. Deionized water was exchanged 4 times per a day. Resulting solution was lyophilized to obtain a white cotton-like solid (19.5 mg).

The foregoing is illustrative of the present invention, and is not to be construed as limiting thereof. The invention is defined by the following claims, with equivalents of the claims to be included therein.

That which is claimed is:

1. A compound having a structure of Formula I:

I

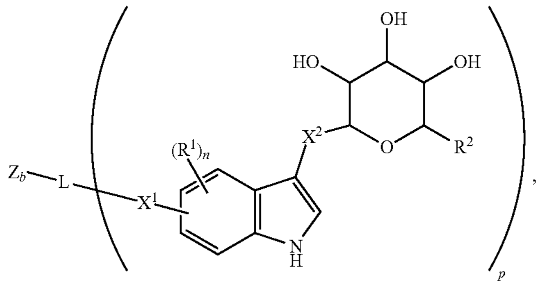

wherein:

Z is each independently a hydroxyl, amino, enzyme, polyiodide binding matrix, a targeting agent, a circulation enhancing agent, water solubilizing group, chromophore, or bioconjugatable group;

L is a linker that comprises a polyethylene glycol;

$X^1$ is absent, —O—, or —S—;

each $R^1$ is independently selected from a halogen, alkyl, alkenyl, alkynyl, —OH, alkoxy, acyloxy, carboxy, carboxylic ester, boronate ester, thioalkoxy, and amino;

each $R^2$ is independently —$CH_2OH$ or —C(O)OH;

each $X^2$ is independently —O—, —S—, or a self-immolative linker;

p is an integer of 1 to 6;

b is an integer of 1 to 6; and each n is independently an integer of 1 to 4;

or a pharmaceutically acceptable salt thereof.

2. The compound of claim 1, wherein $R^2$ is —$CH_2OH$.

3. The compound of claim 1, wherein $R^2$ is —C(O)OH.

4. The compound of claim 1, wherein the compound has a structure of Formula I and Z, L, $X^1$, $R^1$, $R^2$, $X^2$, p, b, and n are each as defined above.

5. The compound of claim 1, wherein $X^2$ is O.

6. The compound of claim 1, wherein $X^2$ is a self-immolative linker.

7. The compound of claim 1, wherein L has a structure of Formula IV:

IV

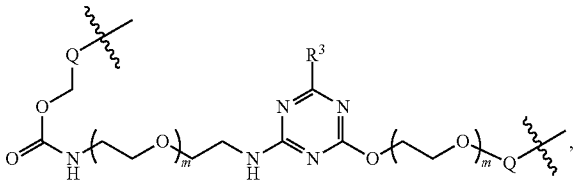

wherein:

each Q is independently absent or is —$(CH_2)_q$—, alkenyl, alkynyl, aryl, —C(O)—, or —$CH_2C(O)$— each of which may be substituted or unsubstituted, where q is an integer of 2 to 5, 10, or 20;

each m is independently an integer of 1 to 100; and $R^3$ is a hydrogen, Z as defined above, a moiety having a structure of Formula I as defined above, or an aryl or heterocycle each of which may be substituted or unsubstituted.

8. The compound of claim 1, wherein L comprises:

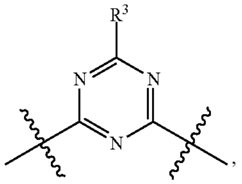

wherein $R^3$ is Z as defined above, a moiety having a structure of Formula I as defined above, or an aryl, alkylamino, alkoxy, or heterocycle, each of which may be substituted or unsubstituted.

9. The compound of claim 8, wherein $R^3$ has a structure of:

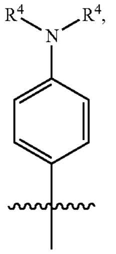

wherein each $R^4$ is independently a hydrogen or is a substituted or unsubstituted alkyl, alkenyl, or alkynyl.

10. The compound of claim 8, wherein $R^3$ has a structure of:

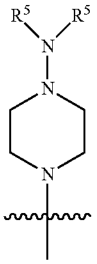

wherein each $R^5$ is independently a hydrogen or is a substituted or unsubstituted alkyl, alkenyl, or alkynyl.

11. The compound of claim 1, wherein Z has a structure of:

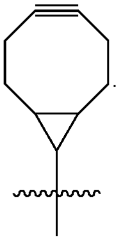 [SMILES: *C1C2CCC#CCCC12]

12. The compound of claim 1, wherein the compound has a structure of Formula I'':

I''

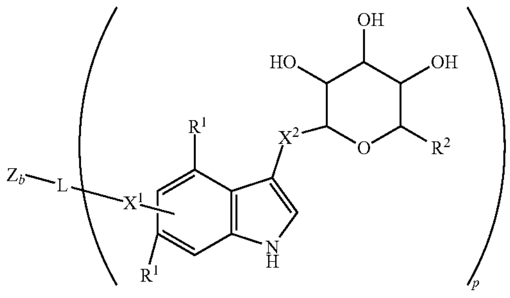

II''

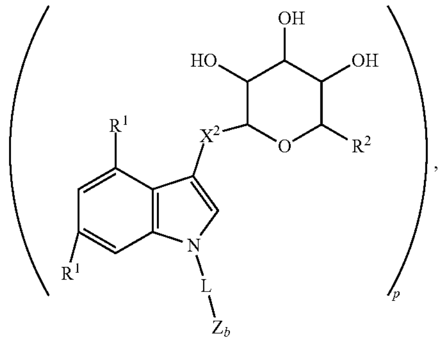

wherein at least one of $R^1$ in Formula I'' is a halogen; and Z, L, $X^1$, $R^1$, $R^2$, $X^2$, p, b, and n are each as defined above.

13. The compound of claim 12, wherein both of $R^1$ in Formula I'' is a halogen.

14. The compound of claim 12, wherein $X^2$ and/or $X^1$ is O.

15. The compound of claim 1, wherein the compound has the following structure:
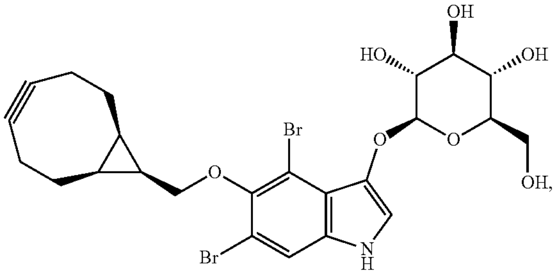
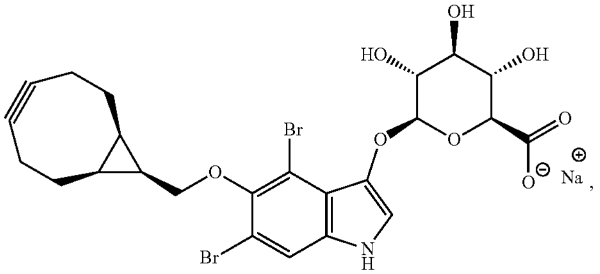
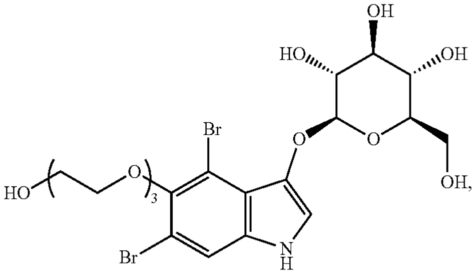
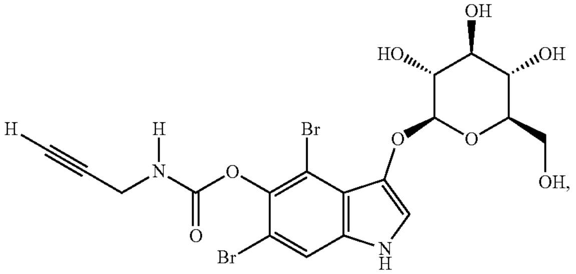
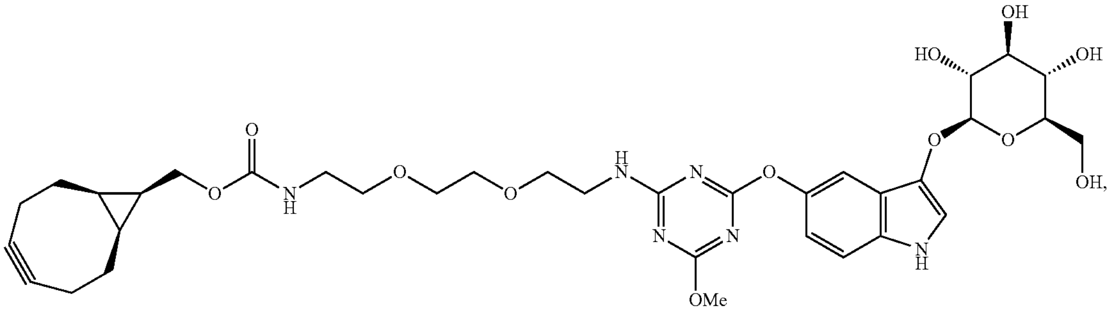
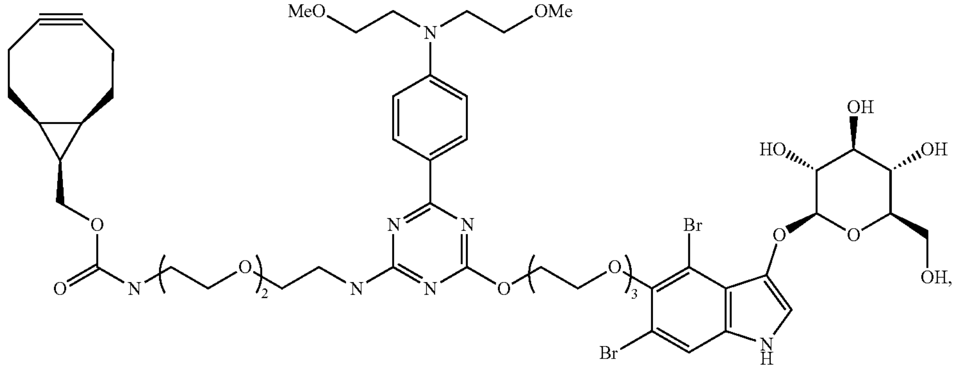
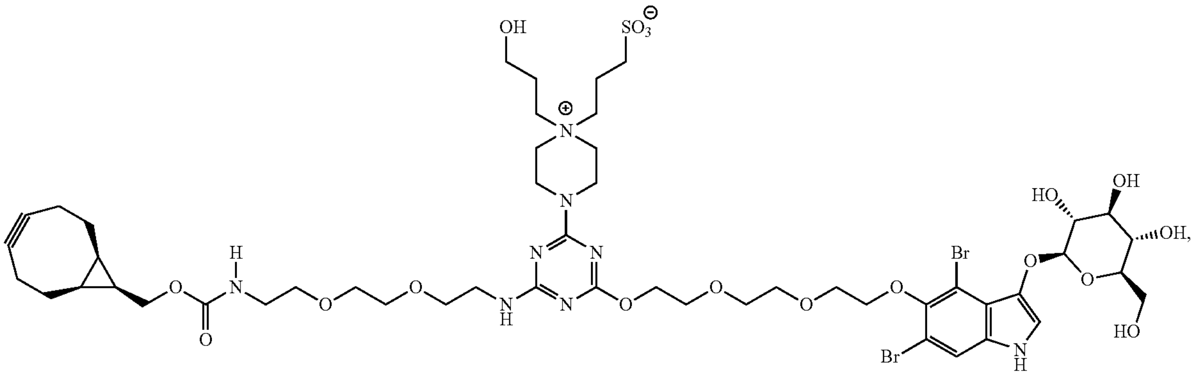

-continued
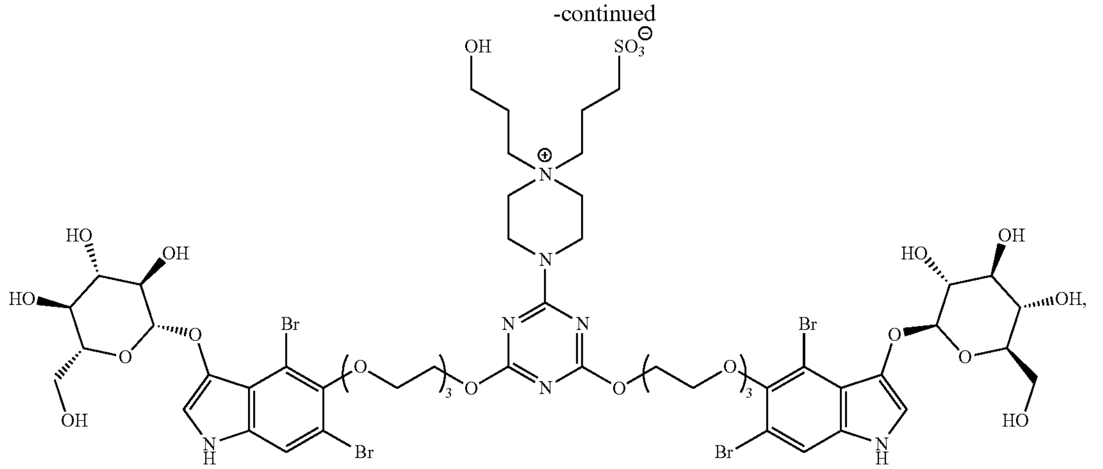
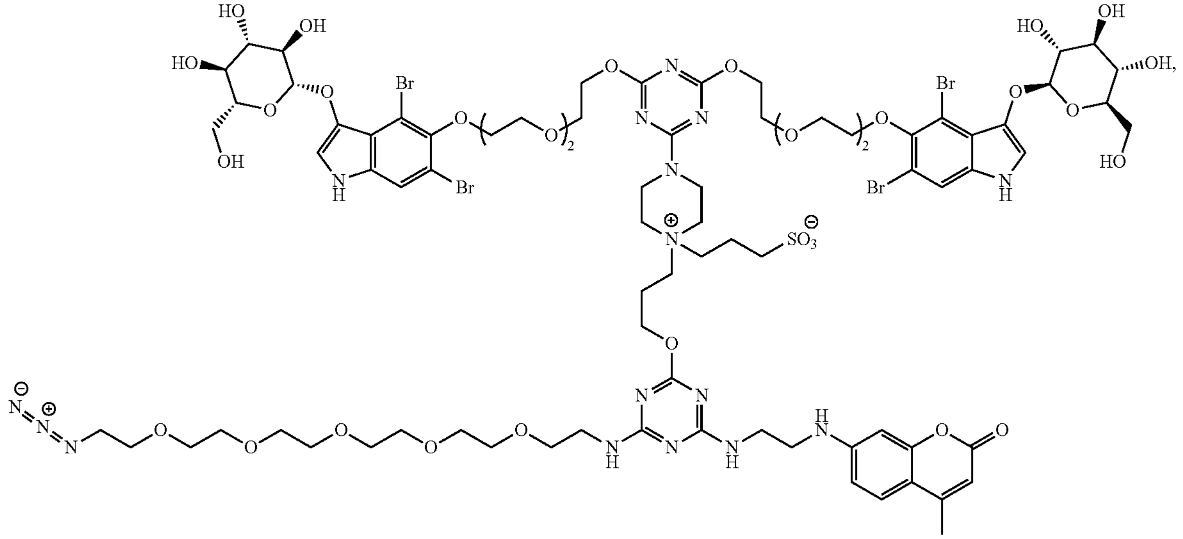
or
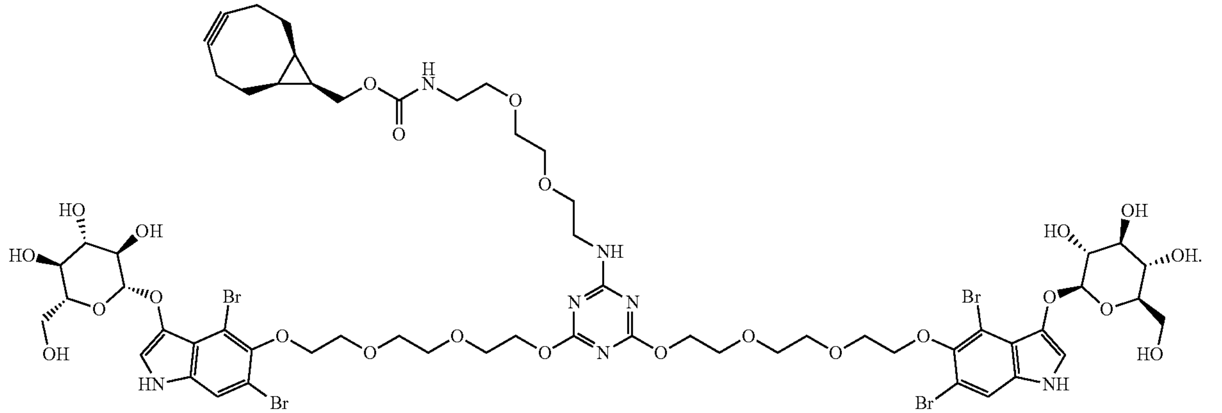
* * * * *